United States Patent
Clark et al.

(10) Patent No.: US 8,436,009 B2
(45) Date of Patent: May 7, 2013

(54) PRODRUG OF TRIAZOLONE COMPOUND

(75) Inventors: Richard Clark, Ibaraki (JP); Fumiyoshi Matsuura, Ibaraki (JP); Masanobu Shinoda, Tokyo (JP); Shinsuke Hirota, Ibaraki (JP); Kazunobu Kira, Ibaraki (JP); Hiroshi Azuma, Ibaraki (JP); Atsushi Takemura, Ibaraki (JP); So Yasui, Ibaraki (JP); Kazutomi Kusano, Ibaraki (JP); Masaki Mikamoto, Ibaraki (JP); Takao Omae, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/695,665

(22) PCT Filed: May 18, 2011

(86) PCT No.: PCT/JP2011/061919
§ 371 (c)(1),
(2), (4) Date: Nov. 1, 2012

(87) PCT Pub. No.: WO2011/145747
PCT Pub. Date: Nov. 24, 2011

(65) Prior Publication Data
US 2013/0053563 A1 Feb. 28, 2013

Related U.S. Application Data

(60) Provisional application No. 61/346,738, filed on May 20, 2010.

(51) Int. Cl.
*A61K 31/506* (2006.01)
*C07D 239/42* (2006.01)

(52) U.S. Cl.
USPC .......................................... 514/275; 544/332

(58) Field of Classification Search ............... 514/230.5, 514/384, 340, 275, 333, 338, 337, 252.05, 514/255.05; 548/263.2; 546/268.4, 256; 544/331, 238, 405, 105, 242
See application file for complete search history.

(56) References Cited

U.S. PATENT DOCUMENTS

| | | | |
|---|---|---|---|
| 7,807,690 | B2 | 10/2010 | Clark et al. |
| 7,816,522 | B2 | 10/2010 | Clark et al. |
| 7,928,228 | B2 | 4/2011 | Clark et al. |
| 8,163,787 | B2 | 4/2012 | Clark et al. |
| 2008/0132507 | A1 | 6/2008 | Clark et al. |
| 2010/0184981 | A1 | 7/2010 | Clark et al. |
| 2010/0240654 | A1 | 9/2010 | Clark et al. |

FOREIGN PATENT DOCUMENTS

| | | |
|---|---|---|
| EP | 1078917 | 2/2001 |
| EP | 2000465 | 12/2008 |
| WO | WO00/35858 | 6/2000 |
| WO | WO00/41531 | 7/2000 |
| WO | WO00/58346 | 10/2000 |
| WO | WO00/66545 | 11/2000 |
| WO | WO2007/111212 | 10/2007 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Bundgaard, "Design of prodrugs: bioreversible derivatives for various functional groups and chemical entities," *Design of Prodrugs*, pp. 1-92 (1985).

(Continued)

*Primary Examiner* — Kristin Bianchi
(74) *Attorney, Agent, or Firm* — Fish & Richardson P.C.

(57) ABSTRACT

By oral administration of a compound represented by the following Formula (I): the blood level of Compound (IV): which has an excellent inhibitory action against blood coagulation factor VIIa and the anticoagulant action, reaches a level sufficient for expression of its pharmacological actions. Therefore, the compound of the present invention is useful as a therapeutic and/or prophylactic agent for diseases caused by thrombus formation.

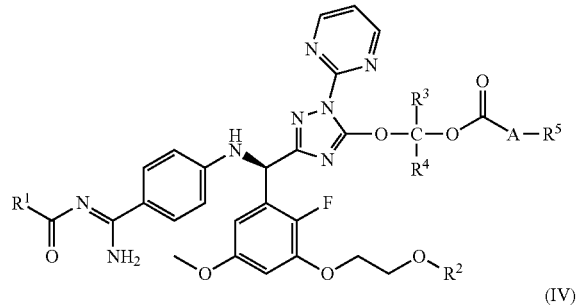

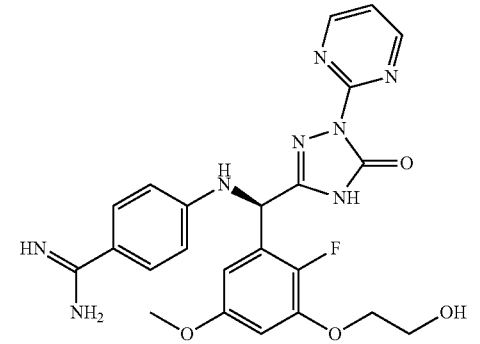

18 Claims, 6 Drawing Sheets

OTHER PUBLICATIONS

Hirota et al., "Discovery and optimization of potent and selective tissue factor/factor VIIa inhibitors," MEDI-352, 242$^{nd}$ ACS National Meeting, 1 page (2011).

International Search Report for PCT Application No. PCT/JP2011/061919, dated Aug. 4, 2011, 2 pages.

Murakami-Tabata et al., "Combined tissue factor/factor VIIa inhibitor and acetylsalicylic acid show increased antithrombotic potency without affecting bleeding time," ATVB 2012, 1 page (2012).

Nagakura et al., "Selective tissue factor/factor VIIa inhibitor ER-410660 and its prodrug E55'39 have an anti-venous thrombotic effect with low risk of bleeding," AHA Scientific Session, 1 page (2011).

Official Letter for Pakistani App. Ser. No. 352/2011, dated Nov. 1, 2012, 2 pages.

Roussel et al., "Inhibition of the Tissue Factor/Factor VIIa complex-lead optimization using combinatorial chemistry," *Tetrahedron*, 55:6219-6230 (1999).

\* cited by examiner

PRODRUG OF TRIAZOLONE COMPOUND

TECHNICAL FIELD

The present invention relates to a prodrug of a triazolone compound or a pharmaceutically acceptable salt thereof which is useful as a pharmaceutical, and a therapeutic or prophylactic agent containing the same as an effective ingredient, for a disease caused by thrombus formation.

BACKGROUND ART

When a blood vessel is ruptured, the body immediately produces thrombin to avoid bleeding to death. On the other hand, an excess amount of thrombin produced due to an inflammatory reaction or the like in a damaged vessel causes thrombosis, leading to impairment of important organ functions. Therefore, for therapy or prophylaxis of thrombosis, a thrombin inhibitor such as heparin or warfarin, which inhibits thrombin production or directly inhibits the thrombin activity, has been used as an anticoagulant for a long time. However, the degree of medical satisfaction with these drugs is not necessarily high, and research and development on novel anticoagulants, having excellent dose-response relationships, a low risk of hemorrhage, and that can be orally administered, is now being pursued on a global scale.

The mechanisms of blood coagulation have been divided into the "intrinsic coagulation pathway", which is initiated by activation of factor XII (FXII) due to contact with a negatively charged substance, and the "extrinsic coagulation pathway", which is activated by tissue factor (TF) and factor VII (FVII). In the case of development of thrombosis, the extrinsic coagulation pathway has been suggested to be important since TF is specifically expressed in the pathological condition. Therefore, it has been thought that compounds that inhibit blood coagulation factor VIIa which is positioned furthest upstream in the extrinsic coagulation pathway are useful as therapeutic and/or prophylactic agents for diseases caused by thrombus formation, such as thrombosis in which the extrinsic coagulation pathway is involved.

Known examples of such compounds that inhibit blood coagulation factor VIIa include amidinonaphthol derivatives (see Non-patent Document 1), amidino derivatives (see Patent Document 1), N-sulfonyldipeptide derivatives (see Patent Document 2), 6-[[(allyl)oxy]methyl]naphthalene-2-carboxylmidamide derivatives (see Patent Document 3) and phenylglycine derivatives (see Patent Documents 4 and 5). Further, triazolone derivatives (see Patent Document 6), which are the active constituents of the prodrugs of the present invention, are known.

However, known compounds are insufficient with respect to their inhibitory activity against blood coagulation factor VIIa, anticoagulant action, therapeutic action against thrombosis, and the like. For triazolone derivatives, further improvement of absorbability upon oral administration has been considered necessary.

CITATION LIST

Non Patent Literature

Non-patent Document 1: Tetrahedron, vol. 55, p. 6219, 1999.

Patent Literature

Patent Document 1: European Patent Application Publication No. 1078917

Patent Document 2: WO 00/58346
Patent Document 3: WO 00/66545
Patent Document 4: WO 00/35858
Patent Document 5: WO 00/41531
Patent Document 6: WO 07/111,212

SUMMARY OF INVENTION

Technical Problem

The present invention aims to provide a prodrug derivative of a triazolone compound which has excellent selective inhibitory activity against blood coagulation factor VIIa, and a pharmaceutically acceptable salt thereof, which has excellent oral absorbability, and a therapeutic and/or prophylactic agent using them for a disease caused by thrombus formation.

Solution to Problem

The present inventors intensively studied solutions of the above-described problems and succeeded in synthesizing novel prodrug derivatives of triazolone compounds having a particular chemical structure, and discovered that these compounds show improved absorbability upon oral administration, that is, improved bioavailability of the active constituent, thereby completing the present invention.

That is, the present invention relates to

<1> a compound represented by the following Formula (I) or a pharmaceutically acceptable salt thereof:

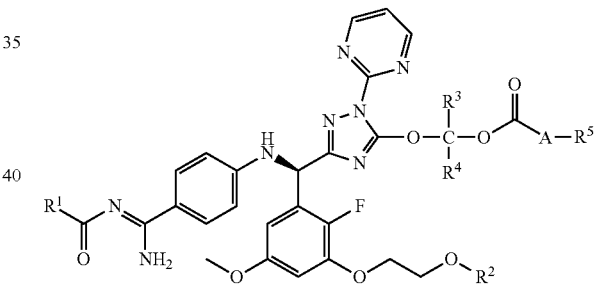

wherein $R^1$ represents phenyl optionally substituted by one to three $C_1$-$C_6$ alkyl groups, $C_1$-$C_6$ alkoxy or $C_2$-$C_6$ alkenyloxy;

$R^2$ represents a hydrogen atom, $C_1$-$C_6$ alkylcarbonyl or pyridylcarbonyl;

$R^3$ and $R^4$ each independently represent a hydrogen atom or $C_1$-$C_6$ alkyl;

A represents a single bond, an oxygen atom, a group represented by Formula (II):

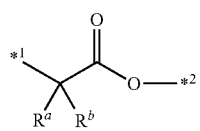

(II)

wherein $R^a$ and $R^b$ each independently represent a hydrogen atom or $C_1$-$C_6$ alkyl, and *1 and *2 mean linking to carbonyl and to $R^5$, respectively, in Formula (I), or a group represented by Formula (III):

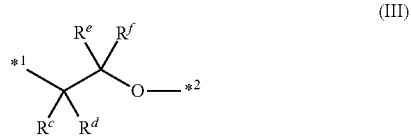

wherein $R^c$, $R^d$, $R^e$ and $R^f$ each independently represent a hydrogen atom or $C_1$-$C_6$ alkyl, and *1 and *2 have the same meanings as described above; and $R^5$ represents $C_1$-$C_6$ alkyl or $C_3$-$C_8$ cycloalkyl, and $C_1$-$C_6$ alkyl or $C_3$-$C_8$ cycloalkyl in $R^5$ is optionally substituted by one to three identical or different substituents selected from the group of substituents consisting of a halogen atom, $C_1$-$C_6$ alkyl and $C_1$-$C_6$ alkoxy.

<2> the compound or the pharmaceutically acceptable salt thereof according to <1>, wherein $R^1$ is phenyl, 4-tolyl, 2,2-dimethyl-1-propyloxy, 2,2-dimethyl-1-butyloxy or 2-methyl-2-propenyloxy;

<3> the compound or the pharmaceutically acceptable salt thereof according to <1>, wherein $R^2$ is a hydrogen atom, acetyl or 4-pyridylcarbonyl;

<4> the compound or the pharmaceutically acceptable salt thereof according to <1>, wherein $R^3$ and $R^4$ are each independently a hydrogen atom, methyl or ethyl;

<5> the compound or the pharmaceutically acceptable salt thereof according to <1>, wherein $R^5$ is $C_1$-$C_6$ alkyl optionally substituted by methoxy, or cyclohexyl optionally substituted by a halogen atom or methyl;

<6> the compound or the pharmaceutically acceptable salt thereof according to <1>, wherein $R^a$, $R^b$, $R^c$, $R^d$, $R^e$ and $R^f$ are each independently a hydrogen atom or methyl;

<7> the compound or the pharmaceutically acceptable salt thereof according to <1>, wherein $R^1$ is 4-tolyl, phenyl, 2,2-dimethyl-1-propyloxy, 2,2-dimethyl-1-butyloxy or 2-methyl-2-propenyloxy;

$R^2$ is a hydrogen atom, acetyl or 4-pyridylcarbonyl;

$R^3$ and $R^4$ are each independently a hydrogen atom, methyl or ethyl;

$R^5$ is $C_1$-$C_6$ alkyl optionally substituted by methoxy, or cyclohexyl optionally substituted by a halogen atom or methyl;

A is a single bond, an oxygen atom, a group represented by Formula (II) or a group represented by Formula (III); and $R^a$, $R^b$, $R^c$, $R^d$, $R^e$ and $R^f$ are each independently a hydrogen atom or methyl;

<8> the compound or the pharmaceutically acceptable salt thereof according to <1>, wherein the compound is (1) 3-methoxymethoxy-2,2-dimethylpropionic acid 5-{(R)-[4-(amino[benzoylimino]methyl)phenylamino]-[2-fluoro-3-(2-hydro xyethoxy)-5-methoxyphenyl]methyl}-2-pyrimidin-2-yl-2H-[1,2,4]triazol-3-yloxymethyl ester, (2) 2,2-dimethylmalonic acid 5-{(R)-(4-{amino(2,2-dimethylpropoxycarbonylimino)methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester t-butyl ester, (3) carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester cyclohexyl ester, (4) 4-pyridinecarboxylic acid 2-(3-{(R)-(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methyl}-2-fluoro-5-methoxyphenoxy)ethyl ester, (5) 2-ethylbutanoic acid 5-[(R)-[3-(2-acetoxyethoxy)-2-fluoro-5-methoxyphenyl]-(4-{amino[2,2-dimethylpropoxycarbonylimino]methyl}phenylamino)methyl]-2-pyrimidin-2-yl-2H-[1,2,4]triazol-3-yloxymethyl ester, (6) 3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester, (7) cyclohexane carboxylic acid 5-[(R)-[3-(2-acetoxyethoxy)-2-fluoro-5-methoxyphenyl]-(4-{amino[2,2-dimethylpropoxycarbonylimino]methyl}phenylamino)methyl]-2-pyrimidin-2-yl-2H-[1,2,4]triazol-3-yloxymethyl ester, (8) 2,2-dimethylmalonic acid 5-{(R)-(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester cyclohexyl ester, (9) carbonic acid 1-(5-{(R)-(4-{amino[4-methylbenzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (1R,2R)-2-methylcyclohexyl ester, (10) 2,2-dimethylmalonic acid 5-{(R)-(4-{amino(2,2-dimethylpropoxycarbonylimino)methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester, (11) carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (R)-1-methylbutyl ester, (12) carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (1S,2S)-2-fluorocyclohexyl ester, (13) carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)propyl ester cyclohexyl ester, (14) carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)propyl ester trans-2-fluoro-cyclohexyl ester, (15) 2,2-dimethylmalonic acid 5-{(R)-(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester ethyl ester, (16) 2,2-dimethylmalonic acid 5-{(R)-(4-{amino(2,2-dimethylpropoxycarbonylimino)methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester isopropyl ester, (17) isonicotinic acid 2-(3-{(R)-(4-{amino[benzoylimino]methyl}phenylamino)-[5-(2,2-dimethyl propionyloxymethoxy)-1-pyrimidin-2-yl-1H-[1,2,4]triazol-3-yl]methyl}-2-fluoro-5-methoxyphenoxy)ethyl ester or (18) 2,2-dimethylmalonic acid 5-{(R)-(4-{amino[2,2-dimethylbutoxycarbonylimino]methyl}phenylamino)-[2-fluoro-3-(2-hydroxyethoxy)-5-methoxyphenyl]methyl}-2-pyrimidin-2-yl-2H-[1,2,4]-triazol-3-yloxymethyl ester 2,2-dimethylpropyl ester;

<9> the compound or the pharmaceutically acceptable salt thereof according to <1>, wherein the compound is (1) 3-methoxymethoxy-2,2-dimethylpropionic acid 5-{(R)-[4-(amino[benzoylimino]methyl)phenylamino]-[2-fluoro-3-(2-hydroxyethoxy)-5-methoxyphenyl]methyl}-2-pyrimidin-2-yl-2H-[1,2,4]triazol-3-yloxymethyl ester, (4) 4-pyridinecarboxylic acid 2-(3-{(R)-(4-{amino[benzoylimino]methyl}phenylamino)-[5-(3-methoxy-2,2-dimethylpropionyloxymethoxy)-1-pyrimidin-2-yl-1H-[1,2,4]

triazol-3-yl]methyl}-2-fluoro-5-methoxyphenoxy)ethyl ester, (5) 2-ethylbutanoic acid 5-[(R)-[3-(2-acetoxyethoxy)-2-fluoro-5-methoxyphenyl]-(4-{amino[2,2-dimethylpropoxycarbonylimino]methyl}phenylamino)methyl]-2-pyrimidin-2-yl-2H-[1,2,4]triazol-3-yloxymethyl ester, (6) 3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester, (13) carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)propyl ester cyclohexyl ester or (18) 2,2-dimethylmalonic acid 5-{(R)-(4-{amino[2,2-dimethylbutoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester;

<10> (1) 3-methoxymethoxy-2,2-dimethylpropionic acid 5-{(R)-[4-(amino[benzoylimino]methyl)phenylamino]-[2-fluoro-3-(2-hydro xyethoxy)-5-methoxyphenyl]methyl}-2-pyrimidin-2-yl-2H-[1,2,4]triazol-3-yloxymethyl ester or a pharmaceutically acceptable salt thereof;

<11> (6) 3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester or a pharmaceutically acceptable salt thereof;

<12> the compound or the pharmaceutically acceptable salt thereof according to <1>, wherein the compound is (51) acetic acid 2-(3-{(R)-(4-{amino[2-methylallyloxycarbonylimino]methyl}phenylamino)-[5-(1-ethylpropoxycarbonyloxymethoxy)-1-pyrimidin-2-yl-1H-[1,2,4]triazol-3-yl]methyl}-2-fluoro-5-methoxyphenoxy)ethyl ester, (52) acetic acid 2-{3-[(R)-(4-{amino[2-methylallyloxycarbonylimino]methyl}phenylamino)-(5-isopropoxycarbonyloxymethoxy-1-pyrimidin-2-yl-1H-[1,2,4]triazol-3-yl)methyl]-2-fluoro-5-methoxyphenoxy}ethyl ester, (53) acetic acid 2-{3-[(R)-(4-{amino[2-methylallyloxycarbonylimino]methyl}phenylamino)-(5-isopropoxycarbonyloxymethoxy-1-pyrimidin-2-yl-1H-[1,2,4]triazol-3-yl)methyl]-2-fluoro-5-methoxyphenoxy}ethyl ester, (54) acetic acid 2-(3-{(R)-(4-{amino[butoxycarbonylimino]methyl}phenylamino)-[5-(1-eth ylpropoxycarbonyloxymethoxy)-1-pyrimidin-2-yl-1H-[1,2,4]triazol-3-yl]methyl}-2-fluoro-5-methoxyphenoxy) ethyl ester, (55) acetic acid 2-(3-{(R)-(4-{amino[isobutoxycarbonylimino]methyl}phenylamino)-[5-(1-ethylpropoxycarbonyloxymethoxy)-1-pyrimidin-2-yl-1H-[1,2,4]triazol-3-yl]methyl}-2-fluoro-5-methoxyphenoxy) ethyl ester, (56) carbonic acid 5-{(R)-(4-{amino-[2-methylallyloxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester, (57) acetic acid 2-(3-{(R)-(4-{amino[2-methylallyloxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester, (58) carbonic acid 5-{(R)-(4-{amino-[2-ethoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester, (59) carbonic acid 5-{(R)-(4-{amino-[2-propoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester, (60) carbonic acid 5-{(R)-(4-{amino-[2-butoxycarbonylimino]methyl}phenylamino)-[2-fluoro-3-(2-hydroxyethoxy)-5-methoxyphenyl]methyl}-2-pyrimidin-2-yl-2H[1,2,4]triazol-3-yloxymethyl ester 2-fluoro-1,1-dimethylethyl ester, (61) acetic acid 2-(3-{(R)-(4-{amino[ethoxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester, (62) acetic acid 2-(3-{(R)-(4-{amino[propoxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester, (63) acetic acid 2-(3-{(R)-(4-{amino[butoxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester, (67) acetic acid 2-{3-[(R)-(4-{amino[butoxycarbonylimino]methyl}phenylamino)-(5-isopropoxycarbonyloxymethoxy-1-pyrimidin-2-yl-1H-[1,2,4]triazol-3-yl)methyl]-2-fluoro-5-methoxyphenoxy)ethyl ester or (68) acetic acid 2-{3-[(R)-(4-{amino[isobutoxycarbonylimino]methyl}phenylamino)-(5-isopropoxycarbonyloxymethoxy-1-pyrimidin-2-yl-1H-[1,2,4]triazol-3-yl)methyl]-2-fluoro-5-methoxyphenoxy)ethyl ester;

<13> a pharmaceutical composition comprising the compound or a pharmaceutically acceptable salt thereof according to any one of <1> to <12>;

<14> a therapeutic and/or prophylactic agent for a disease caused by thrombus formation, the therapeutic and/or prophylactic agent comprising the compound or the pharmaceutically acceptable salt thereof according to any one of <1> to <12>;

<15> the therapeutic and/or prophylactic agent according to <14>, wherein the disease caused by thrombus formation is thrombosis, deep vein thrombosis, pulmonary embolism, cerebral infarction, myocardial infarction, acute coronary syndrome, vascular restenosis, disseminated intravascular coagulation syndrome or a malignant tumor; and <16> the therapeutic and/or prophylactic agent according to <14>, wherein the disease caused by thrombus formation is thrombosis, deep vein thrombosis, pulmonary embolism, cerebral infarction, myocardial infarction, acute coronary syndrome, vascular restenosis or disseminated intravascular coagulation syndrome.

By orally administering the compound of the present invention, the blood level of the following Compound (IV), which has an excellent inhibitory action against blood coagulation factor VIIa and anticoagulant action, reaches a level sufficient for expression of its pharmacological actions.

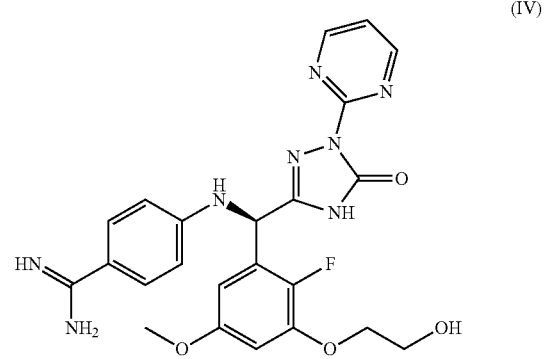 [SMILES: COc1cc(OCCO)c(F)c([C@@H](Nc2ccc(C(=N)N)cc2)c2nn(-c3ncccn3)c(=O)[nH]2)c1]

(IV)

Therefore, the compound of the present invention is useful as a therapeutic and/or prophylactic agent for diseases caused by thrombus formation (such as thrombosis, deep vein thrombosis, pulmonary embolism, cerebral infarction, myocardial infarction, acute coronary syndrome, vascular restenosis and disseminated intravascular coagulation syndrome) (Johannes Ruef & Hugo A Katus, New antithrombotic drugs on the horizon, Expert Opin. Investig. Drugs (2003) 12(5): 781-797).

Further, it has been reported that substances having an inhibitory action against blood coagulation factor VIIa are effective for suppression of metastasis of, and for regression of, malignant tumors. Therefore, the compound of the present invention having an excellent inhibitory action against blood coagulation factor VIIa is useful also as a therapeutic and/or prophylactic agent for malignant tumors and the like (Mattias Belting et al., Regulation of angiogenesis by tissue factor cytoplasmic domain signaling, Nature Medicine (2004) 10(5):502-509; X Jiang et al., Formation of tissue factor-factor VIIa-factor Xa complex promotes cellular signaling and migration of human breast cancer cells, J Thromb Haemost, (2004) 2: 93-101; Hembrough T A. Swartz G M. Papathanasiu A. Vlasuk G P. Roote W E. Green S J. Priblud a V S., Tissue factor/factor VIIa inhibitors block angiogenesis and tumor growth through a nonhemostatic mechanism. Cancer Research. (2003) 63(11):2997-3000).

Effects of Invention

The compound of the present invention shows excellent bioavailability upon its oral administration, and has an excellent action of suppression of blood coagulation. Further, it is safer and has appropriate physicochemical stability, so that the compound of the present invention is useful as a pharmaceutical, especially as a therapeutic and/or prophylactic agent for diseases caused by thrombus formation.

DESCRIPTION OF EMBODIMENTS

Figure 1:
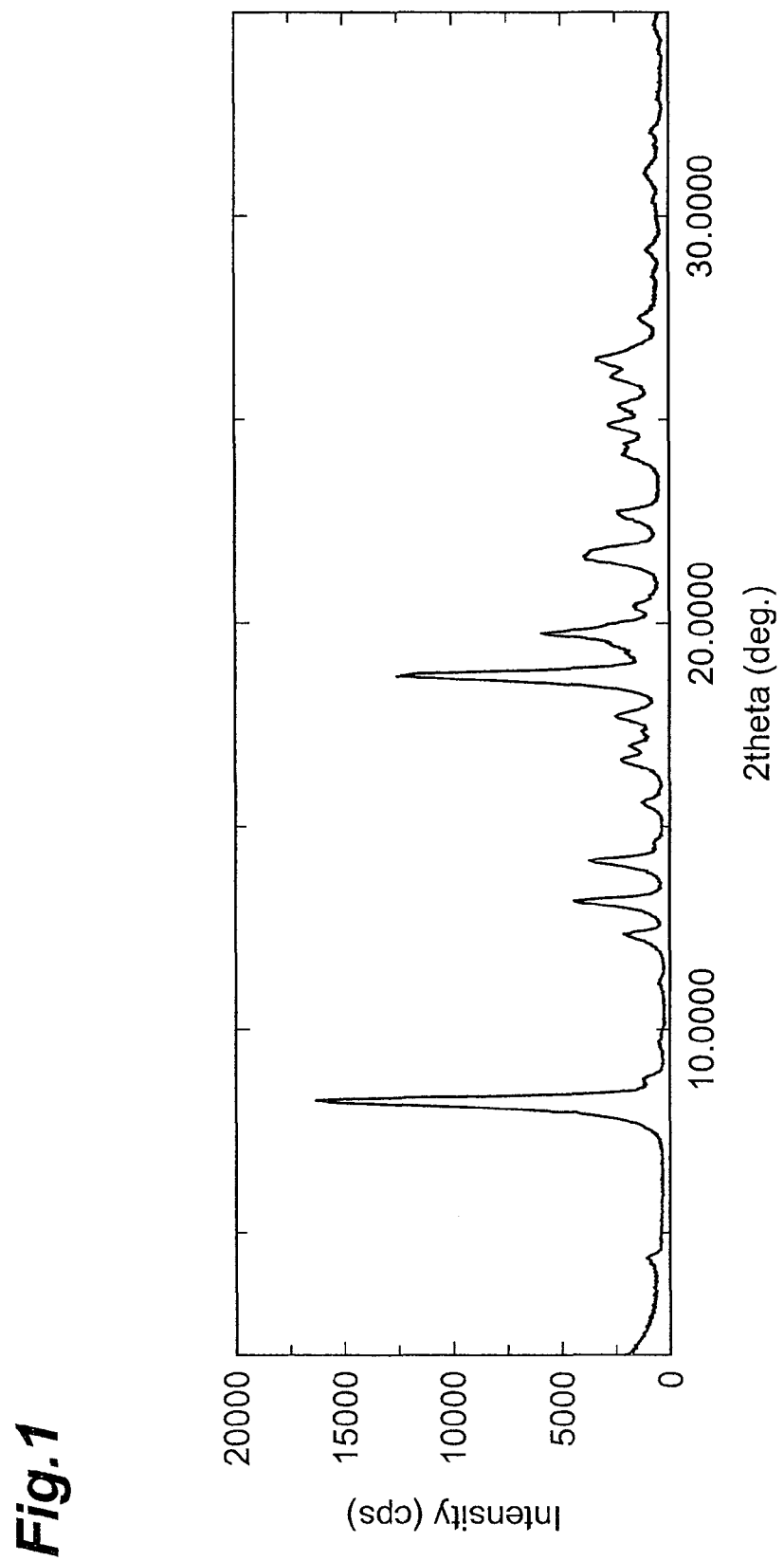
FIG. 1 is a diagram showing the powder X-ray diffraction pattern of the compound of Example 20.

The present invention is now described in detail below.
In the present specification, the structural formula of a compound may represent a particular isomer for convenience. However, all the isomers such as geometric isomers, optical isomers, stereoisomers and tautomers which may be produced due to the structure of the compound, and mixtures of the isomers are included in the present invention. The compound is not restricted to the formula described for convenience, and may be either one of the isomers, or a mixture of the isomers. Therefore, for the compound of the present invention, there may exist a mixture of optically active compounds, racemates or diastereomers, but any of these are included in the present invention without restriction. Further, there may exist crystalline polymorphs but, similarly, the compound is not restricted and may show either a single crystal form or a mixture of different crystal forms. Further, the compound of the present invention includes both anhydride and hydrate.

Examples of tautomers of the compound represented by Formula (I) include the compound represented by the following Formula (Ia):

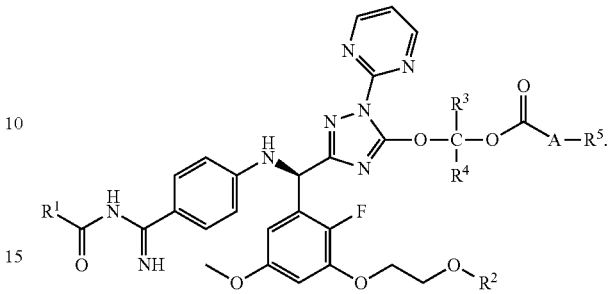

Meanings of the terms, symbols and the like used in the present specification are described below, and the present invention will be described in detail.

The "disease caused by thrombus formation" is not restricted as long as it is a disease which occurs directly or indirectly due to thrombus formation, and particular examples of the disease include thrombosis, deep vein thrombosis, pulmonary embolism, cerebral infarction, myocardial infarction, acute coronary syndrome, vascular restenosis, disseminated intravascular coagulation syndrome and malignant tumors. Preferred examples of the disease include thrombosis, deep vein thrombosis, pulmonary embolism, cerebral infarction, myocardial infarction, acute coronary syndrome, vascular restenosis and disseminated intravascular coagulation syndrome.

The "halogen atom" means a fluorine atom, chlorine atom, bromine atom or iodine atom. Preferred examples of the halogen atom include a fluorine atom and chlorine atom.

"$C_1$-$C_6$ alkyl" means a linear or branched alkyl group having 1 to 6 carbon atoms. Particular examples thereof include methyl, ethyl, 1-propyl (n-propyl), 2-propyl (i-propyl), 2-methyl-1-propyl (1-butyl), 2-methyl-2-propyl (t-butyl), 1-butyl (n-butyl), 2-butyl (s-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl and 2,3-dimethyl-2-butyl.

"$C_2$-$C_6$ alkenyl" means a linear or branched alkenyl group with a double bond having 2 to 6 carbon atoms. Particular examples thereof include vinyl (ethenyl), allyl (2-propenyl), 1-propenyl, isopropenyl (1-methylvinyl), 1-butenyl, 2-butenyl, 3-butenyl, 2-methyl-2-propenyl, pentenyl and hexenyl.

"$C_3$-$C_8$ cycloalkyl" means a monocyclic saturated aliphatic hydrocarbon group having 3 to 8 carbon atoms. Particular examples thereof include cyclopropyl, cyclobutyl, cyclopentyl, cyclohexyl, cycloheptyl and cyclooctyl.

"$C_1$-$C_6$ alkoxy" means an oxy group (oxygen atom) to which the "$C_1$-$C_6$ alkyl" as defined above is linked, and particular examples thereof include methoxy, ethoxy, 1-propyloxy, 2-propyloxy, 2-methyl-1-propyloxy, 2-methyl-2-propyloxy, 1-butyloxy, 2-butyloxy, 1-pentyloxy, 2-pentyloxy, 3-pentyloxy, 2-methyl-1-butyloxy, 3-methyl-1-butyloxy, 2-methyl-2-butyloxy, 3-methyl-2-butyloxy, 2,2-dimethyl-1-propyloxy, 1-hexyloxy, 2-hexyloxy, 3-hexyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2-methyl-3-pentyloxy, 3-methyl-3-pentyloxy, 2,3-dimethyl-1-butyloxy, 3,3-dimethyl-1-butyloxy, 2,2-dimethyl-1-butyloxy, 2-ethyl-1-butyloxy, 3,3-dimethyl-2-butyloxy and 2,3-dimethyl-2-butyloxy.

"$C_2$-$C_6$ alkenyloxy" means an oxy group (oxygen atom) to which the "$C_2$-$C_6$ alkenyl" as defined above is linked, and particular examples thereof include vinyloxy (ethenyloxy), allyloxy (2-propenyloxy), 1-propenyloxy, isopropenyloxy (1-methylvinyloxy), 1-butenyloxy, 2-butenyloxy, 3-butenyloxy, 2-methyl-2-propenyloxy, pentenyloxy and hexenyloxy.

"$C_1$-$C_6$ alkylcarbonyl" means a carbonyl group to which the "$C_1$-$C_6$ alkyl" as defined above is linked, and particular examples thereof include acetyl, propionyl, isopropionyl, butyryl, isobutyryl, valeryl, isovaleryl and pivaloyl.

The salt in the present specification is not restricted as long as it forms a salt with the compound of the present invention and is pharmaceutically acceptable, and examples thereof include inorganic acid salts, organic acid salts and acidic amino acid salts.

Preferred examples of the inorganic acid salts include hydrochloric acid salt, hydrobromic acid salt, sulfuric acid salt, nitric acid salt and phosphoric acid salt, and preferred examples of the organic acid salts include acetic acid salt, succinic acid salt, fumaric acid salt, maleic acid salt, tartaric acid salt, citric acid salt, lactic acid salt, stearic acid salt, benzoic acid salt, methanesulfonic acid salt, ethanesulfonic acid salt, propanesulfonic acid salt, cyclopropanesulfonic acid salt, hydroxyethanesulfonic acid salt, p-toluenesulfonic acid salt and benzenesulfonic acid salt.

Preferred examples of the acidic amino acid salts include aspartic acid salt and glutamic acid salt.

Each substituent in the compounds of the present invention represented by the above General Formulae (I), (II) and (III) is described below.

$R^1$ means phenyl which may be substituted by one to three $C_1$-$C_6$ alkyl group(s), $C_1$-$C_6$ alkoxy or $C_2$-$C_6$ alkenyloxy. Preferred examples of $R^1$ include phenyl which may be substituted by one methyl group or ethyl group, $C_4$-$C_6$ alkoxy and $C_4$-$C_6$ alkenyloxy. Preferred examples of $R^1$ include 4-tolyl, phenyl, 2,2-dimethyl-1-propyloxy, 2,2-dimethyl-1-butyloxy and 2-methyl-2-propenyloxy.

$R^2$ means a hydrogen atom, $C_1$-$C_6$ alkylcarbonyl or pyridylcarbonyl. Preferred examples of $R^2$ include a hydrogen atom, acetyl and 4-pyridylcarbonyl.

$R^3$ and $R^4$ each independently mean a hydrogen atom or $C_1$-$C_6$ alkyl. Preferred examples of each of $R^3$ and $R^4$ include a hydrogen atom, methyl and ethyl, which are selected independently. Most preferred examples of the combination of $R^3$ and $R^4$ include the case wherein both of $R^3$ and $R^4$ represent hydrogen atoms and cases wherein one of $R^3$ and $R^4$ represents methyl or ethyl while the other represents a hydrogen atom.

A means a single bond, an oxygen atom, a group represented by Formula (II):

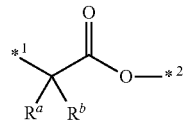

(II)

wherein $R^a$ and $R^b$ each independently represent a hydrogen atom or $C_1$-$C_6$ alkyl, and *1 and *2 mean linking to carbonyl and to $R^5$, respectively, in Formula (I), or a group represented by Formula (III):

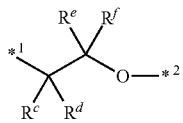

(III)

wherein $R^c$, $R^d$, $R^e$ and $R^f$ each independently represent a hydrogen atom or $C_1$-$C_6$ alkyl, and *1 and *2 have the same meanings as described above.

Preferred examples of each of $R^a$ and $R^b$ include a hydrogen atom and methyl, which are selected independently. Most preferred examples of the combination of $R^a$ and $R^b$ include the case wherein both of these represent methyl.

Preferred examples of each of $R^c$, $R^d$, $R^e$ and $R^f$ include a hydrogen atom and methyl, which are selected independently. Most preferred examples of the combination of $R^c$, $R^d$, $R^e$ and $R^f$ include the case wherein both $R^c$ and $R^d$ are methyl and both $R^e$ and $R^f$ are hydrogen atoms.

$R^5$ means $C_1$-$C_6$ alkyl or $C_3$-$C_8$ cycloalkyl, and $C_1$-$C_6$ alkyl or $C_3$-$C_8$ cycloalkyl in $R^5$ may be substituted by one to three identical or different substituents selected from the group of substituents consisting of a halogen atom, $C_1$-$C_6$ alkyl and $C_1$-$C_6$ alkoxy. Preferred examples of $R^5$ include $C_1$-$C_6$ alkyl which may be substituted by methoxy, and cyclohexyl which may be substituted by a halogen atom or methyl.

Particular examples of the compound of General Formula (I) include the compounds described in Examples 1 to 18 and 51 to 68, but the present invention is not restricted to these compounds.

[General Production Method of Compound of Present Invention]

The compounds of the present invention can be produced by the methods described below. However, the production method of the present invention is not restricted to these.

Each method is described below.

[Production Method A]

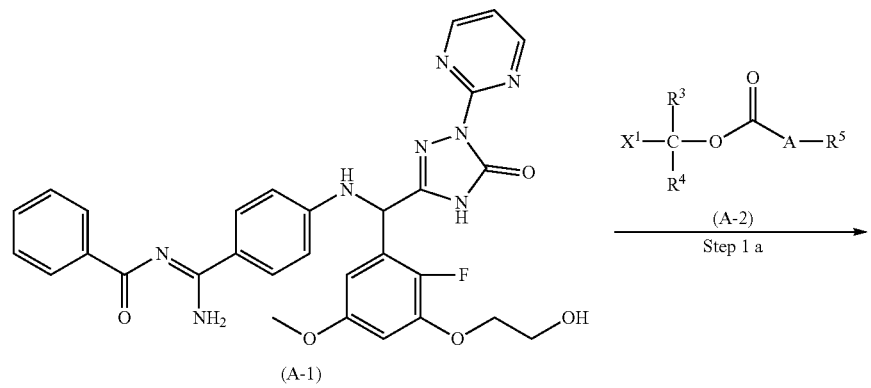

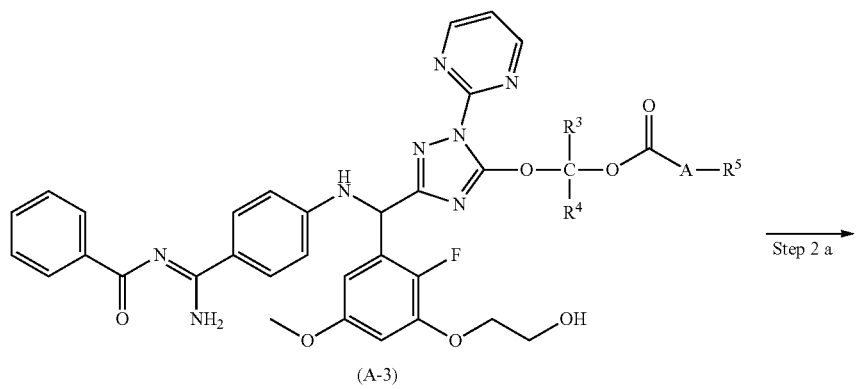

(A-3)

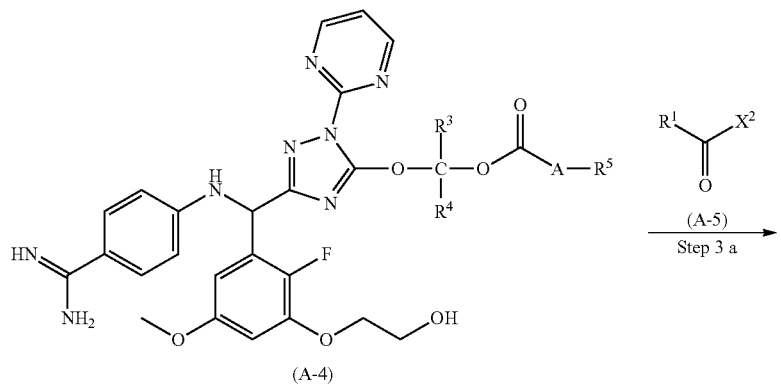

(A-4)

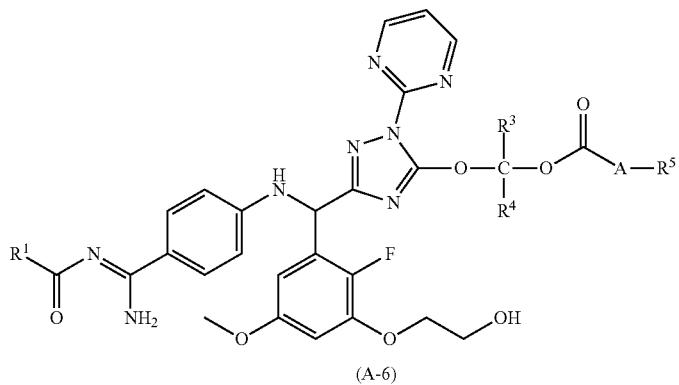

(A-6)

wherein $R^1$, $R^3$, $R^4$, $R^5$ and A have the same meanings as defined above. $X^1$ means a leaving group such as a chlorine atom, bromine atom, iodine atom, methanesulfonyloxy or p-toluenesulfonyloxy, and $X^2$ means a leaving group such as a chlorine atom, 4-nitrophenoxy, 4-bromophenoxy or 4-chlorophenoxy.

[Step 1a]

In this step, Compound (A-1) is allowed to react with Compound (A-2) in a solvent, to produce Compound (A-3). In this reaction step, the reaction is carried out in the presence of a base.

This reaction may also be carried out under the flow or atmosphere of an inert gas such as nitrogen or argon.

As Compound (A-1), the later-mentioned Compounds (Example 1a, 12b) may be used.

As Compound (A-2), commercially available compounds, compounds which can be easily produced from commercially available compounds by methods usually carried out by those skilled in the art, compounds (G-1, H-3) which can be produced by the later-mentioned production methods (Production Methods G and H), and the like can be used. Particular examples of Compound (A-2) which can be used include pivalic acid chloromethyl ester [CAS No. 18997-19-8], 3-methoxy-2,2-dimethylpropionic acid chloromethyl ester, 2,2-dimethylmalonic acid chloromethyl ester ethyl ester, 3-methoxymethoxy-2,2-dimethylpropionic acid chloromethyl ester, 1-chloroethyl isopropyl carbonate [CAS No. 98298-66-9] and 1-chloroethyl cyclohexyl carbonate [CAS No. 99464-83-2].

The solvent to be used in this reaction is not restricted as long as the starting material can be dissolved therein to a certain extent and the reaction is not inhibited therein, and examples of the solvent include amide solvents such as N,N-dimethylformamide and N,N-dimethylacetamide; ether solvents such as tetrahydrofuran, 1,2-dimethoxyethane, t-butyl methyl ether, diethyl ether, diisopropyl ether and 1,4-dioxane; and mixed solvents thereof. The solvent is preferably N,N-dimethylformamide or N,N-dimethylacetamide.

The above-described base means potassium carbonate, potassium hydrogen carbonate, sodium carbonate, sodium hydrogen carbonate, cesium carbonate, cesium hydrogen carbonate, rubidium carbonate or the like. The base is preferably potassium carbonate, potassium hydrogen carbonate or rubidium carbonate.

The reaction temperature usually varies depending on the starting material, the solvent and the other reagents used in the reaction, and is preferably 20° C. to 120° C. (in terms of the internal temperature of the reaction vessel), more preferably about 40° C. to 90° C. (in terms of the internal temperature of the reaction vessel).

The reaction time usually varies depending on the starting material, the solvent, the other reagents used in the reaction, and the reaction temperature, and, after addition of the reagents, the reaction mixture is preferably stirred for 1 to 72 hours, more preferably stirred for 12 to 36 hours at the above-described reaction temperature.

Compound (A-2) can be used in a 1- to 5-fold molar amount, preferably 1.05- to 3-fold molar amount with respect to the Compound (A-1).

The above-described base can be used in a 0.5- to 10-fold molar amount, preferably 0.5- to 3-fold molar amount, more preferably 0.6- to 2-fold molar amount with respect to the Compound (A-1).

[Step 2a]

In this step, Compound (A-4) is produced from Compound (A-3) in a solvent. In this reaction step, the reaction is carried out in an alcohol solvent in the presence of an acid.

This reaction may also be carried out under the flow or atmosphere of an inert gas such as nitrogen or argon.

The solvent to be used in this reaction is not restricted as long as the starting material can be dissolved therein to a certain extent and the reaction is not inhibited therein, and examples of the solvent include alcohol solvents such as methanol, ethanol and 2-propanol, among which methanol is preferred.

The above-described acid means formic acid, acetic acid, hydrochloric acid or the like, and acetic acid is preferred.

The reaction temperature usually varies depending on the starting material, the solvent and the other reagents used in the reaction, and is preferably 20° C. to 60° C. (in terms of the internal temperature of the reaction vessel), more preferably about 30° C. to 50° C. (in terms of the internal temperature of the reaction vessel).

The reaction time usually varies depending on the starting material, the solvent, the other reagents used in the reaction, and the reaction temperature, and, after addition of the reagents, the reaction mixture is preferably stirred for 8 to 24 hours, more preferably stirred for about 12 hours at the above-described reaction temperature.

The above-described acid can be used in an amount of 1 to 100% by volume, preferably in an amount of 10 to 50% by volume, with respect to the solvent (methanol).

[Step 3a]

In this step, Compound (A-4) is allowed to react with Compound (A-5) in a solvent, to produce Compound (A-6). In this reaction step, the reaction is carried out in the presence of a base.

This reaction can be carried out by a method which is commonly used, such as the one described in TETRAHEDRON LETTERS, 1999, 40, 4847.

This reaction may also be carried out under the flow or atmosphere of an inert gas such as nitrogen or argon.

As Compound (A-5), known compounds, commercially available compounds, compounds which can be easily produced from commercially available compounds by methods usually carried out by those skilled in the art, compounds (I-3, J-3) which can be produced by the later-mentioned production methods (Production Methods I and J), and the like can be used. Particular examples of Compound (A-5) which can be used include benzoic acid 4-nitrophenyl ester [CAS No. 959-22-8], 4-methylbenzoic acid 4-nitrophenyl ester [CAS No. 15023-67-3], carbonic acid 2-methyl-2-propenyl ester 4-nitrophenyl ester [CAS No. 218598-29-9], carbonic acid 2-methyl-2-propenyl ester phenyl ester [CAS No. 138621-73-5], carbonic acid 2,2-dimethylpropyl ester 4-nitrophenyl ester [CAS No. 158810-98-1], carbonic acid 2,2-dimethylbutyl ester 4-nitrophenyl ester and benzoyl chloride.

The solvent to be used in this reaction is not restricted as long as the starting material can be dissolved therein to a certain extent and the reaction is not inhibited therein, and examples of the solvent include amide solvents such as N,N-dimethylformamide and N,N-dimethylacetamide; ether solvents such as tetrahydrofuran, 1,2-dimethoxyethane, t-butyl methyl ether, diethyl ether, diisopropyl ether and 1,4-dioxane; dimethyl sulfoxide; and mixed solvents thereof. The solvent is preferably N,N-dimethylformamide or dimethylsulfoxide.

The above-described base means triethylamine, diisopropylethylamine, pyridine, potassium carbonate, potassium hydrogen carbonate, sodium hydrogen carbonate or the like. The base is preferably triethylamine or potassium carbonate.

The reaction temperature usually varies depending on the starting material, the solvent and the other reagents used in the reaction, and is preferably 0° C. to 70° C. (in terms of the internal temperature of the reaction vessel), more preferably 20° C. to 60° C. (in terms of the internal temperature of the reaction vessel).

The reaction time usually varies depending on the starting material, the solvent, the other reagents used in the reaction, and the reaction temperature, and, after addition of the reagents, the reaction mixture is preferably stirred for 0.5 to 24 hours, more preferably stirred for about 4 to 14 hours at the above-described reaction temperature.

Compound (A-5) can be used in a 1- to 3-fold molar amount, preferably 1- to 1.5-fold molar amount, more preferably 1- to 1.2-fold molar amount with respect to the Compound (A-4).

The above-described base can be used in a 1- to 10-fold molar amount, preferably 1- to 3-fold molar amount, more preferably 2-fold molar amount with respect to the Compound (A-4).

[Production Method B]

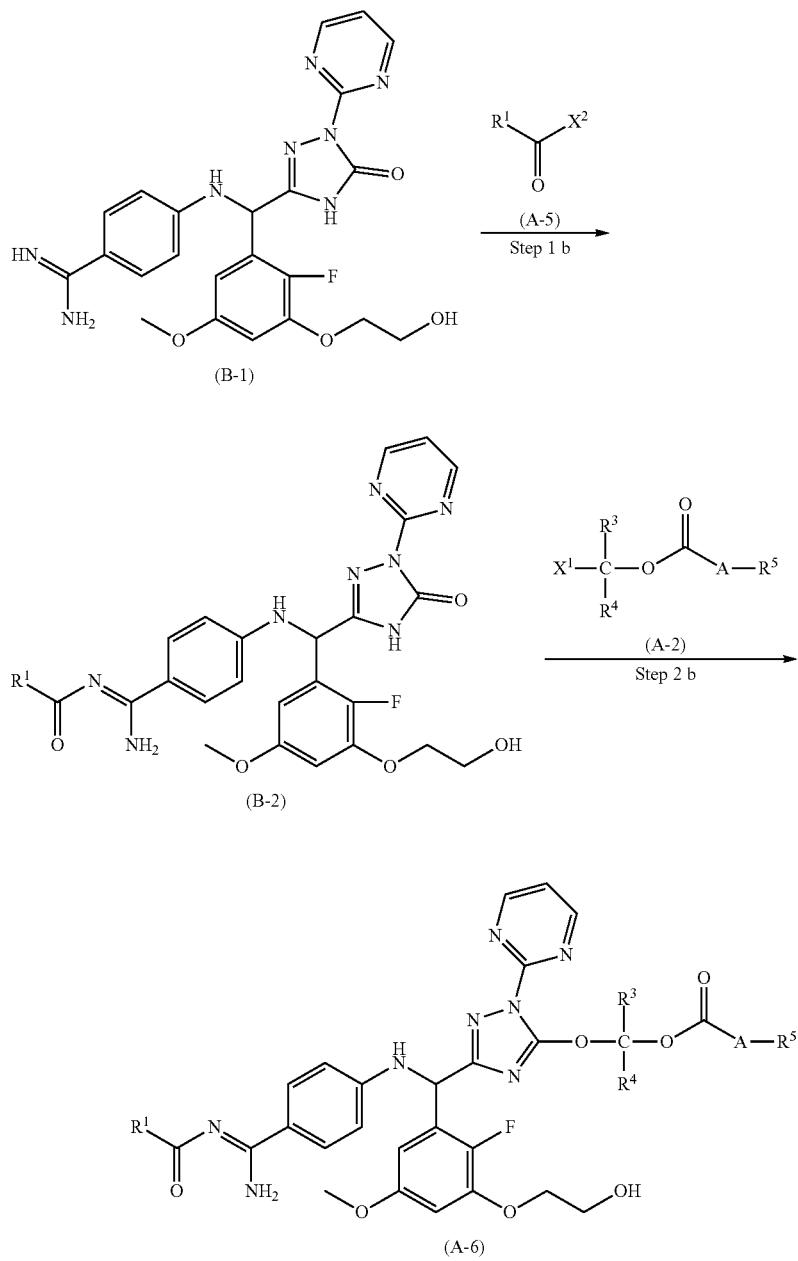

wherein $R^1$, $R^3$, $R^4$, $R^5$, A, $X^1$ and $X^2$ have the same meanings as defined above.

[Step 1b]

In this step, Compound (B-1) is allowed to react with Compound (A-5) in a solvent, to produce Compound (B-2). In this reaction step, the reaction is carried out in the presence of a base.

Examples of Compound (B-1) which may be used include 4-({[2-fluoro-3-(2-hydroxyethoxy)-5-methoxyphenyl]-(5-oxo-1-pyrimidin-2-yl-4,5-dihydro-1H-[1,2,4]triazol-3-yl) methyl}amino)benzamidine acetate [CAS No. 951803-95-5] and 4-{[(R)-[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}benzamidine acetate [CAS No. 951803-91-1].

As the reaction conditions for this step, conditions and operation methods which are the same as those for Step 3a in the above Production Method A may be applied.

[Step 2b]

In this step, Compound (B-2) is allowed to react with Compound (A-2) in a solvent, to produce Compound (A-6). In this reaction step, the reaction is carried out in the presence of a base.

As the reaction conditions for this step, conditions and operation methods which are the same as those for Step 1a in the above Production Method A may be applied.

[Production Method C]
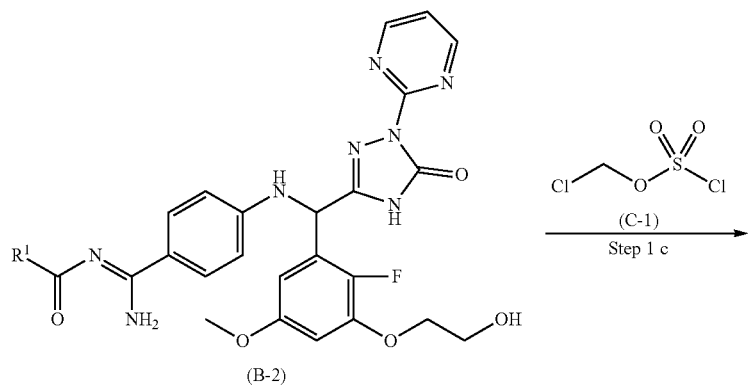
(B-2)
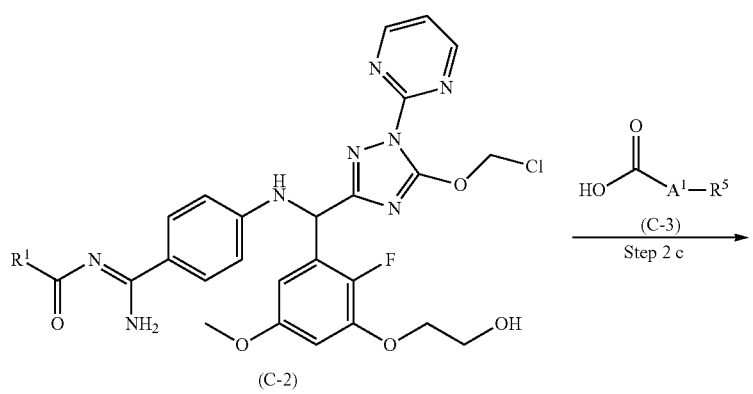
(C-2)
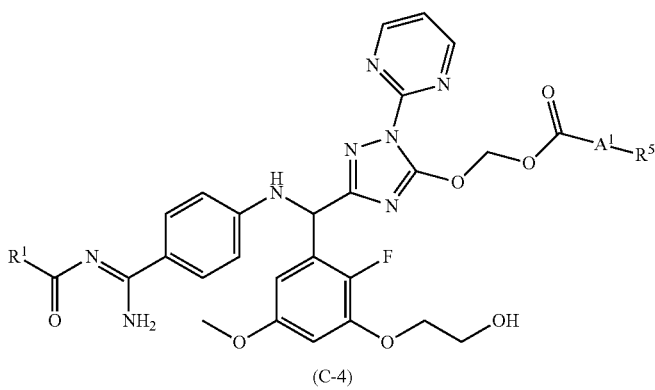
(C-4)
wherein R¹ and R⁵ have the same meanings as defined above; and
A¹ means a single bond, a group represented by Formula (II):
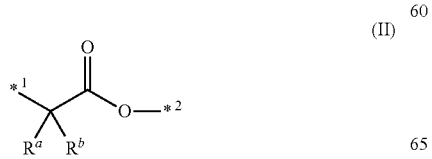
wherein $R^a$ and $R^b$ each independently represent a hydrogen atom or $C_1$-$C_6$ alkyl, and *1 and *2 mean linking to carbonyl and to R⁵, respectively,
or a group represented by Formula (III):
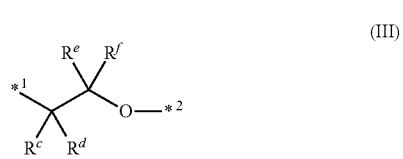

wherein $R^c$, $R^d$, $R^e$ and $R^f$ each independently represent a hydrogen atom or $C_1$-$C_6$ alkyl, and *1 and *2 have the same meanings as described above.

[Step 1c]

In this step, Compound (B-2) is allowed to react with Compound (C-1) in a solvent, to produce Compound (C-2). In this reaction step, the reaction is carried out in the presence of a base, in the presence or absence of a phase-transfer catalyst.

This reaction may also be carried out under the flow or atmosphere of an inert gas such as nitrogen or argon.

As Compound (C-1), chloromethyl chlorosulfate [CAS No. 49715-04-0] may be used.

The solvent to be used in this reaction is not restricted as long as the starting material can be dissolved therein to a certain extent and the reaction is not inhibited therein, and examples of the solvent include ether solvents such as tetrahydrofuran, 1,2-dimethoxyethane, t-butyl methyl ether, cyclopentyl methyl ether, diethyl ether, diisopropyl ether, dibutyl ether, dicyclopentyl ether and 1,4-dioxane; halogenated hydrocarbon solvents such as dichloromethane and chloroform; and mixed solvents thereof; and water. The solvent is preferably a bilayer system of a dichloromethane-tetrahydrofuran mixed solvent and water, or a bilayer system of t-butyl methyl ether and water.

The above-described base means potassium carbonate, potassium hydrogen carbonate, sodium carbonate, sodium hydrogen carbonate, cesium carbonate, dipotassium phosphate or the like. The base is preferably sodium hydrogen carbonate or dipotassium phosphate.

The above-described phase-transfer catalyst means tetrabutylammonium hydrogen sulfate, halogenated tetrabutylammonium or the like. The phase-transfer catalyst is preferably tetrabutylammonium hydrogen sulfate.

The reaction temperature usually varies depending on the starting material, the solvent and the other reagents used in the reaction, and is preferably 0° C. to 50° C. (in terms of the internal temperature of the reaction vessel), more preferably about 10° C. to 30° C. (in terms of the internal temperature of the reaction vessel).

The reaction time usually varies depending on the starting material, the solvent, the other reagents used in the reaction, and the reaction temperature, and, after addition of the reagents, the reaction mixture is preferably stirred for 1 to 50 hours, more preferably stirred for about 20 hours at the above-described reaction temperature.

Compound (C-1) can be used in a 1- to 5-fold molar, preferably 2- to 4-fold molar amount, more preferably 3-fold molar amount with respect to the Compound (B-2).

The above-described base can be used in a 1- to 50-fold molar amount, preferably 5- to 20-fold molar amount, more preferably 5- to 15-fold molar amount with respect to the Compound (B-2).

The above-described phase-transfer catalyst can be used in a 0.01- to 1-fold molar amount, preferably 0.05- to 0.5-fold molar amount, more preferably 0.1- to 0.3-fold molar amount with respect to the Compound (B-2).

[Step 2c]

In this step, Compound (C-2) is allowed to react with a carboxylic acid (C-3) in a solvent, to produce Compound (C-4). In this reaction step, the reaction is carried out in the presence of a base, in the presence or absence of an iodide.

This reaction may also be carried out under the flow or atmosphere of an inert gas such as nitrogen or argon.

As the carboxylic acid (C-3), commercially available compounds, compounds which can be easily produced from commercially available compounds by methods usually carried out by those skilled in the art, and the like can be used. Particular examples of the carboxylic acid (C-3) which can be used include 2,2-dimethylpropionic acid, 3-methoxy-2,2-dimethylpropionic acid [CAS No. 64241-78-7], 3-methoxymethoxy-2,2-dimethylpropionic acid, 2-ethylbutanoic acid [CAS No. 118315-05-2], cyclohexane carboxylic acid, 2,2-dimethylmalonic acid mono-t-butyl ester [CAS No. 143688-40-8], 2,2-dimethylmalonic acid monoethyl ester [CAS No. 5471-77-2], 2,2-dimethylmalonic acid monoisopropyl ester [CAS No. 7695-26-3] and 2,2-dimethylmalonic acid monocyclohexyl ester.

The solvent to be used in this reaction is not restricted as long as Compound (C-2) and the carboxylic acid (C-3) can be dissolved therein to a certain extent and the reaction is not inhibited therein, and examples of the solvent include amide solvents such as N,N-dimethylformamide and N,N-dimethylacetamide; ether solvents such as tetrahydrofuran, 1,2-dimethoxyethane, t-butyl methyl ether, cyclopentyl methyl ether, diethyl ether, diisopropyl ether, dibutyl ether, dicyclopentyl ether and 1,4-dioxane; and mixed solvents thereof. The solvent is preferably N,N-dimethylformamide.

The above-described base means potassium carbonate, potassium hydrogen carbonate, sodium carbonate, sodium hydrogen carbonate, cesium carbonate or the like. The base is preferably potassium hydrogen carbonate.

The above-described iodide means sodium iodide, potassium iodide, tetrabutylammonium iodide or the like. The iodide is preferably sodium iodide.

The reaction temperature usually varies depending on the starting material, the solvent and the other reagents used in the reaction, and is preferably 0° C. to 80° C. (in terms of the internal temperature of the reaction vessel), more preferably about 20° C. to 60° C. (in terms of the internal temperature of the reaction vessel).

The reaction time usually varies depending on the starting material, the solvent, the other reagents used in the reaction, and the reaction temperature, and, after addition of the reagents, the reaction mixture is preferably stirred for 1 to 100 hours, more preferably stirred for about 3 to 64 hours at the above-described reaction temperature.

The carboxylic acid (C-3) can be used in a 1- to 5-fold molar amount, preferably 2- to 4-fold molar amount, more preferably 3-fold molar amount with respect to the Compound (C-2).

The above-described base can be used in a 1- to 50-fold molar amount, preferably 5- to 20-fold molar amount with respect to the Compound (C-2).

The above-described iodide can be used in a 0.1- to 20-fold molar amount, preferably 2- to 10-fold molar amount with respect to the Compound (C-2).

[Production Method D]

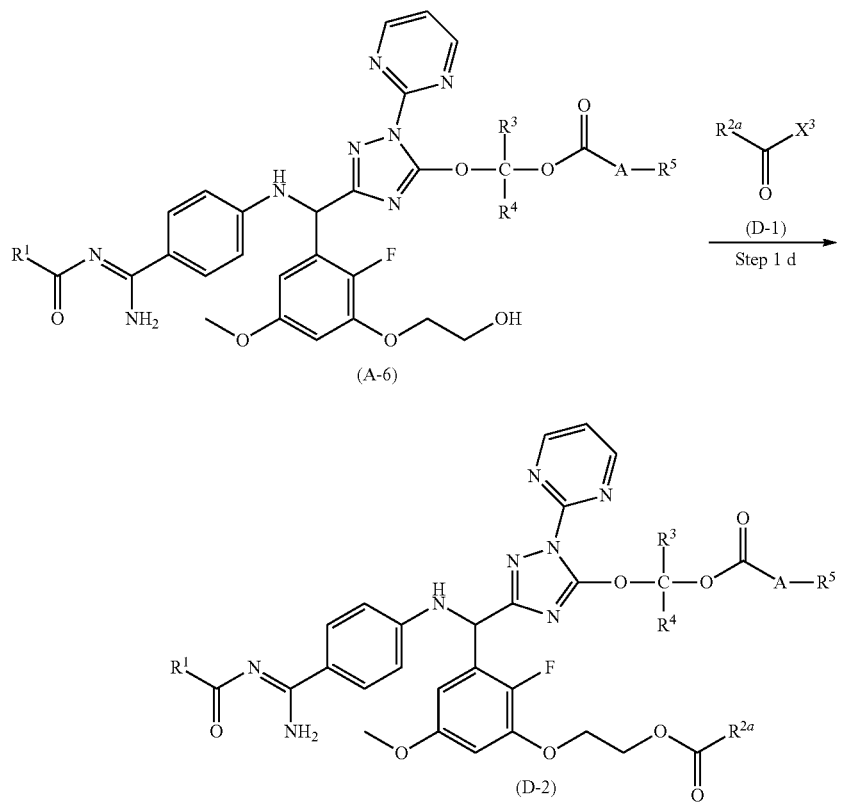

wherein $R^1$, $R^3$, $R^4$, $R^5$ and A have the same meanings as defined above. $R^{2a}$ means $C_1$-$C_6$ alkyl or pyridyl. $X^3$ means a leaving group such as a chlorine atom, fluorine atom or a group represented by Formula:

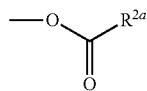

wherein $R^{2a}$ have the same meaning as defined above.

[Step 1d]

In this step, Compound (A-6) is allowed to react with Compound (D-1) in a solvent, to produce Compound (D-2). In this reaction step, the reaction is carried out in the presence of a base, in the presence or absence of an esterification catalyst.

This reaction may also be carried out under the flow or atmosphere of an inert gas such as nitrogen or argon.

As Compound (D-1), commercially available compounds, compounds which can be easily produced from commercially available compounds by methods usually carried out by those skilled in the art, and the like can be used. Particular examples of Compound (D-1) which can be used include acetyl fluoride, which can be produced by adding triethylamine to a mixture of acetic acid, TFFH (fluoro-N,N,N',N'-tetramethylformamidinium hexafluorophosphate) and dichloromethane; isonicotinyl fluoride, which can be produced by adding triethylamine to a mixture of isonicotinic acid, TFFH and dichloromethane; acetyl chloride; isonicotinyl chloride; and acetic anhydride.

The solvent to be used in this reaction is not restricted as long as the starting material can be dissolved therein to a certain extent and the reaction is not inhibited therein, and examples of the solvent which can be used include ether solvents such as tetrahydrofuran, 1,2-dimethoxyethane, t-butyl methyl ether, cyclopentyl methyl ether, diethyl ether, diisopropyl ether, dibutyl ether, dicyclopentyl ether and 1,4-dioxane; halogenated hydrocarbon solvents such as dichloromethane and chloroform; amide solvents such as N,N-dimethylformamide and N,N-dimethylacetamide; sulfoxide solvents such as dimethyl sulfoxide; and mixed solvents thereof.

The solvent is preferably a mixed solvent of dichloromethane-N,N-dimethylformamide.

The above-described base means triethylamine, N,N-diisopropylethylamine, or the like. The base is preferably triethylamine.

The above-described esterification catalyst means 4-dimethylaminopyridine or the like.

The reaction temperature usually varies depending on the starting material, the solvent and the other reagents used in the reaction, and is preferably 0° C. to 50° C. (in terms of the inner temperature of the reaction vessel), more preferably about 10° C. to 30° C. (in terms of the internal temperature of the reaction vessel).

The reaction time usually varies depending on the starting material, the solvent and the other reagents used in the reaction, and the reaction temperature, and, after addition of the reagents, the reaction mixture is preferably stirred for 1 to 12 hours, more preferably stirred for about 2 to 4 hours at the above-described reaction temperature.

Compound (D-1) can be used in a 1.0- to 5-fold molar amount, preferably 1.5- to 3-fold molar amount, more preferably 2-fold molar amount with respect to the Compound (A-6).

The above-described base can be used in a 1- to 10-fold molar amount, preferably 3- to 8-fold molar amount with respect to the Compound (A-6).

The above-described esterification catalyst can be used in a 0.01- to 1-fold molar amount, preferably 0.05- to 0.2-fold molar amount with respect to the Compound (A-6).

[Production Method E]

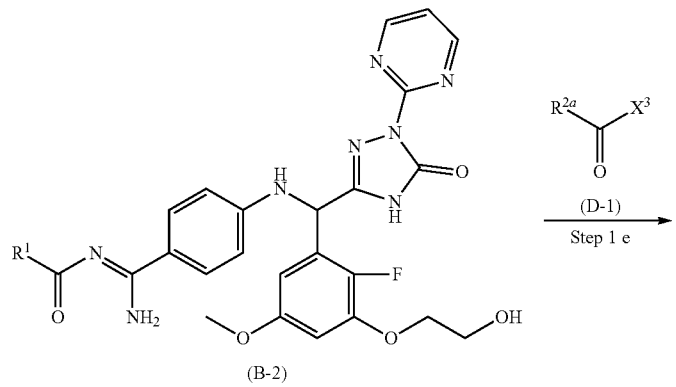

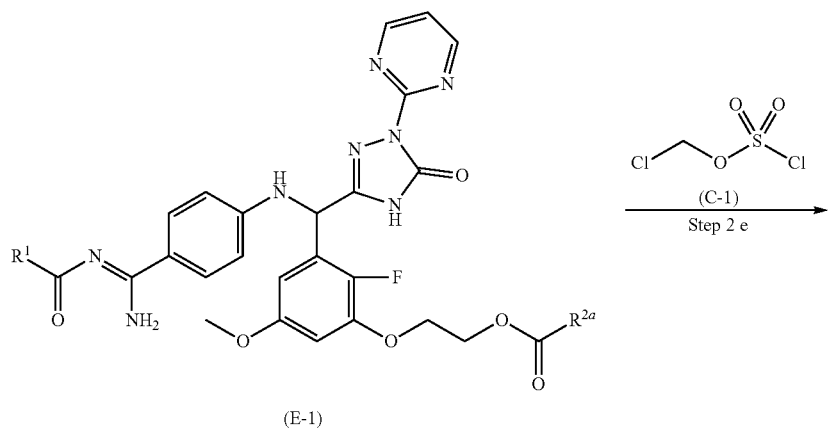

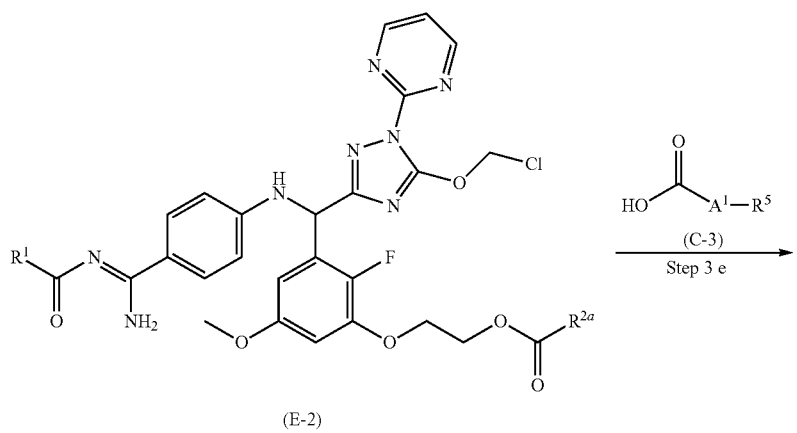

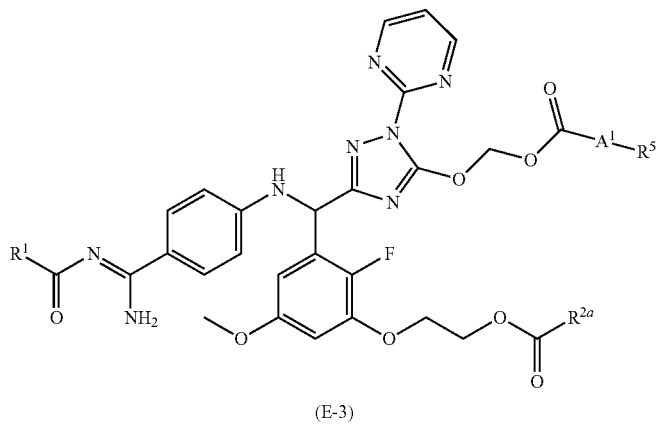

(E-3)

wherein $R^1$, $R^{2a}$, $R^5$, $A^1$ and $X^3$ have the same meanings as defined above.

[Step 1e]

In this step, Compound (B-2) is allowed to react with Compound (D-1) in a solvent, to produce Compound (E-1). As the reaction conditions for this step, conditions and operation methods which are the same as those for Step 1d in the above Production Method D may be applied.

[Step 2e]

In this step, Compound (E-1) is allowed to react with Compound (C-1) in a solvent, to produce Compound (E-2). As the reaction conditions for this step, conditions and operation methods which are the same as those for Step 1c in the above Production Method C may be applied.

[Step 3e]

In this step, Compound (E-2) is allowed to react with the carboxylic acid (C-3) in a solvent, to produce Compound (E-3). As the reaction conditions for this step, conditions and operation methods which are the same as those for Step 2c in the above Production Method C may be applied.

[Production Method F]

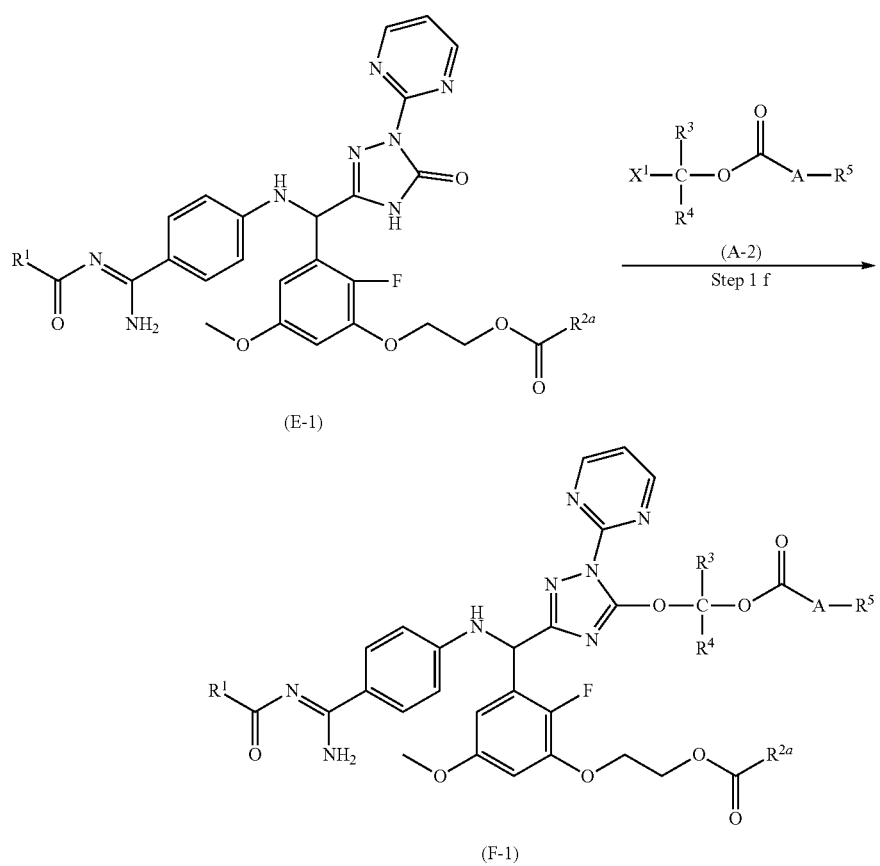

wherein $R^1$, $R^{2a}$, $R^3$, $R^4$, $R^5$, A and $X^1$ have the same meanings as defined above.

[Step 1f]

In this step, Compound (E-1) is allowed to react with Compound (A-2) in a solvent, to produce Compound (F-1). This reaction step is carried out in the presence of a base.

As the reaction conditions for this step, conditions and operation methods which are the same as those for Step 1a in the above Production Method A may be applied.

[Production Method G]

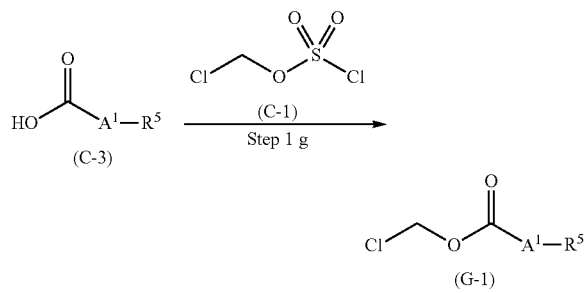

wherein $A^1$ and $R^5$ have the same meanings as defined above.

[Step 1g]

In this step, the carboxylic acid (C-3) is allowed to react with Compound (C-1) in a solvent, to produce Compound (G-1). In this reaction step, the reaction is carried out in the presence of a base.

As the reaction conditions for this step, conditions and operation methods which are the same as those for Step 1c in the above Production Method C may be applied.

[Production Method H]

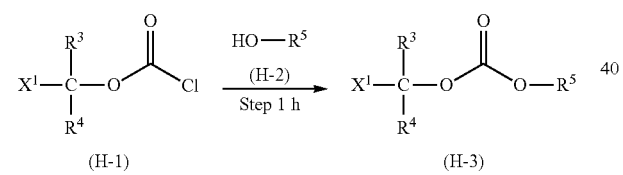

wherein $R^3$, $R^4$, $R^5$ and $X^1$ have the same meanings as defined above.

[Step 1h]

In this step, Compound (H-1) is allowed to react with Compound (H-2) in a solvent, to produce Compound (H-3). This reaction step is carried out in the presence of a base.

This reaction may also be carried out under the flow or atmosphere of an inert gas such as nitrogen or argon.

As Compound (H-1), commercially available compounds, compounds which can be easily produced from commercially available compounds by methods usually carried out by those skilled in the art, and the like can be used. Particular examples of Compound (H-1) which can be used include chloromethyl chloroformate [CAS No. 22128-62-7], 1-chloroethyl chloroformate [CAS No. 50893-53-3] and 1-chloropropyl chloroformate [CAS No. 92600-20-9].

As Compound (H-2), commercially available compounds, compounds which can be easily produced from commercially available compounds by methods usually carried out by those skilled in the art, and the like can be used. Particular examples of Compound (H-2) which can be used include ethanol, 2-propanol, t-butanol, cyclohexanol, 2-pentanol, trans-2-fluorocyclohexanol [CAS No. 14365-32-3], (1S,2S)-2-fluorocyclohexanol [CAS No. 292150-03-9] and (1R,2R)-2-methylcyclohexanol [CAS No. 19043-03-9].

The solvent to be used in this reaction is not restricted as long as the starting material can be dissolved therein to a certain extent and the reaction is not inhibited therein, and examples of the solvent include ether solvents such as tetrahydrofuran, 1,2-dimethoxyethane, t-butyl methyl ether, cyclopentyl methyl ether, diethyl ether, diisopropyl ether, dibutyl ether, dicyclopentyl ether and 1,4-dioxane; halogenated hydrocarbon solvents such as dichloromethane and chloroform; ester solvents such as ethyl acetate and isopropyl acetate; and mixed solvents thereof. The solvent is preferably tetrahydrofuran, ethyl acetate or dichloromethane.

The above-described base means pyridine, collidine, triethylamine or the like. The base is preferably pyridine.

The reaction temperature usually varies depending on the starting material, the solvent and the other reagents used in the reaction, and is preferably −78° C. to 50° C. (in terms of the internal temperature of the reaction vessel), more preferably about −78° C. to 30° C. (in terms of the internal temperature of the reaction vessel).

The reaction time usually varies depending on the starting material, the solvent, the other reagents used in the reaction, and the reaction temperature, and, after addition of the reagents, the reaction mixture is preferably stirred for 1 to 24 hours, more preferably stirred for about 2 to 12 hours at the above-described reaction temperature.

Compound (H-2) can be used in a 1- to 5-fold molar amount, preferably 1.1- to 2-fold molar amount with respect to the Compound (H-1).

The above-described base can be used in a 1- to 5-fold molar amount, preferably 1- to 3-fold molar amount, more preferably 2-fold molar amount with respect to the Compound (H-1).

[Production Method I]

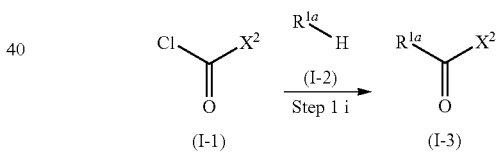

wherein $X^2$ has the same meaning as defined above. $R^{1a}$ means $C_1$-$C_6$ alkoxy or $C_2$-$C_6$ alkenyloxy.

[Step 1i]

In this step, Compound (I-1) is allowed to react with Compound (I-2) in a solvent, to produce Compound (I-3). In this reaction step, the reaction is carried out in the presence of a base.

This reaction may also be carried out under the flow or atmosphere of an inert gas such as nitrogen or argon.

As Compound (I-1), commercially available compounds, compounds which can be easily produced from commercially available compounds by methods usually carried out by those skilled in the art, and the like can be used. Particular examples of Compound (I-1) which can be used include 4-nitrophenyl chloroformate.

As Compound (I-2), commercially available compounds, compounds which can be easily produced from commercially available compounds by methods usually carried out by those skilled in the art, and the like can be used. Particular examples of Compound (I-2) which can be used include ethanol, propanol, 2,2-dimethyl-1-propanol, 2,2-dimethyl-1-butanol and β-methallyl alcohol.

The solvent to be used in this reaction is not restricted as long as the starting material can be dissolved therein to a certain extent and the reaction is not inhibited therein, and examples of the solvent include ether solvents such as tetrahydrofuran, 1,2-dimethoxyethane, t-butyl methyl ether, cyclopentyl methyl ether, diethyl ether, diisopropyl ether, dibutyl ether, dicyclopentyl ether and 1,4-dioxane; halogenated hydrocarbon solvents such as dichloromethane and chloroform; ester solvents such as ethyl acetate and isopropyl acetate; and mixed solvents thereof. The solvent is preferably tetrahydrofuran, ethyl acetate or dichloromethane.

The above-described base means pyridine, collidine, triethylamine or the like. The base is preferably pyridine.

The reaction temperature usually varies depending on the starting material, the solvent and the other reagents used in the reaction, and is preferably −20° C. to 50° C. (in terms of the internal temperature of the reaction vessel), more preferably about 0° C. to 20° C. (in terms of the internal temperature of the reaction vessel).

The reaction time usually varies depending on the starting material, the solvent, the other reagents used in the reaction, and the reaction temperature, and, after addition of the reagents, the reaction mixture is preferably stirred for 1 to 24 hours, more preferably stirred for about 2 to 12 hours at the above-described reaction temperature.

Compound (I-2) can be used in a 1- to 5-fold molar amount, preferably 1- to 2-fold molar amount with respect to the Compound (I-1).

The above-described base can be used in a 1- to 5-fold molar amount, preferably 1- to 3-fold molar amount, more preferably 2-fold molar amount with respect to the Compound (I-1).

[Production Method J]

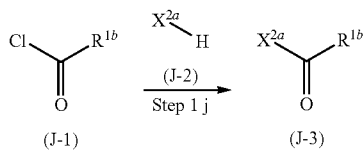

wherein $X^{2a}$ means a leaving group such as 4-nitrophenoxy. $R^{1b}$ means phenyl which may be substituted by one to three $C_1$-$C_6$ alkyl.

[Step 1j]

In this step, Compound (J-1) is allowed to react with Compound (J-2) in a solvent, to produce Compound (J-3). In this reaction step, the reaction is carried out in the presence of a base.

This reaction may also be carried out under the flow or atmosphere of an inert gas such as nitrogen or argon.

As Compound (J-1), commercially available compounds, compounds which can be easily produced from commercially available compounds by methods usually carried out by those skilled in the art, and the like can be used. Particular examples of Compound (J-1) which can be used include benzoyl chloride and p-toluoyl chloride.

As Compound (J-2), commercially available compounds, compounds which can be easily produced from commercially available compounds by methods usually carried out by those skilled in the art, and the like can be used. Particular examples of Compound (I-2) which can be used include 4-nitrophenol.

The solvent to be used in this reaction is not restricted as long as the starting material can be dissolved therein to a certain extent and the reaction is not inhibited therein, and examples of the solvent include ether solvents such as tetrahydrofuran, 1,2-dimethoxyethane, t-butyl methyl ether, cyclopentyl methyl ether, diethyl ether, diisopropyl ether, dibutyl ether, dicyclopentyl ether and 1,4-dioxane; halogenated hydrocarbon solvents such as dichloromethane and chloroform; ester solvents such as ethyl acetate and isopropyl acetate; and mixed solvents thereof. The solvent is preferably tetrahydrofuran, ethyl acetate or dichloromethane.

The above-described base means pyridine, collidine, triethylamine or the like. The base is preferably pyridine.

The reaction temperature usually varies depending on the starting material, the solvent and the other reagents used in the reaction, and is preferably −20° C. to 50° C. (in terms of the internal temperature of the reaction vessel), more preferably about 0° C. to 20° C. (in terms of the internal temperature of the reaction vessel).

The reaction time usually varies depending on the starting material, the solvent and the other reagents used in the reaction, and the reaction temperature, and, after addition of the reagents, the reaction mixture is preferably stirred for 1 to 24 hours, more preferably stirred for about 2 to 12 hours at the above-described reaction temperature.

Compound (J-2) can be used in a 1- to 5-fold molar amount, preferably 1- to 1.5-fold molar amount with respect to the Compound (J-1).

The above-described base can be used in a 1- to 5-fold molar amount, preferably 1- to 3-fold molar amount, more preferably 1- to 2-fold molar amount with respect to the amount of Compound (J-1).

In each of the above-described methods, after the reaction in each step, the compound of interest in the step can be recovered according to a conventional method from the reaction mixture.

For example, in cases where the whole reaction mixture is liquid, the reaction mixture is warmed/cooled to room temperature or cooled on ice if desired, and the acid, alkali, oxidizing agent or reducing agent is neutralized as appropriate, followed by adding water and an organic solvent such as ethyl acetate which is immiscible with water and does not react with the compound of interest, and separating the layer containing the compound of interest. Subsequently, a solvent immiscible with the obtained layer and not reacting with the compound of interest is added to wash the layer containing the compound of interest, and the layers are then separated. Further, in cases where the layer containing the compound of interest is the organic layer, it may be dried using a desiccant such as anhydrous magnesium sulfate or anhydrous sodium sulfate, and the solvent then removed by evaporation, thereby recovering the compound of interest. Further, in cases where the layer containing the compound of interest is the aqueous layer, the compound of interest can be recovered by electric desalting followed by freeze-drying of the layer Further, in cases where the whole reaction mixture is liquid, and this is possible, the compound of interest can be recovered just by evaporating the substances other than the compound of interest (e.g., the solvent and reagents) under normal pressure or reduced pressure.

Further, in cases where only a reagent or a catalyst is present as a solid, or in cases where the whole reaction mixture is liquid and only a reagent or a catalyst is precipitated during the process of the recovery while the compound of interest is dissolved in a solution, the reagent or catalyst is first removed by filtration and the removed reagent or catalyst is washed with an appropriate organic or inorganic solvent, followed by combining the obtained washing liquid with the mother liquid. By processing the resulting mixture in the same manner as in the cases where the whole reaction mixture is liquid, the compound of interest can be recovered.

In particular, in cases where the substances other than the compound of interest, which are contained in the reaction mixture, do not inhibit the subsequent reaction step, the reaction mixture can also be used as it is without isolation of the compound of interest.

In order to increase the purity of the compound of interest recovered by the above method, recrystallization, various chromatography methods and distillation may be carried out as appropriate.

In cases where the recovered compound of interest is a solid, the purity of the compound of interest can be usually increased by recrystallization. In recrystallization, a single solvent or a mixture of solvents which does not react with the compound of interest can be used. More particularly, the compound of interest is first dissolved at room temperature or under heat in a single solvent or a mixture of solvents which does not react with the compound of interest. The obtained mixture is cooled in ice water or the like or left to stand at room temperature, to allow crystallization of the compound of interest from the mixture.

The recovered compound of interest can be subjected to various chromatography methods such as normal-phase column chromatography or reverse-phase column chromatography, to increase the purity of the compound of interest. In general, weakly acidic silica gels such as Silica gel 60 (70-230 mesh or 340-400 mesh) manufactured by Merck or BW-300 (300 mesh) manufactured by Fuji Silysia Chemical Ltd. may be used. In cases where, for example, the compound of interest is basic and shows too strong an adsorption to the above-mentioned silica gels, Propylamine-coated Silica Gel (200-350 mesh) manufactured by Fuji Silysia Chemical Ltd. or the like may also be used. In cases where, for example, the compound of interest is bipolar, or elution with a highly polar solvent such as methanol is necessary, NAM-200H or NAM-300H manufactured by Nagara Science Co., Ltd. may also be used. For purification by chromatography, normal-phase silica gel column chromatography such as FLASH+Cartridge (KP-SIL, 60 Å, 32-63 μm) manufactured by Biotage or Hi-Flash™ Column (40 μm, 60 Å) manufactured by Yamazen Corporation.; or reverse-phase silica gel column chromatography such as YMC*GEL ODS-A manufactured by YMC Co., Ltd. may also be used.

By using one of these silica gels and eluting the compound of interest with a single or multiple solvents which do not react with it, then removing the solvent(s) by evaporation, the compound of interest can be obtained in increased purity.

In cases where the compound of interest which was recovered is liquid, it is also possible to increase the purity of the compound of interest by distillation. In distillation, the compound of interest can be distilled by being placed under reduced pressure at room temperature or under heat.

Representative examples of the production methods of the compounds of the present invention are as described above, but the raw material compounds and the reagents to be used for production of the compounds of the present invention may be in the form of a salt, a solvate or a hydrate, and may vary depending on the starting material, the solvent to be used and the like, and are not restricted as long as they do not inhibit the reaction. Needless to say, the solvent to be used also varies depending on the starting material, the reagents to be used and the like, and is not restricted as long as it does not inhibit the reaction and the starting material can be dissolved therein to some extent. In cases where the compound of the present invention is obtained as a free form, it may be converted to the state of a preparable salt of the compound, or a hydrate thereof, according to a conventional method.

In cases where the compound of the present invention is obtained as a salt or a hydrate, it can be converted to the free form of the compound according to a conventional method.

Various isomers (e.g., geometric isomers, optical isomers, rotational isomers, stereoisomers and tautomers) obtained for the compound of the present invention can be purified and isolated by using a normal separation method including recrystallization, diastereomeric salt method, enzymatic resolution method and various chromatographic methods (e.g., thin-layer chromatography, column chromatography and gas chromatography).

In cases where the compound of the present invention is used as a pharmaceutical, the pharmaceutical is usually formulated by mixing the compound of the present invention with an appropriate additive. However, this does not negate usage as a pharmaceutical of the compound of the present invention as it is.

Examples of the additive include excipients, binders, lubricants, disintegrators, coloring agents, correctives, emulsifiers, surfactants, solubilizers, suspending agents, isotonic agents, buffers, antiseptics, antioxidants, stabilizers and absorption enhancers, which may be used as an appropriate combination, if desired.

Examples of the excipients include lactose, saccharose, glucose, corn starch, mannitol, sorbitol, starch, pregelatinized starch, dextrin, crystalline cellulose, light anhydrous silicic acid, aluminum silicate, calcium silicate, magnesium aluminometasilicate and calcium hydrogen phosphate.

Examples of the binders include polyvinyl alcohol, methyl cellulose, ethyl cellulose, gum arabic, tragacanth, gelatin, shellac, hydroxypropylmethylcellulose, hydroxypropylcellulose, sodium carboxymethylcellulose, polyvinyl pyrrolidone and macrogol.

Examples of the lubricants include magnesium stearate, calcium stearate, sodium stearyl fumarate, talc, polyethylene glycol and colloidal silica.

Examples of the disintegrators include crystalline cellulose, agar, gelatin, calcium carbonate, sodium hydrogen carbonate, calcium citrate, dextrin, pectin, low substituted hydroxypropylcellulose, carboxymethylcellulose, carboxymethylcellulose calcium, croscarmellose sodium, carboxymethyl starch and sodium carboxymethyl starch.

Examples of the coloring agents include those whose addition to pharmaceuticals is permitted, such as iron sesquioxide, yellow iron sesquioxide, carmine, caramel, β-carotene, titanium oxide, talc, riboflavin sodium phosphate and yellow aluminum lake.

Examples of the correctives include cocoa powder, menthol, aromatic powder, peppermint oil, borneol and cinnamon powder.

Examples of the emulsifiers and surfactants include stearyl triethanolamine, sodium lauryl sulfate, laurylamino propionate, lecithin, glycerin monostearate, sucrose fatty acid ester and glycerin fatty acid ester.

Examples of the solubilizers include polyethylene glycol, propylene glycol, benzyl benzoate, ethanol, cholesterol, triethanolamine, sodium carbonate, sodium citrate, polysorbate 80 and nicotinamide.

Examples of the suspending agents include, in addition to the above surfactants, hydrophilic macromolecules such as polyvinyl alcohol, polyvinyl pyrrolidone, methylcellulose, hydroxymethylcellulose, hydroxyethylcellulose and hydroxypropylcellulose.

Examples of the isotonic agents include glucose, sodium chloride, mannitol and sorbitol.

Examples of the buffers include buffer solutions containing a phosphoric acid salt, acetic acid salt, carbonic acid salt or citric acid salt.

Examples of the antiseptics include methylparaben, propylparaben, chlorobutanol, benzyl alcohol, phenethyl alcohol, dehydroacetic acid and sorbic acid.

Examples of the antioxidants include sulfurous acid salts, ascorbic acid and α-tocopherol.

Examples of the stabilizers include those commonly used for pharmaceuticals.

Examples of the absorption enhancers include those commonly used for pharmaceuticals.

Further, examples of the above formulations include oral preparations such as tablets, powders, granules, capsules, syrups, troches and inhalants; and external preparations such as suppositories, ointments, ophthalmic ointments, tapes, eye drops, nasal drops, ear drops, cataplasms and lotions; and injection solutions.

The above oral preparations are formulated by combining the above additives as appropriate. As required, the surfaces of the oral preparations may be coated.

The above external preparations are formulated especially by combining, as appropriate, the excipients, binders, correctives, emulsifiers, surfactants, solubilizers, suspending agents, isotonic agents, antiseptics, antioxidants, stabilizers or absorption enhancers, among the above additives.

The above injection solutions are formulated especially by combining, as appropriate, the emulsifiers, surfactants, solubilizers, suspending agents, isotonic agents, buffers, antiseptics, antioxidants, stabilizers or absorption enhancers, among the above additives.

Although the dose of the pharmaceutical of the present invention varies depending on the symptoms, age, sex, body weight, administration mode, type of salt, sensitivity to the medicament, concrete type of the disease, and the like, the daily dose for an adult is usually about 1 mg to about 1000 mg (preferably about 10 mg to about 500 mg) in the case of oral administration or about 1 mg to about 1000 mg (preferably about 10 to about 500 mg) in the case of an external preparation, or about 1 μg to about 3000 μg (preferably about 3 μg to about 3000 μg) per kg body weight in the case of an injection solution, which is administered once or dividedly in 2 to 6 times per day.

In the cases of the oral preparation and the injection solution, the values indicate their amounts to be actually administered, and, in the case of the external preparation, the value indicates its amount actually absorbed into the living body.

EXAMPLES

The compound of the present invention can be produced, for example, by the process described in the following Examples, and the effect of the compound can be confirmed by the process described in the following Test Examples. It should be understood, however, that these are exemplary only, and that the present invention, in any case, is not limited by the following specific examples and various variations may be made without departing from the scope of the present invention.

Compounds mentioned with reference to published documents are produced according to those documents.

"Silica gel" in "silica gel column chromatography" described in the Examples, unless otherwise specified, is Silica Gel 60 (70-230 mesh or 230-400 mesh) from Merck, FLASH+Cartridge (KP-SIL, 60 Å, 32-63 μm) by Biotage, or Hi-Flash™ Column (40 μm, 60 Å) from Yamazen Corporation.

"Reverse phase silica gel" in "reverse phase silica gel column chromatography" described in the Examples, unless otherwise specified, is YMC*GEL ODS-A (12 nm, S-50 μm) from YMC Co., Ltd.

"NAM silica gel" in "NAM silica gel column chromatography" described in the Examples is NAM-200H or NAM-300H from Nagara Science Co., Ltd.

"SUMICHIRAL OA-2500" or "SUMICHIRAL OA-2500S" described in the Examples is the HPLC column from Sumika Chemical Analysis Service, Ltd.

"Purification by reverse phase high-performance liquid chromatography" described in the Examples were performed, unless otherwise specified, under the following conditions.

[Column]
The column used was as follows:
Company: SHISEIDO
Name: CAPCELL PAK C18
Size: 50 mm×20 mm I.D.
Type: ACR 5 μm

[Mobile Phase]
The combination of (1) and (2) below was used, with a gradient in the ratio range of 100:0-0:100, as a moving bed for liquid chromatography.
(1) 99.9% water (0.1% acetic acid)
(2) 99.9% acetonitrile (0.1% acetic acid)

"Room temperature" in the following Examples generally refers to temperatures between about 10° C. and 35° C. "%" unless otherwise specified, is weight percentages. The other symbols used herein stand for the following:

$^1$H-NMR: proton nuclear magnetic resonance
δ: chemical shift
s: singlet
d: doublet
t: triplet
q: quartet
quint: quintet
sext: sextet
m: multiplet
br: broad
sept: septet
J: coupling constant
Hz: Hertz
M: mol/L
n-: normal
s-: secondary
t-: tertiary
N: normality
$CDCl_3$: deutero chloroform
$d_6$-DMSO: deutero dimethylsulfoxide
$CD_3OD$: deutero methanol
$CD_3CN$: deutero acetonitrile
DMF: N,N-dimethylformamide
DMA: N,N-dimethylacetamide
DMAP: 4-(dimethylamino)pyridine
TBME: t-butyl methyl ether
THF: tetrahydrofuran
TFA: trifluoroacetic acid
DMSO: dimethyl sulfoxide
WSC: hydrochloric acid 1-ethyl-3-(3-dimethylaminopropyl) carbodiimide

Example 1

3-methoxymethoxy-2,2-dimethylpropionic acid 5-{(R)[4-(amino[benzoylimino]methyl)phenylamino]-[2-fluoro-3-(2-hydroxyethoxy)-5-methoxyphenyl]methyl}-2-pyrimidin-2-yl-2H-[1,2,4]triazol-3-yloxymethyl ester (1a) N-[1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide

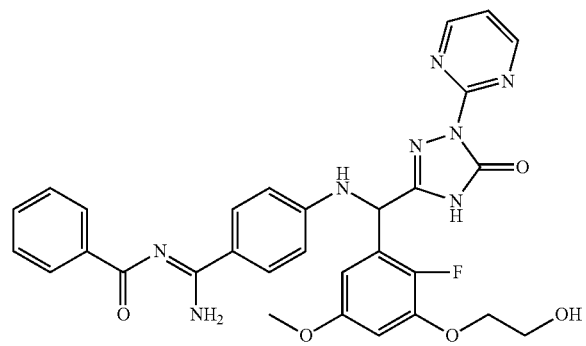 [SMILES: COc1cc(OCCO)c(F)c(C(Nc2ccc(/C(N)=N/C(=O)c3ccccc3)cc2)c2nn(-c3ncccn3)c(=O)[nH]2)c1]

To a mixture of 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine acetic acid salt [CAS No. 951803-95-5] (613 mg) and DMF (5 mL), benzoic acid 4-nitrophenyl ester [CAS No. 959-22-8] (280 mg) and triethylamine (0.2 mL) were added and the resulting mixture was stirred at 50° C. overnight. Acetic acid was added to the reaction solution, and the solvent was evaporated under reduced pressure. The residue obtained was purified by NAM silica gel column chromatography (mixed solvent of methanol-ethyl acetate) to obtain the captioned compound (492 mg).

$^1$H-NMR (CD$_3$OD) δ=3.72 (s, 3H), 3.88 (t, J=4.8 Hz, 2H), 4.10 (t, J=4.8 Hz, 2H), 6.00 (s, 1H), 6.65 (d, J=5.2 Hz, 2H), 6.83 (d, J=8.4 Hz, 2H), 7.35 (t, J=4.8 Hz, 1H), 7.43 (t, J=7.2 Hz, 2H), 7.50 (t, J=7.2 Hz, 1H), 7.98 (d, J=8.4 Hz, 2H), 8.23 (d, J=7.2 Hz, 2H), 8.77 (d, J=4.8 Hz, 2H)

(1b) 3-methoxymethoxy-2,2-dimethylpropionic acid methoxymethyl ester

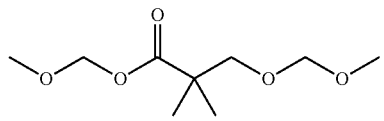

To a mixture of 3-hydroxy-2,2-dimethylpropionic acid [CAS No. 4835-90-9] (10 g) and dichloromethane (350 mL), at 0° C., chloromethyl methyl ether (16.1 mL) dissolved in dichloromethane (30 mL) and N,N-diisopropylethylamine (44.2 mL) were sequentially added. After stirring the mixture overnight at room temperature, aqueous ammonia (50 mL) was added thereto. To the mixture, 2 N hydrochloric acid (500 mL) and diethyl ether (800 mL) were added, and the resulting mixture was shaken, followed by collection of the organic layer. The organic layer was sequentially washed with saturated aqueous sodium hydrogen carbonate solution (300 mL) and saturated aqueous sodium chloride solution (300 mL), and dried over anhydrous magnesium sulfate. The resulting mixture was filtered and the obtained filtrate was concentrated under reduced pressure to obtain the captioned compound (16.5 g).

$^1$H-NMR (CDCl$_3$) δ=1.25 (s, 6H), 3.35 (s, 3H), 3.46 (s, 3H), 3.56 (s, 2H), 4.61 (s, 2H), 5.26 (s, 2H)

(1c) 3-methoxymethoxy-2,2-dimethylpropionic acid

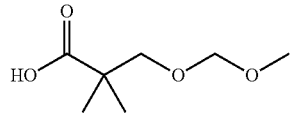

To a mixture of 3-methoxymethoxy-2,2-dimethylpropionic acid methoxymethyl ester (16.5 g) and methanol (30 mL), 5 N aqueous sodium hydroxide solution (30 mL) was added, and the resulting mixture was stirred at room temperature for 4 days. Ice was added to the mixture, and at 0° C., 5 N hydrochloric acid (35 mL) and diethyl ether (300 mL) were added thereto. The mixture was shaken and the organic layer was collected. The organic layer was washed with saturated aqueous sodium chloride solution (100 mL) and dried over anhydrous magnesium sulfate. The resulting mixture was filtered and the obtained filtrate was concentrated under reduced pressure to obtain the captioned compound (14.5 g).

$^1$H-NMR (CDCl$_3$) δ=1.25 (s, 6H), 3.36 (s, 3H), 3.55 (s, 2H), 4.64 (s, 2H)

(1d) 3-methoxymethoxy-2,2-dimethylpropionic acid chloromethyl ester

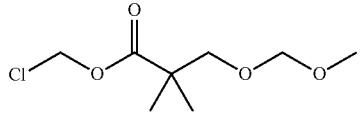

To a mixture of water (240 mL) and TBME (360 mL), dipotassium hydrogen phosphate (246 g), tetrabutylammonium hydrogen sulfate (9.65 g) and 3-methoxymethoxy-2,2-dimethylpropionic acid (45.8 g) were sequentially added. The mixture was cooled to 0° C., and chloromethyl chlorosulfate [CAS No. 49715-04-0] (42.1 mL) was added dropwise thereto with stirring, followed by stirring the resulting mixture overnight at room temperature. Water (1.3 L) and TBME (800 mL) were added to the mixture. After shaking the mixture, the organic layer was collected and washed twice with saturated aqueous sodium chloride solution (300 mL), followed by drying over anhydrous magnesium sulfate. The TFFH: fluoro-N,N,N',N'-tetramethylformamidinium hexafluorophosphate resulting mixture was filtered and the obtained filtrate was concentrated under reduced pressure. The obtained residue was purified by silica gel column chromatography (mixed solvent of heptane-ethyl acetate) to obtain the captioned compound (41.7 g).

¹H-NMR (CDCl₃) δ=1.25 (s, 6H), 3.35 (s, 3H), 3.55 (s, 2H), 4.61 (s, 2H), 5.73 (s, 2H)

(1e) 3-methoxymethoxy-2,2-dimethylpropionic acid 5-{[4-(amino[benzoylimino]methyl)phenylamino]-[2-fluoro-3-(2-hydroxyethoxy)-5-methoxyphenyl]methyl}-2-pyrimidin-2-yl-2H-[1,2,4]triazol-3-yloxymethyl ester

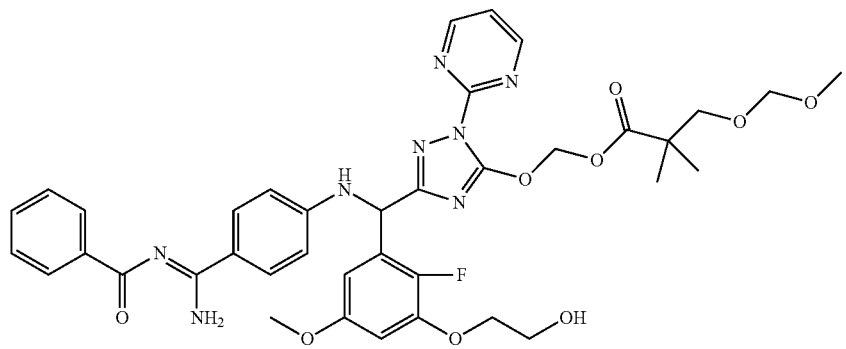 [SMILES: COCOCC(C)(C)C(=O)OCOc1nc(C(Nc2ccc(/C(N)=N/C(=O)c3ccccc3)cc2)c2cc(OC)cc(OCCO)c2F)nn1-c1ncccn1]

To a mixture of N-[1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide (120 mg) and DMF (3 mL), potassium hydrogen carbonate (30 mg) and 3-methoxymethoxy-2,2-dimethylpropionic acid chloromethyl ester (54.8 mg) were sequentially added, and the resulting mixture was stirred at 60° C. for 14 hours. To the mixture, ethyl acetate (100 mL) was added. The resulting mixture was sequentially washed three times with water (50 mL) and with saturated aqueous sodium chloride solution (50 mL), and dried over anhydrous magnesium sulfate. The resulting mixture was filtered and the obtained filtrate was concentrated under reduced pressure. The obtained residue was purified by NAM silica gel column chromatography (mixed solvent of heptane-ethyl acetate and methanol-ethyl acetate) to obtain the captioned compound (40 mg).

¹H-NMR (CD₃CN) δ=1.23 (s, 6H), 3.10 (t, J=5.6 Hz, 1H), 3.17 (s, 3H), 3.43 (s, 2H), 3.73 (s, 3H), 3.85 (q, J=5.6 Hz, 2H), 4.11 (t, J=5.6 Hz, 2H), 4.36 (d, J=7.4 Hz, 1H), 4.38 (d, J=7.4 Hz, 1H), 6.02 (d, J=8.4 Hz, 1H), 6.09 (s, 2H), 6.10 (d, J=8.4 Hz, 1H), 6.62 (dd, J=2.4, 7.4 Hz, 1H), 6.67 (dd, J=2.4, 5.3 Hz, 1H), 6.85 (d, J=8.9 Hz, 2H), 7.44 (t, J=4.3 Hz, 1H), 7.46 (t, J=7.4 Hz, 2H), 7.54 (t, J=7.4 Hz, 1H), 8.00 (d, J=8.9 Hz, 2H), 8.33 (d, J=7.4 Hz, 2H), 8.84 (d, J=4.3 Hz, 2H)

(1f) 3-methoxymethoxy-2,2-dimethylpropionic acid 5-{(R)-[4-(amino[benzoylimino]methyl)phenylamino]-[2-fluoro-3-(2-hydroxyethoxy)-5-methoxyphenyl]methyl}-2-pyrimidin-2-yl-2H-[1,2,4]triazol-3-yloxymethyl ester

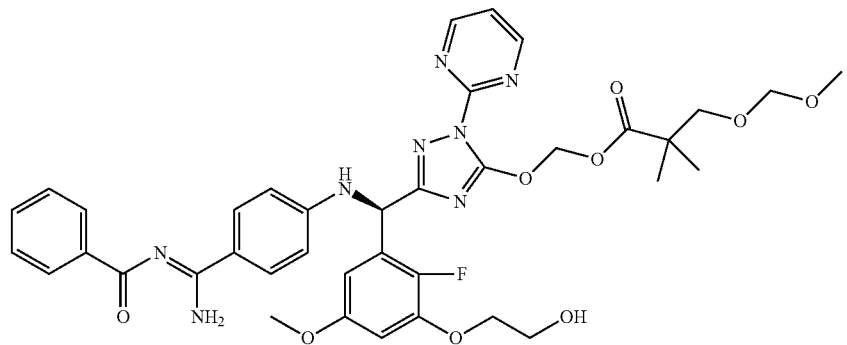 [SMILES: COCOCC(C)(C)C(=O)OCOc1nc([C@H](Nc2ccc(/C(N)=N/C(=O)c3ccccc3)cc2)c2cc(OC)cc(OCCO)c2F)nn1-c1ncccn1]

Using SUMICHIRAL OA-2500 column, 3-methoxymethoxy-2,2-dimethylpropionic acid 5-{[4-(amino[benzoylimino]methyl)phenylamino]-[2-fluoro-3-(2-hydroxyethoxy)-5-methoxyphenyl]methyl}-2-pyrimidin-2-yl-2H-[1,2,4]triazol-3-yloxymethyl ester (568 mg) was separated (optical resolution) under the conditions below to obtain the captioned compound (247.6 mg) in the latter fraction.

HPLC retention time; 15 min (column name: SUMICHIRAL OA-2500, 30 mmφ×25 cm, mobile phase: methanol, elution rate: 30 mL/min)

¹H-NMR (CD₃OD) δ=1.10 (s, 6H), 3.14 (s, 3H), 3.37 (d, J=9.2 Hz, 1H), 3.40 (d, J=9.2 Hz, 1H), 3.73 (s, 3H), 3.89 (t, J=4.8 Hz, 2H), 4.10 (t, J=4.8 Hz, 2H), 4.30 (d, J=6.6 Hz, 1H), 4.33 (d, J=6.6 Hz, 1H), 6.11 (s, 1H), 6.12 (d, J=5.6 Hz, 1H), 6.15 (d, J=5.6 Hz, 1H), 6.62 (dd, J=2.8, 6.8 Hz, 1H), 6.76 (dd, J=2.8, 4.8 Hz, 1H), 6.85 (d, J=9.2 Hz, 2H), 7.41-7.52 (m, 4H), 7.98 (d, J=8.8 Hz, 2H), 8.24 (d, J=8.8 Hz, 2H), 8.87 (d, J=4.8 Hz, 2H)

Example 2

2,2-dimethylmalonic acid 5-{(R)-(4-{amino(2,2-dimethylpropoxycarbonylimino)methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester t-butyl ester (2a) [1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]carbamic acid 2,2-dimethylpropyl ester

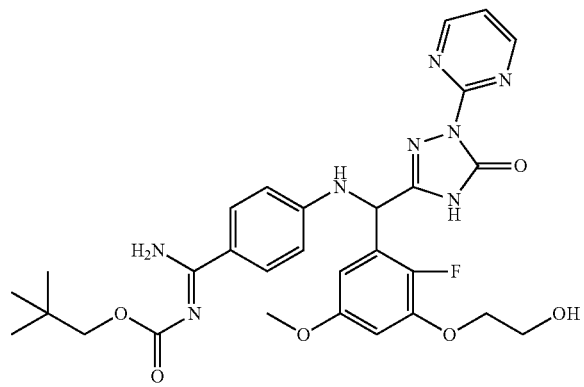 [SMILES: COc1cc(OCCO)c(F)c(C(Nc2ccc(/C(N)=N/C(=O)OCC(C)(C)C)cc2)c2nn(-c3ncccn3)c(=O)[nH]2)c1]

To a mixture of 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine acetic acid salt (6 g) and DMF (500 mL), carbonic acid 2,2-dimethylpropyl ester 4-nitrophenyl ester [CAS No. 158810-98-1] (3.06 g) and triethylamine (4.64 mL) were added, and the resulting mixture was stirred overnight at room temperature. Acetic acid (5 mL) was added to the reaction solution, and the solvent was evaporated under reduced pressure. The residue obtained was purified by NAM silica gel column chromatography (mixed solvent of methanol-ethyl acetate) to obtain the captioned compound (6.5 g).

$^1$H-NMR (CD$_3$OD) δ=0.98 (s, 9H), 3.34 (s, 2H), 3.83 (s, 3H), 3.88 (t, J=4.8 Hz, 2H), 4.10 (t, J=4.8 Hz, 2H), 5.96 (s, 1H), 6.63-6.66 (m, 2H), 6.79 (d, J=8.8 Hz, 2H), 7.33 (t, J=5.0 Hz, 1H), 7.71 (d, J=8.8 Hz, 2H), 7.97 (s, 1H), 8.77 (d, J=4.8 Hz, 2H)

(2b) [1-amino-1-[4-({(5-chloromethoxy-1-pyrimidin-2-yl-1H-[1,2,4]triazol-3-yl)-[2-fluoro-3-(2-hydroxyethoxy)-5-methoxyphenyl]methyl}amino)phenyl]methylidene]carbamic acid 2,2-dimethylpropyl ester

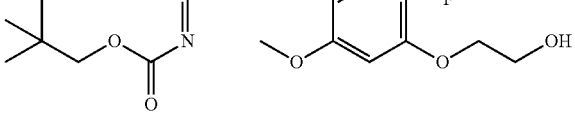

To a mixture of [1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]carbamic acid 2,2-dimethylpropyl ester (4 g) and dichloromethane (80 mL), sodium hydrogen carbonate (6.63 g) and tetrabutylammonium hydrogen sulfate (447 mg) were added at low temperature (−10° C.~5° C.). To the resulting mixture, THF (80 mL) and water (80 mL) were added. To the resulting mixture, chloromethyl chlorosulfate (3.26 g) in dichloromethane/THF (1:1) mixture (10 mL) was added dropwise at −5° C., and the resulting mixture was stirred overnight at room temperature. Under ice-cooling, THF/ethyl acetate (1:4) mixture (500 mL) was added to the mixture, and the resulting mixture was filtered. To the filtrate obtained, water (300 mL) was added, and the resulting mixture was shaken, after which the organic layer was collected. The organic layer was washed with saturated aqueous sodium chloride solution (150 mL). An aqueous layer was extracted with THF/ethyl acetate (1:4) mixture (250 mL, twice). The organic layers were combined and washed with saturated aqueous sodium chloride solution (150 mL). All the organic layers were combined and dried over anhydrous sodium sulfate and anhydrous magnesium sulfate. The resulting mixture was filtered, and the filtrate obtained was concentrated under reduced pressure. The residue obtained was purified by NAM silica gel column chromatography (mixed solvent of methanol-ethyl acetate) to obtain the captioned compound (1.56 g).

$^1$H-NMR (CDCl$_3$) δ=0.98 (s, 9H), 3.49 (s, 2H), 3.70 (s, 3H), 3.85 (s, 2H), 3.97 (t, J=5.2 Hz, 2H), 4.10 (t, J=5.2 Hz, 2H), 5.38 (d, J=7.4 Hz, 1H), 6.15 (d, J=6.0 Hz, 1H), 6.17 (d, J=7.4 Hz, 1H), 6.45 (dd, J=3.2, 7.4 Hz, 1H), 6.68 (dd, J=3.2, 4.8 Hz, 1H), 6.73 (d, J=8.8 Hz, 2H), 7.32 (t, J=4.4 Hz, 1H), 7.71 (d, J=8.8 Hz, 2H), 8.85 (d, J=3.6 Hz, 2H)

(2c) 2,2-dimethylmalonic acid 5-{(R)-(4-{amino(2,2-dimethylpropoxycarbonylimino)methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester t-butyl ester

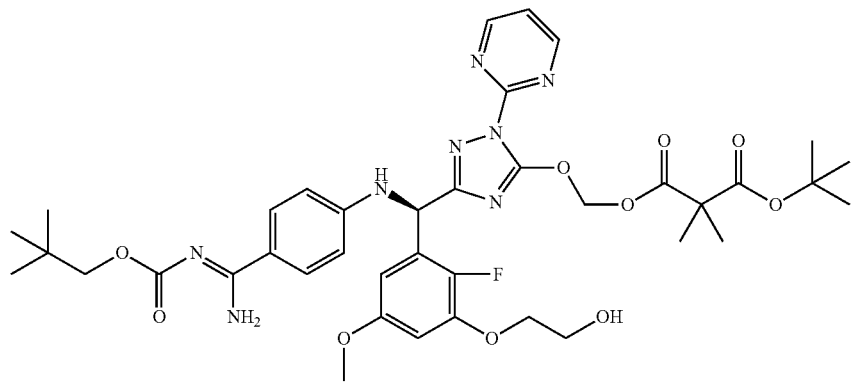 [SMILES: COc1cc(OCCO)c(F)c([C@@H](Nc2ccc(/C(N)=N/C(=O)OCC(C)(C)C)cc2)c2nc(OCOC(=O)C(C)(C)C(=O)OC(C)(C)C)n(-c3ncccn3)n2)c1]

A mixture of [1-amino-1-[4-({(5-chloromethoxy-1-pyrimidin-2-yl-1H-[1,2,4]triazol-3-yl)-[2-fluoro-3-(2-hydroxyethoxy)-5-methoxyphenyl]methyl}amino)phenyl]methylidene]carbamic acid 2,2-dimethylpropyl ester (170 mg), 2,2-dimethylmalonic acid mono-t-butyl ester [CAS No. 143688-40-8] (490 mg), sodium iodide (390 mg), potassium hydrogen carbonate (182 mg), and DMA (25 mL) was stirred at 50° C. overnight. After cooling the mixture to room temperature, 1:1 mixture of water and saturated aqueous sodium chloride and ethyl acetate were added thereto, and the resulting mixture was extracted. The aqueous layer was reextracted with ethyl acetate twice. All the organic layers were combined, washed with water, and dried over anhydrous magnesium sulfate. The desiccant was filtered off, and the filtrate obtained was concentrated under reduced pressure. The residue obtained was purified by silica gel column chromatography (mixed solvent of heptane-ethyl acetate) to obtain a racemate of the captioned compound.

The racemate was optically resolved using SUMICHIRAL OA-2500S column under the conditions below to obtain a crudely purified product of the captioned compound in the former fraction. HPLC retention time; 11 min (column name: SUMICHIRAL OA-2500S, 30 mm$\phi$×25 cm, mobile phase: methanol, elution rate: 20 mL/min)

The crudely purified product obtained was purified again using SUMICHIRAL OA-2500 column (30 mm$\phi$×25 cm, mobile phase: methanol, elution rate: 20 mL/min) to obtain the captioned compound (57.21 mg).

$^1$H-NMR (CD$_3$OD) δ=1.00 (s, 9H), 1.21 (s, 9H), 1.31 (s, 3H), 1.32 (s, 3H), 3.73 (s, 3H), 3.82 (s, 2H), 3.89-3.91 (m, 2H), 4.09-4.11 (m, 2H), 6.07 (s, 1H), 6.16-6.20 (m, 2H), 6.61 (dd, J=3.2, 6.8 Hz, 1H), 6.75 (dd, J=3.2, 4.8 Hz, 1H), 6.79-6.81 (m, 2H), 7.50 (t, J=5.2 Hz, 1H), 7.71-7.73 (m, 2H), 8.89 (d, J=5.2 Hz, 2H)

Example 3-1

Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester cyclohexyl ester (Diastereomer 1)

Example 3-2

Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester cyclohexyl ester (Diastereomer 2)

(3a) Carbonic acid 1-(5-{(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester cyclohexyl ester

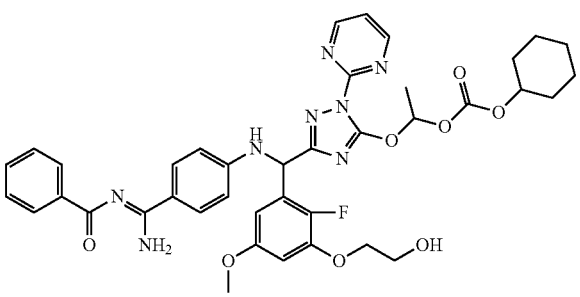 [SMILES: COc1cc(OCCO)c(F)c(C(Nc2ccc(/C(N)=N/C(=O)c3ccccc3)cc2)c2nc(OC(C)OC(=O)OC3CCCCC3)n(-c3ncccn3)n2)c1]

To a mixture of N-[1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide (Example 1a, 1.0 g) and DMF (20 mL), potassium hydrogen carbonate (1.67 g) and 1-chloroethyl cyclohexyl carbonate (2.76 g) were added, and the resulting mixture was stirred at 55° C. for 26 hours. The reaction solution was filtered, and the filtrate obtained was concentrated under reduced pressure. The residue obtained was purified by NAM silica gel column chromatography (mixed solvent of methanol-ethyl acetate) to obtain the captioned compound (680 mg).

Mass spectrum (ESI) m/z: 769 (M+H)+

(3b) Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester cyclohexyl ester

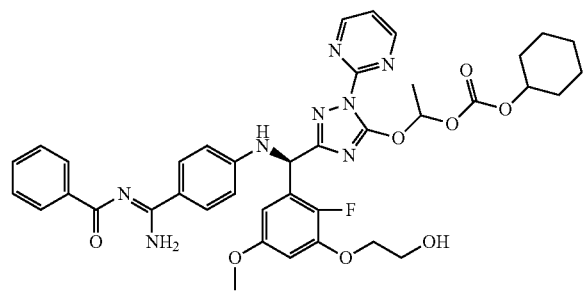 [SMILES: COc1cc(OCCO)c(F)c([C@@H](Nc2ccc(/C(N)=N/C(=O)c3ccccc3)cc2)c2nc(OC(C)OC(=O)OC3CCCCC3)n(-c3ncccn3)n2)c1]

Using SUMICHIRAL OA-2500 column, carbonic acid 1-(5-{(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester cyclohexyl ester (680 mg) was optically resolved under the conditions below to obtain the captioned compounds in the second fraction and the third fraction as a crudely purified product.

HPLC retention time; (the second fraction) 14 min, (the third fraction) 17 min (column name: SUMICHIRAL OA-2500, 30 mmϕ×25 cm, mobile phase: methanol, elution rate: 30 mL/min)

The crudely purified product obtained (the second fraction) was purified using SUMICHIRAL OA-2500S column (20 mmϕ×25 cm, mobile phase: methanol, elution rate: 30 mL/min) to obtain Diastereomer 1 (48.22 mg).

The second fraction (Diastereomer 1)

$^1$H-NMR (CD$_3$OD) δ=1.15-1.90 (m, 13H), 3.71 (s, 3H), 3.84-3.94 (m, 2H), 4.02-4.13 (m, 2H), 4.45-4.57 (m, 1H), 6.08 (s, 1H), 6.59 (dd, J=2.8, 7.2 Hz, 1H), 6.73 (dd, J=2.8, 4.8 Hz, 1H), 6.82 (d, J=8.8 Hz, 2H), 6.91 (q, J=5.6 Hz, 1H), 7.36-7.54 (m, 4H), 7.96 (d, J=8.8 Hz, 2H), 8.16-8.30 (m, 2H), 8.84 (d, J=4.4 Hz, 2H)

Mass spectrum (ESI) m/z: 769 (M+H)+

The crudely purified product obtained (the third fraction) was purified using SUMICHIRAL OA-2500S column (20 mmϕ×25 cm, mobile phase: methanol, elution rate: 30 mL/min) to obtain Diastereomer 2 (46.07 mg).

The third fraction (Diastereomer 2)

$^1$H-NMR (CD$_3$OD) δ=1.10-1.90 (m, 13H), 3.71 (s, 3H), 3.82-3.93 (m, 2H), 4.03-4.14 (m, 2H), 4.42-4.55 (m, 1H), 6.08 (s, 1H), 6.60 (dd, J=2.8, 7.2 Hz, 1H), 6.71 (dd, J=2.8, 4.8 Hz, 1H), 6.82 (d, J=8.8 Hz, 2H), 6.86 (q, J=5.2 Hz, 1H), 7.36-7.53 (m, 4H), 7.97 (d, J=8.8 Hz, 2H), 8.24 (dd, J=1.6, 8.0 Hz, 2H), 8.85 (d, J=4.4 Hz, 2H)

Example 4

4-pyridinecarboxylic acid 2-(3-{(R)-(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methyl}-2-fluoro-5-methoxyphenoxy)ethyl ester (4a) 3-methoxy-2,2-dimethylpropionic acid chloromethyl ester

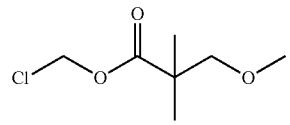

To a mixture of water (25 mL) and TBME (40 mL), dipotassium hydrogen phosphate (45.2 g), tetrabutylammonium hydrogen sulfate (1.76 g), and 3-methoxy-2,2-dimethylpropionic acid [CAS No. 64241-78-7] (6.86 g) were sequentially added. After cooling the resulting mixture to −5° C., a mixture of chloromethyl chlorosulfate (12.8 g) and TBME (10 mL) was added dropwise thereto, and the resulting mixture was stirred overnight at room temperature. Water (50 mL) and TBME (30 mL) were added to the resulting mixture. After shaking the resulting mixture, the organic layer was collected, and TBME (50 mL) was added to the remaining aqueous layer. The resulting mixture was shaken again and the organic layer was collected. The combined organic layers were washed twice with water (30 mL) and with saturated aqueous sodium chloride solution (30 mL), and dried over anhydrous magnesium sulfate. The resulting mixture was filtered, and the filtrate obtained was concentrated under reduced pressure. The residue obtained was distilled (boiling point: 85-86° C./20 mmHg) under reduced pressure to obtain the captioned compound (5.68 g).

$^1$H-NMR (CDCl$_3$) δ=1.23 (s, 6H), 3.34 (s, 3H), 3.41 (s, 2H), 5.75 (s, 2H)

(4b) 3-methoxy-2,2-dimethylpropionic acid 5-({4-[amino(benzoylimino)methyl]phenylamino}-[2-fluoro-3-(2-hydroxyethoxy)-5-methoxyphenyl]methyl)-2-pyrimidin-2-yl-2H-[1,2,4]triazol-3-yloxymethyl ester

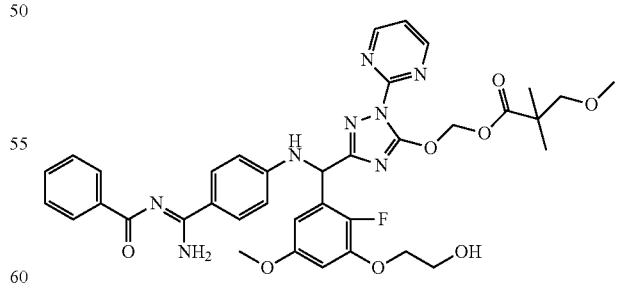

To a mixture of N-[1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide (Example 1a, 45 mg) and DMF (2 mL), cesium carbonate (29 mg) and 3-methoxy-2,2-dimethylpropionic acid chloromethyl ester (20 mg) were sequentially added, and the resulting mixture was stirred at 60° C. for 4 hours. The resulting mixture was poured into ethyl acetate (30 mL) and water (20 mL). After shaking the mixture, the organic layer was collected. The organic layer was sequentially washed twice with water (30 mL) and with saturated aqueous sodium chloride solution (20 mL), and dried over anhydrous magnesium sulfate. The resulting mixture was filtered, and the filtrate obtained was concentrated under reduced pressure. The residue obtained was purified by NAM silica gel column chromatography (mixed solvent of methanol-ethyl acetate) to obtain the captioned compound (20 mg).

$^1$H-NMR (CD$_3$CN) δ=1.10 (s, 6H), 3.05 (s, 3H), 3.09 (br.s, 1H), 3.26 (s, 2H), 3.74 (s, 3H), 3.85 (br.s, 2H), 4.09 (br.s, 2H), 6.03 (d, J=7.6 Hz, 1H), 6.08 (s, 1H), 6.10 (d, J=7.6 Hz, 1H), 6.61 (dd, J=2.4, 7.3 Hz, 1H), 6.67 (dd, J=2.4, 5.0 Hz, 1H), 6.85 (d, J=8.9 Hz, 2H), 7.44 (t, J=4.4 Hz, 1H), 7.46 (t, J=7.8 Hz, 2H), 7.54 (t, J=7.8 Hz, 1H), 8.00 (d, J=8.9 Hz, 2H), 8.33 (d, J=7.8 Hz, 2H), 8.84 (d, J=4.4 Hz, 2H)

(4c) 4-pyridinecarboxylic acid 2-(3-{(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methyl}-2-fluoro-5-methoxyphenoxy)ethyl ester

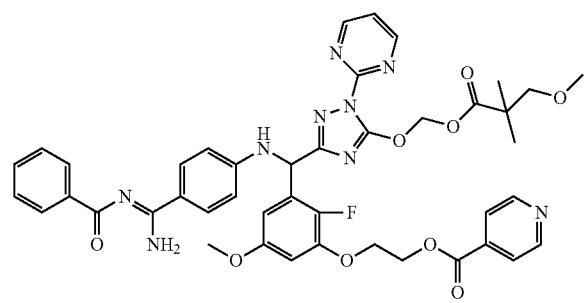 [SMILES: COCC(C)(C)C(=O)OCOc1nc(C(Nc2ccc(/C(N)=N/C(=O)c3ccccc3)cc2)c2cc(OC)cc(OCCOC(=O)c3ccncc3)c2F)nn1-c1ncccn1]

Under nitrogen atmosphere, triethylamine (0.112 mL) was added under ice-cooling to a mixture of 4-pyridinecarboxylic acid [CAS No. 55-22-1] (19.6 mg), TFFH (42.4 mg), and dichloromethane (6 mL), and the resulting mixture was stirred for 1 hour. To the resulting mixture, 3-methoxy-2,2-dimethylpropionic acid 5-({4-[amino(benzoylimino)methyl]phenylamino}-[2-fluoro-3-(2-hydroxyethoxy)-5-methoxyphenyl]methyl)-2-pyrimidin-2-yl-2H-[1,2,4]triazol-3-yloxymethyl ester (14.9 mg) and DMAP (0.27 mg) were added, and the resulting mixture was stirred overnight at room temperature. Under reduced pressure, the solvent in the mixture was distilled off. The residue obtained was purified by reverse phase high-performance liquid chromatography (mixed solvent of acetonitrile-water, containing 0.1% of acetic acid) to obtain the captioned compound (10.4 mg).

$^1$H-NMR (CD$_3$OD) δ=1.04 (s, 3H), 1.05 (s, 3H), 3.00 (s, 3H), 3.17 (d, J=9.6 Hz, 1H), 3.20 (d, J=9.6 Hz, 1H), 3.71 (s, 3H), 4.44 (t, J=4.6 Hz, 2H), 4.72 (t, J=4.6 Hz, 2H), 6.08-6.13 (m, 3H), 6.67 (dd, J=2.8, 6.4 Hz, 1H), 6.78 (dd, J=2.8, 4.6 Hz, 1H), 6.86 (d, J=8.8 Hz, 2H), 7.47-7.52 (m, 4H) 7.87 (d, J=5.4 Hz, 2H), 7.95 (d, J=8.8 Hz, 2H), 8.23 (d, J=6.8 Hz, 2H), 8.67 (d, J=5.4 Hz, 2H), 8.86 (d, J=4.4 Hz, 2H)

(4d) 4-pyridinecarboxylic acid 2-(3-{(R)-(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methyl}-2-fluoro-5-methoxyphenoxy)ethyl ester

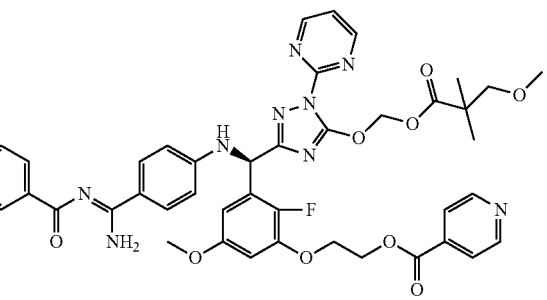

Using SUMICHIRAL OA-2500S column, 4-pyridinecarboxylic acid 2-(3-{(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methl}-2-fluoro-5-methoxyphenoxy)ethyl ester (10.4 mg) was separated (optical resolution) under the conditions below to obtain the captioned compound (3.3 mg) in the former fraction.

HPLC retention time; 14 min (column name: SUMICHIRAL OA-2500S, 30 mmφ×25 cm, mobile phase: acetonitrile, elution rate: 50 mL/min)

$^1$H-NMR (CDCl$_3$) δ=1.14 (s, 3H), 1.15 (s, 3H), 3.16 (s, 3H), 3.31 (d, J=9.6 Hz, 1H), 3.33 (d, J=9.6 Hz, 1H), 3.70 (s, 3H), 4.36 (t, J=4.6 Hz, 2H), 4.70 (t, J=4.6 Hz, 2H), 5.69 (br.s, 1H), 6.09 (br.s, 1H), 6.12 (d, J=5.3 Hz, 1H), 6.22 (d, J=5.3 Hz, 1H), 6.48 (dd, J=2.8, 6.4 Hz, 1H), 6.71 (dd, J=2.8, 4.6 Hz, 1H), 6.76 (d, J=8.8 Hz, 2H), 7.31 (t, J=4.9 Hz, 1H), 7.43 (tt, J=1.6, 6.8 Hz, 2H), 7.50 (tt, J=1.6, 6.8 Hz, 1H), 7.84 (d, J=5.6 Hz, 2H), 7.88 (d, J=8.8 Hz, 2H), 8.30 (dd, J=1.6, 6.8 Hz, 2H), 8.74 (d, J=5.6 Hz, 2H), 8.83 (d, J=4.9 Hz, 2H)

Example 5

2-ethylbutanoic acid 5-[(R)-[3-(2-acetoxyethoxy)-2-fluoro-5-methoxyphenyl]-(4-{amino[2,2-dimethylpropoxycarbonylimino]methyl}phenylamino)methyl]-2-pyrimidin-2-yl-2H-[1,2,4]triazol-3-yloxymethyl ester (5a) 2-ethylbutanoic acid 5-{(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester

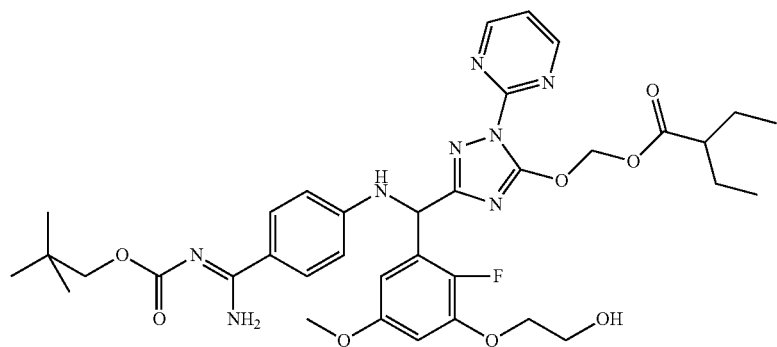 [SMILES: CCC(CC)C(=O)OCOc1nc(C(Nc2ccc(/C(N)=N/C(=O)OCC(C)(C)C)cc2)c2cc(OC)cc(OCCO)c2F)nn1-c1ncccn1]

(5b) 2-ethylbutanoic acid 5-(R)-(4-{amino[2,2-dimethylpropoxycarbonylimino]methyl}phenylamino)-[2-fluoro-3-(2-hydroxyethoxy)-5-methoxyphenyl]methyl-2-pyrimidin-2-yl-2H-[1,2,4]triazol-3-yloxymethyl ester

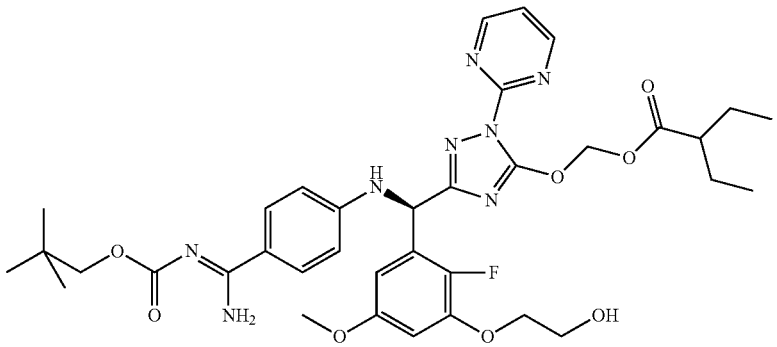 [SMILES: CCC(CC)C(=O)OCOc1nc([C@H](Nc2ccc(/C(N)=N/C(=O)OCC(C)(C)C)cc2)c2cc(OC)cc(OCCO)c2F)nn1-c1ncccn1]

To a mixture of [1-amino-1-[4-({(5-chloromethoxy-1-pyrimidin-2-yl-1H-[1,2,4]triazol-3-yl)-[2-fluoro-3-(2-hydroxyethoxy)-5-methoxyphenyl]methyl}amino)phenyl]methylidene]carbamic acid 2,2-dimethylpropyl ester (Example 2b, 100 mg), potassium hydrogen carbonate (109 mg), and DMF (13.3 mL), 2-ethylbutanoic acid (88.3 mg) and sodium iodide (117 mg) were added, and the resulting mixture was stirred at 45° C. overnight and then cooled to room temperature. To the reaction mixture, ice and saturated aqueous ammonium chloride solution were added, and the resulting mixture was extracted with a mixture of THF and ethyl acetate. The organic layer was washed with saturated aqueous ammonium chloride solution and dried over anhydrous magnesium sulfate.

The resulting mixture was filtered, and the filtrate obtained was concentrated under reduced pressure. The residue obtained was purified by NAM silica gel column chromatography (mixed solvent of methanol-ethyl acetate) to obtain the captioned compound (90 mg).

$^1$H-NMR (CD$_3$OD) δ=0.78 (t, J=7.6 Hz, 6H), 0.98 (s, 9H), 1.42-1.58 (m, 4H), 2.20-2.27 (m, 1H), 3.71 (s, 3H), 3.81 (s, 2H), 3.87 (t, J=6.4 Hz, 2H), 4.08 (t, J=6.4 Hz, 2H), 6.06 (s, 1H), 6.10 (d, J=5.6 Hz, 1H), 6.14 (d, J=5.6 Hz, 1H), 6.60 (dd, J=3.2, 6.4 Hz, 1H), 6.74 (dd, J=2.8, 4.8 Hz, 1H), 6.79 (d, J=7.2 Hz, 2H), 7.47 (t, J=4.8 Hz, 1H), 7.71 (d, J=7.2 Hz, 2H), 8.85 (d, J=4.8 Hz, 2H)

Using SUMICHIRAL OA-2500 column, 2-ethylbutanoic acid 5-{(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester (90 mg) was optically resolved under the conditions below to obtain a crudely purified product of the captioned compound in the latter fraction.

HPLC retention time; 10 min (column name: SUMICHIRAL OA-2500, 30 mmφ×25 cm, mobile phase: methanol, elution rate: 30 mL/min)

The crudely purified product obtained was purified again using SUMICHIRAL OA-2500S column (20 mmφ×25 cm, mobile phase: methanol, elution rate: 30 mL/min) to obtain the captioned compound (37 mg).

(5c) 2-ethylbutanoic acid 5-[(R)-[3-(2-acetoxy-ethoxy)-2-fluoro-5-methoxyphenyl]-(4-{amino[2,2-dimethylpropoxycarbonylimino]methyl}phenylamino)methyl]-2-pyrimidin-2-yl-2H-[1,2,4]triazol-3-yloxymethyl ester

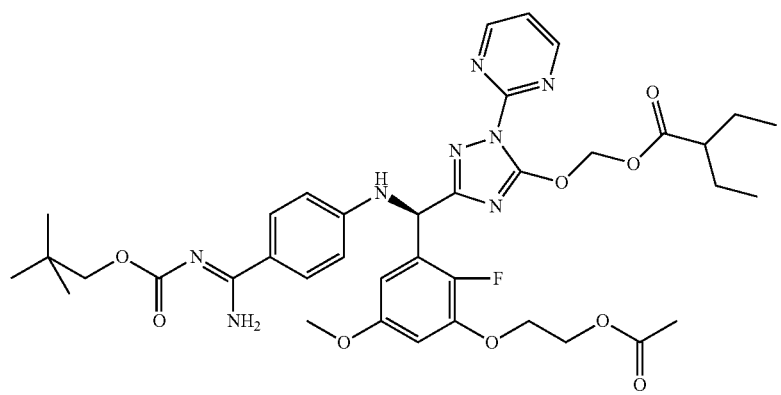 [SMILES: CCC(CC)C(=O)OCOc1nc([C@H](Nc2ccc(/C(N)=N/C(=O)OCC(C)(C)C)cc2)c2cc(OC)cc(OCCOC(C)=O)c2F)nn1-c1ncccn1]

2-ethylbutanoic acid 5-{(R)-(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester (37 mg), DMAP (0.6 mg), and triethylamine (0.056 mL) were dissolved in DMF (2.5 mL) and dichloromethane (2.5 mL). To the solution, a mixture of TFFH (26.5 mg), acetic acid (0.00576 mL), and dichloromethane (3 mL) was slowly added, and the resulting mixture was stirred at room temperature for 3 hours. After concentrating the reaction mixture under reduced pressure, ice, THF, saturated aqueous sodium hydrogen carbonate solution, and saturated aqueous ammonium chloride solution were added to the residue obtained, and the resulting mixture was extracted with the mixture of THF and ethyl acetate. The organic layer was washed with saturated aqueous ammonium chloride solution and dried over anhydrous magnesium sulfate. The resulting mixture was filtered, and the filtrate obtained was concentrated under reduced pressure. The residue obtained was crudely purified by NAM silica gel column chromatography (mixed solvent of methanol-ethyl acetate) to obtain a crudely purified product of the captioned compound.

The crudely purified product obtained was purified using SUMICHIRAL OA-2500 column (20 mmϕ×25 cm, mobile phase: methanol, elution rate: 30 mL/min) to obtain the captioned compound (23.9 mg).

$^1$H-NMR (CD$_3$OD) δ=0.78 (t, J=7.6 Hz, 6H), 0.98 (s, 9H), 1.43-1.58 (m, 4H), 2.05 (s, 3H), 2.20-2.27 (m, 1H), 3.71 (s, 3H), 3.81 (s, 2H), 4.23 (dd, J=1.6, 6.4 Hz, 2H), 4.40 (dd, J=1.6, 6.4 Hz, 2H), 6.06 (s, 1H), 6.11 (d, J=5.6 Hz, 1H), 6.15 (d, J=5.6 Hz, 1H), 6.60 (dd, J=3.2, 6.4 Hz, 1H), 6.74 (dd, J=2.8, 4.8 Hz, 1H), 6.79 (d, J=7.2 Hz, 2H), 7.47 (t, J=4.8 Hz, 1H), 7.71 (d, J=7.2 Hz, 2H), 8.85 (d, J=4.8 Hz, 2H)

Example 6

3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]-triazol-3-yloxymethyl ester (6a) Carbonic acid 2-methylallyl ester 4-nitrophenyl ester

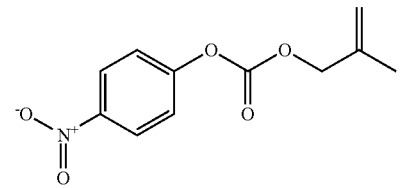

Methallyl alcohol [CAS No. 513-42-8] (5 g) and 4-nitrophenyl chloroformate [CAS No. 7693-46-1] (12.6 g) were dissolved in THF (70 mL), and pyridine (6.69 mL) was added to the resulting mixture under ice-cooling, after which the resulting mixture was stirred overnight at room temperature. To the reaction mixture, ice and saturated aqueous ammonium chloride solution were added, and the resulting mixture was extracted with ethyl acetate. The organic layer was washed with saturated aqueous sodium chloride solution and dried over anhydrous magnesium sulfate. The resulting mixture was filtered, and the filtrate obtained was concentrated under reduced pressure. The residue obtained was purified by silica gel column chromatography (mixed solvent of heptane-ethyl acetate) to obtain the captioned compound (10.5 g).

$^1$H-NMR (CDCl$_3$) δ=1.85 (s, 3H), 4.72 (s, 2H), 5.06 (s, 1H), 5.13 (s, 1H), 7.43 (d, J=8.0 Hz, 2H), 8.32 (d, J=8.0 Hz, 2H)

(6b) Acetic acid 2-{3-[(4-{amino[benzoylimino]methyl}phenylamino)-(5-oxo-1-pyrimidin-2-yl-4,5-dihydro-1H-[1,2,4]triazol-3-yl)methyl]-2-fluoro-5-methoxyphenoxy)ethyl ester

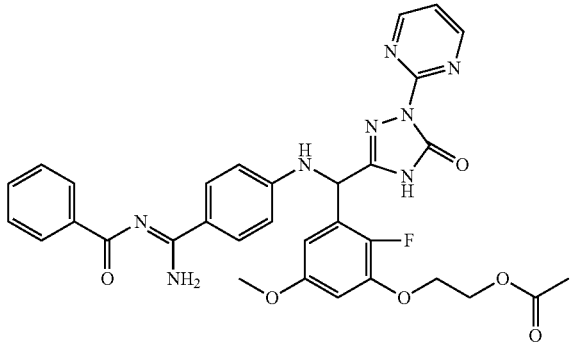 [SMILES: COc1cc(OCCOC(C)=O)c(F)c(C(Nc2ccc(/C(N)=N/C(=O)c3ccccc3)cc2)c2nn(-c3ncccn3)c(=O)[nH]2)c1]

Under nitrogen atmosphere, triethylamine (6.97 mL) was added under ice-cooling to a mixture of acetic acid (601 mg), TFFH (2.64 g), and dichloromethane (50 mL), and the resulting mixture was stirred for 1 hour. To the resulting mixture, a mixture of N-[1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide (Example 1a, 3 g), DMAP (5 mg), and DMF (50 mL) was added dropwise. After stirring the resulting mixture overnight at room temperature, the solvent in the mixture was distilled off under reduced pressure. The residue obtained was dissolved in a small amount of THF, and ethyl acetate (300 mL) and water (100 mL) were added to the resulting mixture. After a buffer (prepared by adding 37 mL of 0.1 M citric acid to 63 mL of 0.2 M disodium hydrogen phosphate) was added to the resulting mixture to adjust the pH to 6, the mixture was shaken, and the organic layer was collected. The organic layer was sequentially washed twice with water (100 mL) and with saturated aqueous sodium chloride solution (100 mL), and dried over anhydrous magnesium sulfate. The resulting mixture was filtered, and the filtrate obtained was concentrated under reduced pressure. The residue obtained was purified by NAM silica gel column chromatography (mixed solvent of methanol-ethyl acetate) to obtain the captioned compound (2.16 g).

$^1$H-NMR ($d_6$-DMSO) δ=2.04 (s, 3H), 3.72 (s, 3H), 4.26-4.29 (m, 2H), 4.34-4.37 (m, 2H), 5.93 (d, J=7.2 Hz, 1H), 6.70 (dd, J=3.1, 4.1 Hz, 1H), 6.76 (dd, J=3.1, 6.2 Hz, 1H), 6.79 (d, J=9.1 Hz, 2H), 7.40-7.55 (m, 4H), 8.05 (d, J=9.1 Hz, 2H), 8.14 (d, J=7.8 Hz, 2H), 8.82 (d, J=5.3 Hz, 2H), 8.99 (br.s, 1H), 10.44 (s, 1H), 12.28 (s, 1H)

(6c) 3-methoxy-2,2-dimethylpropionic acid 5-[[3-(2-acetoxyethoxy)-2-fluoro-5-methoxyphenyl]-(4-{amino[benzoylimino]methyl}phenylamino)methyl]-2-pyrimidin-2-yl-2H-[1,2,4]triazol-3-yloxymethyl ester

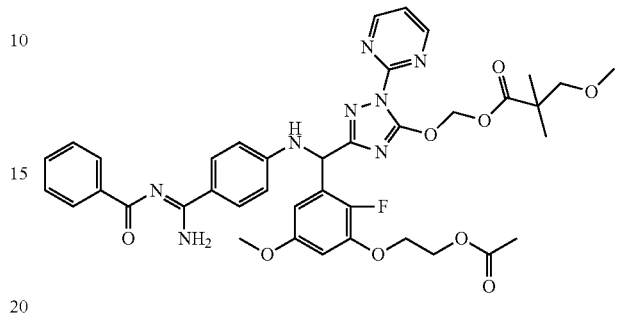

Under nitrogen atmosphere, a mixture of acetic acid 2-{3-[(4-{amino[benzoylimino]methyl}phenylamino)-(5-oxo-1-pyrimidin-2-yl-4,5-dihydro-1H-[1,2,4]triazol-3-yl)methyl]-2-fluoro-5-methoxyphenoxy)ethyl ester (441 mg), 3-methoxy-2,2-dimethylpropionic acid chloromethyl ester (Example 4a, 373 mg), potassium hydrogen carbonate (241 mg), and DMF (20 mL) was stirred at 55° C. for 15 hours. The resulting mixture was poured into ethyl acetate (200 mL) and water (50 mL). After shaking the resulting mixture, the organic layer was collected, sequentially washed twice with water (50 mL) and with saturated aqueous sodium chloride solution (50 mL), and dried over anhydrous magnesium sulfate. The resulting mixture was filtered, and the filtrate obtained was concentrated under reduced pressure. The residue obtained was purified by NAM silica gel column chromatography (mixed solvent of methanol-ethyl acetate) to obtain the captioned compound (184 mg).

$^1$H-NMR (CD$_3$OD) δ=1.06 (s, 3H), 1.07 (s, 3H), 2.02 (s, 3H), 3.00 (s, 3H), 3.19 (d, J=9.0 Hz, 1H), 3.21 (d, J=9.0 Hz, 1H), 3.71 (s, 3H) 4.23-4.26 (m, 2H), 4.39-4.44 (m, 2H), 6.09-6.13 (m, 3H), 6.60 (dd, J=3.0, 7.2 Hz, 1H), 6.78 (dd, J=3.0, 4.5 Hz, 1H), 6.85 (d, J=8.5 Hz, 2H), 7.41-7.51 (m, 4H), 7.98 (d, J=8.5 Hz, 2H), 8.24 (d, J=7.1 Hz, 2H), 8.86 (d, J=4.8 Hz, 2H)

(6d) 3-methoxy-2,2-dimethylpropionic acid 5-[[3-(2-acetoxyethoxy)-2-fluoro-5-methoxyphenyl]-(4-carbamimidoylphenylamino)methyl]-2-pyrimidin-2-yl-2H-[1,2,4]triazol-3-yloxymethyl ester acetate

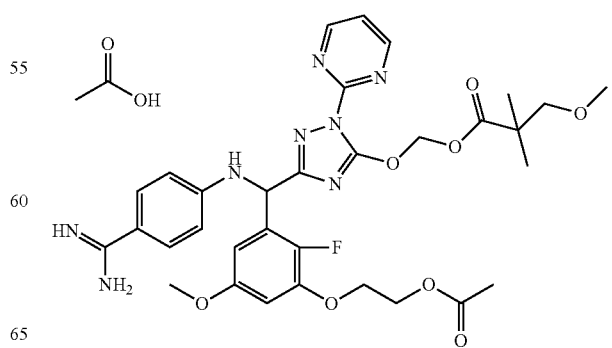

Under nitrogen atmosphere, a mixture of 3-methoxy-2,2-dimethylpropionic acid 5-[[3-(2-acetoxyethoxy)-2-fluoro-5-methoxyphenyl]-(4-{amino[benzoylimino]methyl}phenylamino)methyl]-2-pyrimidin-2-yl-2H-[1,2,4]triazol-3-yloxymethyl ester (184 mg), methanol (10 mL), and acetic acid (1 mL) was stirred at 40° C. for 15 hours. Under reduced pressure, the solvent in the mixture was distilled off. The residue obtained was purified by reverse phase silica gel column chromatography (mixed solvent of acetonitrile-water, containing 0.1% of acetic acid) to obtain the captioned compound (146 mg).

$^1$H-NMR (CD$_3$OD) δ=1.06 (s, 3H), 1.07 (s, 3H), 1.91 (s, 3H), 2.04 (s, 3H), 3.02 (s, 3H), 3.20 (s, 2H), 3.72 (s, 3H), 4.23-4.27 (m, 2H), 4.39-4.43 (m, 2H), 6.09-6.13 (m, 3H), 6.62 (dd, J=2.8, 6.8 Hz, 1H), 6.75 (dd, J=2.8, 4.8 Hz, 1H), 6.87 (dd, J=1.6, 7.6 Hz, 2H), 7.49 (t, J=4.7 Hz, 1H), 7.62 (dd, J=1.6, 7.6 Hz, 2H), 8.87 (d, J=4.7 Hz, 2H)

(6e) 3-methoxy-2,2-dimethylpropionic acid 5-[[3-(2-acetoxyethoxy)-2-fluoro-5-methoxyphenyl]-(4-{amino[2-methylall yloxycarbonylimino]methyl}phenylamino)methyl]-2-pyrimidin-2-yl-2H-[1,2,4]triazol-3-yloxymethyl ester A mixture of 3-methoxy-2,2-dimethylpropionic acid 5-[[3-(2-acetoxyethoxy)-2-fluoro-5-methoxyphenyl]-(4-carbamimidoylphen ylamino)methyl]-2-pyrimidin-2-yl-2H-[1,2,4]triazol-3-yloxymethyl ester acetate (13 mg), triethylamine (0.0074 mL), carbonic acid 2-methylallyl ester 4-nitrophenyl ester (5.6 mg), and DMF (2 mL) was stirred for 3 days at room temperature. The resulting mixture was poured into ethyl acetate (100 mL) and water (30 mL). After shaking the mixture, the organic layer was collected, sequentially washed twice with water (30 mL) and with saturated aqueous sodium chloride solution (30 mL), and dried over anhydrous magnesium sulfate. The resulting mixture was filtered, and the filtrate obtained was concentrated under reduced pressure. The residue obtained was purified by NAM silica gel column chromatography (mixed solvent of methanol-ethyl acetate) to obtain the captioned compound (13 mg).

$^1$H-NMR (CD$_3$CN): δ=1.09 (s, 3H), 1.10 (s, 3H), 1.78 (s, 3H), 2.05 (s, 3H), 3.05 (s, 3H), 3.26 (s, 2H), 3.74 (s, 3H), 4.24-4.27 (m, 2H), 4.37-4.42 (m, 2H), 4.54 (s, 2H), 4.93 (br.s, 1H), 4.98 (br.s, 1H), 5.96 (d, J=7.2 Hz, 1H), 6.06 (d, J=7.2 Hz, 1H), 6.08 (s, 1H), 6.62 (dd, J=3.1, 7.2 Hz, 1H), 6.69 (dd, J=3.1, 5.1 Hz, 1H), 6.78 (d, J=8.8 Hz, 2H), 7.44 (t, J=5.0 Hz, 1H), 7.57 (d, J=8.8 Hz, 2H), 8.84 (d, J=5.0 Hz, 2H)

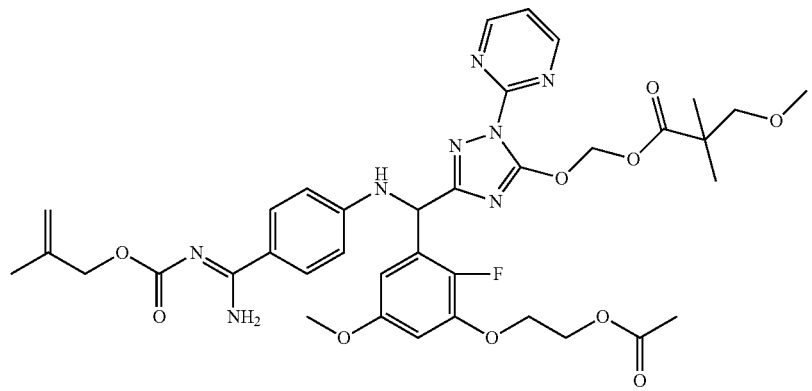 [SMILES: C=C(C)COC(=O)/N=C(\N)c1ccc(NC(c2nc(OCOC(=O)C(C)(C)COC)n(-c3ncccn3)n2)c2cc(OC)cc(OCCOC(C)=O)c2F)cc1]

(6f) 3-methoxy-2,2-dimethylpropionic acid 5-[(R)-[3-(2-acetoxyethoxy)-2-fluoro-5-methoxyphenyl]-(4-{amino[2-meth ylallyloxycarbonylimino]methyl}phenylamino)methyl]-2-pyrimidin-2-yl-2H-[1,2,4]triazol-3-yloxymethyl ester

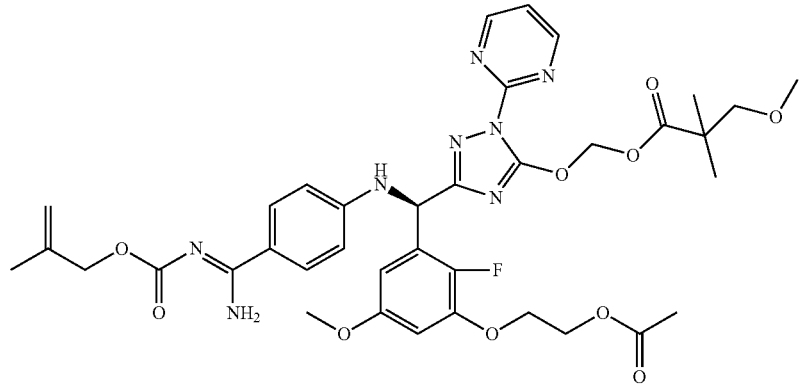 [SMILES: C=C(C)COC(=O)/N=C(\N)c1ccc(N[C@@H](c2nc(OCOC(=O)C(C)(C)COC)n(-c3ncccn3)n2)c2cc(OC)cc(OCCOC(C)=O)c2F)cc1]

Using SUMICHIRAL OA-2500S column, 3-methoxy-2,2-dimethylpropionic acid 5-[[3-(2-acetoxyethoxy)-2-fluoro-5-methoxyphenyl]-(4-{amino[2-methylall yloxycarbonylimino]methyl}phenylamino)methyl]-2-pyrimidin-2-yl-2H-[1,2,4]triazol-3-yloxymethyl ester (13.3 mg) was separated (optical resolution) under the conditions below to obtain the captioned compound (4.8 mg) in the former fraction.

HPLC retention time; 8 min (column name: SUMICHIRAL OA-2500S, 20 mmϕ×25 cm, mobile phase: acetonitrile, elution rate: 15 mL/min)

$^1$H-NMR (CDCl$_3$): δ=1.14 (s, 3H), 1.15 (s, 3H), 1.80 (s, 3H), 2.09 (s, 3H), 3.16 (s, 3H), 3.31 (s, 2H), 3.70 (s, 3H), 4.19-4.21 (m, 2H), 4.41-4.44 (m, 2H), 4.57 (s, 2H), 4.91 (s, 1H), 5.03 (s, 1H), 5.51 (d, J=7.1 Hz, 1H), 6.11 (d, J=6.4 Hz, 1H), 6.12 (d, J=7.1 Hz, 1H), 6.21 (d, J=6.4 Hz, 1H), 6.44 (dd, J=2.9, 6.6 Hz, 1H), 6.68 (dd, J=2.9, 4.8 Hz, 1H), 6.71 (d, J=8.8 Hz, 2H), 7.30 (t, J=5.0 Hz, 1H), 7.73 (d, J=8.8 Hz, 2H), 8.82 (d, J=5.0 Hz, 2H)

Example 7

Cyclohexanecarboxylic acid 5-[(R)-[3-(2-acetoxyethoxy)-2-fluoro-5-methoxyphenyl]-(4-{amino[2,2-dimethylpropoxycarbonylimino]methyl}phenylamino)methyl]-2-pyrimidin-2-yl-2H-[1,2,4]triazol-3-yloxymethyl ester (7a) Cyclohexanecarboxylic acid 5-{(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester

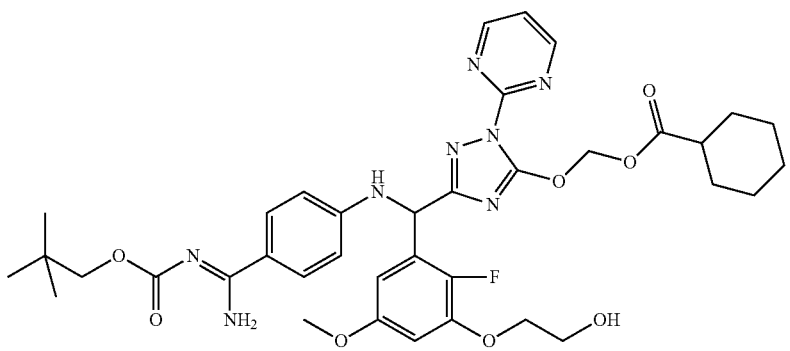 [SMILES: COc1cc(OCCO)c(F)c(C(Nc2ccc(/C(N)=N/C(=O)OCC(C)(C)C)cc2)c2nc(OCOC(=O)C3CCCCC3)n(-c3ncccn3)n2)c1]

To a mixture of [1-amino-1-[4-({(5-chloromethoxy-1-pyrimidin-2-yl-1H-[1,2,4]triazol-3-yl)-[2-fluoro-3-(2-hydroxyethoxy)-5-methoxyphenyl]methyl}amino)phenyl]methylidene]carbamic acid 2,2-dimethylpropyl ester (Example 2b, 120 mg), potassium hydrogen carbonate (131 mg), and DMF (16 mL), sodium iodide (140 mg) and cyclohexanecarboxylic acid (163 mg) were added, and the resulting mixture was stirred at 45° C. overnight. After cooling the reaction mixture to room temperature, ice and saturated aqueous ammonium chloride solution were added thereto, and the resulting mixture was extracted three times with a mixture of THF and ethyl acetate. The organic layer was collected, washed with saturated aqueous ammonium chloride solution, and dried over anhydrous magnesium sulfate. The resulting mixture was filtered, and the filtrate obtained was concentrated under reduced pressure. The residue obtained was purified by NAM silica gel column chromatography (mixed solvent of methanol-ethyl acetate) to obtain the captioned compound (123 mg).

$^1$H-NMR (CD$_3$OD): δ=0.93 (s, 9H), 1.16-1.40 (m, 6H), 1.55-1.65 (m, 2H), 1.70-1.82 (m, 2H), 2.27-2.40 (m, 1H), 3.73 (s, 3H), 3.80 (s, 2H), 3.86 (t, J=6.0 Hz, 2H), 4.08 (t, J=6.0 Hz, 2H), 6.03 (s, 1H), 6.10 (d, J=5.6 Hz, 1H), 6.14 (d, J=5.6 Hz, 1H), 6.60 (dd, J=2.8, 6.8 Hz, 1H), 6.73 (dd, J=2.8, 4.8 Hz, 1H), 6.79 (d, J=7.2 Hz, 2H), 7.47 (t, J=4.8 Hz, 1H), 7.71 (d, J=7.2 Hz, 2H), 8.86 (d, J=4.8 Hz, 2H)

(7b) Cyclohexanecarboxylic acid 5-{(R)-(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester

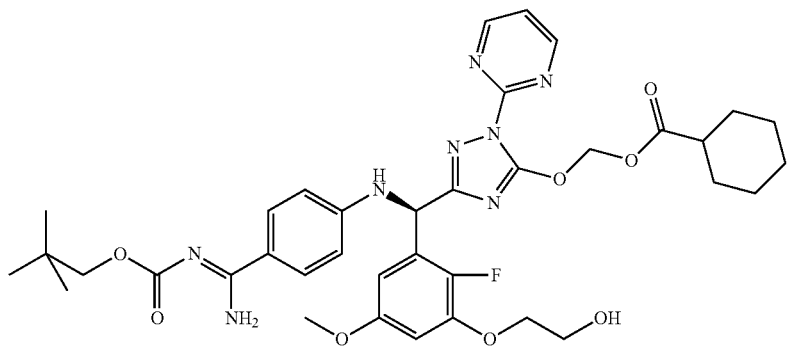 [SMILES: COc1cc(OCCO)c(F)c([C@@H](Nc2ccc(/C(N)=N/C(=O)OCC(C)(C)C)cc2)c2nc(OCOC(=O)C3CCCCC3)n(-c3ncccn3)n2)c1]

Using SUMICHIRAL OA-2500 column, cyclohexanecarboxylic acid 5-{(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester (123 mg) was optically resolved under the conditions below to obtain a crudely purified product of the captioned compound in the latter fraction. HPLC retention time; 11 min (column name: SUMICHIRAL OA-2500, 30 mmφ×25 cm, mobile phase: methanol, elution rate: 30 mL/min)

The crudely purified product obtained was purified again using SUMICHIRAL OA-2500S column (20 mmφ×25 cm, mobile phase: methanol, elution rate: 30 mL/min) to obtain the captioned compound (42 mg).

(7c) Cyclohexanecarboxylic acid 5-[(R)-[3-(2-acetoxyethoxy)-2-fluoro-5-methoxyphenyl]-(4-{amino[2,2-dimethylpropoxycarbonylimino]methyl}phenylamino)methyl]-2-pyrimidin-2-yl-2H-[1,2,4]triazol-3-yloxymethyl ester Cyclohexanecarboxylic acid 5-{(R)-(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]-triazol-3-yloxymethyl ester (42 mg), DMAP (1 mg), and triethylamine (0.0648 mL) were dissolved in DMF (3 mL) and dichloromethane (3 mL). To the solution, a mixture of TFFH (30.7 mg), acetic acid (0.00665 mL), and dichloromethane (3 mL) was slowly added, and the resulting mixture was stirred at room temperature for 3 hours. After concentrating the reaction mixture under reduced pressure, ice, THF, saturated aqueous sodium hydrogen carbonate solution, and saturated aqueous ammonium chloride solution were added to the residue obtained, and the resulting mixture was extracted with a mixture of THF and ethyl acetate. The organic layer was washed with saturated aqueous ammonium chloride solution and dried over anhydrous magnesium sulfate. The resulting mixture was filtered, and the filtrate obtained was concentrated under reduced pressure. The residue obtained was crudely purified by NAM silica gel column chromatography (mixed solvent of methanol-ethyl acetate) to obtain a crudely purified product of the captioned compound.

The crudely purified product obtained was purified using SUMICHIRAL OA-2500 column (30 mmφ×25 cm, mobile phase: methanol solution, elution rate: 30 mL/min) to obtain the captioned compound (34.62 mg).

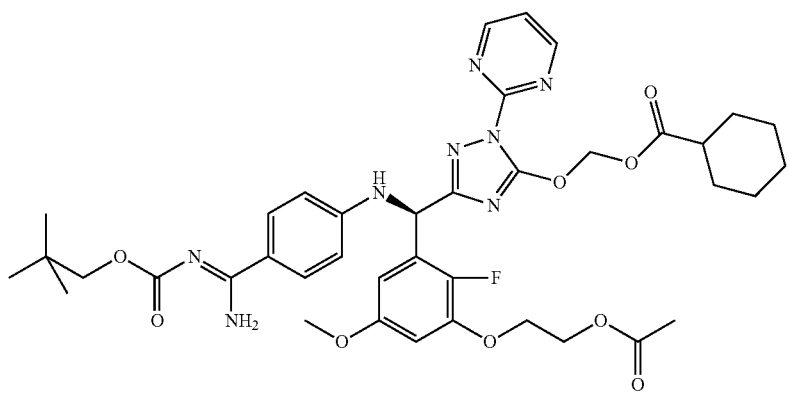 [SMILES: COc1cc(OCCOC(C)=O)c(F)c([C@@H](Nc2ccc(/C(N)=N/C(=O)OCC(C)(C)C)cc2)c2nc(OCOC(=O)C3CCCCC3)n(-c3ncccn3)n2)c1]

¹H-NMR (CD₃OD): δ=0.98 (s, 9H), 1.14-1.38 (m, 6H), 1.55-1.70 (m, 2H), 1.74-1.82 (m, 2H), 2.05 (s, 3H), 2.28-2.37 (m, 1H), 3.72 (s, 3H), 3.82 (s, 2H), 4.23 (t, J=4.4 Hz, 2H), 4.40 (t, J=4.4 Hz, 2H), 6.06 (s, 1H), 6.10 (d, J=5.6 Hz, 1H), 6.12 (d, J=5.6 Hz, 1H), 6.60 (dd, J=2.8, 6.8 Hz, 1H), 6.74 (dd, J=2.8, 4.8 Hz, 1H), 6.79 (d, J=8.0 Hz, 2H), 7.48 (t, J=4.8 Hz, 1H), 7.71 (d, J=8.0 Hz, 2H), 8.86 (d, J=4.8 Hz, 2H)

Example 8

2,2-dimethylmalonic acid 5-{(R)-(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]-triazol-3-yloxymethyl ester cyclohexyl ester (8a) 2,2-dimethylmalonic acid t-butyl ester cyclohexyl ester

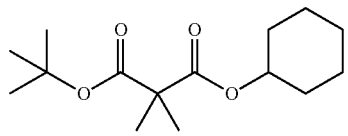 [SMILES: CC(C)(C)OC(=O)C(C)(C)C(=O)OC1CCCCC1]

To a mixture of 2,2-dimethylmalonic acid mono-t-butyl ester [CAS No. 143688-40-8] (800 mg), DMAP (104 mg), and dichloromethane (8 mL), cyclohexanol (0.494 mL) and WSC (976 mg) were sequentially added at 0° C. The resulting mixture was stirred overnight at room temperature, and TBME (50 mL) was added thereto. The resulting mixture was sequentially washed with water (30 mL) and saturated aqueous sodium chloride solution (30 mL), and dried over anhydrous magnesium sulfate. The resulting mixture was filtered, and the filtrate obtained was concentrated under reduced pressure. The residue obtained was purified by silica gel column chromatography (mixed solvent of heptane-ethyl acetate) to obtain the captioned compound (817 mg).

¹H-NMR (CDCl₃): δ=1.24-1.56 (m, 6H), 1.37 (s, 6H), 1.44 (s, 9H), 1.69-1.74 (m, 2H), 1.79-1.85 (m, 2H), 4.77-4.83 (m, 1H)

(8b) 2,2-dimethylmalonic acid monocyclohexyl ester

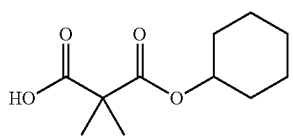

To a mixture of 2,2-dimethylmalonic acid t-butyl ester cyclohexyl ester (817 mg) and dichloromethane (7.5 mL), TFA (1.5 mL) was added, and the resulting mixture was stirred at room temperature for 2.5 hours. To the resulting mixture, ethyl acetate (100 mL) was added. The resulting mixture was sequentially washed with water (30 mL) and saturated aqueous sodium chloride solution (30 mL), and dried over anhydrous magnesium sulfate. The resulting mixture was filtered, and toluene (10 mL) was added to the filtrate obtained, after which the filtrate was concentrated under reduced pressure to obtain the captioned compound (571 mg).

¹H-NMR (CDCl₃): δ=1.28-1.54 (m, 6H), 1.47 (s, 6H), 1.66-1.73 (m, 2H), 1.78-1.83 (m, 2H), 4.81-4.87 (m, 1H)

(8c) 2,2-dimethylmalonic acid 5-{(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester cyclohexyl ester

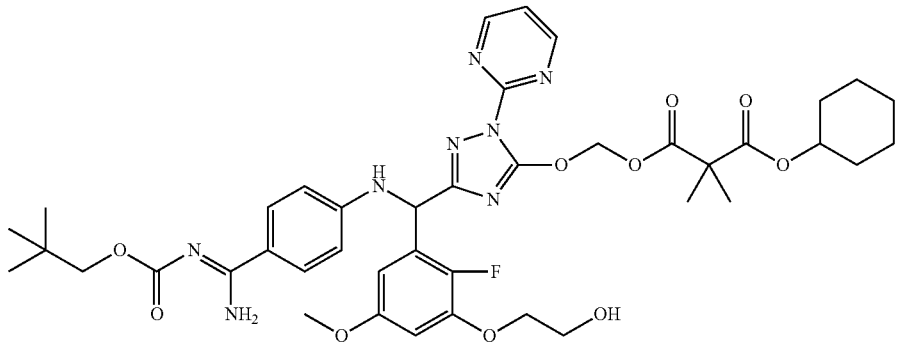 [SMILES: COc1cc(OCCO)c(F)c(C(Nc2ccc(/C(N)=N/C(=O)OCC(C)(C)C)cc2)c2nc(OCOC(=O)C(C)(C)C(=O)OC3CCCCC3)n(-c3ncccn3)n2)c1]

To a mixture of [1-amino-1-[4-({(5-chloromethoxy-1-pyrimidin-2-yl-1H-[1,2,4]triazol-3-yl)-[2-fluoro-3-(2-hydroxyethoxy)-5-methoxyphenyl]methyl}amino)phenyl]methylidene]carbamic acid 2,2-dimethylpropyl ester (Example 2b, 80 mg) and DMF (5 mL), sodium iodide (183 mg), potassium hydrogen carbonate (85.5 mg), and 2,2-dimethylmalonic acid monocyclohexyl ester (261 mg) were added, and the resulting mixture was stirred at room temperature for 3 days. Ethyl acetate (30 mL) and water (10 mL) were added to the mixture, and the resulting mixture was shaken, after which the organic layer was collected. Ethyl acetate (20 mL) was added to the aqueous layer, and the resulting mixture was shaken, after which the organic layer was collected. All the organic layers were combined, washed with saturated aqueous sodium chloride solution (10 mL), and dried over anhydrous magnesium sulfate. The resulting mixture was filtered, and the filtrate obtained was concentrated under reduced pressure. The residue obtained was purified by NAM silica gel column chromatography (mixed solvent of heptane-ethyl acetate) to obtain the captioned compound (97.9 mg).

¹H-NMR (CDCl₃): δ=0.99 (s, 9H), 1.10-1.27 (m, 5H), 1.39 (s, 6H), 1.41-1.44 (m, 1H), 1.51-1.61 (m, 4H), 3.68 (s, 3H), 3.85 (s, 2H), 3.96 (t, J=4.4 Hz, 2H), 4.09 (t, J=4.4 Hz, 2H), 4.64-4.67 (m, 1H), 5.56 (d, J=7.2 Hz, 1H), 6.08 (d, J=7.2 Hz, 1H), 6.16 (d, J=5.6 Hz, 1H), 6.18 (d, J=5.6 Hz, 1H), 6.44 (dd, J=3.0, 6.6 Hz, 1H), 6.63 (dd, J=3.0, 4.6 Hz, 1H), 6.70 (d, J=8.8 Hz, 2H), 7.30 (t, J=4.8 Hz, 1H), 7.70 (d, J=8.8 Hz, 2H), 8.82 (d, J=4.8 Hz, 2H)

(8d) 2,2-dimethylmalonic acid 5-{(R)-(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester cyclohexyl ester

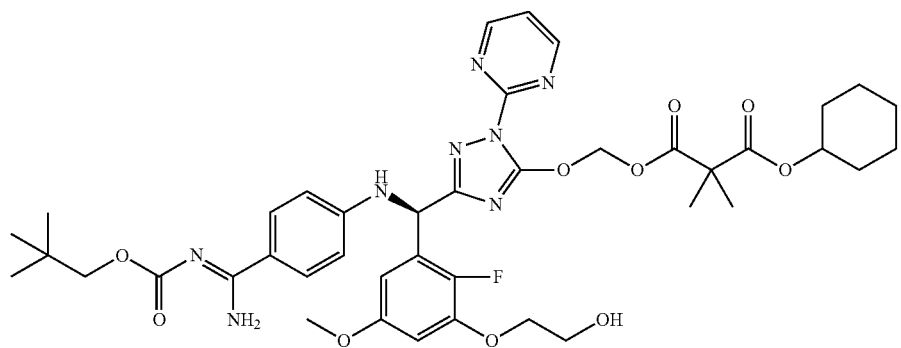 [SMILES: COc1cc(OCCO)c(F)c([C@@H](Nc2ccc(/C(N)=N/C(=O)OCC(C)(C)C)cc2)c2nc(OCOC(=O)C(C)(C)C(=O)OC3CCCCC3)n(-c3ncccn3)n2)c1]

Using SUMICHIRAL OA-2500S column, 2,2-dimethylmalonic acid 5-{(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester cyclohexyl ester (97.8 mg) was separated (optical resolution) under the conditions below to obtain the captioned compound (34.8 mg) in the former fraction.

HPLC retention time; 12 min (column name: SUMICHIRAL OA-2500S, 30 mmφ×25 cm, mobile phase: methanol, elution rate: 20 mL/min)

$^1$H-NMR (CDCl$_3$): δ=0.99 (s, 9H), 1.10-1.27 (m, 5H), 1.39 (s, 6H), 1.41-1.44 (m, 1H), 1.51-1.61 (m, 4H), 3.68 (s, 3H), 3.85 (s, 2H), 3.96 (t, J=4.4 Hz, 2H), 4.09 (t, J=4.4 Hz, 2H), 4.64-4.67 (m, 1H), 5.56 (d, J=7.2 Hz, 1H), 6.08 (d, J=7.2 Hz, 1H), 6.16 (d, J=5.6 Hz, 1H), 6.18 (d, J=5.6 Hz, 1H), 6.44 (dd, J=3.0, 6.6 Hz, 1H), 6.63 (dd, J=3.0, 4.6 Hz, 1H), 6.70 (d, J=8.8 Hz, 2H), 7.30 (t, J=4.8 Hz, 1H), 7.70 (d, J=8.8 Hz, 2H), 8.82 (d, J=4.8 Hz, 2H)

Example 9

Carbonic acid 1-(5-{(R)-(4-{amino[4-methylbenzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (1R,2R)-2-methylcyclohexyl ester (9a) N-[1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]-4-methylbenzamide

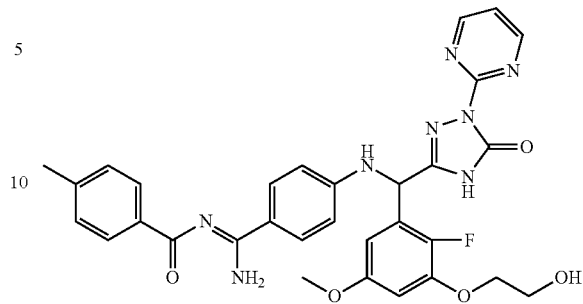

To a mixture of 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine acetic acid salt (1.6 g) and DMF (120 mL), 4-methylbenzoic acid 4-nitrophenyl ester [CAS No. 15023-67-3] (815 mg) and triethylamine (1.21 mL) were added, and the resulting mixture was stirred overnight at room temperature. The solvent in the reaction solution was distilled off under reduced pressure. The residue obtained was purified by NAM silica gel column chromatography (mixed solvent of methanol-ethyl acetate) to obtain the captioned compound (1.01 g).

$^1$H-NMR (CD$_3$OD): δ=2.39 (s, 3H), 3.73 (s, 3H), 3.89 (t, J=4.8 Hz, 2H), 4.11 (t, J=4.8 Hz, 2H), 6.00 (s, 1H), 6.65-6.67 (m, 2H), 6.83 (d, J=8.8 Hz, 2H), 7.25 (d, J=8.2 Hz, 2H), 7.35 (t, J=5.2 Hz, 1H), 7.96 (d, J=8.8 Hz, 2H), 8.12 (d, J=8.2 Hz, 2H), 8.78 (d, J=5.2 Hz, 2H)

(9b) Carbonic acid 1-chloroethyl ester (1R,2R)-2-methylcyclohexyl ester

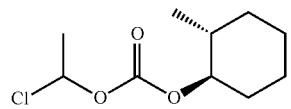

To a mixture of 1-chloroethyl chloroformate [CSA No. 50893-53-3] (0.416 mL), pyridine (0.624 mL), and THF (25 mL), (1R,2R)-2-methylcyclohexanol [CSA No. 19043-03-9] (441 mg) dissolved in THF (5 mL) was added at −78° C. After stirring the mixture overnight at room temperature, ethyl acetate (100 mL) and heptane (100 mL) were added to the mixture. The resulting mixture was sequentially washed with 0.5 N hydrochloric acid (50 mL), saturated aqueous sodium hydrogen carbonate solution (50 mL), water (50 mL), and saturated aqueous sodium chloride solution (50 mL), and dried over anhydrous magnesium sulfate. The resulting mixture was filtered, and the filtrate obtained was concentrated under reduced pressure to obtain the captioned compound (482 mg).

$^1$H-NMR (CDCl$_3$): δ=0.95 (d, J=6.0 Hz, 1.5H), 0.97 (d, J=6.4 Hz, 1.5H), 1.03-1.13 (m, 1H), 1.18-1.28 (m, 1H), 1.31-1.40 (m, 2H), 1.56-1.66 (m, 2H), 1.68-1.82 (m, 2H), 1.84 (d, J=10.0 Hz, 1.5H), 1.86 (d, J=9.6 Hz, 1.5H), 2.03-2.11 (m, 1H), 4.32 (q, J=9.6 Hz, 0.5H), 4.33 (q, J=10.0 Hz, 0.5H), 6.42-6.48 (m, 1H)

(9c) Carbonic acid 1-(5-{(4-{amino[4-methylbenzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (1R,2R)-2-methylcyclohexyl ester

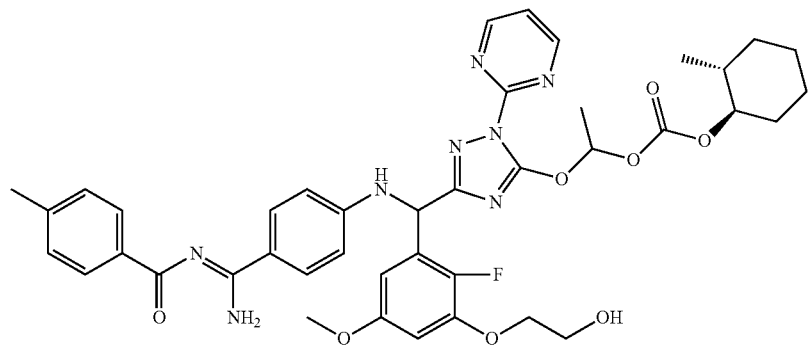 [SMILES: COc1cc(OCCO)c(F)c(C(Nc2ccc(/C(N)=N/C(=O)c3ccc(C)cc3)cc2)c2nc(OC(C)OC(=O)O[C@@H]3CCCC[C@H]3C)n(-c3ncccn3)n2)c1]

To a mixture of N-[1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]-4-methylbenzamide (230 mg) and DMF (3 mL), potassium hydrogen carbonate (113 mg) and carbonic acid 1-chloroethyl ester (1R,2R)-2-methylcyclohexyl ester (250 mg) were sequentially added, and the resulting mixture was stirred at 55° C. for 24 hours and at room temperature for another 2 days. The reaction solution was purified by reverse phase silica gel column chromatography (mixed solvent of acetonitrile-water) to obtain the captioned compound (129.2 mg).

(9d) Carbonic acid 1-(5-{(R)-(4-{amino[4-methylbenzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (1R,2R)-2-methylcyclohexyl ester Using SUMICHIRAL OA-2500 column, carbonic acid 1-(5-{(4-{amino[4-methylbenzoylimino]methyl} phenylamino)-[2-fluoro-3-(2-hydroxyethoxy)-5-methoxyphenyl]methyl}-2-pyrimidin-2-yl-2H-[1,2,4]triazol-3-yloxy)ethyl ester (1R,2R)-2-methylcyclohexyl ester (129 mg) was separated (optical resolution) under the conditions below to obtain a crudely purified product of the captioned compound, a diastereomer mixture, in the third fraction.

HPLC retention time; 15 min (column name: SUMICHIRAL OA-2500, 30 mmφ×25 cm, mobile phase: methanol, elution rate: 30 mL/min)

The crudely purified product obtained was purified again using SUMICHIRAL OA-2500 column (30 mmφ×25 cm, mobile phase: methanol, elution rate: 30 mL/min) to obtain the captioned compound (15.6 mg) as a diastereomer mixture.

$^1$H-NMR (CDCl$_3$): δ=0.91 (d, J=6.4 Hz, 3H), 0.98-1.08 (m, 1H), 1.11-1.27 (m, 3H), 1.48-1.55 (m, 1H), 1.56-1.61 (m, 1H), 1.68-1.76 (m, 2H), 1.78 (d, J=5.2 Hz, 3H), 1.91-1.95 (m, 1H), 2.40 (s, 3H), 3.70 (s, 3H), 3.97 (t, J=4.4 Hz, 2H), 4.10 (t, J=4.4 Hz, 2H), 4.23 (dt, J=4.4, 10.0 Hz, 1H), 5.54 (d, J=6.8 Hz, 1H), 6.13 (d, J=6.8 Hz, 1H), 6.44 (dd, J=2.8, 6.8 Hz, 1H), 6.64 (dd, J=2.8, 4.8 Hz, 1H), 6.74 (d, J=8.8 Hz, 2H), 6.97 (q, J=5.2 Hz, 1H), 7.23 (d, J=8.4 Hz, 2H), 7.28 (t, J=5.2 Hz, 1H), 7.88 (d, J=8.8 Hz, 2H), 8.24 (d, J=8.4 Hz, 2H), 8.81 (d, J=5.2 Hz, 2H)

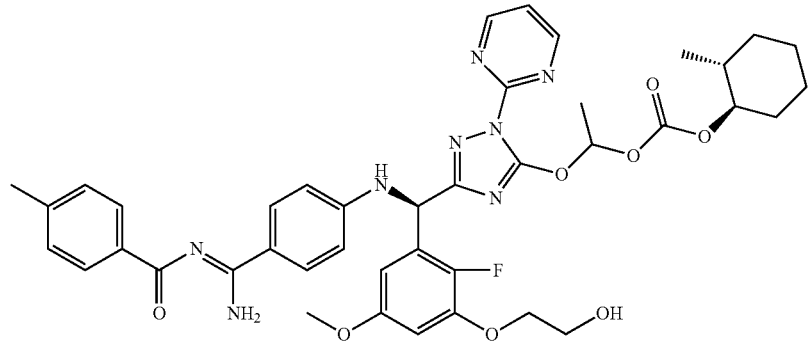 [SMILES: COc1cc(OCCO)c(F)c([C@@H](Nc2ccc(/C(N)=N/C(=O)c3ccc(C)cc3)cc2)c2nc(OC(C)OC(=O)O[C@@H]3CCCC[C@H]3C)n(-c3ncccn3)n2)c1]

Example 10

2,2-dimethylmalonic acid 5-{(R)-(4-{amino(2,2-dimethylpropoxylcarbonylimino)methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester

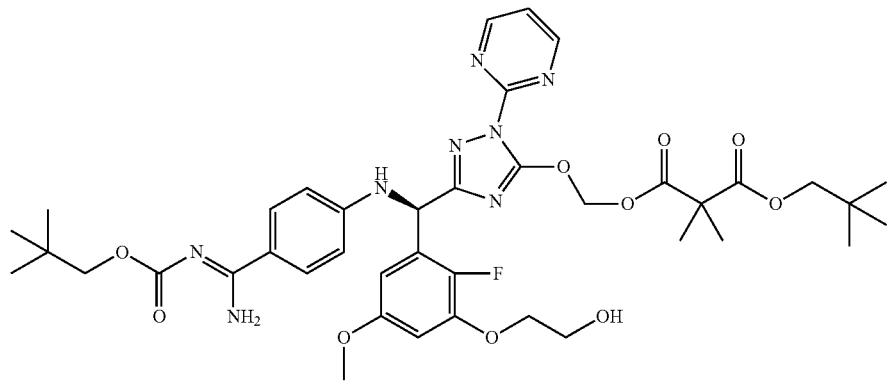 [SMILES: COc1cc(OCCO)c(F)c([C@@H](Nc2ccc(/C(N)=N/C(=O)OCC(C)(C)C)cc2)c2nc(OCOC(=O)C(C)(C)C(=O)OCC(C)(C)C)n(-c3ncccn3)n2)c1]

To a mixture of 2,2-dimethylmalonic acid 5-{(4-carbamimidoylphenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester acetate (Example 18e, 70 mg) and DMA (2 mL), carbonic acid 2,2-dimethylpropyl ester 4-nitrophenyl ester [CAS No. 158810-98-1] (70 mg) and triethylamine (0.07 mL) were added, and the resulting mixture was stirred overnight at room temperature. The reaction solution was concentrated under reduced pressure. The residue obtained was purified by silica gel column chromatography (mixed solvent of heptane-ethyl acetate) to obtain a racemate of the captioned compound.

The racemate was optically resolved under the conditions below using SUMICHIRAL OA-2500 column to obtain a crudely purified product of the captioned compound in the latter fraction.

HPLC retention time; 14 min (column name: SUMICHIRAL OA-2500, 30 mmϕ×25 cm, mobile phase: methanol, elution rate: 20 mL/min)

The crudely purified product obtained was purified again using SUMICHIRAL OA-2500S column (30 mmϕ×25 cm, mobile phase: methanol, elution rate: 15 mL/min) to obtain the captioned compound (15.77 mg).

$^1$H-NMR (CD$_3$OD): δ=0.71 (s, 9H), 0.98 (s, 9H), 1.35 (s, 3H), 1.37 (s, 3H), 3.55 (d, J=10.4 Hz, 1H), 3.59 (d, J=10.4 Hz, 1H), 3.72 (s, 3H), 3.81 (s, 2H), 3.88 (t, J=4.8 Hz, 2H), 4.08 (t, J=4.8 Hz, 2H), 6.06 (s, 1H), 6.13-6.17 (m, 2H), 6.60 (dd, J=2.8, 6.8 Hz, 1H), 6.74 (dd, J=2.8, 4.8 Hz, 1H), 6.78-6.80 (m, 2H), 7.48 (t, J=4.8 Hz, 1H), 7.70-7.72 (m, 2H), 8.87 (d, J=4.8 Hz, 2H)

Example 11-1

Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (R)-1-methylbutyl ester (Diastereomer 1)

Example 11-2

Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (R)-1-methylbutyl ester (Diastereomer 2)

(11a) Carbonic acid 1-chloroethyl ester (R)-1-methylbutyl ester

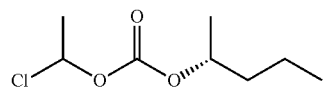

To a mixture of 1-chloroethyl chloroformate (1.19 mL), pyridine (1.49 mL), and THF (100 mL), (R)-(−)-2-pentanol [CSA No. 31087-44-2] (1 mL) dissolved in THF (3 mL) was added at −78° C. After stirring the mixture overnight at room temperature, ethyl acetate and heptane were added to the reaction mixture. The resulting mixture was sequentially washed with 0.5 N hydrochloric acid, saturated aqueous sodium hydrogen carbonate solution, water, and saturated aqueous sodium chloride solution, and dried over anhydrous magnesium sulfate. The resulting mixture was filtered, and the filtrate obtained was concentrated under reduced pressure to obtain the captioned compound (1.8 g) as a crude product.

$^1$H-NMR (CDCl$_3$): δ=0.93 (td, J=7.2, 2.4 Hz, 3H), 1.31 (dd, J=7.2, 6.4 Hz, 3H), 1.36-1.44 (m, 2H), 1.47-1.57 (m, 1H), 1.62-1.73 (m, 1H), 1.83 (d, J=5.6 Hz, 3H), 4.80-4.87 (m, 1H), 6.43 (q, J=5.6 Hz, 1H)

(11b) Carbonic acid 1-(5-{(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (R)-1-methylbutyl ester pyrimidin-2-yl-2H-[1,2,4]triazol-3-yloxy)ethyl ester (R)-1-methylbutyl ester (130 mg) was separated (optical resolution) under the conditions below to obtain the captioned compound in the third fraction (23.7 mg) and the fourth fraction (26.8 mg).

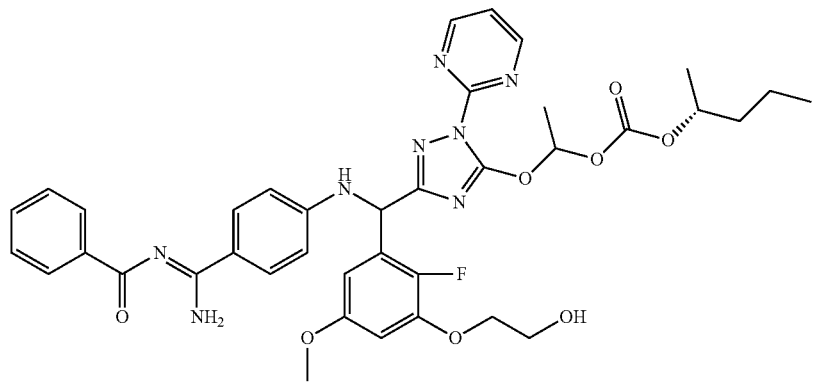 [SMILES: CCC[C@@H](C)OC(=O)OC(C)Oc1nc(C(Nc2ccc(/C(N)=N/C(=O)c3ccccc3)cc2)c2cc(OC)cc(OCCO)c2F)nn1-c1ncccn1]

To a mixture of N-[1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide (Example 1a, 150 mg) and DMF (3 mL), potassium hydrogen carbonate (150 mg) and carbonic acid 1-chloroethyl ester (R)-1-methylbutyl ester (150 mg) were sequentially added, and the resulting mixture was stirred at 55° C. for 18 hours. The reaction mixture was purified by reverse phase silica gel column chromatography (mixed solvent of acetonitrile-water) to obtain the captioned compound (130 mg).

(11c) Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (R)-1-methylbutyl ester HPLC retention time; (the third fraction) 12 min, (the fourth fraction) 14 min (column name: SUMICHIRAL OA-2500, 30 mmφ×25 cm, mobile phase: methanol, elution rate: 30 mL/min)

The third fraction (Diastereomer 1)

$^1$H-NMR (CDCl$_3$): δ=0.86 (t, J=7.2 Hz, 3H), 1.26 (d, J=6.4 Hz, 3H), 1.26-1.40 (m, 2H), 1.42-1.52 (m, 1H), 1.58-1.68 (m, 1H), 1.74 (d, J=5.6 Hz, 3H), 3.70 (s, 3H), 3.98 (t, J=4.8 Hz, 2H), 4.12 (t, J=4.8 Hz, 2H), 4.76-4.79 (m, 1H), 5.61 (d, J=6.8 Hz, 1H), 6.12 (d, J=6.8 Hz, 1H), 6.45 (dd, J=6.8, 2.8 Hz, 1H), 6.62 (dd, J=4.8, 2.8 Hz, 1H), 6.77 (d, J=8.8 Hz, 2H), 6.95 (q, J=5.6 Hz, 1H), 7.28 (t, J=5.2 Hz, 1H), 7.40-7.49 (m, 3H), 7.90 (d, J=8.8 Hz, 2H), 8.34-8.37 (m, 2H), 8.82 (d, J=5.2 Hz, 2H)

The fourth fraction (Diastereomer 2)

$^1$H-NMR (CDCl$_3$): δ=0.89 (t, J=7.6 Hz, 3H), 1.19 (d, J=6.4 Hz, 3H), 1.26-1.40 (m, 2H), 1.42-1.52 (m, 1H), 1.56-1.68 (m, 1H), 1.77 (d, J=5.6 Hz, 3H), 3.69 (s, 3H), 3.69-3.98 (m, 2H),

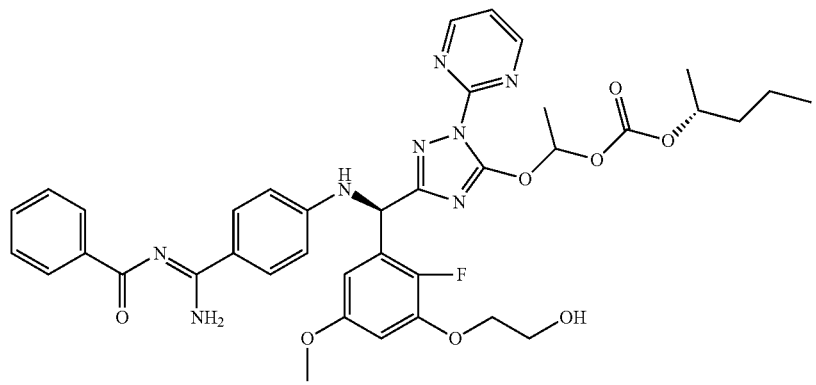 [SMILES: CCC[C@@H](C)OC(=O)OC(C)Oc1nc([C@H](Nc2ccc(/C(N)=N/C(=O)c3ccccc3)cc2)c2cc(OC)cc(OCCO)c2F)nn1-c1ncccn1]

Using SUMICHIRAL OA-2500 column, carbonic acid 1-(5-{(4-{amino[benzoylimino]methyl}phenylamino)-[2-fluoro-3-(2-hydroxyethoxy)-5-methoxyphenyl]methyl}-2-

4.08-4.12 (m, 2H), 4.72-4.77 (m, 1H), 5.58 (d, J=6.8 Hz, 1H), 6.13 (d, J=6.8 Hz, 1H), 6.44 (dd, J=6.8, 2.8 Hz, 1H), 6.64 (dd, J=4.8, 2.8 Hz, 1H), 6.75 (d, J=8.8 Hz, 2H), 6.96 (q, J=5.6 Hz,

1H), 7.28 (t, J=5.2 Hz, 1H), 7.40-7.49 (m, 3H), 7.90 (d, J=8.8 Hz, 2H), 8.34-8.37 (m, 2H), 8.81 (d, J=5.2 Hz, 2H)

Example 12

Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (1S,2S)-2-fluorocyclohexyl ester (12a) Carbonic acid 1-chloroethyl ester (1S,2S)-2-fluorocyclohexyl ester

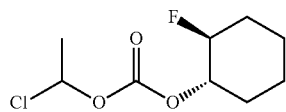

To a mixture of 1-chloroethyl chloroformate (1.0 mL), pyridine (1.0 mL), and dichloromethane (30 mL), (1S,2S)-2-fluorocyclohexanol [CSA No. 292150-03-9] (900 mg) dissolved in dichloromethane (10 mL) was added at −78° C. After stirring the resulting mixture overnight at room temperature, dichloromethane (30 mL) was added to the mixture. The resulting mixture was sequentially washed with 0.5 N hydrochloric acid and saturated aqueous sodium chloride solution, and dried over anhydrous magnesium sulfate. The resulting mixture was filtered, and the filtrate obtained was concentrated under reduced pressure. The residue obtained was purified by silica gel column chromatography (mixed solvent of heptane-ethyl acetate) to obtain the captioned compound (480 mg).

$^1$H-NMR (CDCl$_3$): δ=1.24-1.64 (m, 4H), 1.70-1.81 (m, 2H), 1.84 (d, J=5.6 Hz, 3H), 2.08-2.22 (m, 2H), 4.36-4.57 (m, 1H), 4.72-4.82 (m, 1H), 6.27 (q, J=5.6 Hz, 1H)

(12b) [1-amino-1-(4-{[(R)-[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide

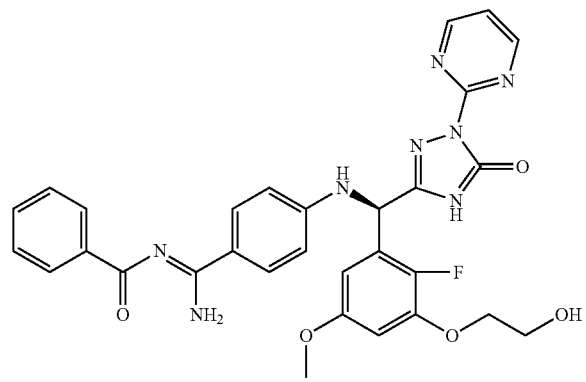

To a mixture of 4-{[(R)-[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}benzamidine acetic acid salt [CAS No. 951803-91-1] (5.6 g) and DMF (200 mL), benzoic acid 4-nitrophenyl ester (2.89 g) and triethylamine (4.7 mL) were added, and the resulting mixture was stirred overnight at room temperature. Acetic acid (6.5 mL) was added to the reaction solution, and then the solvent was evaporated under reduced pressure. The residue obtained was crudely purified by reverse phase silica gel column chromatography (mixed solvent of acetonitrile-water, containing 0.1% of acetic acid), and the crudely purified product obtained was purified by NAM silica gel column chromatography (mixed solvent of methanol-ethyl acetate) to obtain the captioned compound (4.48 g).

$^1$H-NMR (CD$_3$OD): δ=3.73 (s, 3H), 3.35-3.43 (m, 2H), 4.08-4.15 (m, 2H), 6.00 (s, 1H), 6.61-6.71 (m, 2H), 6.85 (d, J=8.8 Hz, 2H), 7.37 (t, J=4.8 Hz, 1H), 7.42-7.56 (m, 3H), 7.98 (d, J=8.8 Hz, 2H), 8.22 (dd, J=1.2, 7.2 Hz, 2H), 8.79 (d, J=4.8 Hz, 2H)

(12c) Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (1S,2S)-2-fluorocyclohexyl ester

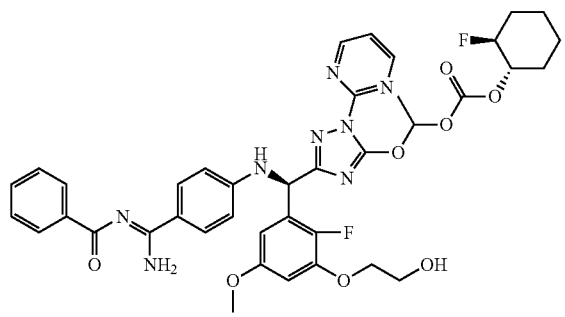 [SMILES: COc1cc(OCCO)c(F)c([C@@H](Nc2ccc(/C(N)=N/C(=O)c3ccccc3)cc2)c2nc(OC(C)OC(=O)O[C@H]3CCCC[C@@H]3F)n(-c3ncccn3)n2)c1]

To a mixture of N-[1-amino-1-(4-{[(R)-[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide (200 mg) and DMF (3 mL), potassium hydrogen carbonate (200 mg), carbonic acid 1-chloroethyl ester (1S,2S)-2-fluorocyclohexyl ester (200 mg), and sodium iodide (100 mg) were sequentially added, and the resulting mixture was stirred at 55° C. for 24 hours. The reaction mixture was crudely purified by NAM silica gel column chromatography (mixed solvent of ethyl acetate-methanol) to obtain the captioned compound (110 mg) as a crudely purified product.

The crudely purified product obtained was purified using SUMICHIRAL OA-2500 (30 mmφ×25 cm, mobile phase: methanol, elution rate: 30 mL/min) to obtain the captioned compound (60.5 mg) as a diastereomer mixture.

$^1$H-NMR (CD$_3$OD): δ=1.24-1.64 (m, 4H), 1.70-1.81 (m, 2H), 1.75, 1.78 (each d, J=5.6 Hz, J=5.2 Hz, total 3H), 2.05-2.22 (m, 2H), 3.69, 3.73 (each s, total 3H), 3.98 (br.s, 2H), 4.09-4.13 (m, 2H), 4.32-4.55 (m, 1H), 4.68-4.80 (m, 1H), 5.54-5.57 (m, 1H), 6.12, 6.17 (each d, J=7.2 Hz, J=7.6 Hz, total 1H), 6.43-6.47 (m, 1H), 6.30, 6.72 (each dd, J=4.8, 3.2 Hz, J=4.4, 2.8 Hz, total 1H), 6.77 (d, J=8.8 Hz, 2H), 6.92, 6.98 (each q, J=4.4 Hz, total 1H), 7.26-7.30 (m, 1H), 7.41-7.49 (m, 3H), 7.88-7.91 (m, 2H), 8.36 (d, J=7.2 Hz, 2H), 8.81-8.83 (m, 2H)

Example 13

Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]-triazol-3-yloxy)propyl ester cyclohexyl ester

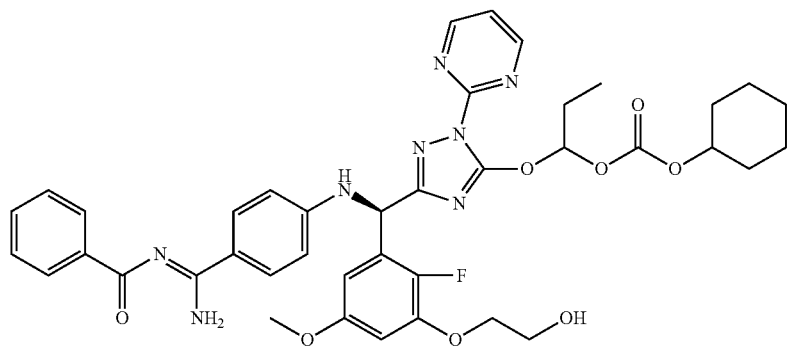 [SMILES: CCC(OC(=O)OC1CCCCC1)Oc1nc([C@H](Nc2ccc(/C(N)=N/C(=O)c3ccccc3)cc2)c2cc(OC)cc(OCCO)c2F)nn1-c1ncccn1]

To a mixture of N-[1-amino-1-(4-{[(R)-[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide (Example 12b, 200 mg) and DMA (2 mL), carbonic acid 1-chloropropyl ester cyclohexyl ester [CAS No. 108098-53-9] (300 mg) and potassium hydrogen carbonate (100 mg) were added, and the resulting mixture was stirred at 55° C. for 36 hours. The resulting mixture was poured into ethyl acetate and water. After shaking the mixture, the organic layer was collected, sequentially washed twice with water and with saturated aqueous sodium chloride solution, and dried over anhydrous magnesium sulfate. The resulting mixture was filtered, and the filtrate obtained was concentrated under reduced pressure. The residue obtained was crudely purified by NAM silica gel column chromatography (mixed solvent of methanol-ethyl acetate) to obtain a crudely purified product (120 mg).

The crudely purified product obtained was purified using SUMICHIRAL OA-2500S (30 mmϕ×25 cm, mobile phase: methanol, elution rate: 30 mL/min) to obtain the captioned compound (101 mg) as a diastereomer mixture.

$^1$H-NMR (CD$_3$OD): δ=1.06, 1.08 (each t, J=7.2 Hz, 3H), 1.22-1.39 (m, 5H), 1.47-1.52 (m, 1H), 1.59-1.87 (m, 4H), 1.98-2.06 (m, 2H), 3.72, 3.73 (each s, 3H), 3.89 (t, J=4.4 Hz, 2H), 4.10 (t, J=4.4 Hz, 2H), 4.47-4.54 (m, 1H), 6.08 (s, 1H), 6.61 (dd, J=2.4, 6.4 Hz, 1H), 6.71-6.84 (m, 4H), 7.41-7.52 (m, 4H), 7.97 (d, J=8.4 Hz, 2H), 8.24 (d, J=8.4 Hz, 2H), 8.87 (d, J=4.8 Hz, 2H)

Example 14

Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)propyl ester trans-2-fluoro-cyclohexyl ester

(14a) Carbonic acid 1-chloropropyl ester trans-2-fluorocyclohexyl ester

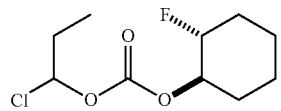

1-Chloropropyl chloroformate [CAS No. 92600-20-9] (2.99 g) and pyridine (1.62 mL) were dissolved in dichloromethane (30 mL), and a solution of trans-2-fluorocyclohexanol [CAS No. 14365-32-3] (2.36 g) in dichloromethane was added dropwise thereto under ice-cooling. After stirring the resulting mixture overnight at room temperature, the reaction mixture was diluted with ethyl acetate, and sequentially washed with 1 N hydrochloric acid, water, and saturated aqueous sodium chloride solution. The organic layer was dried over anhydrous magnesium sulfate. The resulting mixture was filtered, and the filtrate obtained was concentrated under reduced pressure. The residue obtained was purified by silica gel column chromatography (mixed solvent of heptane-ethyl acetate) to obtain the captioned compound (2.731 g).

$^1$H-NMR (CDCl$_3$): δ=1.08 (t, J=7.2 Hz, 3H), 1.22-1.52 (m, 3H), 1.52-1.62 (m, 1H), 1.70-1.81 (m, 2H), 2.03-2.21 (m, 4H), 4.37-4.57 (m, 1H), 4.73-4.81 (m, 1H), 6.27 (q, J=7.2 Hz, 1H)

(14b) Carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)propyl ester trans-2-fluoro-cyclohexyl ester

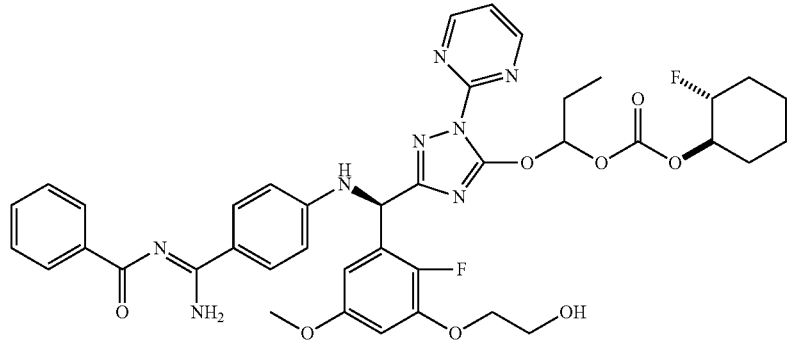

To a mixture of N-[1-amino-1-(4-{[(R)-[2-fluoro-3-(2-hydroxyethoxy)-5-methoxyphenyl]-(5-oxo-1-pyrimidin-2-yl-4,5-dihydro-1H[1,2,4]-triazol-3-yl)methyl]amino}phenyl)methylidene]benzamide (Example 12b, 500 mg) and DMF (5 mL), carbonic acid 1-chloropropyl ester trans-2-fluorocyclohexyl ester (998 mg), sodium iodide (625 mg), and potassium hydrogen carbonate (100 mg) were added, and the resulting mixture was stirred at 40° C. for 76 hours. Water was added to the mixture, and the resulting mixture was extracted with ethyl acetate. The organic layer was sequentially washed twice with water and with saturated aqueous sodium chloride solution, and dried over anhydrous magnesium sulfate. The resulting mixture was filtered, and the filtrate obtained was concentrated under reduced pressure. The residue obtained was crudely purified by silica gel column chromatography (mixed solvent of methanol-ethyl acetate) to obtain a crudely purified product.

The crudely purified product obtained was purified using SUMICHIRAL OA-2500S under the conditions below to obtain the captioned compound (114 mg) as a diastereomer mixture.

HPLC retention time; 11 min (column name: SUMICHIRAL OA-2500S, 30 mmϕ×25 cm, mobile phase: methanol, elution rate: 30 mL/min)

$^1$H-NMR (CD$_3$OD): δ=1.07, 1.09 (each t, J=7.2 Hz, 3H), 1.18-1.36 (m, 3H), 1.40-1.54 (m, 1H), 1.58-1.64 (m, 2H), 1.94-2.10 (m, 4H), 3.73 (s, 3H), 3.89 (t, J=4.4 Hz, 2H), 4.10 (t, J=4.4 Hz, 2H), 4.23-4.44 (m, 1H), 4.52-4.64 (m, 1H), 6.07-6.11 (m, 1H), 6.59-6.63 (m, 1H), 6.72-6.84 (m, 4H), 7.41-7.52 (m, 4H), 7.97 (d, J=8.8 Hz, 2H), 8.24 (d, J=8.4 Hz, 2H), 8.86, 8.87 (each d, J=4.4 Hz, 2H)

Example 15

2,2-dimethylmalonic acid 5-{(R)-(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester ethyl ester

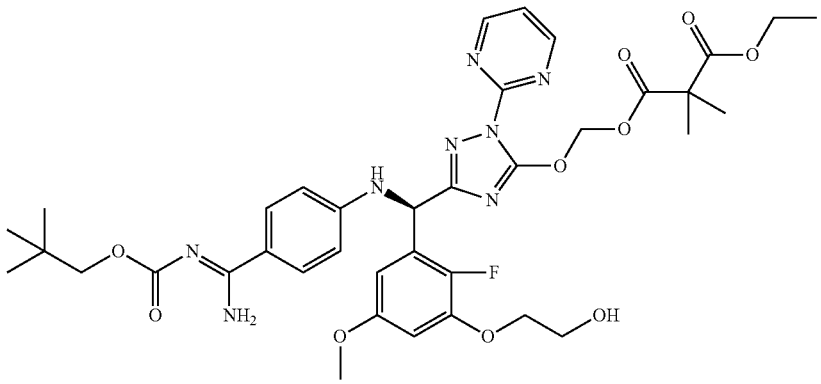 [SMILES: CCOC(=O)C(C)(C)C(=O)OCOc1nc([C@H](Nc2ccc(/C(N)=N/C(=O)OCC(C)(C)C)cc2)c2cc(OC)cc(OCCO)c2F)nn1-c1ncccn1]

To a mixture of [1-amino-1-[4-({(5-chloromethoxy-1-pyrimidin-2-yl-1H-[1,2,4]triazol-3-yl)-[2-fluoro-3-(2-hydroxyethoxy)-5-methoxyphenyl]methyl}amino)phenyl]methylidene]carbamic acid 2,2-dimethylpropyl ester (Example 2b, 100 mg), potassium hydrogen carbonate (107 mg), and DMF (8 mL), sodium iodide (113 mg) and 2,2-dimethylmalonic acid monoethyl ester [CAS No. 5471-77-2] (121 mg) were added, and the resulting mixture was stirred at 45° C. overnight. The reaction mixture was filtered, and the filtrate obtained was concentrated under reduced pressure. The residue obtained was purified by NAM silica gel column chromatography (mixed solvent of methanol-ethyl acetate) to obtain a racemate of the captioned compound.

Using SUMICHIRAL OA-2500 column, the racemate of the captioned compound was separated (optical resolution) under the conditions below to obtain the captioned compound (36 mg) in the latter fraction.
HPLC retention time; 11 min (column name: SUMICHIRAL OA-2500, 30 mmϕ×25 cm, mobile phase: methanol, elution rate: 30 mL/min)
¹H-NMR (CDCl₃): δ=0.96 (s, 9H), 1.05 (t, J=6.8 Hz, 3H), 1.37 (s, 6H), 3.66 (s, 3H), 3.83 (s, 2H), 3.94-4.02 (m, 4H), 4.08 (t, J=5.2 Hz, 2H), 5.59 (d, J=7.2 Hz, 1H), 6.06 (d, J=6.8 Hz, 1H), 6.14 (d, J=6.4 Hz, 1H), 6.16 (J=6.4 Hz, 1H), 6.42 (dd, J=2.8, 6.8 Hz, 1H), 6.59 (dd, J=3.2, 4.6 Hz, 1H), 6.67 (d, J=8.8 Hz, 2H), 7.29 (t, J=4.8 Hz, 1H), 7.65 (d, J=8.8 Hz, 2H), 8.80 (d, J=5.2 Hz, 2H)

Example 16

2,2-dimethylmalonic acid 5-{(R)-(4-{amino(2,2-dimethylpropoxycarbonylimino)methyl}phenylamino)-[2-fluoro-3-(2-hydroxyethoxy)-5-methoxyphenyl]methyl}-2-pyrimidin-2-yl-2H-[1,2,4]-triazol-3-yloxymethyl ester isopropyl ester

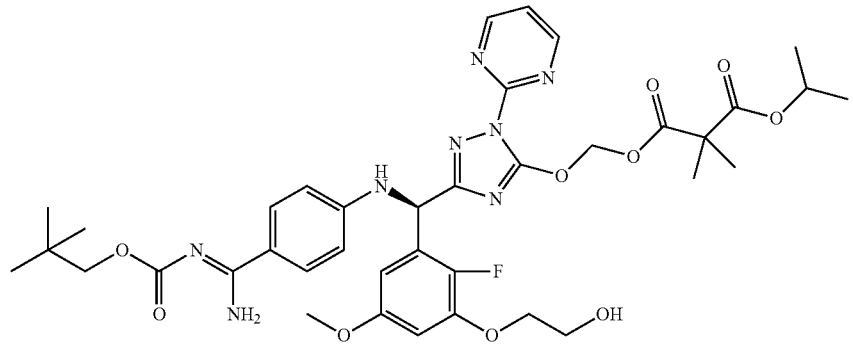 [SMILES: COc1cc(OCCO)c(F)c([C@@H](Nc2ccc(/C(N)=N/C(=O)OCC(C)(C)C)cc2)c2nc(OCOC(=O)C(C)(C)C(=O)OC(C)C)n(-c3ncccn3)n2)c1]

To a mixture of [1-amino-1-[4-({(5-chloromethoxy-1-pyrimidin-2-yl-1H-[1,2,4]triazol-3-yl)-[2-fluoro-3-(2-hydroxyethoxy)-5-methoxyphenyl]methyl}amino)phenyl]methylidene]carbamic acid 2,2-dimethylpropyl ester (Example 2b, 70 mg), potassium hydrogen carbonate (74 mg), and DMF (5 mL), sodium iodide (79 mg) and 2,2-dimethylmalonic acid monoisopropyl ester [CAS No. 7695-26-3] (92 mg) were added, and the resulting mixture was stirred at 45° C. overnight. The reaction mixture was filtered, and the filtrate obtained was concentrated under reduced pressure. The residue obtained was purified by NAM silica gel column chromatography (mixed solvent of methanol-ethyl acetate) to obtain a racemate of the captioned compound.
Using SUMICHIRAL OA-2500 column, the racemate obtained was separated (optical resolution) under the conditions below to obtain the captioned compound (28 mg) in the latter fraction.
HPLC retention time; 11 min (column name: SUMICHIRAL OA-2500, 30 mmϕ×25 cm, mobile phase: methanol, elution rate: 30 mL/min)
¹H-NMR (CDCl₃): δ=0.99 (s, 9H), 1.06 (d, 6.4 Hz, 3H), 1.07 (d, 6.4 Hz, 3H), 1.38 (s, 6H), 3.70 (s, 3H), 3.86 (s, 2H), 3.96 (t, J=3.6 Hz, 2H), 4.11 (t, J=4.4 Hz, 2H), 4.90 (sept, J=6.0 Hz, 1H), 5.51 (d, J=7.2 Hz, 1H), 6.10 (d, J=7.2 Hz, 1H), 6.16 (d, J=5.6 Hz, 1H), 6.19 (d, J=5.6 Hz, 1H), 6.45 (dd, J=2.8, 6.6 Hz, 1H), 6.63 (dd, J=2.8, 4.6 Hz, 1H), 6.71 (d, J=8.4 Hz, 2H), 7.31 (t, J=4.8 Hz, 1H), 7.71 (d, J=8.4 Hz, 2H), 8.83 (d, J=4.8 Hz, 2H)

Example 17

Isonicotinic acid 2-(3-{(R)-(4-{amino[benzoylimino]methyl}phenylamino)-[5-(2,2-dimethyl propionyloxymethoxy)-1-pyrimidin-2-yl-1H-[1,2,4]triazol-3-yl]methyl}-2-fluoro-5-methoxyphenoxy)ethyl ester (17a) Isonicotinic acid 2-{3-[(4-{amino[benzoylimino]methyl}phenylamino)-(5-oxo-1-pyrimidin-2-yl-4,5-dihydro-1H-[1,2,4]triazol-3-yl)methyl]-2-fluoro-5-methoxyphenoxy}ethyl ester

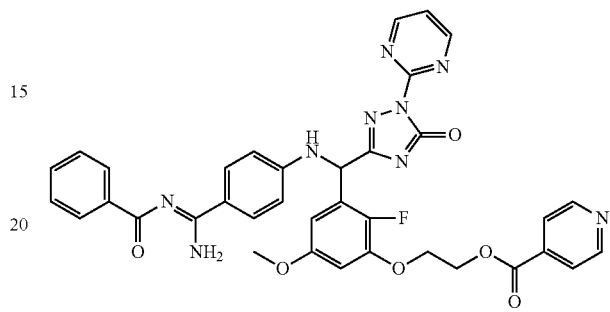

Under nitrogen atmosphere, triethylamine (0.348 mL) was added under ice-cooling to a mixture of 4-pyridinecarboxylic acid [CAS No. 55-22-1] (61.6 mg), TFFH (132 mg), and dichloromethane (5 mL), and the resulting mixture was stirred for 1 hour. To the mixture, a mixture of N-[1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide (Example 1a, 150 mg), DMAP (5 mg), and DMF (2.5 mL) was added dropwise. After stirring the resulting mixture at room temperature for 3 days, the solvent in the mixture was concentrated under reduced pressure. The residue obtained was purified by reverse phase silica gel column chromatography (mixed solvent of acetonitrile-water, containing 0.1% of acetic acid) to obtain the captioned compound (188 mg).
¹H-NMR (CD₃OD): δ=3.71 (s, 3H), 4.43 (t, J=4.4 Hz, 2H), 4.71 (t, J=4.4 Hz, 2H), 6.02 (s, 1H), 6.64-6.67 (m, 1H), 6.75-6.78 (m, 1H), 6.86 (d, J=8.8 Hz, 2H), 7.35 (t, J=4.8 Hz, 1H), 7.48 (t, J=6.8 Hz, 2H), 7.57 (t, J=6.8 Hz, 1H), 7.87 (d, J=6.0 Hz, 2H), 7.90 (d, J=8.8 Hz, 2H), 8.16 (d, J=6.8 Hz, 2H), 8.66 (d, J=6.0 Hz, 2H), 8.76 (d, J=4.8 Hz, 2H)

(17b) Isonicotinic acid 2-(3-{(4-{amino[benzoylimino]methyl}phenylamino)-[5-(2,2-dimethylpropionyloxymethoxy)-1-pyrimidin-2-yl-1H-[1,2,4]triazol-3-yl]methyl}-2-fluoro-5-methoxyphenoxy) ethyl ester

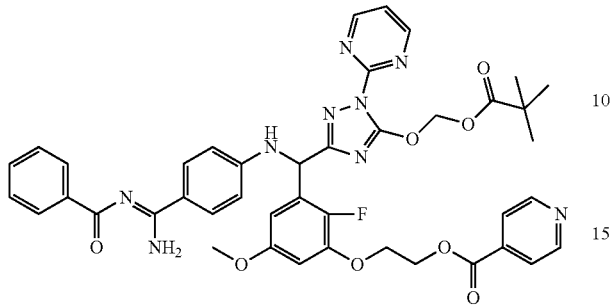

Under nitrogen atmosphere, a mixture of isonicotinic acid 2-{3-[(4-{amino[benzoylimino]methyl}phenylamino)-(5-oxo-1-pyrimidin-2-yl-4,5-dihydro-1H-[1,2,4]triazol-3-yl)methyl]-2-fluoro-5-methoxyphenoxy}ethyl ester (31.3 mg), 2,2-dimethylpropionic acid chloromethyl ester (9.1 mg), potassium hydrogen carbonate (6.7 mg), and DMF (2 mL) was stirred at 45° C. for 20 hours. The mixture was poured into ethyl acetate (100 mL) and water (20 mL). After shaking the mixture, the organic layer was collected, sequentially washed three times with water (20 mL) and with saturated aqueous sodium chloride solution (20 mL), and dried over anhydrous magnesium sulfate. The resulting mixture was filtered, and the filtrate obtained was concentrated under reduced pressure. The residue obtained was purified by NAM silica gel column chromatography (mixed solvent of methanol-ethyl acetate) to obtain the captioned compound (12.2 mg).

$^1$H-NMR (CDCl$_3$): δ=1.15 (s, 9H), 3.70 (s, 3H), 4.37 (t, J=5.0 Hz, 2H), 4.72 (t, J=5.0 Hz, 2H), 5.52 (d, J=7.0 Hz, 1H), 6.14 (d, J=6.3 Hz, 1H), 6.15 (d, J=6.3 Hz, 1H), 6.16 (d, J=7.0 Hz, 1H), 6.49 (dd, J=2.9, 6.6 Hz, 1H), 6.69 (dd, J=2.9, 5.3 Hz, 1H), 6.77 (d, J=9.0 Hz, 2H), 7.31 (t, J=4.9 Hz, 1H), 7.43 (tt, J=1.3, 7.5 Hz, 2H), 7.49 (tt, J=1.3, 7.5 Hz, 1H), 7.85 (dd, J=1.1, 6.6 Hz, 2H), 7.89 (d, J=9.0 Hz, 2H), 8.36 (dd, J=1.3, 7.5 Hz, 2H), 8.77 (dd, J=1.1, 6.6 Hz, 2H), 8.84 (d, J=4.9 Hz, 2H)

(17c) Isonicotinic acid 2-(3-{(R)-(4-{amino[benzoylimino]methyl}phenylamino)-[5-(2,2-dimethylpropionyloxymethoxy)-1-pyrimidin-2-yl-1H-[1,2,4]triazol-3-yl]methyl}-2-fluoro-5-methoxyphenoxy) ethyl ester

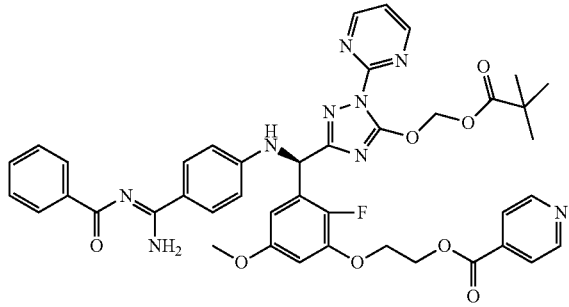 [SMILES: COc1cc(OCCOC(=O)c2ccncc2)c(F)c([C@@H](Nc2ccc(/C(N)=N/C(=O)c3ccccc3)cc2)c2nc(OCOC(=O)C(C)(C)C)n(-c3ncccn3)n2)c1]

Using SUMICHIRAL OA-2500S column, isonicotinic acid 2-(3-{(4-{amino[benzoylimino]methyl}phenylamino)-[5-(2,2-dimethylpropionyloxymethoxy)-1-pyrimidin-2-yl-1H-[1,2,4]triazol-3-yl]methyl}-2-fluoro-5-methoxyphenoxy)ethyl ester (12.2 mg) was separated (optical resolution) under the conditions below to obtain the captioned compound (3.8 mg) in the former fraction.

HPLC retention time; 10 min (column name: SUMICHIRAL OA-2500S, 20 mmφ×25 cm, mobile phase: acetonitrile, elution rate: 20 mL/min)

Example 18

2,2-dimethylmalonic acid 5-{(R)-(4-{amino[2,2-dimethylbutoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester

(18a) Carbonic acid 2,2-dimethylbutyl ester 4-nitrophenyl ester

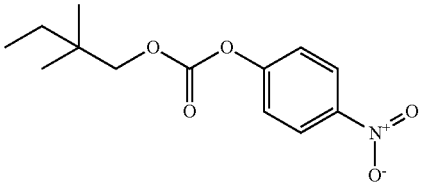 [SMILES: CCC(C)(C)COC(=O)Oc1ccc([N+](=O)[O-])cc1]

To a mixture of 4-nitrophenyl chloroformate (1.97 g), 2,2-dimethylbutan-1-ol [CAS No. 1185-33-7] (1 g), and dichloromethane (30 mL), pyridine (1.58 mL) was added, and the resulting mixture was stirred at room temperature for 3 days. To the mixture, ethyl acetate and 1 N hydrochloric acid were added. After shaking the resulting mixture, the organic layer was collected, sequentially washed twice with water and with saturated aqueous sodium chloride solution, and dried over anhydrous sodium sulfate. The desiccant was filtered off, and the filtrate obtained was concentrated under reduced pressure. The residue obtained was purified by silica gel column chromatography (mixed solvent of heptane-ethyl acetate) to obtain the captioned compound (2.23 g).

$^1$H-NMR (CDCl$_3$): δ=0.89 (t, J=7.6 Hz, 3H), 0.97 (s, 6H), 1.38 (q, J=7.6 Hz, 2H), 4.02 (s, 2H), 7.38 (d, J=8.8 Hz, 2H), 8.29 (d, J=8.8 Hz, 2H)

(18b) 2,2-dimethylmalonic acid mono-(2,2-dimethylpropyl)ester

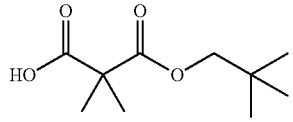

To a mixture of 2,2-dimethylmalonic acid mono-t-butyl ester (10 g), 2,2-dimethyl-1-propanol [CAS No. 75-84-3] (5.15 g), DMAP (1.3 g), and dichloromethane (100 mL), WSC (12.2 g) was added with stirring under ice-cooling, and the resulting mixture was stirred at room temperature for 2 days. TBME and water were added to the mixture, and the resulting mixture was extracted. The organic layer was sequentially washed with water and saturated aqueous sodium chloride solution, and dried over anhydrous magnesium sulfate. The desiccant was filtered off, and the filtrate obtained was concentrated under reduced pressure. The residue obtained was purified by silica gel column chromatography (mixed solvent of heptane-ethyl acetate) to obtain 2,2-dimethylmalonic acid t-butyl ester(2,2-dimethylpropyl)ester (12 g).

To a solution of the obtained 2,2-dimethylmalonic acid t-butyl ester (2,2-dimethylpropyl)ester (12 g) in dichloromethane (100 mL), TFA (20 mL) was added, and the resulting mixture was stirred at room temperature for 3 hours. Ethyl acetate and water were added to the mixture. After shaking the resulting mixture, the organic layer was collected, sequentially washed with water and saturated aqueous sodium chloride solution, and dried over anhydrous magnesium sulfate. The desiccant was filtered off, and toluene was added to the filtrate obtained, after which the resulting mixture was concentrated under reduced pressure to obtain the captioned compound (8.7 g).

$^1$H-NMR (CD$_3$OD): δ=0.94 (s, 9H), 1.41 (s, 6H), 3.81 (s, 2H)

(18c) N-[1-amino-1-[4-({(5-chloromethoxy-1-pyrimidin-2-yl-1H-[1,2,4]triazol-3-yl)-[2-fluoro-3-(2-hydroxyethoxy)-5-methoxyphenyl]methyl}amino)phenyl]methylidene]benzamide

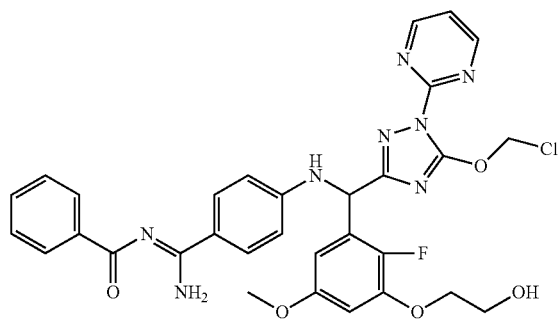 [SMILES: COc1cc(OCCO)c(F)c(C(Nc2ccc(/C(N)=N/C(=O)c3ccccc3)cc2)c2nc(OCCl)n(-c3ncccn3)n2)c1]

To a mixture of dichloromethane (20 mL), THF (20 mL), and water (20 mL), N-[1-amino-1-(4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}phenyl)methylidene]benzamide (Example 1a, 901 mg), sodium hydrogen carbonate (632 mg), and tetrabutylammonium hydrogen sulfate (102 mg) were sequentially added. After cooling the resulting mixture to −10° C., a mixture of chloromethyl chlorosulfate (373 mg) and dichloromethane (5 mL) was added dropwise thereto with stirring, and the resulting mixture was stirred overnight at room temperature. Dichloromethane (10 mL), THF (10 mL), and water (10 mL) were added to the mixture, and the resulting mixture was cooled again to −10° C., after which a mixture of chloromethyl chlorosulfate (373 mg) and dichloromethane (5 mL) was added dropwise thereto with stirring, and the resulting mixture was stirred overnight at room temperature. Ethyl acetate (300 mL) and water (100 mL) were added to the mixture, and the resulting mixture was shaken, after which the organic layer was collected. Ethyl acetate (80 mL) and THF (20 mL) were added to the aqueous layer, and the resulting mixture was shaken again, after which the organic layer was collected. The combined organic layers were dried over anhydrous magnesium sulfate. The mixture was filtered, and the filtrate obtained was concentrated under reduced pressure. The residue obtained was purified by NAM silica gel column chromatography (mixed solvent of heptane-ethyl acetate) to obtain the captioned compound (340 mg).

$^1$H-NMR (CD$_3$OD): δ=3.73 (s, 3H), 3.88 (t, J=5.0 Hz, 2H), 4.09 (t, J=5.0 Hz, 2H), 6.14 (s, 1H), 6.23 (d, J=6.8 Hz, 1H), 6.29 (d, J=6.8 Hz, 1H), 6.62 (dd, J=3.6, 8.3 Hz, 1H), 6.78 (dd, J=3.6, 5.1 Hz, 1H), 6.85 (d, J=8.7 Hz, 2H), 7.44 (t, J=7.6 Hz, 2H), 7.50 (t, J=4.7 Hz, 1H), 7.51 (t, J=7.6 Hz, 1H), 7.97 (d, J=8.7 Hz, 2H), 8.25 (d, J=7.6 Hz, 2H), 8.88 (d, J=4.7 Hz, 2H)

(18d) 2,2-dimethylmalonic acid 5-{(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester

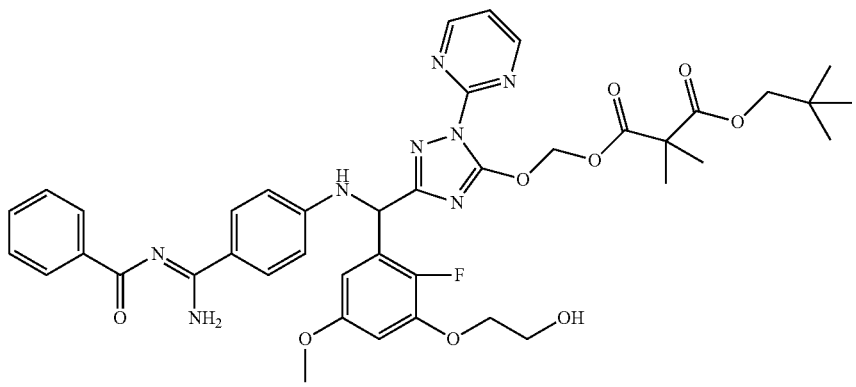 [SMILES: COc1cc(OCCO)c(F)c(C(Nc2ccc(/C(N)=N/C(=O)c3ccccc3)cc2)c2nc(OCOC(=O)C(C)(C)C(=O)OCC(C)(C)C)n(-c3ncccn3)n2)c1]

A mixture of N-[1-amino-1-[4-({(5-chloromethoxy-1-pyrimidin-2-yl-1H-[1,2,4]triazol-3-yl)-[2-fluoro-3-(2-hydroxyethoxy)-5-methoxyphenyl]methyl}amino)phenyl]methylidene]benzamide (500 mg), 2,2-dimethylmalonic acid mono-(2,2-dimethylpropyl)ester (1.56 g), sodium iodide (1.16 g), potassium hydrogen carbonate (543 mg), and DMA (50 mL) was stirred at 50° C. for 7 hours. After cooling the mixture to room temperature, ethyl acetate was added thereto, and the resulting mixture was sequentially washed twice with water and with saturated aqueous sodium chloride solution, and dried over anhydrous magnesium sulfate. The desiccant was filtered off, and the filtrate obtained was concentrated under reduced pressure. The residue obtained was purified by NAM silica gel column chromatography (mixed solvent of methanol-ethyl acetate) to obtain the captioned compound (500 mg).

$^1$H-NMR (CD$_3$OD): δ=0.70 (s, 9H), 1.36 (s, 3H), 1.37 (s, 3H), 3.55 (d, J=10.4 Hz, 1H), 3.59 (d, J=10.4 Hz, 1H), 3.73 (s,

3H), 3.85-3.93 (m, 2H), 4.05-4.12 (m, 2H), 6.10 (s, 1H), 6.15 (d, J=6.0 Hz, 1H), 6.16 (d, J=6.0 Hz, 1H), 6.61 (dd, J=2.8, 6.8 Hz, 1H), 6.76 (dd, J=2.8, 4.4 Hz, 1H), 6.84 (d, J=8.8 Hz, 2H), 7.40-7.53 (m, 4H), 7.98 (d, J=8.8 Hz, 2H), 8.22-8.28 (m, 2H), 8.87 (d, J=4.8 Hz, 2H)

(18e) 2,2-dimethylmalonic acid 5-{(4-carbamimidoylphenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester acetate

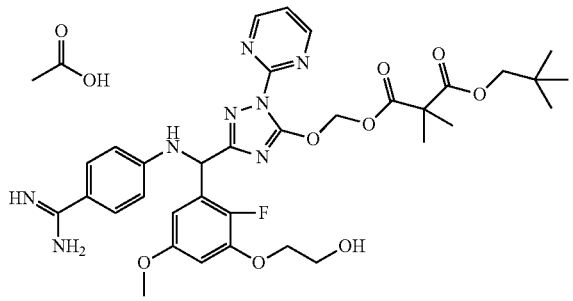

To a mixture of 2,2-dimethylmalonic acid 5-{(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester (500 mg) and methanol (4 mL), acetic acid (1 mL) was added, and the resulting mixture was stirred at 40° C. for 4 hours. The mixture was concentrated under reduced pressure, and the residue obtained was purified by reverse phase silica gel column chromatography (mixed solvent of acetonitrile-water, containing 0.1% of acetic acid) to obtain the captioned compound (430 mg).

(18f) 2,2-dimethylmalonic acid 5-{(4-{amino[2,2-dimethylbutoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester

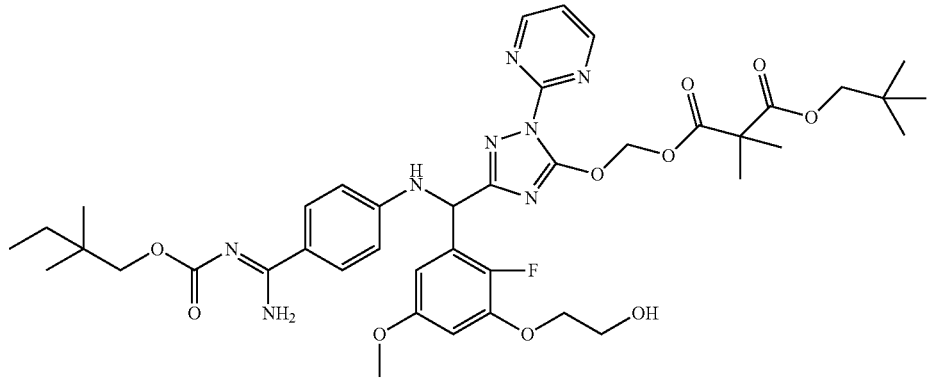 [SMILES: CCC(C)(C)COC(=O)/N=C(\N)c1ccc(NC(c2nc(OCOC(=O)C(C)(C)C(=O)OCC(C)(C)C)n(-c3ncccn3)n2)c2cc(OC)cc(OCCO)c2F)cc1]

To a mixture of 2,2-dimethylmalonic acid 5-{(4-carbamimidoylphenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester acetate (270 mg), carbonic acid 2,2-dimethylbutyl ester 4-nitrophenyl ester (141 mg), and THF (10 mL), triethylamine (0.17 mL) was added, and the resulting mixture was stirred at room temperature for 26 hours. Acetic acid (0.3 mL) was added to the reaction solution, and the resulting mixture was concentrated under reduced pressure. The residue obtained was purified by NAM silica gel column chromatography (mixed solvent of methanol-ethyl acetate) to obtain the captioned compound.

(18 g) 2,2-dimethylmalonic acid 5-{(R)-(4-{amino[2,2-dimethylbutoxycarbonylimino]methyl}phenylamino)-[2-fluoro-3-(2-hydroxy ethoxy)-5-methoxyphenyl]methyl}-2-pyrimidin-2-yl-2H-[1,2,4]triazol-3-yloxymethyl ester 2,2-dimethylpropyl ester

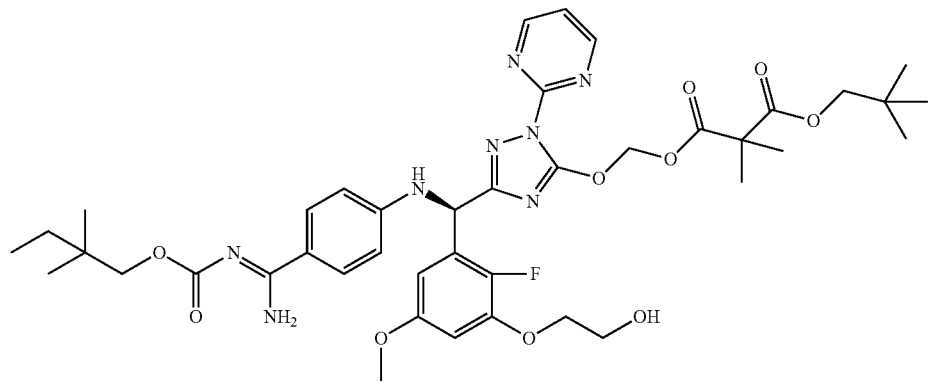 [SMILES: CCC(C)(C)COC(=O)/N=C(\N)c1ccc(N[C@@H](c2nc(OCOC(=O)C(C)(C)C(=O)OCC(C)(C)C)n(-c3ncccn3)n2)c2cc(OC)cc(OCCO)c2F)cc1]

Using SUMICHIRAL OA-2500 column, 2,2-dimethylmalonic acid 5-{(4-{amino[2,2-dimethylbutoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester was separated (optical resolution) under the conditions below to obtain a crudely purified product of the captioned compound in the latter fraction.

HPLC retention time; 13 min (column name: SUMICHIRAL OA-2500, 30 mmφ×25 cm, mobile phase: methanol, elution rate: 20 mL/min)

The crudely purified product obtained was purified again using SUMICHIRAL OA-2500S column (30 mmφ×25 cm, mobile phase: methanol, elution rate: 20 mL/min) to obtain the captioned compound (88.80 mg).

$^1$H-NMR (CD$_3$OD): δ=0.74 (s, 9H), 0.87 (t, J=7.6 Hz, 3H), 0.93 (s, 6H), 1.32-1.43 (m, 8H), 3.55 (d, J=10.4 Hz, 1H), 3.59 (d, J=10.4 Hz, 1H), 3.71 (s, 3H), 3.83 (s, 2H), 3.85-3.91 (m, 2H), 4.05-4.11 (m, 2H), 6.06 (s, 1H), 6.14 (d, J=6.0 Hz, 1H), 6.15 (d, J=6.0 Hz, 1H), 6.59 (dd, J=2.8, 6.8 Hz, 1H), 6.74 (dd, J=2.8, 4.8 Hz, 1H), 6.79 (d, J=8.8 Hz, 2H), 7.48 (t, J=4.8 Hz, 1H), 7.70 (d, J=8.8 Hz, 2H), 8.86 (d, J=4.8 Hz, 2H)

Example 19

3-methoxymethoxy-2,2-dimethylpropionic acid 5-{(R)-[4-(amino[benzoylimino]methyl)phenylamino]-[2-fluoro-3-(2-hydroxyethoxy)-5-methoxyphenyl]methyl}-2-pyrimidin-2-yl-2H-[1,2,4]triazol-3-yloxymethyl ester hydrochloride

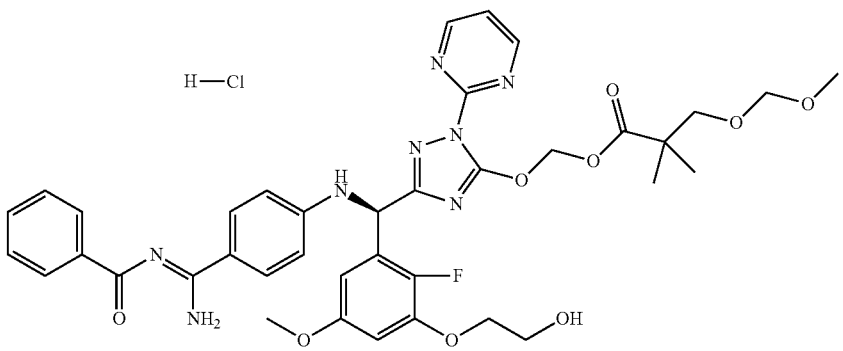 [SMILES: COCOCC(C)(C)C(=O)OCOc1nc([C@H](Nc2ccc(/C(N)=N/C(=O)c3ccccc3)cc2)c2cc(OC)cc(OCCO)c2F)nn1-c1ncccn1 ; Cl]

To a mixture of 3-methoxymethoxy-2,2-dimethylpropionic acid 5-{(R)-[4-(amino[benzoylimino]methyl)phenylamino]-[2-fluoro-3-(2-hydroxyethoxy)-5-methoxyphenyl]methyl}-2-pyrimidin-2-yl-2H-[1,2,4]triazol-3-yloxymethyl ester (Example 1f, 300 mg), TBME (4 mL), toluene (4 mL), and isopropyl alcohol (2 mL), 4 N hydrogen chloride-ethyl acetate solution (0.098 mL) was slowly added, and the resulting mixture was stirred at room temperature for 5 minutes. The solvent in the reaction solution was distilled off under reduced pressure to obtain the captioned compound (333 mg).

$^1$H-NMR (CD$_3$OD): δ=1.10 (s, 6H), 3.15 (s, 3H), 3.40 (s, 2H), 3.72 (s, 3H), 3.89 (t, J=4.8 Hz, 2H), 4.09 (t, J=4.8 Hz, 2H), 4.32 (d, J=6.6 Hz, 1H), 4.34 (d, J=6.6 Hz, 1H), 6.11 (d, J=5.6 Hz, 1H), 6.14 (s, 1H), 6.15 (d, J=5.6 Hz, 1H), 6.63 (dd, J=2.8, 7.0 Hz, 1H), 6.73 (dd, J=2.8, 4.4 Hz, 1H), 6.94 (d, J=9.0 Hz, 2H), 7.49 (t, J=4.8 Hz, 1H), 7.55 (t, J=7.6 Hz, 2H), 7.67 (t, J=7.6 Hz, 1H), 7.83 (d, J=9.0 Hz, 2H), 8.09 (d, J=7.6 Hz, 2H), 8.87 (d, J=4.8 Hz, 2H)

Example 20

3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]-triazol-3-yloxymethyl ester methanesulfonate

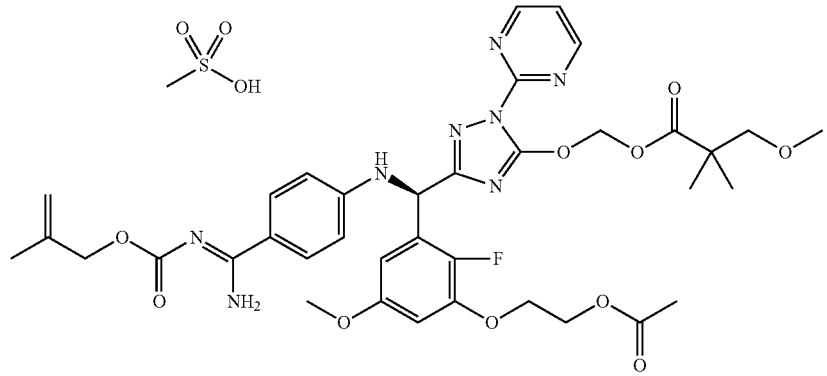

At room temperature, 3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester (Example 6f, 50 mg) was dissolved in ethyl acetate (5 mL), and a solution of methanesulfonic acid (0.0041 mL) in ethyl acetate (0.5 mL) was added dropwise thereto. The resulting mixture was stirred overnight at room temperature, and the precipitated solid was filtered. The filtrate obtained was washed with ethyl acetate and TBME, and dried. The captioned compound (48 mg) was obtained.

$^1$H-NMR (d$_6$-DMSO): δ=0.988 (s, 3H), 0.994 (s, 3H), 1.75 (s, 3H), 2.02 (s, 3H), 2.27 (s, 3H), 2.97 (s, 3H), 3.18 (s, 2H), 3.69 (s, 3H), 4.21-4.27 (m, 2H), 4.29-4.34 (m, 2H), 4.68 (s, 2H), 4.98 (s, 1H), 5.07 (s, 1H), 6.04 (s, 2H), 6.06 (d, J=3.2 Hz, 1H), 6.68 (dd, J=2.4, 4.4 Hz, 1H), 6.72 (dd, J=2.4, 6.4 Hz, 1H), 6.87 (d, J=9.2 Hz, 2H), 7.59 (t, J=4.4 Hz, 1H), 7.65 (d, J=9.2 Hz, 2H), 7.82 (d, J=7.6 Hz, 1H), 8.92 (d, J=5.2 Hz, 2H), 10.06 (br.s, 1H), 10.70 (br.s, 1H), 11.97 (br.s, 1H)

Example 21

4-pyridinecarboxylic acid 2-(3-{(R)-(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methyl}-2-fluoro-5-methoxyphenoxy)ethyl ester hydrochloride

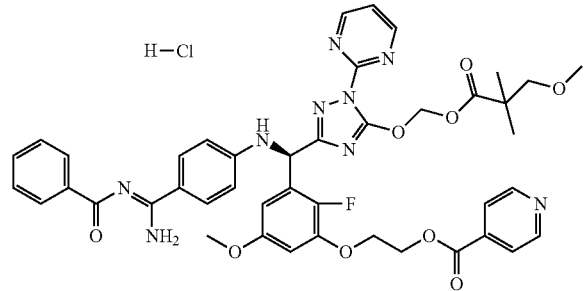 [SMILES: COCC(C)(C)C(=O)OCOc1nc([C@H](Nc2ccc(/C(N)=N/C(=O)c3ccccc3)cc2)c2cc(OC)cc(OCCOC(=O)c3ccncc3)c2F)nn1-c1ncccn1 ; Cl]

To a mixture of 4-pyridinecarboxylic acid 2-(3-{(R)-(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methyl}-2-fluoro-5-methoxyphenoxy)ethyl ester (Example 4d, 208 mg), dichloromethane (3 mL), and TBME (6 mL), 0.4 M hydrogen chloride-ethyl acetate solution (0.62 mL) was added dropwise at room temperature. TBME (6 mL) was added to the resulting mixture, and after stirring the resulting mixture for 10 minutes, the mixture was sonicated for 2 minutes. The precipitates were recovered by filtration, washed twice with TBME (5 mL), and dried under reduced pressure. The captioned compound (192 mg) was obtained.

$^1$H-NMR (CDCl$_3$): δ=1.13 (s, 3H), 1.14 (s, 3H), 3.16 (s, 3H), 3.33 (d, J=9.4 Hz, 1H), 3.34 (d, J=9.4 Hz, 1H), 3.70 (s, 3H), 4.36 (t, J=5.0 Hz, 2H), 4.71 (t, J=5.0 Hz, 2H), 6.09 (s, 1H), 6.10 (d, J=5.3 Hz, 1H), 6.23 (d, J=5.3 Hz, 1H), 6.48 (dd, J=2.8, 6.4 Hz, 1H), 6.67 (dd, J=2.8, 4.4 Hz, 1H), 6.75 (d, J=8.9 Hz, 2H), 7.28 (m, 1H), 7.50 (t, J=7.5 Hz, 2H), 7.61 (t, J=7.5 Hz, 1H), 7.83 (d, J=5.3 Hz, 2H), 7.94 (d, J=8.9 Hz, 2H), 8.19 (d, J=7.5 Hz, 2H), 8.69 (d, J=5.3 Hz, 2H), 8.78 (d, J=4.9 Hz, 2H)

Example 22

4-pyridinecarboxylic acid 2-(3-{(R)-(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methyl}-2-fluoro-5-methoxyphenoxy)ethyl ester methanesulfonate

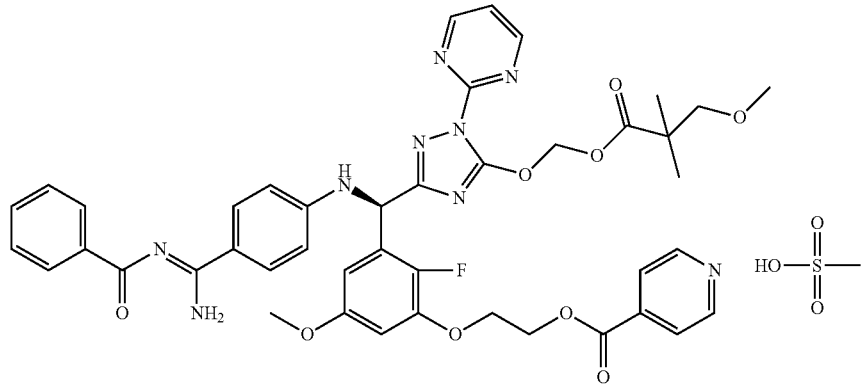

To a mixture of 4-pyridinecarboxylic acid 2-(3-{(R)-(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methyl}-2-fluoro-5-methoxyphenoxy)ethyl ester (219 mg), dichloromethane (3 mL), and TBME (6 mL), a mixture of methanesulfonic acid (0.0171 mL) and dichloromethane (1 mL) was added dropwise at room temperature. TBME (6 mL) was added to the resulting mixture, and after stirring the resulting mixture for 10 minutes, the mixture was sonicated for 2 minutes. The precipitates were recovered by filtration, washed twice with TBME (5 mL), and dried under reduced pressure. The captioned compound (206 mg) was obtained.

$^1$H-NMR (CDCl$_3$): δ=1.13 (s, 3H), 1.14 (s, 3H), 2.31 (s, 3H), 3.18 (s, 3H), 3.33 (d, J=9.4 Hz, 1H), 3.34 (d, J=9.4 Hz, 1H), 3.59 (s, 3H), 4.31 (t, J=5.1 Hz, 2H), 4.70 (t, J=5.1 Hz, 2H), 6.07 (d, J=5.5 Hz, 1H), 6.08 (s, 1H), 6.17 (d, J=5.5 Hz, 1H), 6.35 (dd, J=2.8, 6.4 Hz, 1H), 6.54 (dd, J=2.8, 4.4 Hz, 1H), 6.73 (d, J=8.8 Hz, 2H), 7.05 (br.s, 1H), 7.16 (t, J=4.8 Hz, 1H), 7.48 (t, J=7.3 Hz, 2H), 7.60 (t, J=7.3 Hz, 1H), 7.85 (d, J=8.8 Hz, 2H), 7.87 (d, J=5.2 Hz, 2H), 8.04 (d, J=7.3 Hz, 2H), 8.61 (d, J=5.2 Hz, 2H), 8.74 (d, J=4.8 Hz, 2H)

Example 23

3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester hydrochloride

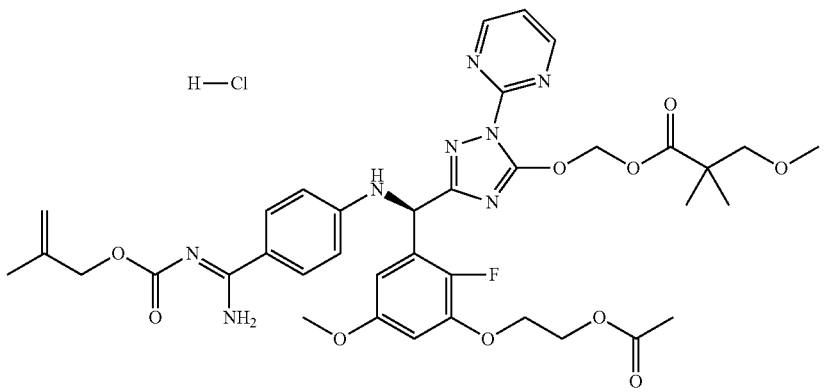 [SMILES: C=C(C)COC(=O)/N=C(\N)c1ccc(N[C@@H](c2nc(OCOC(=O)C(C)(C)COC)n(-c3ncccn3)n2)c2cc(OC)cc(OCCOC(C)=O)c2F)cc1 ; Cl]

To a mixture of 3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester (Example 6f, 20 mg) and toluene (4 mL), under stirring at room temperature, a dilution (0.2 mL) prepared by adding 4 M hydrogen chloride-ethyl acetate solution (0.32 mL) to ethyl acetate (10 mL) was added dropwise. The solvent in the mixture was distilled off under reduced pressure to obtain the captioned compound (20 mg).

$^1$H-NMR (d$_6$-DMSO): δ=1.007 (s, 3H), 1.010 (s, 3H), 1.76 (s, 3H), 2.04 (s, 3H), 2.99 (s, 3H), 3.19 (s, 2H), 3.71 (s, 3H), 4.21-4.29 (m, 2H), 4.31-4.38 (m, 2H), 4.65 (br.s, 2H), 4.98 (s, 1H), 5.06 (s, 1H), 6.05 (s, 3H), 6.68-6.78 (m, 2H), 6.86 (d, J=8.0 Hz, 2H), 7.60 (t, J=4.8 Hz, 1H), 7.68 (d, J=8.0 Hz, 2H), 8.94 (d, J=4.8 Hz, 2H)

Mass spectrum (ESI) m/z: 779 (M+H)$^+$

Example 24

3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]-triazol-3-yloxymethyl ester ethanesulfonate

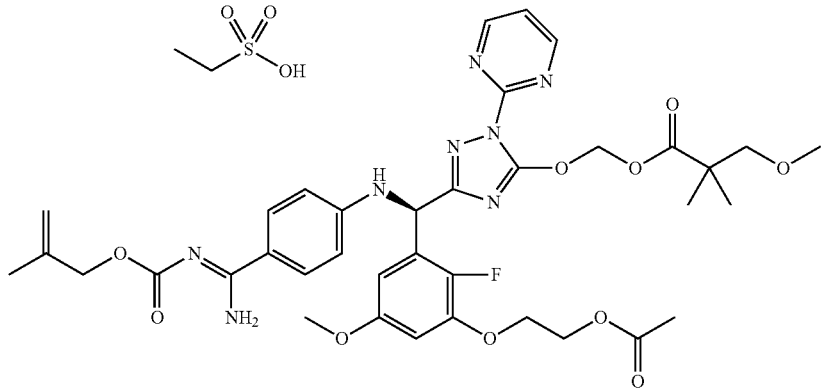

At room temperature, 3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4] triazol-3-yloxymethyl ester (Example 6f, 100 mg) was dissolved in ethyl acetate (10 mL), and a solution of ethanesulfonic acid (14.2 mg) in ethyl acetate (1 mL) was added dropwise thereto. The resulting mixture was stirred at room temperature for 1 hour, and the precipitated solid was filtered. The filtrate obtained was washed with TBME and dried. The captioned compound (103 mg) was obtained.

$^1$H-NMR (CD$_3$OD): δ=1.068 (s, 3H), 1.073 (s, 3H), 1.29 (t, J=7.2 Hz, 3H), 1.82 (s, 3H), 2.06 (s, 3H), 2.79 (q, J=7.2 Hz, 2H), 3.03 (s, 3H), 3.22 (s, 2H), 3.73 (s, 3H), 4.23-4.25 (m, 2H), 4.39-4.42 (m, 2H), 4.75 (s, 2H), 5.02 (s, 1H), 5.10 (s, 1H), 6.11-6.13 (m, 3H), 6.63 (dd, J=3.2, 6.4 Hz, 1H), 6.74 (dd, J=3.2, 4.8 Hz, 1H), 6.91 (d, J=9.2 Hz, 2H), 7.50 (t, J=4.8 Hz, 1H), 7.66 (d, J=9.2 Hz, 2H), 8.88 (d, J=4.8 Hz, 2H)

Example 25

3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}-phenylamino)methyl]-2-pyrimidin-2-yl-2H-[1,2,4] triazol-3-yloxymethyl ester propanesulfonate

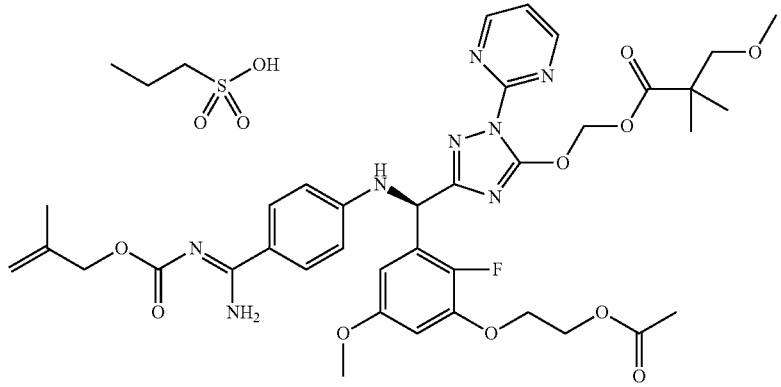

At room temperature, 3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4] triazol-3-yloxymethyl ester (Example 6f, 100 mg) was dissolved in ethyl acetate (10 mL), a solution of 1-propanesulfonic acid [CAS No. 5284-66-2] (13.5 mg) in ethyl acetate (1 mL) was added dropwise thereto. The resulting mixture was stirred at room temperature for 22 hours, and the precipitated solid was filtered. The solids recovered by filtration were washed with ethyl acetate and TBME, and dried. The captioned compound (90 mg) was obtained.

$^1$H-NMR (CD$_3$OD): δ=1.02 (t, J=7.2 Hz, 3H), 1.068 (s, 3H), 1.073 (s, 3H), 1.76-1.86 (m, 2H), 1.82 (s, 3H), 2.05 (s, 3H), 2.73-2.78 (m, 2H), 3.03 (s, 3H), 3.22 (d, J=0.8 Hz, 2H), 3.73 (s, 3H), 4.23-4.25 (m, 2H), 4.39-4.42 (m, 2H), 4.75 (s, 2H), 5.02 (s, 1H), 5.10 (s, 1H), 6.11-6.13 (m, 3H), 6.63 (dd, J=3.2, 7.2 Hz, 1H), 6.74 (dd, J=3.2, 4.8 Hz, 1H), 6.91 (d, J=9.2 Hz, 2H), 7.50 (t, J=4.8 Hz, 1H), 7.66 (d, J=9.2 Hz, 2H), 8.88 (d, J=4.8 Hz, 2H)

Example 26

2-fluoro-5-methoxyphenol

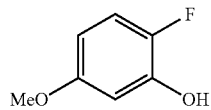

To a flask, 4-fluoroanisole (20.00 g, 159 mmol), N,N,N',N",N"-pentamethyldiethylenetriamine (27.75 g, 160 mmol), and tetrahydrofuran (100 mL) were added, and the resulting mixture was cooled to −70° C. under nitrogen atmosphere. To the solution, n-butyllithium (59.2 mL, 163 mmol, 2.76 M, in hexane) was added dropwise, and trimethyl borate (39.8 mL, 357 mmol) was added three hours later. One hour later, the reaction mixture was warmed to −10° C., and acetic acid (28.0 mL) was added thereto. The reaction temperature was then changed to 5° C., and 30% aqueous hydrogen peroxide solution (30 mL) was added dropwise to the reaction mixture, after which the resulting mixture was stirred overnight at room temperature. To the reaction mixture, 10% aqueous sodium sulfite solution was added, and the resulting mixture was extracted with tert-butyl methyl ether. To the organic layer, a 2 N aqueous sodium hydroxide solution was added, and the resulting mixture was extracted. After adding 5 N hydrochloric acid to the aqueous layer to adjust the pH to 6, the resulting mixture was extracted with tert-butyl methyl ether. The organic layer was sequentially washed with water and 5% saline, dried over anhydrous magnesium sulfate, and then filtered. The filtrate obtained was concentrated under reduced pressure to obtain the captioned compound (21.7 g) as a colorless oil.

$^1$H-NMR (400 MHz, CDCl$_3$): δ=3.76 (s, 3H), 5.43 (bs, 1H), 6.34-6.40 (m, 1H), 6.57 (dd, J=3.1, 7.3 Hz, 1H), 6.97 (dd, J=9.0, 10.3 Hz, 1H).

Example 27 tert-butyl(2-fluoro-5-methoxyphenoxy)dimethylsilane

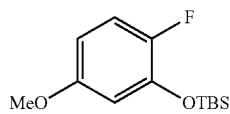

To a flask, 2-fluoro-5-methoxyphenol (6.00 g, 42 mmol), triethylamine (5.77 g, 57 mmol), and tetrahydrofuran (36.0 mL) were added, and the resulting mixture was cooled in an ice water bath under nitrogen atmosphere. To the solution, a solution of tert-butyldimethylsilyl chloride (6.89 g, 44 mmol) in tetrahydrofuran (30.0 mL) was added dropwise, and the resulting mixture was stirred overnight at room temperature. To the reaction mixture, heptane and a 2 N aqueous sodium hydroxide solution were added, and the resulting mixture was extracted. The organic layer was washed with water, and concentrated under reduced pressure to obtain the captioned compound (10.2 g) as a light brownish-red oil.

$^1$H-NMR (400 MHz, CDCl$_3$): δ=0.19 (s, 6H), 1.00 (s, 9H), 3.74 (s, 3H), 6.38-6.44 (m, 1H), 6.47 (dd, J=3.0, 7.1 Hz, 1H), 6.94 (dd, J=8.9, 10.4 Hz, 1H).

Example 28

2-fluoro-3-hydroxy-5-methoxybenzaldehyde

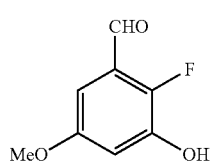 [SMILES: COc1cc(O)c(F)c(C=O)c1]

To a flask, tert-butyl(2-fluoro-5-methoxyphenoxy)dimethylsilane (6.00 g, 23 mmol), N,N,N',N",N"-pentamethyldiethylenetriamine (4.87 g, 28 mmol), and tetrahydrofuran (48.0 mL) were added, and the resulting mixture was cooled to −72° C. under nitrogen atmosphere. To the solution, n-butyllithium (10.2 mL, 28 mmol, 2.76 M, in hexane) was added dropwise, and the resulting mixture was stirred at −56° C. for 3 hours. To the solution, a solution of N,N-dimethylformamide (3.42 g, 47 mmol) in tetrahydrofuran (6.0 mL) was added, and the resulting mixture was warmed to 10° C., after which water was added thereto, and the two-layer reaction solution was stirred overnight at room temperature. Heptane was added to the reaction mixture, and the aqueous layer was collected. Toluene was added to the aqueous layer. To the resulting mixture, 5 N hydrochloric acid was added to adjust the pH to 2, and the resulting mixture was extracted. The organic layer was washed with water and concentrated under reduced pressure, after which a mixture of toluene and ethyl acetate was added to the resulting concentration residue, and the resulting mixture was purified by suspension. The purified product obtained was filtered and dried to obtain the captioned compound (3.16 g) as a light brown solid.

$^1$H-NMR (400 MHz, CDCl$_3$): δ=3.81 (s, 3H), 6.80-6.90 (m, 2H), 10.30 (s, 1H).

Example 29

4-{[cyano(2-fluoro-3-hydroxy-5-methoxyphenyl)methyl]amino}benzonitrile

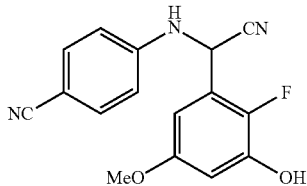 [SMILES: COc1cc(O)c(F)c(C(C#N)Nc2ccc(C#N)cc2)c1]

Under nitrogen atmosphere, a solution of 2-fluoro-3-hydroxy-5-methoxybenzaldehyde (17.01 g, 100 mmol), 4-aminobenzonitrile (11.81 g, 100 mmol), and guanidine hydrochloride (287 mg, 3 mmol) in methanol (85 mL) was stirred at 40° C. for 1.5 hours. Trimethylsilylcyanide (18.1 mL, 130 mmol) was then added dropwise thereto, and the resulting mixture was stirred at 40° C. for 22 hours. After cooling the mixture, under cooling at 15° C., 3% aqueous sodium hydrogen carbonate solution (87.65 g) was added dropwise thereto, and the resulting mixture was stirred for 1 hour under cooling at 10° C. The precipitated solid was filtered and dried to obtain the captioned compound (27.91 g) as a white solid.

$^1$H-NMR (400 MHz, CDCl$_3$): δ=3.76 (s, 3H), 5.61 (d, J=6.0 Hz, 1H), 6.27 (d, J=5.2 Hz, 1H), 6.59-6.63 (m, 2H), 6.80 (d, J=6.8 Hz, 2H), 7.49 (d, J=6.8 Hz, 2H), 9.44 (brs, 1H).

Example 30

4-({cyano[2-fluoro-3-(2-hydroxyethoxy)-5-methoxyphenyl]methyl}amino)benzonitrile

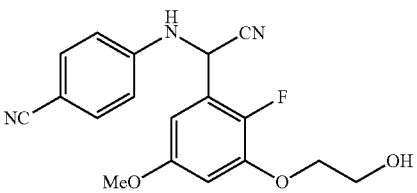 [SMILES: COc1cc(OCCO)c(F)c(C(C#N)Nc2ccc(C#N)cc2)c1]

Under nitrogen atmosphere, a mixture of 4-{[cyano(2-fluoro-3-hydroxy-5-methoxyphenyl)methyl]amino}benzonitrile (1.49 g, 5 mmol), 2-chloroethanol (1.61 g, 20 mmol), sodium iodide (3.00 g, 20 mmol), potassium carbonate (967 mg, 7 mmol), and N,N-dimethylformamide (7.43 mL) was stirred at 70° C. for 13.5 hours. After cooling the mixture, ethyl acetate and water were added to the reaction mixture, and the resulting mixture was extracted. The organic layer was washed with 10% saline, and then concentrated under reduced pressure to obtain a crude product of the captioned compound (2.77 g) as a yellow-brown oil.

$^1$H-NMR (400 MHz, CDCl$_3$): δ=3.82 (s, 3H), 3.98-4.02 (m, 2H), 4.08-4.17 (m, 3H), 4.55 (d, J=7.2 Hz, 1H), 5.62 (d, J=7.2 Hz, 1H), 6.62-6.69 (m, 2H), 6.78 (d, J=8.4 Hz, 2H), 7.56 (d, J=8.4 Hz, 2H).

Example 31

2-(4-cyanophenylamino)-2-[2-fluoro-3-(2-hydroxyethoxy)-5-methoxyphenyl]thioacetamide

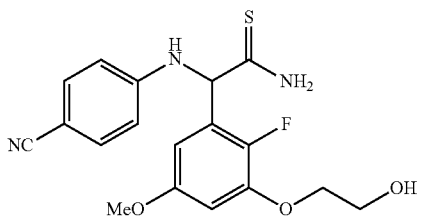 [SMILES: COc1cc(OCCO)c(F)c(C(Nc2ccc(C#N)cc2)C(N)=S)c1]

The crude product of 4-({cyano[2-fluoro-3-(2-hydroxyethoxy)-5-methoxyphenyl]methyl}amino)benzonitrile (2.77 g) obtained in Example 30 was dissolved in tetrahydrofuran (4.26 mL) and methanol (4.26 mL), and 20% aqueous ammonium sulfide solution (8.54 mL, 25 mmol) was added dropwise thereto at room temperature, and the resulting mixture was stirred at the same temperature. After completion of the reaction, water (4.26 mL) was added dropwise to the reaction mixture, and the resulting mixture was stirred at the same temperature for 0.5 hours. The precipitated solid was filtered. The filtrate obtained was sequentially washed with water and tert-butyl methyl ether, and dried to obtain the captioned compound (1.87 g) as a pale yellow solid.

$^1$H-NMR (400 MHz, DMSO-d$_6$): δ=3.68-3.73 (m, 5H), 4.02-4.07 (m, 2H), 4.90 (t, J=5.6 Hz, 1H), 5.44 (d, J=5.6 Hz, 1H), 6.60-6.64 (m, 1H), 6.68-6.73 (m, 3H), 7.15 (d, J=6.0 Hz, 1H), 7.52 (d, J=9.2 Hz, 2H), 9.53 (brs, 1H), 9.94 (brs, 1H).

Example 32

2-fluoro-3-(2-hydroxyethoxy)-5-methoxybenzaldehyde

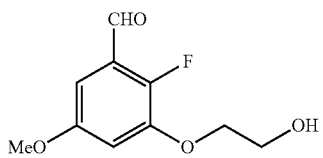 [SMILES: COc1cc(C=O)c(F)c(OCCO)c1]

Under nitrogen atmosphere, a mixture of 2-fluoro-3-hydroxy-5-methoxybenzaldehyde (17.01 g, 100 mmol), 2-chloroethanol (8.72 mL, 130 mmol), sodium iodide (19.49 g, 130 mmol), potassium carbonate (17.97 g, 130 mmol), and N,N-dimethylformamide (85 mL) was stirred at 100° C. for 4.25 hours, after which 2-chloroethanol (4.70 mL, 70 mmol), sodium iodide (10.49 g, 70 mmol), potassium carbonate (9.68 g, 70 mmol), and N,N-dimethylformamide (17 mL) were added thereto, and the resulting mixture was stirred at the same temperature for 4.25 hours. To the mixture, 2-chloroethanol (2.01 mL, 30 mmol), sodium iodide (4.50 g, 30 mmol), and potassium carbonate (4.15 g, 30 mmol) were added, and the resulting mixture was stirred at 100° C. for 7 hours, after which 2-chloroethanol (2.01 mL, 30 mmol) was added thereto, and the resulting mixture was stirred at the same temperature for 2.5 hours. After cooling the mixture, ethyl acetate and water were added to the reaction mixture, and the resulting mixture was extracted. The organic layer was washed with water and concentrated under reduced pressure to obtain a crude product containing the captioned compound (17.70 g) as a red-brown solid.

$^1$H-NMR (400 MHz, CDCl$_3$): δ=2.17 (t, J=6.4 Hz, 1H), 3.82 (s, 3H), 3.98-4.04 (m, 2H), 4.14-4.17 (m, 2H), 6.78-6.82 (m, 1H), 6.85-6.89 (m, 1H), 10.36 (s, 1H).

Example 33

2-(4-cyanophenylamino)-2-[2-fluoro-3-(2-hydroxyethoxy)-5-methoxyphenyl]thioacetamide

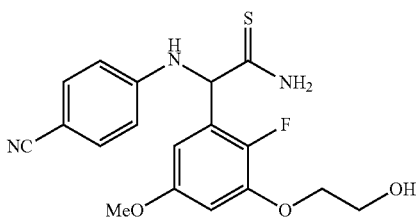 [SMILES: COc1cc(OCCO)c(F)c(C(Nc2ccc(C#N)cc2)C(N)=S)c1]

Under nitrogen atmosphere, to a solution of the crude product containing 2-fluoro-3-(2-hydroxyethoxy)-5-methoxybenzaldehyde (16.68 g, 77.9 mmol), 4-aminobenzonitrile (9.20 g, 77.9 mmol), and guanidine hydrochloride (372 mg, 3.9 mmol) in methanol (132 mL), trimethylsilylcyanide (12.09 g, 116.9 mmol) was added at room temperature, and the resulting mixture was stirred at 40° C. for 19 hours. After cooling the mixture, tetrahydrofuran (132 mL) was added thereto under water cooling, and 20% aqueous ammonium sulfide solution (133 mL) was added dropwise to the resulting mixture, after which the resulting mixture was stirred at room temperature. After completion of the reaction, ethyl acetate and 5% saline were added to the reaction mixture, and the resulting mixture was extracted. The organic layer was washed with 5% saline and then concentrated under reduced pressure. Methanol (100 mL) was added to the residue obtained, and the resulting mixture was concentrated under reduced pressure. Further, methanol (100 mL) was added to the residue obtained, and the resulting mixture was concentrated under reduced pressure. Methanol (120 mL) was added to the residue obtained, and the resulting mixture was stirred overnight at room temperature. The precipitated solid was filtered and dried to obtain the captioned compound (20.46 g) as a pale purple solid.

$^1$H-NMR (400 MHz, DMSO-d$_6$): δ=3.68-3.73 (m, 5H), 4.02-4.07 (m, 2H), 4.90 (t, J=5.6 Hz, 1H), 5.44 (d, J=5.6 Hz,

1H), 6.60-6.64 (m, 1H), 6.68-6.73 (m, 3H), 7.15 (d, J=6.0 Hz, 1H), 7.52 (d, J=9.2 Hz, 2H), 9.53 (brs, 1H), 9.94 (brs, 1H).

Example 34

2-(4-cyanophenylimino)-2-[2-fluoro-3-(2-hydroxyethoxy)-5-methoxyphenyl]thioacetimidate methyl ester

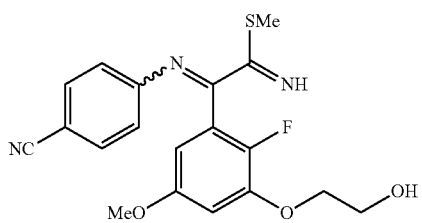 [SMILES: COc1cc(OCCO)c(F)c(C(=Nc2ccc(C#N)cc2)C(=N)SC)c1]

To a suspension of 2-(4-cyanophenylamino)-2-[2-fluoro-3-(2-hydroxyethoxy)-5-methoxypheny l]thioacetamide (100 g, 267 mmol) in acetonitrile (600 mL), under water cooling, trimethyloxonium tetrafluoroborate (39.5 g, 267 mmol) was added over 20 minutes, and the resulting mixture was stirred at room temperature for 0.5 hours. To the solution, under water cooling, manganese dioxide (139 g, 1.602 mmol) was added over 10 minutes, and the resulting mixture was stirred at room temperature for 1 hour. Toluene (500 mL) was added to the reaction mixture, and the resulting mixture was filtered, after which the resulting filter cake was washed with ethyl acetate. The filtrate obtained and a washing solution were combined, and the resulting mixture was sequentially washed with saturated aqueous sodium hydrogen carbonate solution, water, and saturated saline, dried over anhydrous magnesium sulfate, and then filtered. The filtrate obtained was concentrated under reduced pressure to obtain a crude product of the captioned compound as an oily product.
$^1$H-NMR (400 MHz, CDCl$_3$): δ=2.35 and 2.40 (s, 3H), 3.64 (s, 3H), 3.91-3.98 (m, 2H), 4.05 (t, J=5.2 Hz, 2H), 6.01-6.06 (m, 1H), 6.48-6.55 (m, 1H), 6.84 (d, J=8.4H, 2H), 7.15-7.20 (m, 1H), 7.50 (d, J=8.4 Hz, 2H).

Example 35

Carbonic acid {3-[1-(4-cyanophenylimino)-2-methoxycarbonylimino-2-methylsulfanylethyl]-2-fluoro-5-methoxyphenoxy}ethyl ester methyl ester

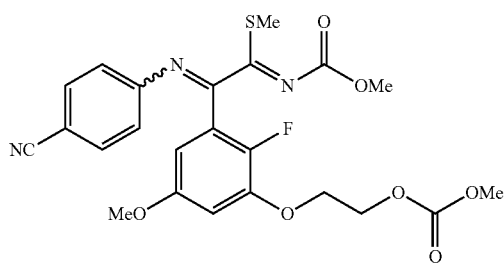 [SMILES: COC(=O)/N=C(\SC)C(=Nc1ccc(C#N)cc1)c1cc(OC)cc(OCCOC(=O)OC)c1F]

To a solution of the crude product of 2-(4-cyanophenylimino)-2-[2-fluoro-3-(2-hydroxyethoxy)-5-methoxyphenyl]thioacetimidate methyl ester obtained in Example 34 in ethyl acetate (100 mL), toluene (700 mL) followed by methyl chloroformate (61.9 mL, 801 mmol) and 2,4,6-collidine (123 mL, 935 mmol) was added, and the resulting mixture was stirred at 85° C. overnight. After cooling the mixture, ethyl acetate and 1 N hydrochloric acid were added to the reaction mixture, and the resulting mixture was extracted. The organic layer was sequentially washed with saturated aqueous sodium hydrogen carbonate solution and saturated saline, dried over anhydrous magnesium sulfate, and then filtered. The filtrate obtained was passed through a silica gel pad and then concentrated under reduced pressure to obtain a crude product of the captioned compound (119.4 g) as an oily product.
$^1$H-NMR (400 MHz, CDCl$_3$): δ=2.34 and 2.48 (s, 3H), 3.59-3.84 (m, 9H), 4.15 and 4.25 (d, J=4.8 Hz, 2H), 4.44 and 4.51 (d, J=4.8 Hz, 2H), 6.18 and 6.98 (dd, J=3.2, 4.4 Hz, 1H), 6.52 and 6.71 (dd, J=3.2, 6.8 Hz, 1H), 6.82 and 7.08 (d, J=8.8 Hz, 2H), 7.50 and 7.61 (d, J=8.8 Hz, 2H).

Example 36

Carbonic acid 2-{3-[(4-cyanophenylimino)-(5-oxo-1-pyrimidin-2-yl-4,5-dihydro-1H-[1,2,4]-triazol-3-yl)methyl]-2-fluoro-5-methoxyphenoxy}ethyl ester methyl ester

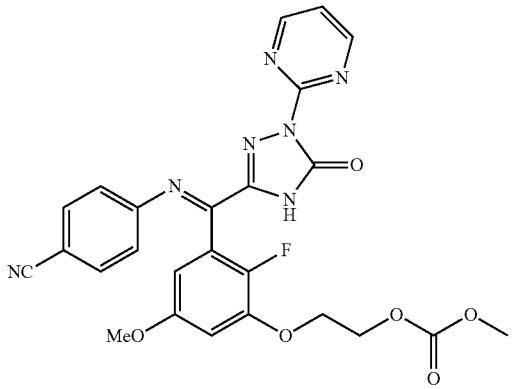 [SMILES: COC(=O)OCCOc1cc(OC)cc(/C(=N\c2ccc(C#N)cc2)c2nn(-c3ncccn3)c(=O)[nH]2)c1F]

A mixture of the crude product containing carbonic acid {3-[1-(4-cyanophenylimino)-2-methoxycarbonylimino-2-methylsulfanylethyl]-2-fluoro-5-methoxyphenoxy}ethyl ester methyl ester (37 g, 73.4 mmol), toluene (740 mL), pyrimidin-2-yl-hydrazine (8.08 g, 73.4 mmol), and triethylamine (12.3 mL, 88.2 mmol) was heated at 50° C. for 10 minutes under stirring, gradually heated to 110° C., and heated at 110° C. for 4 hours under stirring. The mixture was gradually cooled to room temperature, and then the precipitate was filtered and dried to obtain the captioned compound (23.89 g) as a pale yellow powder.
$^1$H-NMR (400 MHz, CDCl$_3$): δ=3.68 (s, 3H), 3.80 (s, 3H), 4.15 (t, J=4.4 Hz, 2H), 4.43 (t, J=4.4 Hz, 2H), 6.29 (t, J=3.2 Hz, 1H), 6.54 (dd, J=3.2, 6.4 Hz, 1H), 6.86 (d, J=8.4 Hz, 2H), 7.26 (t, J=4.8 Hz, 1H), 7.53 (d, J=8.4 Hz, 2H), 8.83 (d, J=4.8 Hz, 2H), 9.43 (brs, 1H).

Example 37

Carbonic acid 2-{3-[(4-cyanophenylamino)-(5-oxo-1-pyrimidin-2-yl-4,5-dihydro-1H-[1,2,4]-triazol-3-yl)methyl]-2-fluoro-5-methoxyphenoxy}ethyl ester methyl ester

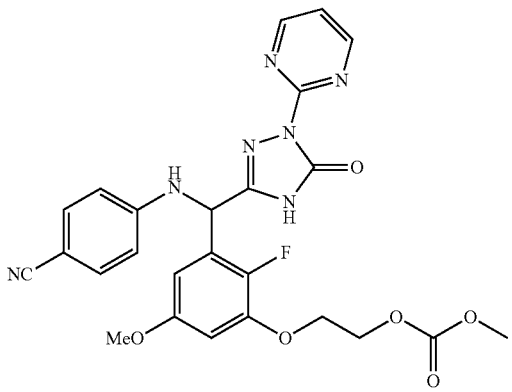 [SMILES: COC(=O)OCCOc1cc(OC)cc(C(Nc2ccc(C#N)cc2)c2nn(-c3ncccn3)c(=O)[nH]2)c1F]

To a mixture of carbonic acid 2-{3-[(4-cyanophenylimino)-(5-oxo-1-pyrimidin-2-yl-4,5-dihydro-1H-[1,2,4]-triazol-3-yl)methyl]-2-fluoro-5-methoxyphenoxy}ethyl ester methyl ester (2.0 g, 3.75 mmol), 2-methylpyridine borane [CAS No. 3999-38-0] (0.802 mg, 7.5 mmol), methanol (6 mL), and water (6 mL), acetic acid (6 mL) was added dropwise, and the resulting mixture was stirred at room temperature for 24 hours. The reaction solution was filtered and washed with tetrahydrofuran (6 mL). The solid obtained was dried under air flow to obtain a crude product of the captioned compound (2.02 g) as a white solid.

$^1$H-NMR (400 MHz, DMSO-$d_6$): δ=3.71 (s, 6H), 4.25-4.35 (m, 2H), 4.40-4.50 (m, 2H), 5.89 (d, J=7.6 Hz, 1H), 6.60-6.68 (m, 1H), 6.72-6.85 (m, 3H), 7.41 (t, J=5.6 Hz, 1H), 7.52 (d, J=8.4 Hz, 2H), 7.64 (d, J=7.2 Hz, 1H), 8.81 (d, J=5.6 Hz, 2H), 12.26 (brs, 1H)

Example 38

4-{[[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}benzonitrile

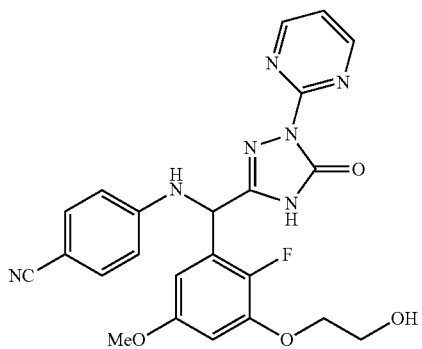 [SMILES: COc1cc(OCCO)c(F)c(C(Nc2ccc(C#N)cc2)c2nn(-c3ncccn3)c(=O)[nH]2)c1]

To a mixture of the crude product of carbonic acid 2-{3-[(4-cyanophenylamino)-(5-oxo-1-pyrimidin-2-yl-4,5-dihydro-1H-[1,2,4]-triazol-3-yl)methyl]-2-fluoro-5-methoxyphenoxy}ethyl ester methyl ester (2.02 g), methanol (6 mL), tetrahydrofuran (6 mL), and water (2.3 mL), 5 N aqueous sodium hydroxide solution (3.71 mL, 18.6 mmol) was added. Methanol (2 mL), tetrahydrofuran (2 mL), and water (2 mL) were added to the reaction solution, and the resulting mixture was stirred at room temperature for 23 hours and 30 minutes. Acetic acid (4.25 mL) was added to the reaction solution, and the resulting mixture was stirred for 20 minutes, after which water (20 mL) was added dropwise thereto, and the resulting mixture was stirred at room temperature for 1 day. The precipitated solid was filtered and washed with water (6 mL) and tert-butyl methyl ether (6 mL). The solid obtained was dried under air flow to obtain the captioned compound (1.576 g) as a white solid.

$^1$H-NMR (DMSO-$d_6$): δ=3.66-3.78 (m, 5H), 4.07 (d, J=5.2 Hz, 2H), 4.92 (t, J=5.2 Hz, 1H), 5.88 (d, J=7.6 Hz, 1H), 6.55-6.65 (m, 1H), 6.70-6.82 (m, 3H), 7.41 (t, J=4.8 Hz, 1H), 7.52 (d, J=8.8 Hz, 2H), 7.63 (d, J=7.6 Hz, 1H), 8.81 (d, J=4.8 Hz, 2H), 12.26 (brs, 1H).

Example 39

4-{[[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}benzonitrile

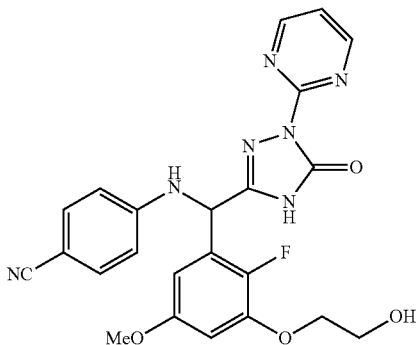 [SMILES: COc1cc(OCCO)c(F)c(C(Nc2ccc(C#N)cc2)c2nn(-c3ncccn3)c(=O)[nH]2)c1]

A suspension of carbonic acid 2-{3-[(4-cyanophenylimino)-(5-oxo-1-pyrimidin-2-yl-4,5-dihydro-1H-[1,2,4]-triazol-3-yl)methyl]-2-fluoro-5-methoxyphenoxy}ethyl ester methyl ester (25.0 g, 47.1 mmol) and methanol (90 mL) was cooled to 15° C. Sodium cyanoborohydride (5.45 g, 87 mmol) was added thereto, and was rinsed with methanol (10 mL). Acetic acid (21.5 mL, 375 mmol) was added dropwise thereto, and the resulting mixture was stirred at room temperature for 28 hours. The mixture was cooled in an ice-water bath, and tetrahydrofuran (100 mL) and a 5 N aqueous sodium hydroxide solution (113 mL, 565 mmol) were added thereto. After stirring the resulting mixture for 18 hours, the mixture was cooled to 15° C. or below, and acetic acid (81 mL, 1.410 mol) was added thereto. To the solution obtained, a seed crystal (5.0 mg) of the captioned compound was added at room temperature, and water (250 mL) was added dropwise to the resulting mixture, after which the resulting mixture was stirred at 4° C. for 21.5 hours. The suspension obtained was filtered and was washed with 25% aqueous methanol (100 mL) and dried at 40° C. under reduced pressure to obtain the captioned compound (21.1 g) as a white solid.

¹H-NMR (400 MHz, DMSO-d₆): δ=3.70 (s, 3H), 3.73 (dt, J=5.2, 5.2 Hz, 2H), 4.07 (t, J=4.8 Hz, 2H), 4.92 (t, J=4.8 Hz, 1H), 5.88 (d, J=7.2 Hz, 1H), 6.53-6.63 (m, 1H), 6.70-6.84 (m, 3H), 7.41 (dt, J=1.2, 4.8 Hz, 1H), 7.53 (d, J=8.0 Hz, 2H), 7.63 (d, J=7.6 Hz, 1H), 8.81 (dd, J=1.2, 4.8 Hz, 2H), 12.26 (brs, 1H).

Example 40

4-{[[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}benzamidine hydrochloride

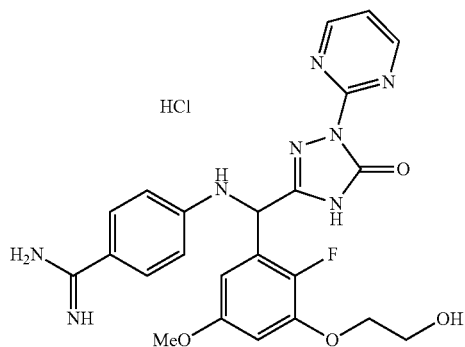 [SMILES: COc1cc(OCCO)c(F)c(C(Nc2ccc(C(=N)N)cc2)c2nn(-c3ncccn3)c(=O)[nH]2)c1 ; Cl]

A suspension of 4-{[[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}benzonitrile (5.12 g, 97.6% purity, 10.5 mmol) and methanol (15 mL) was cooled to 5° C. or below. Acetyl chloride (15 mL, 211 mmol) was slowly added thereto, and the resulting mixture was stirred at 10° C. or below for 18.5 hours. To the mixture obtained, methanol (25 mL) was added, and the resulting mixture was stirred for 1 hour or more. The mixture was concentrated at 10° C. or below under reduced pressure, and further subjected to azeotropic distillation twice with methanol (20 mL). The methanol (15 mL) was added to the residue to dissolve the same, and the resulting mixture was cooled to 10° C. or below. Ammonium chloride (5.05 g, 94.5 mmol) followed by a solution of triethylamine (14.6 mL, 105 mmol) in methanol (15 mL) was added thereto at 20° C. or below. The resulting mixture was stirred at room temperature for 18 hours, and 2 N hydrochloric acid (50 mL) was added thereto at 20° C. or below, and the resulting mixture was stirred at room temperature for 18 hours or more. After cooling to 10° C. or below, the suspension obtained was filtered and sequentially washed with water (10 mL) and tert-butyl methyl ether (10 mL). The solid obtained was dried at 40° C. under reduced pressure to obtain the captioned compound (4.7 g) as a white solid.

¹H-NMR (CD₃OD): δ=3.73 (s, 3H), 3.89 (t, J=4.8 Hz, 2H), 4.11 (t, J=4.8 Hz, 2H), 6.01 (s, 1H), 6.60-6.64 (m, 1H), 6.66-6.72 (m, 1H), 6.87 (d, J=8.8 Hz, 2H), 7.37 (t, J=5.2 Hz, 1H), 7.63 (d, J=8.8 Hz, 2H), 8.79 (d, J=5.2 Hz, 2H).

Example 41

4-{[(R)-[2-fluoro-3-(2-hydroxyethoxy)-5-methoxyphenyl](5-oxo-1-pyrimidin-2-yl-4,5-dihydro-1H-1,2,4-triazol-3-yl)methyl]amino}benzamidine (R)-methoxyphenylacetate

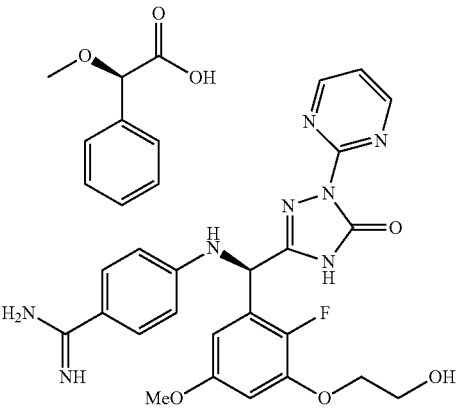

A suspension of 4-{[[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}benzamidine hydrochloride (4.73 g, purity 92%, 8.2 mmol) and methanol (131 mL) was heated to 60° C. to bring into solution. Triethylamine (1.71 mL, 12.3 mmol) was added thereto at 60° C., and the resulting mixture was stirred for minutes or more. To the suspension obtained, (R)-(−)-α-methoxyphenylacetic acid (2.73 g, 16.4 mmol) and acetic acid (4.35 mL) were added to bring the same into solution. The solution obtained was allowed to cool to 35° C., and a seed crystal of the captioned compound was added thereto, and the resulting mixture was stirred at room temperature for 20 hours and at 0° C. for 3 hours. The resulting solid was filtered, sequentially washed with ethanol (13 mL) and tert-butyl methyl ether (13 mL), and then dried at room temperature under reduced pressure to obtain the captioned compound (2.1 g) as a white solid.

¹H-NMR (CD₃OD): δ=3.35 (s, 3H), 3.73 (s, 3H), 3.89 (t, J=4.4 Hz, 2H), 4.11 (t, J=4.4 Hz, 2H), 4.56 (s, 1H), 6.00 (s, 1H), 6.60-6.64 (m, 1H), 6.65-6.71 (m, 1H), 6.87 (d, J=8.8 Hz, 2H), 7.22-7.32 (m, 3H), 7.35 (t, J=4.8 Hz, 1H), 7.47 (dd, J=1.6, 7.6 Hz, 2H), 7.63 (dd, J=2.0, 7.2 Hz, 2H), 8.78 (d, J=4.8 Hz, 2H).

Example 42

4-{[(R)-[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}benzamidine hydrochloride

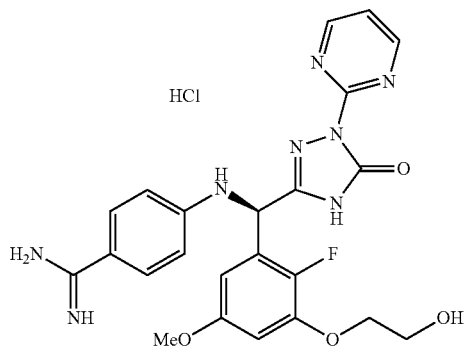 [SMILES: COc1cc(OCCO)c(F)c([C@@H](Nc2ccc(C(=N)N)cc2)c2nn(-c3ncccn3)c(=O)[nH]2)c1 ; Cl]

To a mixture of 4-{[(R)-[2-fluoro-3-(2-hydroxyethoxy)-5-methoxyphenyl](5-oxo-1-pyrimidin-2-yl-4,5-dihydro-1H-1,2,4-triazol-3-yl)methyl]amino}benzamidine (R)-methoxyphenylacetate (20 g, 30.2 mmol), methanol (200 mL), and ethanol (400 mL), 5 N hydrochloric acid (20 mL, 100 mmol) was added to dissolve the same. A seed crystal of the captioned compound was added to the reaction solution, and the resulting mixture was stirred overnight at room temperature. The precipitated solid was filtered and sequentially washed with a mixed solvent of ethanol and methanol (ethanol: methanol=2:1, 50 mL) and tert-butyl methyl ether (50 mL). The solid obtained was dried under air flow to obtain the captioned compound (14.52 g) as a white solid.

$^1$H-NMR (CD$_3$OD): δ=3.73 (s, 3H), 3.89 (t, J=4.8 Hz, 2H), 4.11 (t, J=4.8 Hz, 2H), 6.01 (s, 1H), 6.60-6.64 (m, 1H), 6.66-6.72 (m, 1H), 6.87 (d, J=8.8 Hz, 2H), 7.37 (t, J=5.2 Hz, 1H), 7.63 (d, J=8.8 Hz, 2H), 8.79 (d, J=5.2 Hz, 2H).

Mass spectrum (ESI): m/z 495 (M+H)$^+$

Example 43

[1-amino(4-{[(R)-[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}phenyl)methylene]carbamic acid 2-methylallyl ester

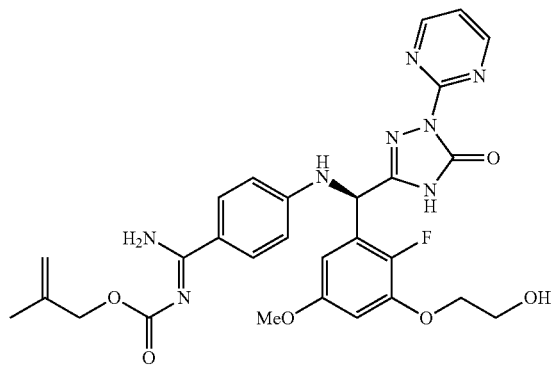 [SMILES: C=C(C)COC(=O)/N=C(\N)c1ccc(N[C@@H](c2nn(-c3ncccn3)c(=O)[nH]2)c2cc(OC)cc(OCCO)c2F)cc1]

To a mixture of 4-{[(R)-[2-fluoro-3-(2-hydroxyethoxy)-5-methoxyphenyl](5-oxo-1-pyrimidin-2-yl-4,5-dihydro-1H-1,2,4-triazol-3-yl)methyl]amino}benzamidine (R)-methoxyphenylacetate (0.5 g, 0.755 mmol), potassium carbonate (104 mg, 0.755 mmol), and dimethyl sulfoxide (1.5 mL), carbonic acid 2-methylallyl ester phenyl ester [CAS No. 138621-73-5] (145 mg, 0.755 mmol) was added, and the resulting mixture was stirred at 60° C. for 2 hours and 30 minutes. After cooling the mixture, the reaction solution was added to a mixture of ethyl acetate (5 mL) and water (15 mL), and an aqueous acetic acid solution (prepared from acetic acid (0.1 mL) and water (5 mL)) was added dropwise to the resulting mixture with stirring. The precipitated solid was filtered and sequentially washed with ethyl acetate (10 mL) and water (10 mL). The solid obtained was dried under air flow to obtain the captioned compound (361 mg) as a yellow solid.

$^1$H-NMR (CD$_3$OD): δ=1.79 (s, 3H), 3.71 (s, 3H), 3.87 (t, J=4.8 Hz, 2H), 4.09 (t, J=4.8 Hz, 2H), 4.55 (s, 2H), 4.91 (s, 1H), 5.02 (s, 1H), 5.96 (s, 1H), 6.60-6.67 (m, 2H), 6.78 (d, J=8.8 Hz, 2H), 7.34 (t, J=4.8 Hz, 1H), 7.71 (d, J=8.8 Hz, 2H), 8.77 (d, J=4.8 Hz, 2H)

Mass spectrum (ESI): m/z 593 (M+H)$^+$

Example 44

[1-amino(4-{[(R)-[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}phenyl)methylene]carbamic acid 2-methylallyl ester

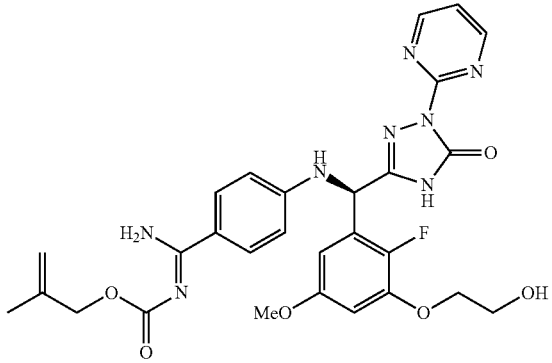 [SMILES: C=C(C)COC(=O)/N=C(\N)c1ccc(N[C@@H](c2nn(-c3ncccn3)c(=O)[nH]2)c2cc(OC)cc(OCCO)c2F)cc1]

To a mixture of 4-{[(R)-[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}benzamidine hydrochloride (5.0 g, 9.41 mmol), potassium carbonate (2.6 g, 18.8 mmol), and dimethyl sulfoxide (15 mL), carbonic acid 2-methylallyl ester phenyl ester [CAS No. 138621-73-5] (1.57 g, 8.19 mmol) was added, and the resulting mixture was stirred at room temperature for 4 days. Ethyl acetate (100 mL) and water (200 mL) were added to the reaction solution, and the aqueous layer was collected. Acetic acid (1.62 mL, 28.2 mmol) was added dropwise to the aqueous layer with stirring, and the precipitated solid was filtered and sequentially washed with water (20 mL) and diethyl ether (20 mL). The solid obtained was suspended in ethyl acetate, filtered, and then dried under air flow. The dried solid was suspended in ethyl acetate (50 mL), and the suspension was stirred for 1 day. The suspension was filtered, and the solid obtained was washed with ethyl acetate and dried under air flow to obtain the captioned compound (4.87 g) as a yellow solid.

$^1$H-NMR (CD$_3$OD): δ=1.79 (s, 3H), 3.71 (s, 3H), 3.87 (t, J=4.8 Hz, 2H), 4.09 (t, J=4.8 Hz, 2H), 4.55 (s, 2H), 4.91 (s, 1H), 5.02 (s, 1H), 5.96 (s, 1H), 6.60-6.67 (m, 2H), 6.78 (d, J=8.8 Hz, 2H), 7.34 (t, J=4.8 Hz, 1H), 7.71 (d, J=8.8 Hz, 2H), 8.77 (d, J=4.8 Hz, 2H)

Mass spectrum (ESI): m/z 593 (M+H)$^+$

Example 45

Acetic acid 2-{3-[(R)-{4-[amino(2-methylallyloxycarbonylimino)methyl]phenylamino}-(5-oxo-1-pyrimidin-2-yl-4,5-dihydro-1H-[1,2,4]-triazol-3-yl)methyl]-2-fluoro-5-methoxyphenoxy}ethyl ester

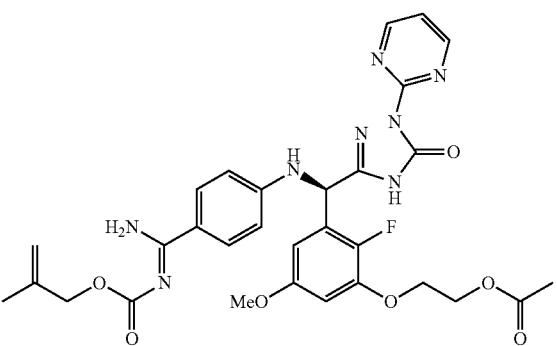 [SMILES: C=C(C)COC(=O)/N=C(\N)c1ccc(N[C@@H](C(=N)NC(=O)Nc2ncccn2)c2cc(OC)cc(OCCOC(C)=O)c2F)cc1]

To a mixture of 4-{[(R)-[2-fluoro-3-(2-hy droxy ethoxy)-5-methoxyphenyl] (5-oxo-1-pyrimidi n-2-yl-4,5-dihydro-1H-1,2,4-triazol-3-yl)methyl]amino}benzamidine (R)-methoxyphenylacetate (0.5 g, 0.755 mmol), carbonic acid 2-methylallyl ester 4-nitrophenyl ester [CAS No. 218598-29-9] (179 mg, 0.755 mmol), and N,N-dimethylformamide (1.5 mL), triethylamine (0.532 mL, 3.78 mmol) was added, and the resulting mixture was stirred overnight at room temperature. To the reaction solution, 4-dimethylaminopyridine (2.78 mg, 0.0228 mmol) and acetic anhydride (0.157 mL, 1.66 mmol) were added, and the resulting mixture was stirred at room temperature for 1 hour and 20 minutes. A buffer of pH 6 was added to the reaction solution, and the resulting mixture was extracted four times with a mixture of ethyl acetate and tetrahydrofuran (ethyl acetate:tetrahydrofuran=1:1). All the organic layers were combined, washed with saturated aqueous sodium chloride solution, dried over anhydrous magnesium sulfate, and then filtered. The filtrate obtained was concentrated under reduced pressure, after which acetone (3 mL) was added to the residue obtained, and the resulting mixture was stirred at room temperature for 3 days. The precipitated solid was filtered and washed with acetone (1.5 mL). The solid obtained was dried under air flow to obtain the captioned compound (246 mg).

$^1$H-NMR (CD$_3$OD): δ=1.79 (s, 3H), 2.05 (s, 3H), 3.72 (s, 3H), 4.22-4.27 (m, 2H), 4.37-4.44 (m, 2H), 4.55 (s, 2H), 4.90 (s, 1H), 5.02 (s, 1H), 5.96 (s, 1H), 6.62-6.69 (m, 2H), 6.78 (d, J=9.2 Hz, 2H), 7.35 (t, J=4.8 Hz, 1H), 7.72 (d, J=9.2 Hz, 2H), 8.77 (d, J=4.8 Hz, 2H)

Mass spectrum (ESI): m/z 635 (M+H)$^+$

Example 46

Acetic acid 2-{3-[(R)-{4-[amino(2-methylallyloxy-carbonylimino)methyl]phenylamino}-(5-oxo-1-pyrimidin-2-yl-4,5-dihydro-1H-[1,2,4]-triazol-3-yl)methyl]-2-fluoro-5-methoxyphenoxy}ethyl ester

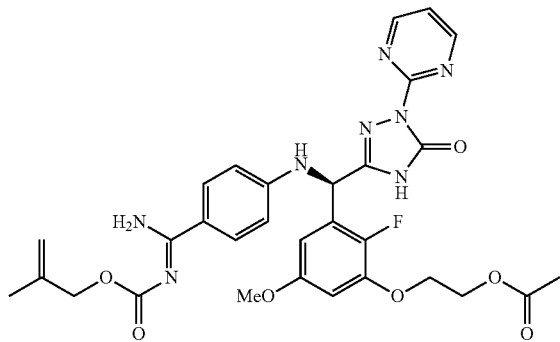 [SMILES: C=C(C)COC(=O)/N=C(\N)c1ccc(N[C@@H](c2nn(-c3ncccn3)c(=O)[nH]2)c2cc(OC)cc(OCCOC(C)=O)c2F)cc1]

At room temperature, 4-{[(R)-[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}benzamidine hydrochloride (5.058 g, 9.42 mmol) was dissolved in dimethyl sulfoxide (15 mL), and potassium carbonate (3.91 g, 28.3 mmol) was added thereto. To the resulting mixture, 2-methyl-allyl phenyl carbonate (1.81 g, 9.42 mmol) was added under stirring at room temperature, and the resulting mixture was stirred for 18 hours. Thereafter, 4-dimethylaminopyridine (57.5 mg, 0.471 mmol) and acetic anhydride (2.23 mL, 23.6 mmol) were added to the reaction solution, and the resulting mixture was stirred for 1.5 hours. Further, acetic anhydride (0.223 mL, 2.36 mmol) was added to the mixture, and the resulting mixture was stirred for 2 hours. To the reaction solution, tetrahydrofuran (20 mL) and ethyl acetate (40 mL) were added, and 5% aqueous sodium hydrogen carbonate solution (50 g) was added to quench the reaction, after which the layers were separated at 50° C. Furthermore, the aqueous layer was extracted twice with a mixture of tetrahydrofuran (20 mL) and ethyl acetate (40 mL). The organic layer was combined, washed twice with 5% aqueous sodium hydrogen carbonate solution (25 g) and once with 5% saline, and then concentrated under reduced pressure. Acetone (30 mL) was added to the residue obtained, and the resulting mixture was stirred at room temperature for 3 hours, after which tert-butyl methyl ether (25 mL) was added to the mixture, and the resulting mixture was stirred at 4° C. for 16 hours. The precipitate was filtered and dried to obtain the captioned compound (3.74 g) as a pale yellow solid.

$^1$H-NMR (400 MHz, DMSO-d$_6$): δ=1.72 (s, 3H), 2.04 (s, 3H), 3.71 (s, 3H), 4.27 (m, 2H), 4.34 (m, 2H), 4.44 (s, 2H), 4.87 (s, 1H), 4.94 (s, 1H), 5.90 (d, J=7.6 Hz, 1H), 6.67 (m, 1H), 6.73 (d, J=8.8 Hz, 2H), 6.76 (m, 1H), 7.34 (d, J=7.6 Hz, 1H), 7.41 (t, J=4.8 Hz, 1H), 7.82 (d, J=8.8 Hz, 2H), 8.81 (d, J=4.8 Hz, 1H), 12.27 (brs, 1H).

Mass spectrum (ESI): m/z 635 (M+H)$^+$

Example 47

3-methoxy-2,2-dimethylpropionic acid 5-[(R)-[3-(2-acetoxyethoxy)-2-fluoro-5-methoxyphenyl]-(4-{amino[2-methylallyloxycarbonylimino] methyl}phenylamino)methyl]-2-pyrimidin-2-yl-2H-[1,2,4]triazol-3-yloxymethyl ester

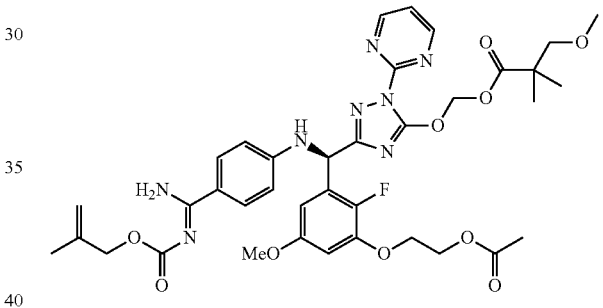

Under nitrogen atmosphere, a mixture of acetic acid 2-{3-[(R)-{4-[amino(2-methylallyloxycarbonylimino)methyl] phenylamino}-(5-oxo-1-pyrimidin-2-yl-4,5-dihydro-1H-[1,2,4]-triazol-3-yl)methyl]-2-fluoro-5-methoxyphenoxyl} ethyl ester (1.0 g, 1.57 mmol), 3-methoxy-2,2-dimethylpropionic acid chloromethyl ester (598 mg, 3.31 mmol), rubidium carbonate (255 mg, 1.10 mmol), and N,N-dimethylacetamide (20 mL) was stirred at 85° C. for 75 minutes. After cooling to room temperature, ethyl acetate (100 mL) and water (100 mL) were added to the reaction mixture. The organic layer was collected, sequentially washed with water (100 mL) and saturated aqueous sodium chloride solution, and dried over anhydrous magnesium sulfate. The desiccant was filtered off, and the filtrate obtained was concentrated under reduced pressure. The residue obtained was purified by silica gel column chromatography (mixed solvent of heptane-ethyl acetate) to obtain the captioned compound (560 mg) as a solid.

$^1$H-NMR (CDCl$_3$): δ=1.14 (s, 3H), 1.15 (s, 3H), 1.80 (s, 3H), 2.09 (s, 3H), 3.16 (s, 3H), 3.31 (s, 2H), 3.70 (s, 3H), 4.19-4.21 (m, 2H), 4.41-4.44 (m, 2H), 4.57 (s, 2H), 4.91 (s, 1H), 5.03 (s, 1H), 5.51 (d, J=7.1 Hz, 1H), 6.11 (d, J=6.4 Hz, 1H), 6.12 (d, J=7.1 Hz, 1H), 6.21 (d, J=6.4 Hz, 1H), 6.44 (dd, J=2.9, 6.6 Hz, 1H), 6.68 (dd, J=2.9, 4.8 Hz, 1H), 6.71 (d, J=8.8 Hz, 2H), 7.30 (t, J=5.0 Hz, 1H), 7.73 (d, J=8.8 Hz, 2H), 8.82 (d, J=5.0 Hz, 2H).

Example 48

3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]-triazol-3-yloxymethyl ester

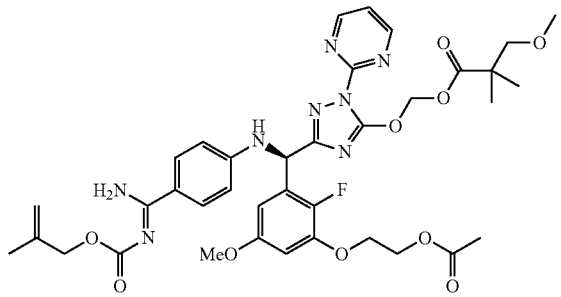 [SMILES: C=C(C)COC(=O)/N=C(\N)c1ccc(N[C@@H](c2nc(OCOC(=O)C(C)(C)COC)n(-c3ncccn3)n2)c2cc(OC)cc(OCCOC(C)=O)c2F)cc1]

Under nitrogen atmosphere, a mixture of [1-amino(4-{[(R)-[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}phenyl)methylene]carbamic acid 2-methylallyl ester (1.0 g, 1.69 mmol), 3-methoxy-2,2-dimethylpropionic acid chloromethyl ester (641 mg, 3.55 mmol), rubidium carbonate (312 mg, 1.35 mmol), and N,N-dimethylacetamide (30 mL) was stirred at 85° C. for 115 minutes. After cooling to room temperature, pyridine (0.69 mL, 8.45 mmol), 4-dimethylaminopyridine (20.7 mg, 0.169 mmol), and acetic anhydride (0.32 mL, 3.39 mmol) were added to the reaction solution, and the resulting mixture was stirred at room temperature for 2 hours. Ethyl acetate (150 mL) and water (150 mL) were added to the reaction mixture, and the resulting mixture was extracted. The organic layer was collected, sequentially washed with water (100 mL) and saturated aqueous sodium chloride solution, and dried over anhydrous magnesium sulfate. The desiccant was filtered off, and the filtrate obtained was concentrated under reduced pressure. The residue obtained was purified by silica gel column chromatography (mixed solvent of ethyl acetate-methanol) to obtain the captioned compound (610 mg) as a solid.

$^1$H-NMR (CDCl$_3$): δ=1.14 (s, 3H), 1.15 (s, 3H), 1.80 (s, 3H), 2.09 (s, 3H), 3.16 (s, 3H), 3.31 (s, 2H), 3.70 (s, 3H), 4.19-4.21 (m, 2H), 4.41-4.44 (m, 2H), 4.57 (s, 2H), 4.91 (s, 1H), 5.03 (s, 1H), 5.51 (d, J=7.1 Hz, 1H), 6.11 (d, J=6.4 Hz, 1H), 6.12 (d, J=7.1 Hz, 1H), 6.21 (d, J=6.4 Hz, 1H), 6.44 (dd, J=2.9, 6.6 Hz, 1H), 6.68 (dd, J=2.9, 4.8 Hz, 1H), 6.71 (d, J=8.8 Hz, 2H), 7.30 (t, J=5.0 Hz, 1H), 7.73 (d, J=8.8 Hz, 2H), 8.82 (d, J=5.0 Hz, 2H).

Example 49

3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester ethanesulfonate

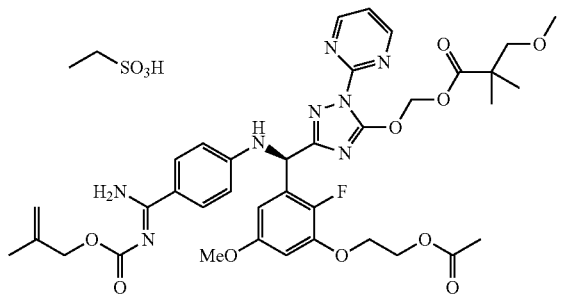

At room temperature, 3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester (1.0 g, 1.28 mmol) was dissolved in acetone (80 mL), and a solution of ethanesulfonic acid (127 mg, 1.15 mmol) in acetone (20 mL) was added dropwise thereto. To the resulting mixture, a seed crystal of the captioned compound was added, and the resulting mixture was stirred overnight at room temperature. The precipitated solid was filtered, washed with acetone, and then dried to obtain the captioned compound (889 mg) as a white powder.

$^1$H-NMR (CD$_3$OD): δ=1.068 (s, 3H), 1.073 (s, 3H), 1.29 (t, J=7.2 Hz, 3H), 1.82 (s, 3H), 2.06 (s, 3H), 2.79 (q, J=7.2 Hz, 2H), 3.03 (s, 3H), 3.22 (s, 2H), 3.73 (s, 3H), 4.23-4.25 (m, 2H), 4.39-4.42 (m, 2H), 4.75 (s, 2H), 5.02 (s, 1H), 5.10 (s, 1H), 6.11-6.13 (m, 3H), 6.63 (dd, J=3.2, 6.4 Hz, 1H), 6.74 (dd, J=3.2, 4.8 Hz, 1H), 6.91 (d, J=9.2 Hz, 2H), 7.50 (t, J=4.8 Hz, 1H), 7.66 (d, J=9.2 Hz, 2H), 8.88 (d, J=4.8 Hz, 2H).

Example 50

3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester propanesulfonate

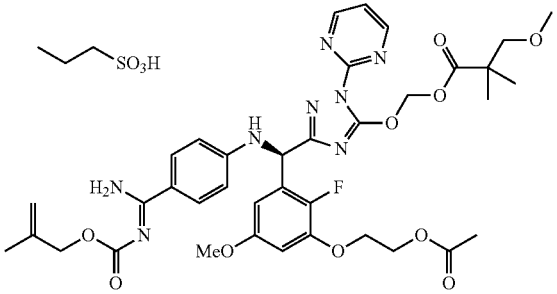

At room temperature, 3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester (1.0 g, 1.28 mmol) was dissolved in ethyl acetate (100 mL), a solution of 1-propanesulfonic acid [CAS No. 5284-66-2] (151 mg, 1.22 mmol) in ethyl acetate (5 mL) was added dropwise thereto. To the resulting mixture, a seed crystal of the captioned compound was added, and the resulting mixture was stirred overnight at room temperature. The precipitated solid was filtered, sequentially washed with ethyl acetate and tert-butyl methyl ether, and then dried to obtain the captioned compound (950 mg) as a white powder.

$^1$H-NMR (CD$_3$OD): δ=1.02 (t, J=7.2 Hz, 3H), 1.068 (s, 3H), 1.073 (s, 3H), 1.76-1.86 (m, 2H), 1.82 (s, 3H), 2.05 (s, 3H), 2.73-2.78 (m, 2H), 3.03 (s, 3H), 3.22 (d, J=0.8 Hz, 2H), 3.73 (s, 3H), 4.23-4.25 (m, 2H), 4.39-4.42 (m, 2H), 4.75 (s, 2H), 5.02 (s, 1H), 5.10 (s, 1H), 6.11-6.13 (m, 3H), 6.63 (dd, J=3.2, 7.2 Hz, 1H), 6.74 (dd, J=3.2, 4.8 Hz, 1H), 6.91 (d, J=9.2 Hz, 2H), 7.50 (t, J=4.8 Hz, 1H), 7.66 (d, J=9.2 Hz, 2H), 8.88 (d, J=4.8 Hz, 2H).

Example 51

Acetic acid 2-(3-{(R)-(4-{amino[2-methylallyloxycarbonylimino]methyl}phenylamino)-[5-(1-ethylpropoxycarbonyloxymethoxy)-1-pyrimidin-2-yl-1H-[1,2,4]triazol-3-yl]methyl}-2-fluoro-5-methoxyphenoxy)ethyl ester

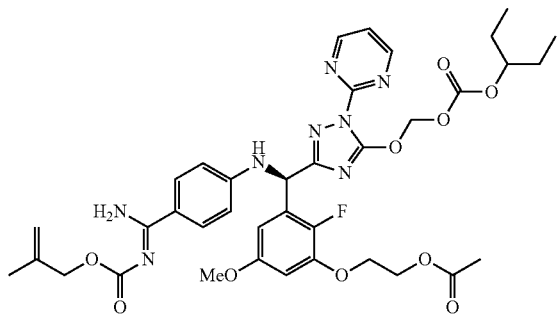 [SMILES: C=C(C)COC(=O)/N=C(\N)c1ccc(N[C@@H](c2nc(OCOC(=O)OC(CC)CC)n(-c3ncccn3)n2)c2cc(OC)cc(OCCOC(C)=O)c2F)cc1]

Under nitrogen atmosphere, a mixture of acetic acid 2-{3-[(R)-{4-[amino(2-methylallyloxycarbonylimino)methyl]phenylamino}-(5-oxo-1-pyrimidin-2-yl-4,5-dihydro-1H-[1,2,4]-triazol-3-yl)methyl]-2-fluoro-5-methoxyphenoxyl}ethyl ester (Example 45, 300 mg), carbonic acid chloromethyl ester 1-ethylpropyl ester [CAS No. 176310-42-2] (177 mg), potassium carbonate (80 mg) and N,N-dimethylformamide (5 mL) was stirred at 85° C. for 60 minutes. After cooling the mixture to room temperature, ethyl acetate and water were added thereto. The organic layer was collected, the aqueous layer was reextracted with ethyl acetate, and all the organic layers were combined. The organic layer was sequentially washed with water and with saturated aqueous sodium chloride solution, and dried over anhydrous magnesium sulfate. The desiccant was filtered off, and the filtrate obtained was concentrated under reduced pressure. The residue obtained was purified by silica gel column chromatography (mixed solvent of heptane-ethyl acetate-methanol) to obtain the captioned compound (130 mg) as a solid.

$^1$H-NMR (CD$_3$OD): δ=0.84 (dt, J=1.6, 7.6 Hz, 6H), 1.56 (m, 4H), 1.78 (s, 3H), 2.04 (s, 3H), 3.69 (s, 3H), 4.20-4.23 (m, 2H), 4.37-4.40 (m, 2H), 4.53 (s, 2H), 4.58 (m, 1H), 4.89 (br.s, 1H), 5.01 (br.s, 1H), 6.06 (s, 1H), 6.10 (d, J=6.0 Hz, 1H), 6.13 (d, J=6.0 Hz, 1H), 6.57 (dd, J=2.8, 6.8 Hz, 1H), 6.74 (dd, J=2.8, 4.4 Hz, 1H), 6.77 (d, J=9.2 Hz, 2H), 7.46 (t, J=5.2 Hz, 1H), 7.71 (d, J=8.8 Hz, 2H), 8.84 (d, J=5.2 Hz, 2H).

Example 52

Acetic acid 2-{3-[(R)-(4-{amino[2-methylallyloxycarbonylimino]methyl}phenylamino)-(5-isopropoxycarbonyloxymethoxy-1-pyrimidin-2-yl-1H-[1,2,4]triazol-3-yl)methyl]-2-fluoro-5-methoxyphenoxy}ethyl ester

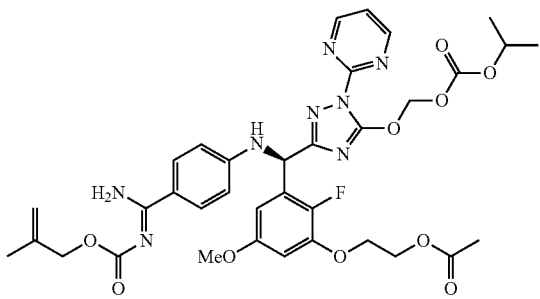 [SMILES: C=C(C)COC(=O)/N=C(\N)c1ccc(N[C@@H](c2nc(OCOC(=O)OC(C)C)n(-c3ncccn3)n2)c2cc(OC)cc(OCCOC(C)=O)c2F)cc1]

Under nitrogen atmosphere, a mixture of acetic acid 2-{3-[(R)-{4-[amino(2-methylallyloxycarbonylimino)methyl]phenylamino}-(5-oxo-1-pyrimidin-2-yl-4,5-dihydro-1H-[1,2,4]-triazol-3-yl)methyl]-2-fluoro-5-methoxyphenoxy}ethyl ester (Example 45, 75 mg), carbonic acid chloromethyl ester isopropyl ester [CAS No. 35180-01-9] (44.3 mg), potassium carbonate (33.3 mg) and N,N-dimethylformamide (3 mL) was stirred at 85° C. for 60 minutes. After cooling the reaction mixture to room temperature, ethyl acetate and water were added thereto. The organic layer was collected, the aqueous layer was reextracted with ethyl acetate, and all the organic layers were combined. The organic layer was sequentially washed with water and with saturated aqueous sodium chloride solution, and dried over anhydrous magnesium sulfate. The desiccant was filtered off, and the filtrate obtained was concentrated under reduced pressure. The residue obtained was purified by silica gel column chromatography (mixed solvent of heptane-ethyl acetate) to obtain the captioned compound (28.9 mg) as a solid.

$^1$H-NMR (CD$_3$CN): δ=1.26 (d, J=6.4 Hz, 6H), 1.78 (s, 3H), 2.04 (s, 3H), 3.72 (s, 3H), 4.23-4.26 (m, 2H), 4.38-4.40 (m, 2H), 4.52 (s, 2H), 4.87 (quint, J=6.0 Hz, 1H), 4.92 (br.s, 1H), 4.98 (br.s, 1H), 6.00 (d, J=7.6 Hz, 1H), 6.05 (d, J=7.6 Hz, 1H), 6.07 (s, 2H), 6.60 (dd, J=2.8, 6.8 Hz, 1H), 6.67 (dd, J=2.8, 4.8 Hz, 1H), 6.77 (d, J=8.8 Hz, 2H), 7.42 (t, J=4.8 Hz, 1H), 7.77 (d, J=8.8 Hz, 2H), 8.83 (d, J=4.8 Hz, 2H).

Example 53

Acetic acid 2-(3-{(R)-(4-{amino[propoxycarbonylimino]methyl}phenylamino)-[5-(1-ethylpropoxylcarbonyloxymethoxy)-1-pyrimidin-2-yl-1H-[1,2,4]-triazol-3-yl]methyl}-2-fluoro-5-methoxyphenoxy) ethyl ester (53a) Acetic acid 2-(3-{(R)-(4-carbamimidoylphenylamino)-[5-(1-ethylpropoxycarbonyloxymethoxy)-1-pyrimidin-2-yl-1H-[1,2,4]triazol-3-yl]methyl}-2-fluoro-5-methoxyphenoxy)ethyl ester acetic acid salt

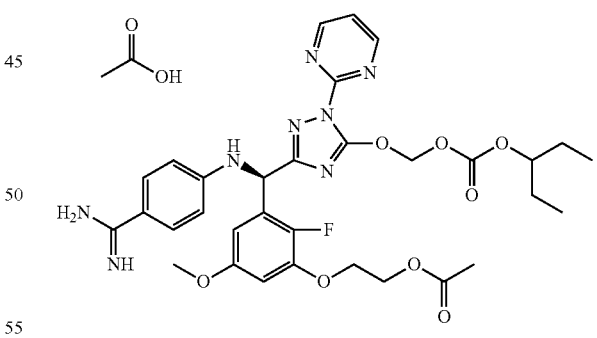

To a mixture of acetic acid 2-(3-{(R)-(4-{amino[2-methylallyloxycarbonylimino]methyl}phenylamino)-[5-(1-ethylpropoxycarbonyloxymethoxy)-1-pyrimidin-2-yl-1H-[1,2,4]triazol-3-yl]methyl}-2-fluoro-5-methoxyphenoxy)ethyl ester (Example 51, 266 mg), DMF (2 mL) and acetic acid (0.196 mL), tetrakis(triphenylphosphine) palladium (0) (20 mg) was added, and the resulting mixture was stirred overnight at an external temperature of 45° C. After cooling the mixture to room temperature, the reaction solution containing the captioned compound was divided into 4 equal lots, and used for the following reactions.

(53b) Acetic acid 2-(3-{(R)-(4-{amino[propoxycar-bonylimino]methyl}phenylamino)-[5-(1-ethylpro-poxycarbonyloxymethoxy)-1-pyrimidin-2-yl-1H-[1,2,4]triazol-3-yl]methyl}-2-fluoro-5-methoxyphenoxy)ethyl ester

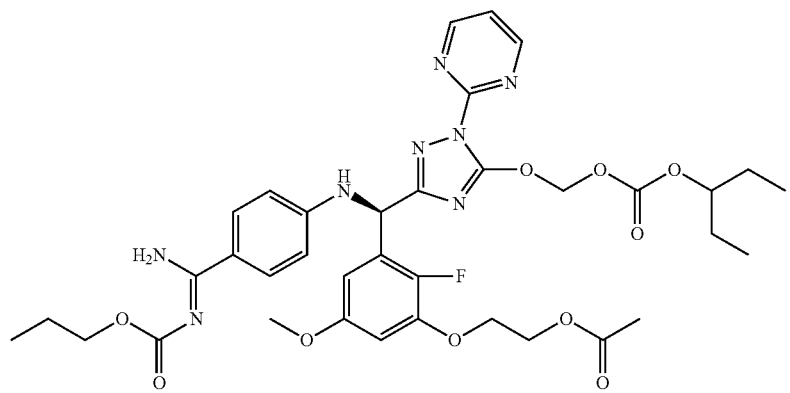 [SMILES: CCCOC(=O)/N=C(\N)c1ccc(N[C@@H](c2nc(OCOC(=O)OC(CC)CC)n(-c3ncccn3)n2)c2cc(OC)cc(OCCOC(C)=O)c2F)cc1]

To a mixture of one lot containing acetic acid 2-(3-{(R)-(4-carbamimidoylphenylamino)-[5-(1-ethylpropoxycarbo-nyloxym ethoxy)-1-pyrimidin-2-yl-1H-[1,2,4]triazol-3-yl]methyl}-2-fluoro-5-methoxyphenoxy)ethyl ester acetic acid salt (corresponding to 63.2 mg) obtained in Example 53a and DMF (3 ml), carbonic acid 4-nitrophenyl ester propyl ester [CAS No. 67036-12-8] (38.4 mg) and pyridine (55.2 μL) were added, and the resulting mixture was stirred at room temperature for 2 days. Ethyl acetate and water were added to the mixture, and the organic layer was collected. The organic layer was sequentially washed twice with water and with saturated aqueous sodium chloride solution, and dried over anhydrous sodium sulfate. The desiccant was filtered off, and the filtrate obtained was concentrated under reduced pressure. The residue obtained was purified by NAM silica gel column chromatography (mixed solvent of hexane-ethyl acetate) to obtain the captioned compound (23.21 mg).

$^1$H-NMR (CDCl$_3$): δ=0.86-0.91 (m, 6H), 0.98 (t, J=7.2 Hz, 3H), 1.58-1.66 (m, 4H), 1.70-1.78 (m, 2H), 2.1 (s, 3H), 3.70 (s, 3H), 4.08 (t, J=6.8 Hz), 4.20 (t, J=4.4 Hz, 2H), 4.43 (t, J=4.4 Hz, 2H), 4.61-4.67 (m, 1H), 5.44 (d, J=7.2 Hz, 1H), 6.13 (d, J=7.2 Hz, 1H), 6.16-6.19 (m, 2H), 6.43-6.45 (m, 1H), 6.66-6.68 (m, 1H), 6.71 (d, J=8.4 Hz, 2H), 7.30 (t, J=4.8 Hz, 1H), 7.72 (d, J=8.8 Hz, 2H), 8.82 (d, J=4.8 Hz, 2H).

Example 54

Acetic acid 2-(3-{(R)-(4-{amino[butoxycarbon-ylimino]methyl}phenylamino)-[5-(1-ethylpropoxy-carbonyloxymethoxy)-1-pyrimidin-2-yl-1H-[1,2,4]triazol-3-yl]methyl}-2-fluoro-5-methoxyphenoxy) ethyl ester

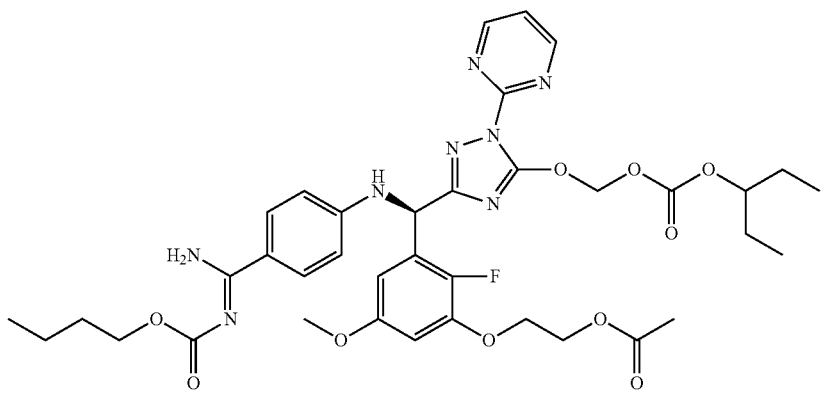 [SMILES: CCCCOC(=O)/N=C(\N)c1ccc(N[C@@H](c2nc(OCOC(=O)OC(CC)CC)n(-c3ncccn3)n2)c2cc(OC)cc(OCCOC(C)=O)c2F)cc1]

To a mixture of one lot containing acetic acid 2-(3-{(R)-(4-carbamimidoylphenylamino)-[5-(1-ethylpropoxycarbo-nyloxymethoxy)-1-pyrimidin-2-yl-1H-[1,2,4]triazol-3-yl]methyl}-2-fluoro-5-methoxyphenoxy)ethyl ester acetic acid salt (corresponding to 63.2 mg) obtained in Example 53a and DMF (3 ml), carbonic acid butyl ester 4-nitrophenyl ester [CAS No. 67036-13-9] (40.8 mg) and pyridine (55.2 μL) were added, and the resulting mixture was stirred at room temperature for 2 days. Ethyl acetate and water were added to the mixture, and the organic layer was collected. The organic layer was sequentially washed twice with water and with saturated aqueous sodium chloride solution, and dried over anhydrous sodium sulfate. The desiccant was filtered off, and the filtrate obtained was concentrated under reduced pressure. The residue obtained was purified by NAM silica gel column chromatography (mixed solvent of hexane-ethyl acetate) to obtain the captioned compound. This compound was dis-solved in methanol, and was purified again using SUM- ICHIRAL OA-2500 column (30 mmφ×25 cm, mobile phase: methanol, elution rate: 30 mL/min) to obtain the captioned compound (18.85 mg).

¹H-NMR (CDCl₃): δ=0.86-0.91 (m, 6H), 0.94 (t, J=7.2 Hz, 3H), 1.39-1.48 (m, 2H), 1.58-1.73 (m, 6H), 2.1 (s, 3H), 3.70 (s, 3H), 4.13 (t, J=6.8 Hz, 2H), 4.20 (t, J=4.4 Hz, 2H), 4.43 (t, J=4.4 Hz, 2H), 4.61-4.67 (m, 1H), 5.43 (d, J=7.6 Hz, 1H), 6.13 (d, J=7.2 Hz, 1H), 6.16-6.19 (m, 2H), 6.43-6.45 (m, 1H), 6.66-6.68 (m, 1H), 6.72 (d, J=8.8 Hz, 2H), 7.30 (t, J=4.8 Hz, 1H), 7.72 (d, J=8.8 Hz, 2H), 8.82 (d, J=4.8 Hz, 2H).

Example 55

Acetic acid 2-(3-{(R)-(4-{amino[isobutoxycarbonylimino]methyl}phenylamino)-[5-(1-ethylpropoxycarbonyloxymethoxy)-1-pyrimidin-2-yl-1H-[1,2,4]triazol-3-yl]methyl}-2-fluoro-5-methoxyphenoxy) ethyl ester

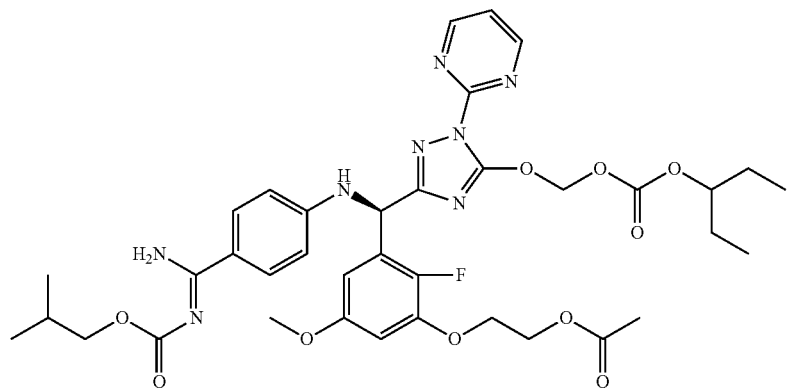 [SMILES: CCC(CC)OC(=O)OCOc1nc([C@H](Nc2ccc(/C(N)=N/C(=O)OCC(C)C)cc2)c2cc(OC)cc(OCCOC(C)=O)c2F)nn1-c1ncccn1]

To a mixture of one lot containing acetic acid 2-(3-{(R)-(4-carbamimidoylphenylamino)-[5-(1-ethylpropoxycarbonyloxymethoxy)-1-pyrimidin-2-yl-1H-[1,2,4]triazol-3-yl]methyl}-2-fluoro-5-methoxyphenoxy)ethyl ester acetic acid salt (corresponding to 63.2 mg) obtained in Example (53a) and DMF (3 ml), carbonic acid isobutyl ester 4-nitrophenyl ester [CAS No. 112240-73-0] (40.8 mg) and pyridine (55.2 μL) were added, and the resulting mixture was stirred at room temperature for 2 days. Ethyl acetate and water were added to the mixture, and the organic layer was collected. The organic layer was sequentially washed twice with water and with saturated aqueous sodium chloride solution, and dried over anhydrous sodium sulfate. The desiccant was filtered off, and the filtrate obtained was concentrated under reduced pressure. The residue obtained was purified by NAM silica gel column chromatography (mixed solvent of hexane-ethyl acetate) to obtain the captioned compound. This compound was dissolved in methanol, and was purified again using SUMICHIRAL OA-2500 column (30 mmφ×25 cm, mobile phase: methanol, elution rate: 30 mL/min) to obtain the captioned compound (26.74 mg).

¹H-NMR (CDCl₃): δ=0.86-0.91 (m, 6H), 0.97 (d, J=6.8 Hz, 6H), 1.58-1.66 (m, 4H), 1.99-2.07 (m, 1H), 2.1 (s, 3H), 3.69 (s, 3H), 3.91 (d, J=6.8 Hz, 2H), 4.20 (t, J=4.0 Hz, 2H), 4.43 (t, J=4.0 Hz, 2H), 4.61-4.67 (m, 1H), 5.44 (d, J=7.2 Hz, 1H), 6.13 (d, J=7.2 Hz, 1H), 6.16-6.19 (m, 2H), 6.43-6.45 (m, 1H), 6.66-6.67 (m, 1H), 6.72 (d, J=8.8 Hz, 2H), 7.30 (t, J=4.8 Hz, 1H), 7.72 (d, J=8.8 Hz, 2H), 8.82 (d, J=4.8 Hz, 2H).

Example 56

Carbonic acid 5-{(R)-(4-{amino-[2-methylallyloxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester (56a) Carbonic acid chloromethyl ester 2-fluoro-1,1-dimethylethyl ester

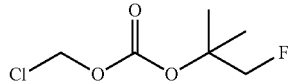

Under nitrogen atmosphere, to a mixture of 1-fluoro-2-methylpropane-2-ol (THF solution, 5.25 g) [CAS No. 353-80-0](Biorg. Med. Chem., volume 19, page 1580, 2011), THF (95 ml) and chloromethyl chloroformate (7 ml), pyridine (6.4 ml) was added dropwise at −78° C. The resulting mixture was stirred overnight at room temperature, and then ethyl acetate (200 mL) and heptane (200 mL) were added to the mixture. The resulting mixture was sequentially washed with 0.5 N hydrochloric acid (300 mL), saturated aqueous sodium hydrogen carbonate solution (200 mL), water (200 mL), and saturated aqueous sodium chloride solution (200 mL), and dried over anhydrous magnesium sulfate. The resulting mixture was filtered, and the filtrate obtained was concentrated under reduced pressure. The residue obtained was distilled under reduced pressure to obtain the captioned compound (5.25 g).

¹H-NMR (CDCl₃): δ=1.55 (d, J=1.6 Hz, 6H), 4.46 (d, J=47.2 Hz, 2H), 5.69 (s, 2H).

(56b) Carbonic acid 5-{(R)-(4-{amino[2-methylallyloxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester

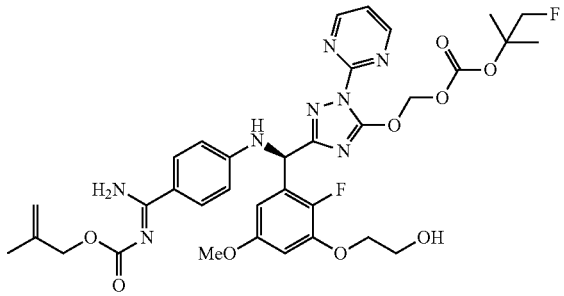 [SMILES: C=C(C)COC(=O)/N=C(\N)c1ccc(N[C@@H](c2nc(OCOC(=O)OC(C)(C)CF)n(-c3ncccn3)n2)c2cc(OC)cc(OCCO)c2F)cc1]

Under nitrogen atmosphere, a mixture of [1-amino(4-{[(R)-[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}phenyl)methylene]carbamic acid 2-methylallyl ester (Example 44, 474 mg), carbonic acid chloromethyl ester 2-fluoro-1,1,dimethylethyl ester (295 mg), rubidium carbonate (166 mg) and N,N-dimethylacetamide (15 mL) was stirred at 85° C. for 60 minutes. After cooling the mixture to room temperature, the reaction solution was concentrated under reduced pressure. The obtained residue was purified by reverse phase silica gel column chromatography (mixed solvent of methanol-water containing 0.1% of acetic acid), and then the obtained compound was further purified by silica gel column chromatography (mixed solvent of heptane-ethyl acetate-methanol) to obtain the captioned compound (98 mg).

¹H-NMR (CDCl₃): δ=1.50 (d, J=1.6 Hz, 6H), 1.80 (s, 3H), 2.35 (br.s, 1H), 3.69 (s, 3H), 3.97 (t, J=4.2 Hz, 2H), 4.10 (t, J=4.2 Hz, 2H), 4.44 (d, J=47.2 Hz, 2H), 4.57 (s, 2H), 4.90 (s, 1H), 5.04 (s, 1H), 5.46 (d, J=7.2 Hz, 1H), 6.13 (m, 3H), 6.44 (dd, J=2.8, 6.4 Hz, 1H), 6.65 (dd, J=2.8, 5.0 Hz, 1H), 6.71 (d, J=8.8 Hz, 2H), 7.30 (t, J=4.8 Hz, 1H), 7.72 (d, J=8.8 Hz, 2H), 8.83 (d, J=4.8 Hz, 2H).

Example 57

Acetic acid 2-(3-{(R)-(4-{amino[2-methylallyloxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester

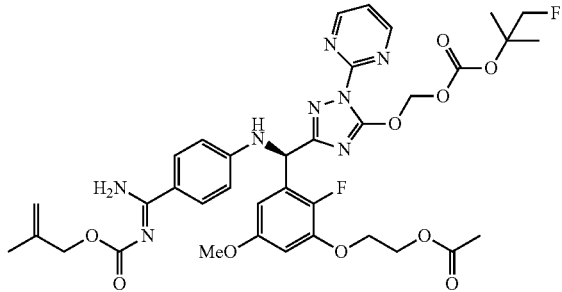 [SMILES: C=C(C)COC(=O)/N=C(\N)c1ccc(N[C@@H](c2nc(OCOC(=O)OC(C)(C)CF)n(-c3ncccn3)n2)c2cc(OC)cc(OCCOC(C)=O)c2F)cc1]

Under nitrogen atmosphere, a mixture of acetic acid 2-{3-[(R)-{4-[amino(2-methylallyloxycarbonylimino)methyl]phenylamino}-(5-oxo-1-pyrimidin-2-yl-4,5-dihydro-1H-[1,2,4]-triazol-3-yl)methyl]-2-fluoro-5-methoxyphenoxy}ethyl ester (Example 45, 508 mg), carbonic acid chloromethyl ester 2-fluoro-1,1,dimethylethyl ester (Example 56a, 295 mg), rubidium carbonate (166 mg) and N,N-dimethylacetamide (15 mL) was stirred at 85° C. for 60 minutes. After cooling the mixture to room temperature, the reaction solution was concentrated under reduced pressure. The obtained residue was purified by reverse phase silica gel column chromatography (mixed solvent of methanol-water containing 0.1% of acetic acid), and then the obtained compound was further purified by silica gel column chromatography (mixed solvent of heptane-ethyl acetate-methanol) to obtain the captioned compound (104 mg).

¹H-NMR (CDCl₃): δ=1.50 (d, J=1.6 Hz, 6H), 1.80 (s, 3H), 2.10 (s, 3H), 3.69 (s, 3H), 4.20 (t, J=4.8 Hz, 2H), 4.41 (t, J=4.8 Hz, 2H), 4.45 (d, J=47.2 Hz, 2H), 4.57 (s, 2H), 4.91 (s, 1H), 5.04 (s, 1H), 5.46 (d, J=7.6 Hz, 1H), 6.14 (m, 3H), 6.44 (dd, J=3.1, 6.5 Hz, 1H), 6.65 (dd, J=3.1, 4.9 Hz, 1H), 6.71 (d, k=8.8 Hz, 2H), 7.30 (t, J=4.4 Hz, 1H), 7.72 (d, J=8.8 Hz, 2H), 8.83 (d, J=4.4 Hz, 2H).

Example 58

Carbonic acid 5-{(R)-(4-{amino-[2-ethoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester (58a) Carbonic acid 5-{(R)-(4-carbamimidoylphenylamino)-[2-fluoro-3-(2-hydroxyethoxy)-5-m ethoxyphenyl]methyl}-2-pyrimidin-2-yl-2H-[1,2,4]triazol-3-yloxymethyl ester 2-fluoro-1,1-dimethylethyl ester acetic acid salt

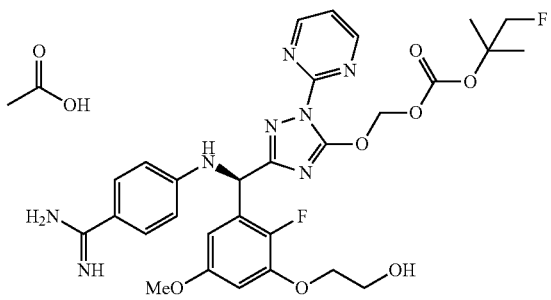

Under nitrogen atmosphere, to a mixture of carbonic acid 5-{(R)-(4-{amino-[2-methylallyloxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester (Example 56b, 63.5 mg), acetic acid (49 μL) and N,N-dimethylformamide (0.70 ml), tetrakis(triphenylphosphine) palladium (0) (4.9 mg) was added, and the resulting mixture was stirred at 45° C. for 15 hours. After cooling the mixture to room temperature, the reaction solution containing the captioned compound was divided into 3 equal lots, and used for the following reactions.

(58b) Carbonic acid 5-{(R)-(4-{amino-[2-ethoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester

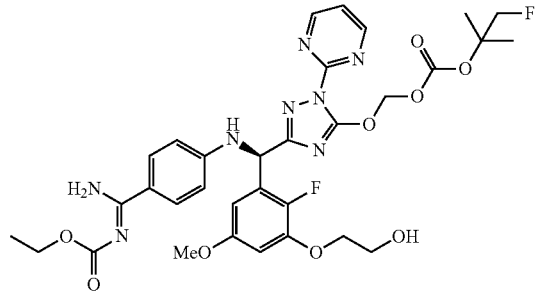 [SMILES: CCOC(=O)/N=C(\N)c1ccc(N[C@@H](c2nc(OCOC(=O)OC(C)(C)CF)n(-c3ncccn3)n2)c2cc(OC)cc(OCCO)c2F)cc1]

To one lot obtained in Example (58a), pyridine (18 μL) and carbonic acid ethyl ester 4-nitrophenyl ester [CAS No. 6132-45-2] (12 mg) were added, and the resulting mixture was stirred overnight at room temperature. Ethyl acetate (5 ml) and water (4 ml) were added to the mixture, and the organic layer was collected. The aqueous layer was extracted with ethyl acetate (5 ml), all the organic layers were combined, and dried over anhydrous magnesium sulfate. The resulting mixture was filtered, and the filtrate obtained was concentrated under reduced pressure. The residue obtained was purified by silica gel column chromatography (mixed solvent of heptane-ethyl acetate-methanol) to obtain the captioned compound (4.9 mg).

$^1$H-NMR (CDCl$_3$): δ=1.37 (t, J=6.9 Hz, 3H), 1.50 (d, J=1.6 Hz, 6H), 3.70 (s, 3H), 3.97 (t, J=4.2 Hz, 2H), 4.10 (t, J=4.2 Hz, 2H), 4.19 (q, J=6.9 Hz, 2H), 4.44 (d, J=47.2 Hz, 2H), 5.47 (d, J=7.5 Hz, 1H), 6.12 (m, 3H), 6.45 (dd, J=2.8, 6.4 Hz, 1H), 6.65 (dd, J=2.8, 4.7 Hz, 1H), 6.71 (d, J=8.8 Hz, 2H), 7.30 (t, J=5.2 Hz, 1H), 7.72 (d, J=8.8 Hz, 2H), 8.83 (d, J=5.2 Hz, 2H).

Example 59

Carbonic acid 5-{(R)-(4-{amino-[2-propoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester

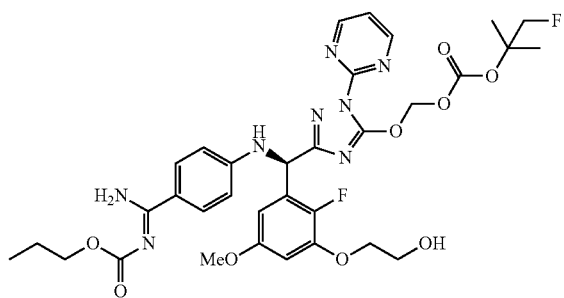 [SMILES: CCCOC(=O)/N=C(\N)c1ccc(N[C@@H](C(=N)/N=C(\Nc2ncccn2)OCOC(=O)OC(C)(C)CF)c2cc(OC)cc(OCCO)c2F)cc1]

To one lot obtained in Example (58a), pyridine (18 μL) and carbonic acid 4-nitrophenyl ester propyl ester (13 mg) were added, and the resulting mixture was stirred overnight at room temperature. Ethyl acetate (5 ml) and water (4 ml) were added to the mixture, and the organic layer was collected. The aqueous layer was extracted with ethyl acetate (5 ml), all the organic layers were combined, and dried over anhydrous magnesium sulfate. The resulting mixture was filtered, and the filtrate obtained was concentrated under reduced pressure. The residue obtained was purified by silica gel column chromatography (mixed solvent of heptane-ethyl acetate-methanol) to obtain the captioned compound (7.0 mg).

$^1$H-NMR (CDCl$_3$): δ=0.98 (t, J=7.4 Hz, 3H), 1.50 (d, J=1.6 Hz, 6H), 1.74 (sext, J=7.4 Hz, 2H), 3.70 (s, 3H), 3.97 (t, J=4.2 Hz, 2H), 4.09 (m, 4H), 4.44 (d, J=47.2 Hz, 2H), 5.44 (d, J=7.5 Hz, 1H), 6.13 (m, 3H), 6.45 (dd, J=3.0, 6.5 Hz, 1H), 6.65 (dd, J=3.0, 4.8 Hz, 1H), 6.71 (d, J=8.8 Hz, 2H), 7.30 (t, J=4.4 Hz, 1H), 7.72 (d, J=8.8 Hz, 2H), 8.83 (d, J=4.4 Hz, 2H).

Example 60

Carbonic acid 5-{(R)-(4-{amino-[2-butoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester

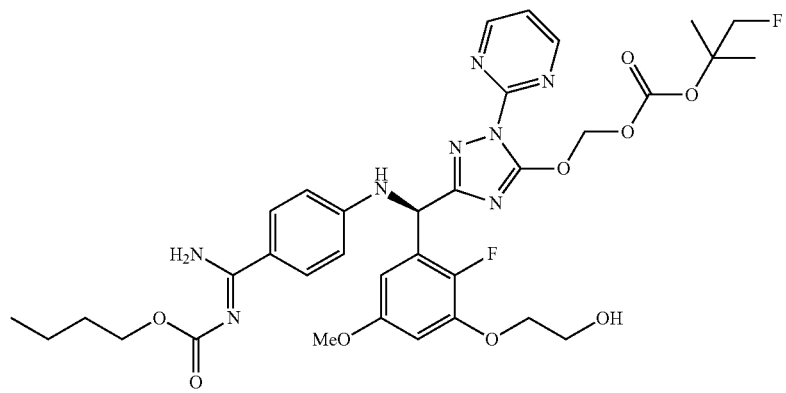 [SMILES: CCCCOC(=O)/N=C(\N)c1ccc(N[C@@H](c2nc(OCOC(=O)OC(C)(C)CF)n(-c3ncccn3)n2)c2cc(OC)cc(OCCO)c2F)cc1]

To one lot obtained in Example (58a), pyridine (18 μL) and carbonic acid butoxy ester 4-nitrophenyl ester (14 mg) were added, and the resulting mixture was stirred overnight at room temperature. Ethyl acetate (5 ml) and water (4 ml) were added to the mixture, and the organic layer was collected. The aqueous layer was extracted with ethyl acetate (5 ml), all the organic layers were combined, and dried over anhydrous magnesium sulfate. The resulting mixture was filtered, and the filtrate obtained was concentrated under reduced pressure. The residue obtained was purified by silica gel column chromatography (mixed solvent of heptane-ethyl acetate-methanol) to obtain the captioned compound (8.9 mg).

$^1$H-NMR (CDCl$_3$): δ=0.94 (t, J=7.2 Hz, 3H), 1.41 (sext, J=7.2 Hz, 2H), 1.50 (d, J=1.7 Hz, 6H), 1.71 (quint, J=7.2 Hz, 2H), 3.70 (s, 3H), 3.97 (dd, J=4.0, 4.8 Hz, 2H), 4.11 (m, 4H), 4.44 (d, J=47.2 Hz, 2H), 4.97 (d, J=7.3 Hz, 1H), 6.12 (m, 3H), 6.45 (dd, J=2.8, 6.3 Hz, 1H), 6.64 (dd, J=2.8, 4.8 Hz, 1H), 6.71 (d, J=8.8 Hz, 2H), 7.30 (t, J=4.8 Hz, 1H), 7.72 (d, J=8.8 Hz, 2H), 8.83 (d, J=4.8 Hz, 2H).

Example 61

Acetic acid 2-(3-{(R)-(4-{amino[ethoxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester (61a) Acetic acid 2-(3-{(R)-(carbamimidoylphenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester acetic acid salt

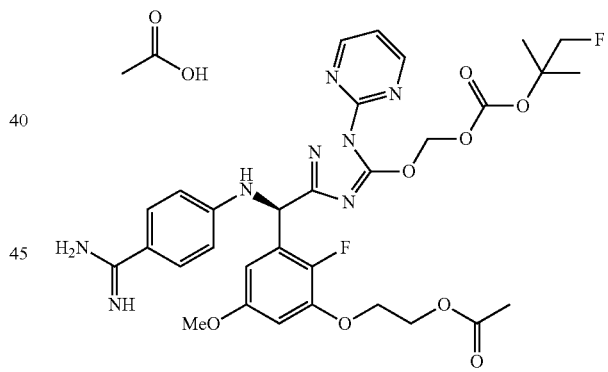

Under nitrogen atmosphere, to a mixture of acetic acid 2-(3-{(R)-(4-{amino[2-methylallyloxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester (Example 57, 72.4 mg), acetic acid (53 μL) and N,N-dimethylformamide (0.80 ml), tetrakis(triphenylphosphine) palladium (0) (5.4 mg) was added, and the resulting mixture was stirred at 45° C. for 15 hours. After cooling the mixture to room temperature, the reaction solution containing the captioned compound was divided into 3 equal lots, and used for the following reactions.

(61b) Acetic acid 2-(3-{(R)-(4-{amino[ethoxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester

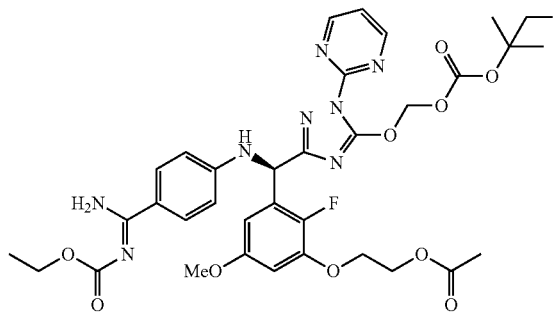

To one lot obtained in Example (61a), pyridine (18 μL) and carbonic acid ethyl ester 4-nitrophenyl ester (12 mg) were added, and the resulting mixture was stirred overnight at room temperature. Ethyl acetate (5 ml) and water (4 ml) were added to the mixture, and the organic layer was collected. The aqueous layer was extracted with ethyl acetate (5 ml), all the organic layers were combined, and dried over anhydrous magnesium sulfate. The resulting mixture was filtered, and the filtrate obtained was concentrated under reduced pressure. The residue obtained was purified by silica gel column chromatography (mixed solvent of heptane-ethyl acetate-methanol) to obtain the captioned compound (8.4 mg).

$^1$H-NMR (CDCl$_3$): δ=1.33 (t, J=7.0 Hz, 3H), 1.50 (d, J=1.6 Hz, 6H), 2.10 (s, 3H), 3.70 (s, 3H), 4.16 (m, 4H), 4.43 (t, J=4.8 Hz, 2H), 4.44 (d, J=47.2 Hz, 2H), 5.43 (d, J=7.2 Hz, 1H), 6.12 (m, 3H), 6.45 (dd, J=2.8, 6.5 Hz, 1H), 6.65 (dd, J=2.8, 4.7 Hz, 1H), 6.72 (d, J=8.8 Hz, 2H), 7.30 (t, J=4.8 Hz, 1H), 7.73 (d, J=8.8 Hz, 2H), 8.83 (d, J=4.8 Hz, 2H).

Example 62

Acetic acid 2-(3-{(R)-(4-{amino[propoxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester

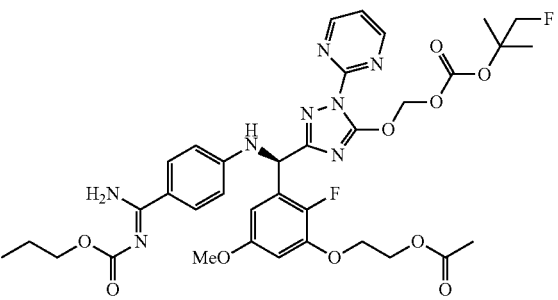 [SMILES: CCCOC(=O)/N=C(\N)c1ccc(N[C@@H](c2nc(OCOC(=O)OC(C)(C)CF)n(-c3ncccn3)n2)c2cc(OC)cc(OCCOC(C)=O)c2F)cc1]

To one lot obtained in Example (61a), pyridine (18 μL) and carbonic acid 4-nitrophenyl ester propyl ester (13 mg) were added, and the resulting mixture was stirred overnight at room temperature. Ethyl acetate (5 ml) and water (4 ml) were added to the mixture, and the organic layer was collected. The aqueous layer was extracted with ethyl acetate (5 ml), all the organic layers were combined, and dried over anhydrous magnesium sulfate. The resulting mixture was filtered, and the filtrate obtained was concentrated under reduced pressure. The residue obtained was purified by silica gel column chromatography (mixed solvent of heptane-ethyl acetate-methanol) to obtain the captioned compound (9.2 mg).

$^1$H-NMR (CDCl$_3$): δ=0.98 (t, J=7.6 Hz, 3H), 1.50 (d, J=1.6 Hz, 6H), 1.74 (sext, J=7.6 Hz, 2H), 2.10 (s, 3H), 3.70 (s, 3H), 4.09 (t, J=7.6 Hz, 2H), 4.20 (t, J=4.8 Hz), 4.43 (t, J=4.8 Hz, 2H), 4.44 (d, J=47.2 Hz, 2H), 5.43 (d, J=7.9 Hz, 1H), 6.13 (m, 3H), 6.44 (dd, J=3.1, 6.3 Hz, 1H), 6.67 (dd, J=3.1, 4.7 Hz, 1H), 6.72 (d, J=8.8 Hz, 2H), 7.30 (t, J=4.9 Hz, 1H), 7.72 (d, J=8.8 Hz, 2H), 8.83 (d, J=4.9 Hz, 2H).

Example 63

Acetic acid 2-(3-{(R)-(4-{amino[butoxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester

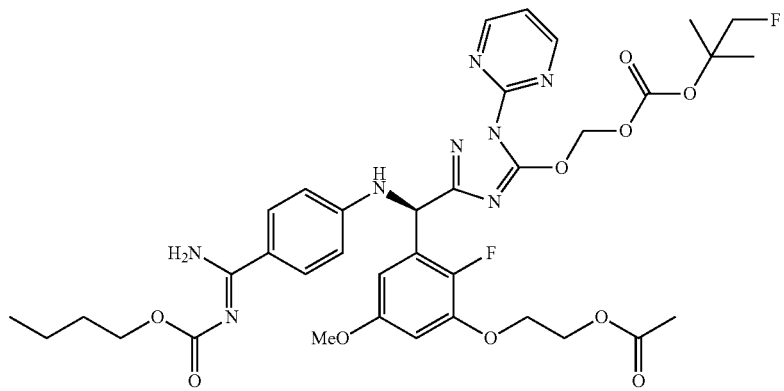 [SMILES: CCCCOC(=O)/N=C(\N)c1ccc(N[C@@H](C(=N)/N=C(\Nc2ncccn2)OCOC(=O)OC(C)(C)CF)c2cc(OC)cc(OCCOC(C)=O)c2F)cc1]

To one lot obtained in Example (61a), pyridine (18 μL) and carbonic acid butoxy ester 4-nitrophenyl ester (14 mg) were added, and the resulting mixture was stirred overnight at room temperature. Ethyl acetate (5 ml) and water (4 ml) were added to the mixture, and the organic layer was collected. The aqueous layer was extracted with ethyl acetate (5 ml), all the organic layers were combined, and dried over anhydrous magnesium sulfate. The resulting mixture was filtered, and the filtrate obtained was concentrated under reduced pressure. The residue obtained was purified by silica gel column chromatography (mixed solvent of heptane-ethyl acetate-methanol) to obtain the captioned compound (9.4 mg).

$^1$H-NMR (CDCl$_3$): δ=0.94 (t, J=7.2 Hz, 3H), 1.41 (sext, J=7.2 Hz, 2H), 1.51 (d, J=1.7 Hz, 6H), 1.70 (quint, J=7.2 Hz, 2H) 2.10 (s, 3H), 3.70 (s, 3H), 4.14 (t, J=7.4 Hz, 2H), 4.20 (t, J=5.0 Hz, 2H), 4.43 (t, J=5.0 Hz, 2H), 4.44 (d, J=47.2 Hz, 2H), 5.42 (d, J=7.1 Hz, 1H), 6.12 (m, 3H), 6.45 (dd, J=2.8, 6.4 Hz, 1H), 6.64 (dd, J=2.8, 4.8 Hz, 1H), 6.71 (d, J=8.8 Hz, 2H), 7.30 (t, J=4.8 Hz, 1H), 7.72 (d, J=8.8 Hz, 2H), 8.83 (d, J=4.8 Hz, 2H).

Example 64

Carbonic acid 2-(3-{1-(4-cyanophenylamino)-2-[ethoxycarbonylimino]-2-methylsulfanylethyl]-2-fluoro-5-methoxyphenoxy)ethyl ester ethyl ester

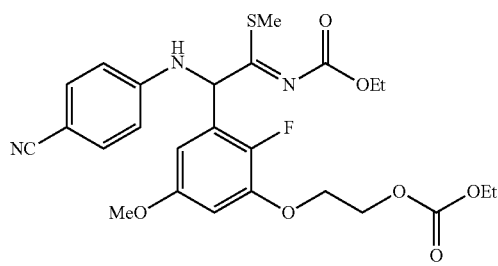 [SMILES: CCOC(=O)/N=C(\SC)C(Nc1ccc(C#N)cc1)c1cc(OC)cc(OCCOC(=O)OCC)c1F]

After the atmosphere in the reaction vessel had been replaced with nitrogen, toluene (1126 mL) and acetonitrile (1126 mL) were added. While stirring the resulting mixture at room temperature, 2-(4-cyanophenylamino)-2-[2-fluoro-3-(2-hydroxyethoxy)-5-methoxypheny l]thioacetamide (837.5 g, net weight 750.4 g, 1.999 mol) was added portionwise. After rinsing in with a mixed solvent of toluene:acetonitrile=1:1 (750 mL), the bath temperature was set at 18° C. To this mixture, trimethyloxonium tetrafluoroborate (311 g, 1.999 mol) was added portionwise over a period of about 2 hours, rinsing in with acetonitrile (750 mL), and the mixture was stirred 3 hours at a bath temperature of 22° C. Trimethyloxonium tetrafluoroborate (15.6 g, 0.100 mol) was additionally added, the mixture was further stirred for about 2 hours, and then the bath temperature was set at 0° C. and the mixture was stirred for 12 hours. At the bath temperature of 0° C., ethyl chloroformate (911 g, 8.395 mol) was added dropwise to the reaction solution obtained, followed by dropwise addition of pyridine (889 g, 11.233 mol) at an internal temperature of 16° C. or less. Thereafter, the resulting mixture was stirred at a bath temperature of 22° C. for 2 hours, ethyl acetate (7504 mL) and water (7504 mL) were added to the mixture, and the organic layer was collected. The organic layer was sequentially washed with water (7504 mL) and 5% sodium bicarbonate water, then with 10% aqueous sodium chloride solution (7504 g) twice, and concentrated under reduced pressure to about 2300 mL. To the residue obtained, tetrahydrofuran was added and the mixture was further subjected to azeotropic distillation three times (2500 mL, 2500 mL, then 2250 mL of tetrahydrofuran was used) to obtain a tetrahydrofuran solution of the captioned compound.

Example 65

Carbonic acid 2-{3-[(4-cyanophenylamino)-(5-oxo-1-pyrimidin-2-yl-4,5-dihydro-1H-[1,2,4]-triazol-3-yl)methyl]-2-fluoro-5-methoxyphenoxy}ethyl ester ethyl ester

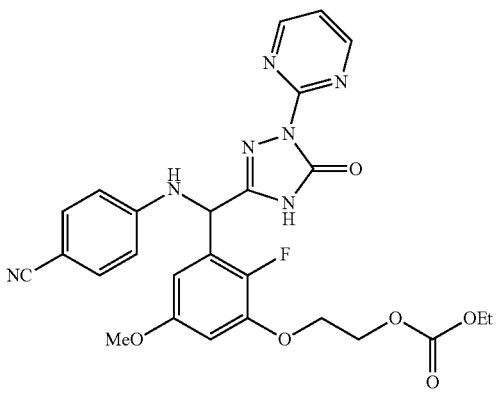 [SMILES: CCOC(=O)OCCOc1cc(OC)cc(C(Nc2ccc(C#N)cc2)c2nn(-c3ncccn3)c(=O)[nH]2)c1F]

After the atmosphere in the reaction vessel had been replaced with nitrogen, the tetrahydrofuran solution containing Carbonic acid 2-(3-{1-(4-cyanophenylamino)-2-[ethoxycarbonylimino]-2-methylsulfanylethyl]-2-fluoro-5-methoxyphenoxy)ethyl ester ethyl ester obtained in Example 64 was added, rinsing in with tetrahydrofuran (1250 mL) and stirred. Thereafter, pyrimidin-2-yl-hydrazine (275 g, 2.497 mol) was added portionwise at a bath temperature of 15° C., rinsing in with tetrahydrofuran (1000 mL), and the mixture was stirred at a bath temperature of 22° C. for 14 hours. Pyrimidin-2-yl-hydrazine (8.2 g, 0.074 mol) was additionally added, rinsing in with tetrahydrofuran (30 mL), and stirring was continued for one hour. Thereafter, the bath temperature was set at 15° C., 1,8-diazabicyclo[5.4.0]undec-7-ene (304 g, 1.999 mol) was added dropwise to the mixture, rinsing in with tetrahydrofuran (50 mL), and then the bath temperature was set at 22° C. and the mixture was stirred for 2.5 hours. Thereafter, the bath temperature was set at 15° C., and ethyl acetate (7504 mL) and 1 N hydrochloric acid (7504 mL) were added to the reaction solution. Then, the bath temperature was set at 22° C., the organic layer was collected, and the aqueous layer was further extracted with ethyl acetate (3752 mL). All the organic layers were combined, the organic layer was washed with 10% aqueous sodium chloride solution (7504 g) twice, and concentrated under reduced pressure. The residue obtained was subjected to azeotropic distillation three times with methanol (1250 mL of methanol was used, each time). To the residue obtained, tetrahydrofuran (375 mL) and methanol (475 mL) were added to obtain the suspension of the captioned compound.

¹H-NMR (400 MHz, DMSO-d₆): δ=1.20 (t, J=7.2, 3H), 3.71 (s, 3H), 4.13 (q, J=7.2, 2H), 4.26-4.32 (m, 2H), 4.38-4.43 (m, 2H), 5.89 (d, J=7.2 Hz, 1H), 6.60-6.66 (m, 1H), 6.72-6.82 (m, 3H), 7.41 (dt, J=4.8, 0.4 Hz, 1H), 7.52 (d, J=8.8 Hz, 2H), 7.64 (d, J=7.2 Hz, 1H), 8.81 (dd, J=4.8, 0.4 Hz, 2H), 12.26 (bs, 1H).

Example 66

4-{[[2-fluoro-3-(2-hydroxyethoxy)-5-methoxyphenyl](5-oxo-1-pyrimidin-2-yl-4,5-dihydro-1H-[1,2,4]-triazol-3-yl)methyl]amino}benzonitrile

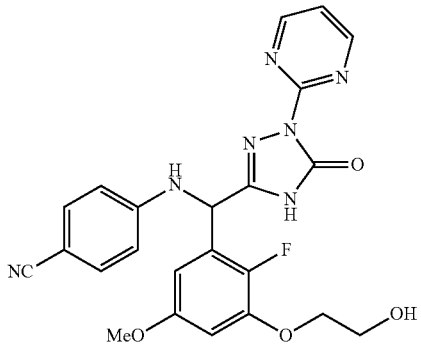 [SMILES: COc1cc(OCCO)c(F)c(C(Nc2ccc(C#N)cc2)c2nn(-c3ncccn3)c(=O)[nH]2)c1]

After the atmosphere in the reaction vessel had been replaced with nitrogen, the suspension containing carbonic acid 2-{3-[(4-cyanophenylamino)-(5-oxo-1-pyrimidin-2-yl-4,5-dihydro-1H-[1,2,4]-triazol-3-yl)methyl]-2-fluoro-5-methoxyphenoxy}ethyl ester ethyl ester obtained in Example 65 was added at a bath temperature of 15° C., and rinsing in with methanol (2407 mL) and tetrahydrofuran (826 mL). 5 N aqueous sodium hydroxide solution (1599 mL, 7.995 mol) was added dropwise to the mixture at the bath temperature of 15° C., then the bath temperature was set at 20° C., and the reaction suspension was stirred for 16 hours. Thereafter, the bath temperature was set at 15° C., and acetic acid (2288 mL) was added dropwise to the solution obtained. Then, the bath temperature was set at 22° C., and water (3750 mL) was added dropwise. Seed crystals of the captioned compound (374 mg, 0.836 mmol) were added to the mixture which was then stirred for 20 minutes. Then, water (3754 mL) was added dropwise, and the bath temperature was cooled to 0° C. over a period of about 2 hours. Stirring was maintained for 16 hours at the bath temperature of 0° C. The precipitate was filtered, washed with water (2250 mL), and dried under reduced pressure at 40 to 50° C. to obtain the captioned compound (660 g, net weight 631.6 g) as a pale yellow white powder.

¹H-NMR (400 MHz, DMSO-d₆): δ=3.70 (s, 3H), 3.73 (dt, J=5.2, 5.2 Hz, 2H), 4.07 (t, J=4.8 Hz, 2H), 4.92 (t, J=4.8 Hz, 1H), 5.88 (d, J=7.2 Hz, 1H), 6.53-6.63 (m, 1H), 6.70-6.84 (m, 3H), 7.41 (dt, J=1.2, 4.8 Hz, 1H), 7.53 (d, J=8.0 Hz, 2H), 7.63 (d, J=7.6 Hz, 1H), 8.81 (dd, J=1.2, 4.8 Hz, 2H), 12.26 (brs, 1H).

Example 67

Acetic acid 2-{3-[(R)-(4-{amino[butoxycarbonylimino]methyl}phenylamino)-(5-isopropoxycarbonyloxymethoxy-1-pyrimidin-2-yl-1H-[1,2,4]triazol-3-yl)methyl]-2-fluoro-5-methoxyphenoxy)ethyl ester (67a) Acetic acid 2-{3-[(R)-(4-carbamimidoylphenylamino)-(5-isopropoxycarbonyloxymethoxy-1-pyrimidin-2-yl-1H-[1,2,4]triazol-3-yl)methyl]-2-fluoro-5-methoxyphenoxy}ethyl ester acetic acid salt

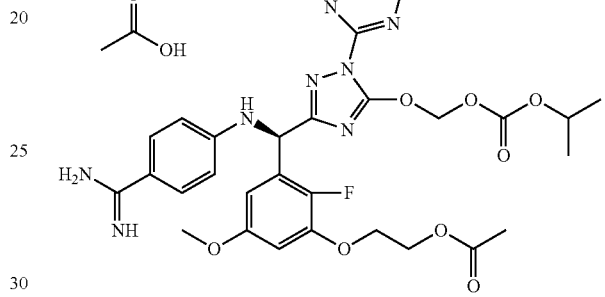

Under nitrogen atmosphere, a mixture of acetic acid 2-{3-[(R)-{4-[amino(2-methylallyloxycarbonylimino)methyl]phenylamino}-(5-oxo-1-pyrimidin-2-yl-4,5-dihydro-1H-[1,2,4]-triazol-3-yl)methyl]-2-fluoro-5-methoxyphenoxy}ethyl ester (Example 45, 250 mg), carbonic acid chloromethyl ester isopropyl ester [CAS No. 35180-01-9] (121 mg), rubidium carbonate (73.2 mg) and DMA (10 mL) was stirred at 85° C. for 90 minutes. After cooling the mixture to room temperature, ethyl acetate and water were added thereto. The organic layer was collected, the aqueous layer was reextracted with ethyl acetate, and all the organic layers were combined. The organic layer was sequentially washed with water and with saturated aqueous sodium chloride solution, and dried over anhydrous magnesium sulfate. The desiccant was filtered off, and the filtrate obtained was concentrated under reduced pressure. The residue obtained was purified by silica gel column chromatography (mixed solvent of heptane-ethyl acetate-methanol) to obtain the acetic acid 2-{3-[(R)-(4-{amino[2-methylallyloxycarbonylimino]methyl}phenylamino)-(5-isopropoxycarbonyloxymethoxy-1-pyrimidin-2-yl-1H-[1,2,4]triazol-3-yl)methyl]-2-fluoro-5-methoxyphenoxy]ethyl ester as a solid.

To a mixture of obtained solid, DMF (3 mL) and acetic acid (0.3 mL), tetrakis(triphenylphosphine) palladium (22.9 mg) was added, and the resulting mixture was stirred for 24 h at 45° C. After cooling the mixture to room temperature, the reaction mixture was purified by reverse phase silica gel column chromatography (mixed solvent of methanol-water containing 0.1% of acetic acid) to obtain the captioned compound (95 mg).

(67b) Acetic acid 2-{3-[(R)-(4-{amino[butoxycarbonylimino]methyl}phenylamino)-(5-isopropoxycarbonyloxymethoxy-1-pyrimidin-2-yl-1H-[1,2,4]triazol-3-yl)methyl]-2-fluoro-5-methoxyphenoxy)ethyl ester

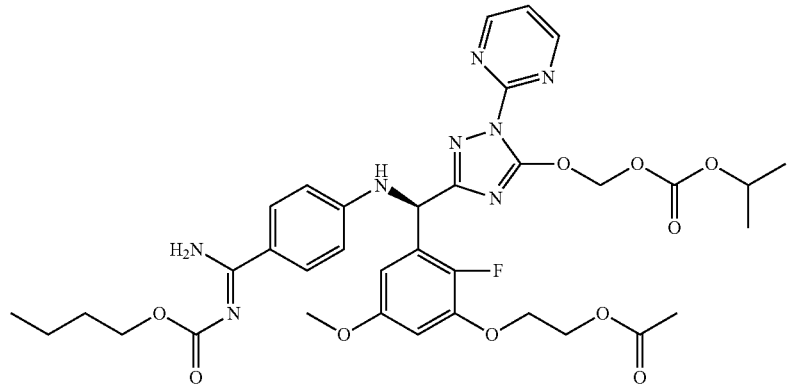 [SMILES: CCCCOC(=O)/N=C(\N)c1ccc(N[C@@H](c2nc(OCOC(=O)OC(C)C)n(-c3ncccn3)n2)c2cc(OC)cc(OCCOC(C)=O)c2F)cc1]

To a mixture of Acetic acid 2-{3-[(R)-(4-carbamimidoylphenylamino)-(5-isopropoxycarbonyloxymethoxy-1-pyrimidin-2-yl-1H-[1,2,4]triazol-3-yl)methyl]-2-fluoro-5-methoxyphenoxy}ethyl ester acetic acid salt (23 mg) obtained in Example 67a and DMF (1 ml), carbonic acid butyl ester 4-nitrophenyl ester [CAS No. 67036-13-9] (10 mg) and triethylamine (50 μL) were added, and the resulting mixture was stirred at room temperature for 63 h. Ethyl acetate and water were added to the mixture, and the organic layer was collected. The organic layer was sequentially washed with water and with saturated aqueous sodium chloride solution, and dried over anhydrous magnesium sulfate. The desiccant was filtered off, and the filtrate obtained was concentrated under reduced pressure. The residue obtained was purified by silica gel column chromatography (mixed solvent of heptane-ethyl acetate) to obtain the captioned compound (16.80 mg).

$^1$H-NMR (CD$_3$OD) δ 0.95 (t, J=7.2 Hz, 3H), 1.24 (d, J=6.0 Hz, 6H), 1.44 (m, 2H), 1.65 (m, 2H), 2.04 (s, 3H), 3.70 (s, 3H), 4.09 (t, J=6.4 Hz, 2H), 4.20-4.24 (m, 2H), 4.37-4.39 (m, 2H), 4.85 (quint, J=6.0 Hz, 1H), 6.05 (s, 1H), 6.08 (d, J=5.6 Hz, 1H), 6.11 (d, J=5.6 Hz, 1H), 6.57 (dd, J=2.8, 6.8 Hz, 1H), 6.74 (dd, J=2.8, 4.8 Hz, 1H), 6.77 (d, J=8.8 Hz, 2H), 7.46 (t, J=4.8 Hz, 1H), 7.69 (d, J=8.8 Hz, 2H), 8.85 (d, J=4.8 Hz, 2H)

Example 68

Acetic acid 2-{3-[(R)-(4-{amino[isobutoxycarbonylimino]methyl}phenylamino)-(5-isopropoxycarbonyloxymethoxy-1-pyrimidin-2-yl-1H-[1,2,4]-triazol-3-yl)methyl]-2-fluoro-5-methoxyphenoxy)ethyl ester

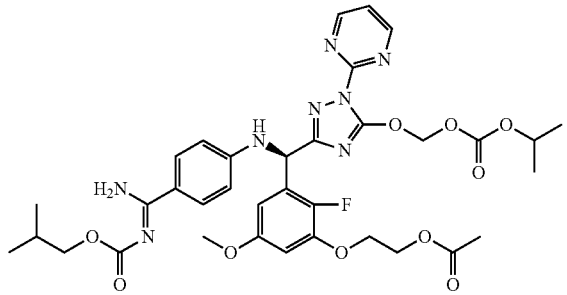 [SMILES: COc1cc(OCCOC(C)=O)c(F)c([C@@H](Nc2ccc(/C(N)=N/C(=O)OCC(C)C)cc2)c2nc(OCOC(=O)OC(C)C)n(-c3ncccn3)n2)c1]

To a mixture of Acetic acid 2-{3-[(R)-(4-carbamimidoylphenylamino)-(5-isopropoxycarbonyloxymethoxy-1-pyrimidin-2-yl-1H-[1,2,4]triazol-3-yl)methyl]-2-fluoro-5-methoxyphenoxy}ethyl ester acetic acid salt (23 mg) obtained in Example 67a and DMF (1 ml), carbonic acid isobutyl ester 4-nitrophenyl ester [CAS No. 112240-73-0] (10 mg) and triethylamine (50 μL) were added, and the resulting mixture was stirred at room temperature for 64 h. Ethyl acetate and water were added to the mixture, and the organic layer was collected. The organic layer was sequentially washed with water and with saturated aqueous sodium chloride solution, and dried over anhydrous magnesium sulfate. The desiccant was filtered off, and the filtrate obtained was concentrated under reduced pressure. The residue obtained was purified by silica gel column chromatography (mixed solvent of heptane-ethyl acetate) to obtain the captioned compound (14.99 mg).

$^1$H-NMR (CD$_3$OD) δ 0.97 (d, J=6.8 Hz, 6H), 1.24 (d, J=6.4 Hz, 6H), 1.95 (m, 1H), 2.05 (s, 3H), 3.70 (s, 3H), 3.87 (d, J=6.8 Hz, 2H), 4.20-4.24 (m, 2H), 4.37-4.40 (m, 2H), 4.85 (quint, J=6.4 Hz, 1H), 6.06 (s, 1H), 6.08 (d, J=5.6 Hz, 1H), 6.12 (d, J=5.6 Hz, 1H), 6.57 (dd, J=2.8, 6.8 Hz, 1H), 6.75 (dd, J=2.8, 4.8 Hz, 1H), 6.77 (d, J=9.2 Hz, 2H), 7.46 (t, J=4.8 Hz, 1H), 7.69 (d, J=9.2 Hz, 2H), 8.85 (d, J=4.8 Hz, 2H)

[Measurement of Powder X-Ray Diffraction Patterns]

For the compound crystals obtained in Example 20, 24, and 25, powder X-ray diffraction patterns were measured under the conditions below.

[Measurement Conditions]
X-ray used: CuKa ray
Voltage: 50 kV
Current: 300 mA
Divergence slit: 0.50 mm
Scattering slit: open
Receiving slit: open
Scan rate: 2°/min FIG. 1 shows the powder X-ray diffraction patterns of the compound of Example 20, and Table 1 shows the peaks of angle of diffraction [2θ] and the peak intensity.

TABLE 1

| 2theta (degree) | Relative Intensity |
|---|---|
| 4.4 | 7 |
| 8.3 | 100 |
| 8.8 | 8 |
| 12.3 | 12 |
| 13.2 | 27 |
| 14.1 | 23 |
| 14.6 | 5 |
| 15.6 | 8 |
| 16.6 | 14 |
| 17.0 | 12 |

TABLE 1-continued

| 2theta (degree) | Relative Intensity |
|---|---|
| 17.3 | 8 |
| 17.7 | 16 |
| 18.7 | 75 |
| 19.7 | 37 |
| 20.4 | 10 |
| 21.6 | 24 |
| 22.7 | 15 |
| 24.1 | 14 |
| 24.4 | 13 |
| 24.9 | 17 |
| 25.3 | 14 |
| 26.0 | 17 |
| 26.5 | 21 |
| 27.5 | 9 |
| 28.5 | 5 |
| 29.2 | 7 |
| 30.4 | 5 |
| 31.1 | 7 |
| 31.8 | 4 |
| 32.1 | 5 |

Figure 2:
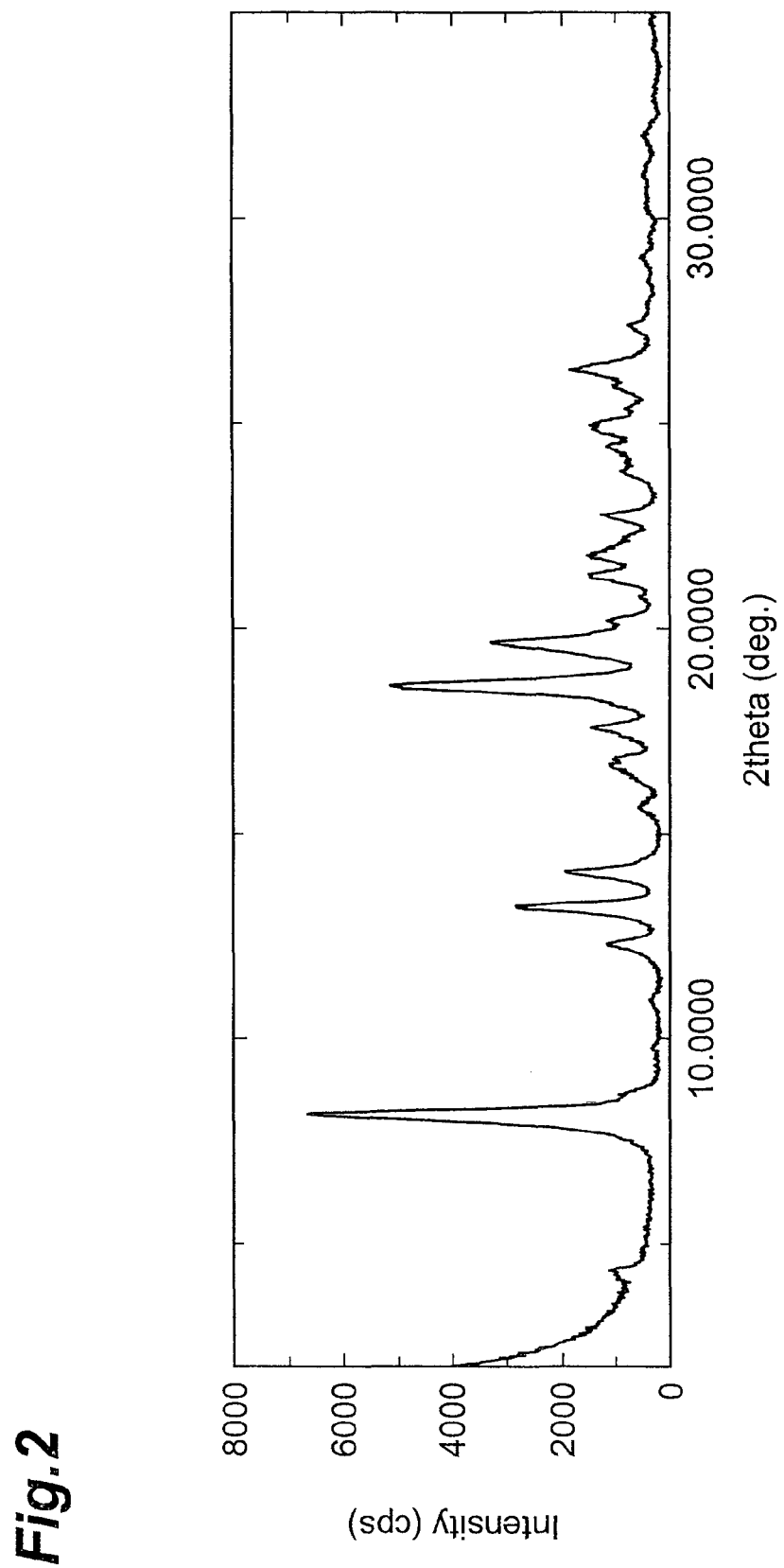
FIG. 2 is a diagram showing the powder X-ray diffraction pattern of the compound of Example 24.

FIG. 2 shows the powder X-ray diffraction patterns of the compound of Example 24, and Table 2 shows the peaks of angle of diffraction [2θ] and the peak intensity.

TABLE 2

| 2theta (degree) | Relative Intensity |
|---|---|
| 4.3 | 17 |
| 8.2 | 100 |
| 8.6 | 15 |
| 12.3 | 17 |
| 13.2 | 40 |
| 14.1 | 29 |
| 15.6 | 9 |
| 16.7 | 17 |
| 16.8 | 16 |
| 17.6 | 22 |
| 18.6 | 78 |
| 19.7 | 48 |
| 20.2 | 18 |
| 20.8 | 9 |
| 21.3 | 22 |
| 21.8 | 23 |
| 22.2 | 13 |
| 22.8 | 18 |
| 23.8 | 14 |
| 24.4 | 18 |
| 24.9 | 22 |
| 25.4 | 12 |
| 25.9 | 16 |
| 26.3 | 27 |
| 27.4 | 12 |
| 29.1 | 7 |
| 31.0 | 7 |
| 32.0 | 8 |

Figure 3:
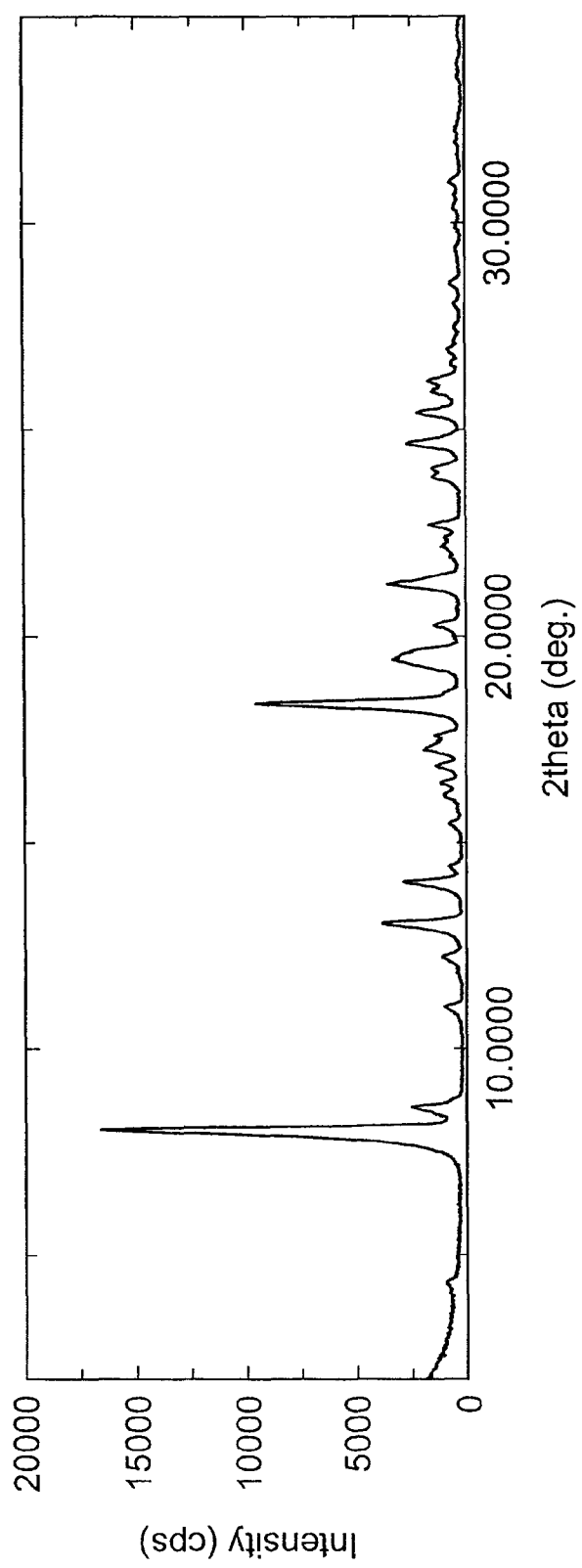
FIG. 3 is a diagram showing the powder X-ray diffraction pattern of the compound of Example 25.

FIG. 3 shows the powder X-ray diffraction patterns of the compound of Example 25, and Table 3 shows the peak of angle of diffraction [2θ] and the peak intensity.

TABLE 3

| 2theta (degree) | Relative Intensity |
|---|---|
| 8.1 | 100 |
| 8.6 | 16 |
| 11.0 | 7 |
| 12.2 | 8 |
| 13.0 | 24 |
| 14.0 | 18 |
| 14.4 | 5 |
| 15.5 | 5 |

TABLE 3-continued

| 2theta (degree) | Relative Intensity |
|---|---|
| 16.2 | 7 |
| 16.4 | 8 |
| 16.9 | 9 |
| 17.3 | 12 |
| 17.6 | 9 |
| 18.4 | 60 |
| 19.3 | 13 |
| 19.3 | 17 |
| 19.5 | 19 |
| 19.7 | 15 |
| 20.3 | 10 |
| 21.2 | 19 |
| 21.3 | 23 |
| 22.4 | 6 |
| 22.7 | 11 |
| 23.8 | 10 |
| 24.1 | 10 |
| 24.7 | 17 |
| 25.4 | 14 |
| 25.9 | 10 |
| 26.2 | 11 |
| 26.9 | 6 |

[Measurement of $^{13}$C Solid NMR Spectrum]

The $^{13}$C solid NMR spectrum of the compounds obtained in Example 20, 24, and 25 was measured under the conditions below.

[Measurement Conditions]

Figure 4:
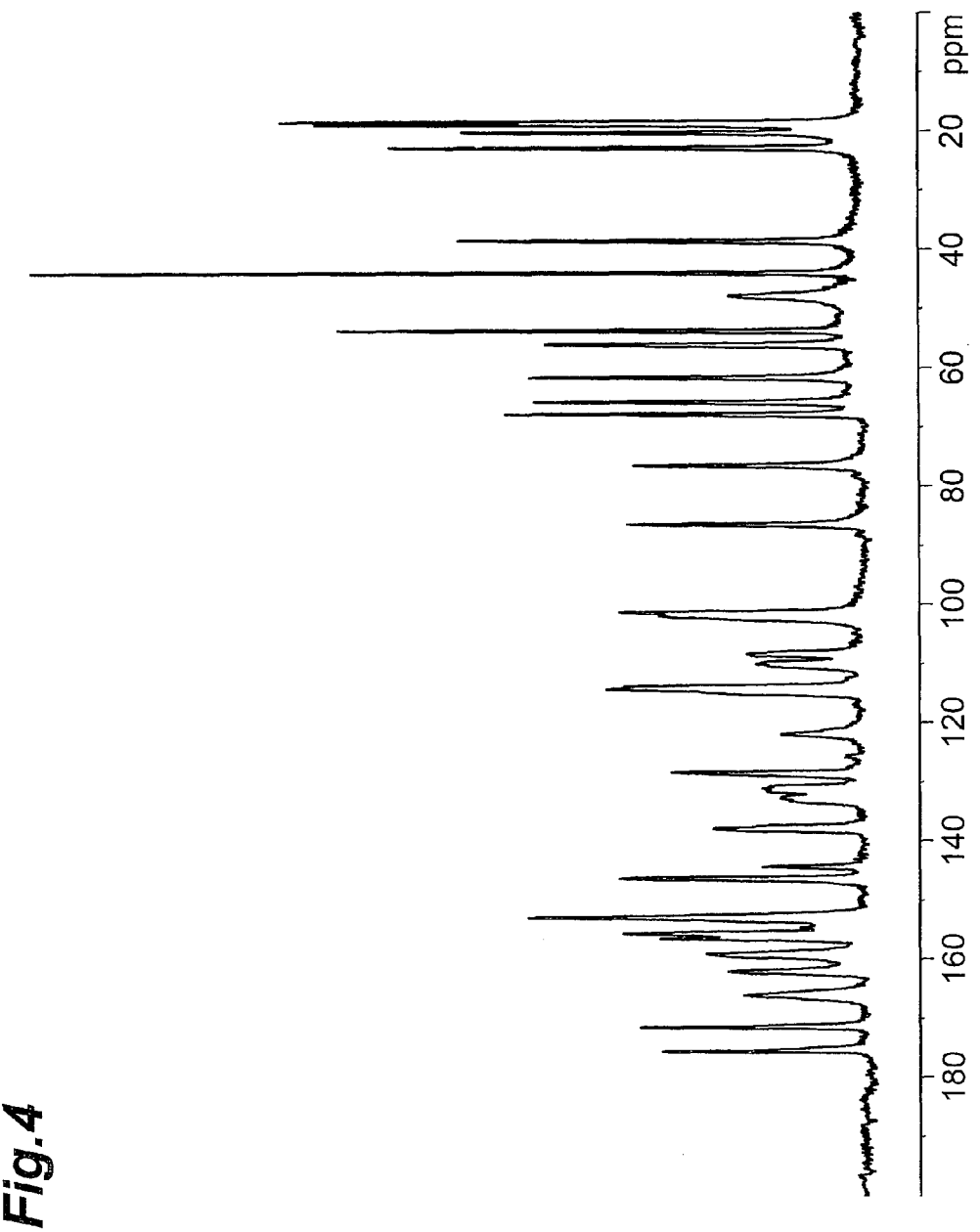
FIG. 4 is a diagram showing the $^{13}$C solid-state NMR spectrum of the compound of Example 20.

Measurement temperature: room temperature (~23° C.)
Reference material: glycine (external reference: carbonyl carbon, 176.03 ppm)
Measured nuclear: $^{13}$C (100.625 MHz)
Pulse mode: CP/TOSS measurement
Accumulations: 4096
Pulse repetition time: 3 seconds FIG. 4 shows the $^{13}$C solid NMR spectrum of the compound of Example 20, and the chemical shift of the signal is shown below.

δ (ppm) 175.6, 171.5, 166.1, 162.1, 159.1, 156.5, 155.7, 154.6, 153.0, 146.4, 144.3, 138.0, 132.8, 131.1, 128.4, 122.0, 114.4, 110.0, 108.4, 101.4, 86.6, 76.6, 67.9, 65.9, 61.7, 56.1, 53.8, 48.0, 44.1, 38.7, 23.0, 20.4, 19.1, 18.6

Figure 5:
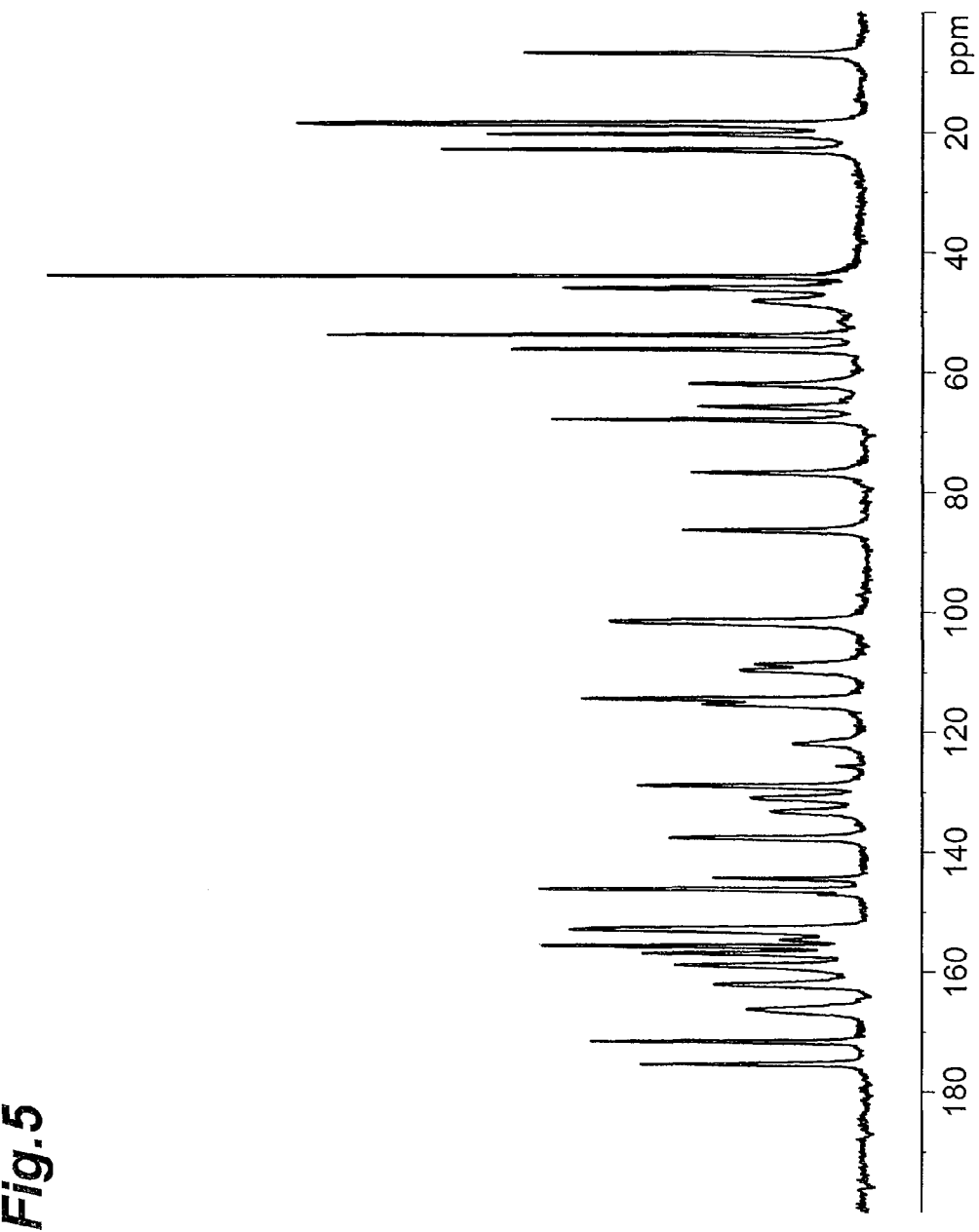
FIG. 5 is a diagram showing the $^{13}$C solid-state NMR spectrum of the compound of Example 24.

FIG. 5 shows the $^{13}$C solid NMR spectrum of the compound of Example 24, and the chemical shift of the signal is shown below.

δ (ppm) 175.5, 171.7, 166.3, 162.1, 158.9, 156.9, 155.7, 154.6, 153.0, 147.0, 146.3, 144.4, 137.7, 133.2, 131.0, 128.9, 121.9, 115.4, 114.5, 109.7, 108.7, 101.6, 86.4, 76.8, 68.0, 65.8, 62.1, 56.3, 53.9, 48.3, 46.2, 44.2, 23.2, 20.5, 18.8, 7.1

Figure 6:
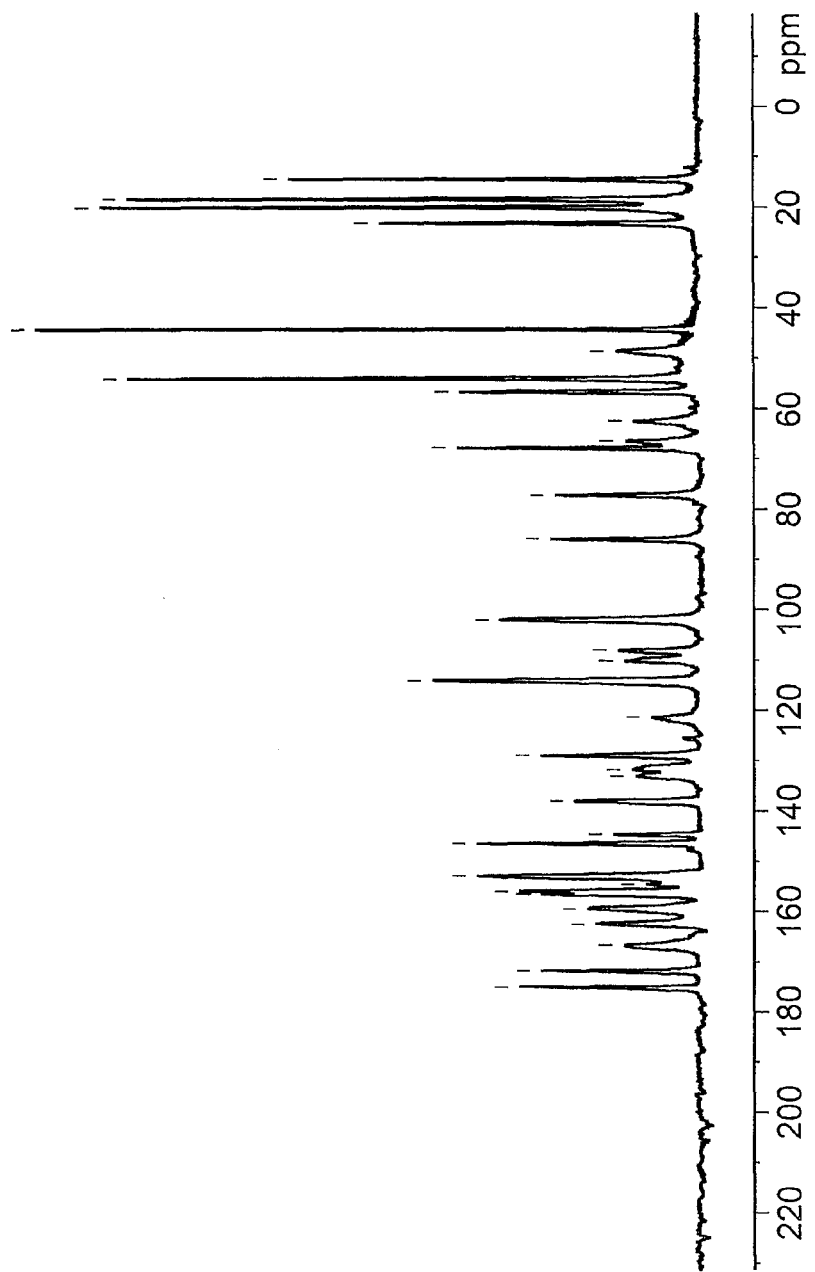
FIG. 6 is a diagram showing the $^{13}$C solid-state NMR spectrum of the compound of Example 25.

FIG. 6 shows the $^{13}$C solid NMR spectrum of the compound of Example 25, and the chemical shift of the signal is shown below.

δ (ppm) 175.0, 171.7, 166.7, 162.4, 159.4, 156.6, 156.0, 154.5, 152.9, 146.5, 144.7, 138.0, 133.0, 131.8, 129.0, 121.3, 114.1, 110.2, 108.1, 102.0, 86.0, 77.2, 67.9, 66.5, 62.5, 56.8, 54.2, 48.7, 44.3, 23.2, 20.1, 18.5, 14.5

Test Example 1

Measurement of Blood Level in Rhesus Monkey by Oral Administration (1) Animal:

Brood male rhesus monkeys aged 4 years or older were used.

(2) Evaluation Sample:

DMSO (Wako Pure Chemical Industries, Ltd.) was added to the compound of the present invention to prepare a solution (A) having a concentration of 10 mg/mL. The solution (A) was stored at −20° C. until use in assay.

(3) Method for Preparing a Solution for Administration:

To 1.2 mL of the solution (A) above, 3 mL of polyoxyethylene (20) sorbitan monolaurate (Wako Pure Chemical Industries, Ltd.) and 25.8 mL of ultrapure water (water obtained by purifying tap water with MQ Gradient-A10 (instrument) and Elix-UV5 (filter) (MILLIPORE)) were added, and the resulting mixture was mixed to prepare a solution for administration (B) (final concentration of the solution for administration (B): 0.4 mg/mL).

(4) Administration, Blood Collection, and Plasma Collection:

Using a disposable glass syringe of 10 or 20 mL capacity, the solution for administration (B) of 2.5 mL per 1 kg of body weight of rhesus monkeys was orally administered to the rhesus monkeys (dose: 1 mg/kg). About 0:5 mL each of blood was collected from a vein at 0.25, 0.5, 1, 2, 4, 6, and 8 hours after the administration. To a 1.5 mL polypropylene tube (Eppendorf) to which (p-amidinophenyl)methanesulfonyl fluoride hydrochloride (Wako Pure Chemical Industries, Ltd.) was added to a final concentration of 2-5 mM, the blood collected above was added, and the resulting mixture was stored under ice-cooling. This solution was centrifuged at 10000 rpm for 5 minutes at 4° C., and accurately 50 μL of plasma was collected and stored until analysis at 20° C.

(5) Method for Measuring Compound Concentration in Plasma:

Concentration of the compound in plasma was determined by using a liquid chromatograph mass spectrometer (LC-MS/MS). To imipramine hydrochloride (SIGMA), a mixed solvent of acetonitrile and methanol (1:1) was added to a concentration of 100 ng/mL to prepare an internal standard substance solution (IS solution) for measurement of concentration. After thawing plasma, acetonitrile (5 μL) followed by 0.3 mL of the IS solution was added thereto, and the resulting mixture was mixed and centrifuged (deproteinized) at 2700 rpm for 10 minutes at 4° C. The supernatant obtained was filtered with a Millipore filter (MILLIPORE) to obtain a filtrate (C).

The filtrate (C) (3-5 μL) was analyzed by LC-MS/MS. For the chromatograms obtained, peak areas of the compounds measured and peak areas corresponding to the internal standard substance were analyzed using MassLynx (MicroMass) to calculate the concentration of the compound contained in the plasma by the internal standard method.

(6) Results

By oral administering the compound of the present invention to rhesus monkeys, the existence of the compound (IV) in venous blood was confirmed. The above test was performed twice for each compound to determine, by moment analysis, maximum plasma concentration ($C_{max}$) of the compound (IV) and area under the plasma concentration curve (AUC) extrapolated to infinite time. The $C_{max}$ and AUC (average of two tests) of each compound are shown in Table 4 below.

TABLE 4

|  | Maximum concentration (Cmax, μg/mL) | Area under the plasma concentration curve (AUC, μg · h/mL) |
| --- | --- | --- |
| Compound (IV) Hydrochloride | 0.010 | 0.130 |
| Example 1 | 0.052 | 0.365 |
| Example 2 | 0.039 | 0.698 |
| Example 3-2 | 0.075 | 0.626 |

TABLE 4-continued

|  | Maximum concentration (Cmax, μg/mL) | Area under the plasma concentration curve (AUC, μg · h/mL) |
| --- | --- | --- |
| Example 4 | 0.036 | 0.314 |
| Example 5 | 0.063 | 0.809 |
| Example 6 | 0.065 | 0.400 |
| Example 7 | 0.058 | 0.576 |
| Example 8 | 0.071 | 0.524 |
| Example 9 | 0.101 | 0.663 |
| Example 10 | 0.064 | 0.402 |
| Example 11-2 | 0.058 | 0.440 |
| Example 12 | 0.051 | 0.492 |
| Example 13 | 0.052 | 0.477 |
| Example 14 | 0.048 | 0.379 |
| Example 15 | 0.069 | 0.371 |
| Example 16 | 0.046 | 0.511 |
| Example 17 | 0.041 | 0.319 |
| Example 18 | 0.034 | 0.497 |

Test Example 2

Measurement of Blood Level in Rhesus Monkey by Oral Administration (1) Animal:

Brood male rhesus monkeys aged 4 years or older were used.

(2) Evaluation Sample:

DMSO (Wako Pure Chemical Industries, Ltd.) was added to the compound of the present invention to prepare a solution (A) having a concentration of 10 mg/mL. The solution (A) was stored at −20° C. until use in assay.

(3) Method for Preparing a Solution for Administration:

To 1.1 mL of the solution (A) above, 2.2 mL of polyoxyethylene (80) sorbitan monolaurate (Tokyo Chemical Industry Co., Ltd.) and 18.7 mL of distilled water for injection (Otsuka Pharmaceutical Co., Ltd.) were added, and the resulting mixture was mixed to prepare a solution for administration (B) (final concentration of the solution for administration (B): 0.5 mg/mL).

(4) Administration, Blood Collection, and Plasma Collection:

Using a disposable glass syringe of 10 or 20 mL capacity, the solution for administration (B) of 2.0 mL per 1 kg of body weight of rhesus monkeys was orally administered to the rhesus monkeys (dose: 1 mg/kg). About 0.5 mL each of blood was collected from a vein at 0.5, 1, 2, 4, 6, and 8 hours after the administration, and stored under ice-cooling. This solution was centrifuged at 10000 rpm for 5 minutes at 4° C., and accurately 50 μL of plasma was collected and stored until analysis at 20° C.

(5) Method for Measuring Compound Concentration in Plasma:

Concentration of the compound in plasma was determined by using a liquid chromatograph mass spectrometer (LC-MS/MS). To imipramine hydrochloride (SIGMA), a mixed solvent of acetonitrile and methanol (1:1) was added to a concentration of 100 ng/mL to prepare an internal standard substance solution (IS solution) for measurement of concentration. After thawing plasma, acetonitrile (5 μL) followed by 0.3 mL of the IS solution was added thereto, and the resulting mixture was mixed and centrifuged (deproteinized) at 2700 rpm for 10 minutes at 4° C. The supernatant obtained was filtered with a Millipore filter (MILLIPORE) to obtain a filtrate (C).

The filtrate (C) (3-5 μL) was analyzed by LC-MS/MS. For the chromatograms obtained, peak areas of the compounds measured and peak areas corresponding to the internal standard substance were analyzed using MassLynx (MicroMass) to calculate the concentration of the compound contained in the plasma by the internal standard method.

(6) Results

By oral administering the compound of the present invention to rhesus monkeys, the existence of the compound (IV) in venous blood was confirmed. The above test was performed twice for each compound to determine, by moment analysis, maximum plasma concentration ($C_{max}$) of the compound (IV) and area under the plasma concentration curve (AUC) extrapolated to infinite time. The $C_{max}$ and AUC (average of two tests) of each compound are shown in Table 5 below.

TABLE 5

| | Maximum concentration (Cmax, µg/mL) | Area under the plasma concentration curve (AUC, µg · h/mL) |
| --- | --- | --- |
| Example 51 | 0.057 | 0.502 |
| Example 52 | 0.056 | 0.279 |
| Example 53 | 0.045 | 0.244 |
| Example 54 | 0.059 | 0.434 |
| Example 55 | 0.048 | 0.272 |
| Example 57 | 0.061 | 0.378 |
| Example 67 | 0.051 | 0.396 |
| Example 68 | 0.063 | 0.371 |

INDUSTRIAL APPLICABILITY

By oral administration of the compound of the present invention, excellent inhibitory action on blood coagulation factor VIIa and blood concentration of the compound (IV) having an anti-blood coagulation effect reach the level sufficient to exhibit pharmacological action. Therefore, the compound of the present invention is useful as a therapeutic and/or prophylactic agent for diseases caused by thrombus formation.

The invention claimed is:

1. A compound represented by the following Formula (I) or a pharmaceutically acceptable salt thereof:

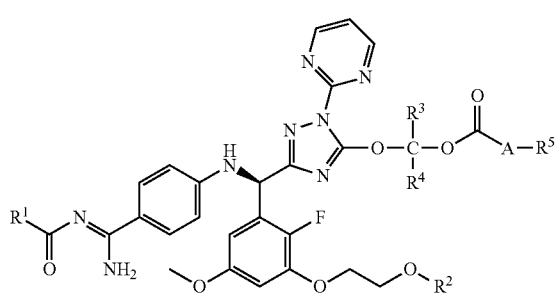

(I)

wherein $R^1$ represents phenyl optionally substituted by one to three $C_1$-$C_6$ alkyl groups, $C_1$-$C_6$ alkoxy or $C_2$-$C_6$ alkenyloxy;
$R^2$ represents a hydrogen atom, $C_1$-$C_6$ alkylcarbonyl or pyridylcarbonyl;
$R^3$ and $R^4$ each independently represent a hydrogen atom or $C_1$-$C_6$ alkyl;
A represents a single bond, an oxygen atom, a group represented by Formula (II):

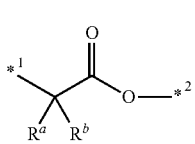

(II)

wherein $R^a$ and $R^b$ each independently represent a hydrogen atom or $C_1$-$C_6$ alkyl, and *1 and *2 mean linking to carbonyl and to $R^5$, respectively, in Formula (I),
or a group represented by Formula (III):

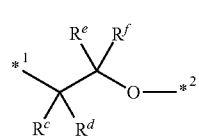

(III)

wherein $R^c$, $R^d$, $R^e$ and $R^f$ each independently represent a hydrogen atom or $C_1$-$C_6$ alkyl, and *1 and *2 have the same meanings as described above; and
$R^5$ represents $C_1$-$C_6$ alkyl or $C_3$-$C_8$ cycloalkyl, and $C_1$-$C_6$ alkyl or $C_3$-$C_8$ cycloalkyl in $R^5$ is optionally substituted by one to three identical or different substituents selected from the group of substituents consisting of a halogen atom, $C_1$-$C_6$ alkyl and $C_1$-$C_6$ alkoxy.

2. The compound or the pharmaceutically acceptable salt thereof according to claim 1, wherein $R^1$ is phenyl, 4-tolyl, 2,2-dimethyl-1-propyloxy, 2,2-dimethyl-1-butyloxy or 2-methyl-2-propenyloxy.

3. The compound or the pharmaceutically acceptable salt thereof according to claim 1, wherein $R^2$ is a hydrogen atom, acetyl or 4-pyridylcarbonyl.

4. The compound or the pharmaceutically acceptable salt thereof according to claim 1, wherein $R^3$ and $R^4$ are each independently a hydrogen atom, methyl or ethyl.

5. The compound or the pharmaceutically acceptable salt thereof according to claim 1, wherein $R^5$ is $C_1$-$C_6$ alkyl optionally substituted by methoxy, or cyclohexyl optionally substituted by a halogen atom or methyl.

6. The compound or the pharmaceutically acceptable salt thereof according to claim 1, wherein $R^a$, $R^b$, $R^c$, $R^d$, $R^e$ and $R^f$ are each independently a hydrogen atom or methyl.

7. The compound or the pharmaceutically acceptable salt thereof according to claim 1, wherein
$R^1$ is 4-tolyl, phenyl, 2,2-dimethyl-1-propyloxy, 2,2-dimethyl-1-butyloxy or 2-methyl-2-propenyloxy;
$R^2$ is a hydrogen atom, acetyl or 4-pyridylcarbonyl;
$R^3$ and $R^4$ are each independently a hydrogen atom, methyl or ethyl;
$R^5$ is $C_1$-$C_6$ alkyl optionally substituted by methoxy, or cyclohexyl optionally substituted by a halogen atom or methyl;
A is a single bond, an oxygen atom, a group represented by Formula (II) or a group represented by Formula (III); and
$R^a$, $R^b$, $R^c$, $R^d$, $R^e$ and $R^f$ are each independently a hydrogen atom or methyl.

8. The compound or the pharmaceutically acceptable salt thereof according to claim 1, wherein the compound is 3-methoxymethoxy-2,2-dimethylpropionic acid 5-{(R)-[4-(amino[benzoylimino]methyl)phenylamino]-[2- fluoro-3-(2-hydroxyethoxy)-5-methoxyphenyl]methyl}-2-pyrimidin-2-yl-2H-[1,2,4]triazol-3-yloxymethyl ester,
2,2-dimethylmalonic acid 5-{(R)-(4-{amino(2,2-dimethylpropoxycarbonylimino)methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester t-butyl ester,
carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester cyclohexyl ester,
4-pyridinecarboxylic acid 2-(3-{(R)-(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methyl}-2-fluoro-5-methoxyphenoxy)ethyl ester,
2-ethylbutanoic acid 5-[(R)-[3-(2-acetoxyethoxy)-2-fluoro-5-methoxyphenyl]-(4-{amino[2,2-dimethylpropoxycarbonylimino]methyl}phenylamino)methyl]-2-pyrimidin-2-yl-2H-[1,2,4]triazol-3-yloxymethyl ester,
3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester,
cyclohexane carboxylic acid 5-[(R)-[3-(2-acetoxyethoxy)-2-fluoro-5-methoxyphenyl]-(4-{amino[2,2-dimethylpropoxycarbonylimino]methyl}phenylamino)methyl]-2-pyrimidin-2-yl-2H-[1,2,4]triazol-3-yloxymethyl ester,
2,2-dimethylmalonic acid 5-{(R)-(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester cyclohexyl ester,
carbonic acid 1-(5-{(R)-(4-{amino[4-methylbenzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (1R,2R)-2-methylcyclohexyl ester,
2,2-dimethylmalonic acid 5-{(R)-(4-{amino(2,2-dimethylpropoxycarbonylimino)methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester,
carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (R)-1-methylbutyl ester,
carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)ethyl ester (1S,2S)-2-fluorocyclohexyl ester,
carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)propyl ester cyclohexyl ester,
carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)propyl ester trans-2-fluorocyclohexyl ester,
2,2-dimethylmalonic acid 5-{(R)-(4-{amino[2,2-dimethylpropoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester ethyl ester,
2,2-dimethylmalonic acid 5-{(R)-(4-{amino(2,2-dimethylpropoxycarbonylimino)methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester isopropyl ester,
isonicotinic acid 2-(3-{(R)-(4-{amino[benzoylimino]methyl}phenylamino)-[5-(2,2-dimethylpropionyloxymethoxy)-1-pyrimidin-2-yl-1H-[1,2,4]triazol-3-yl]methyl}-2-fluoro-5-methoxyphenoxy)ethyl ester, or
2,2-dimethylmalonic acid 5-{(R)-(4-{amino[2,2-dimethylbutoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester,
or a pharmaceutically acceptable salt thereof.

9. The compound or the pharmaceutically acceptable salt thereof according to claim 1, wherein the compound is
3-methoxymethoxy-2,2-dimethylpropionic acid 5-{(R)-[4-(amino[benzoylimino]methyl)phenylamino]-[2-fluoro-3-(2-hydroxyethoxy)-5-methoxyphenyl]methyl}-2-pyrimidin-2-yl-2H-[1,2,4]triazol-3-yloxymethyl ester,
4-pyridinecarboxylic acid 2-(3-{(R)-(4-{amino[benzoylimino]methyl}phenylamino)-[5-(3-methoxy-2,2-dimethylpropionyloxymethoxy)-1-pyrimidin-2-yl-1H-[1,2,4]triazol-3-yl]methyl}-2-fluoro-5-methoxyphenoxy)ethyl ester,
2-ethylbutanoic acid 5-[(R)-[3-(2-acetoxyethoxy)-2-fluoro-5-methoxyphenyl]-(4-{amino[2,2-dimethylpropoxycarbonylimino]methyl}phenylamino)methyl]-2-pyrimidin-2-yl-2H-[1,2,4]triazol-3-yloxymethyl ester,
3-methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester,
carbonic acid 1-(5-{(R)-(4-{amino[benzoylimino]methyl}phenylamino)-[2-fluoro-3-(2-hydroxyethoxy)-5-methoxyphenyl]methyl}-2-pyrimidin-2-yl-2H-[1,2,4]triazol-3-yloxy)propyl ester cyclohexyl ester, or
2,2-dimethylmalonic acid 5-{(R)-(4-{amino[2,2-dimethylbutoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2,2-dimethylpropyl ester,
or a pharmaceutically acceptable salt thereof.

10. 3-Methoxymethoxy-2,2-dimethylpropionic acid 5-{(R)-[4-(amino[benzoylimino]methyl)phenylamino]-[2-fluoro-3-(2-hydroxyethoxy)-5-methoxyphenyl]methyl}-2-pyrimidin-2-yl-2H-[1,2,4]triazol-3-yloxymethyl ester or a pharmaceutically acceptable salt thereof.

11. 3-Methoxy-2,2-dimethylpropionic acid 5-[(R)-[3-(2-acetoxyethoxy)-2-fluoro-5-methoxyphenyl]-(4-{amino[2-methylallyloxycarbonylimino]methyl}phenylamino)methyl]-2-pyrimidin-2-yl-2H-[1,2,4]triazol-3-yloxymethyl ester or a pharmaceutically acceptable salt thereof.

12. The compound or the pharmaceutically acceptable salt thereof according to claim 1, wherein the compound is acetic acid 2-(3-{(R)-(4-{amino[2-methylallyloxycarbonylimino]methyl}phenylamino)-[5-(1-ethylpropoxycarbonyloxymethoxy)-1-pyrimidin-2-yl-1H-[1,2,4]triazol-3-yl]methyl}-2-fluoro-5-methoxyphenoxy)ethyl ester,
acetic acid 2-{3-[(R)-(4-{amino[2-methylallyloxycarbonylimino]methyl}phenylamino)-(5-isopropoxycarbonyloxymethoxy-1-pyrimidin-2-yl-1H-[1,2,4]triazol-3-yl)methyl]-2-fluoro-5-methoxyphenoxy}ethyl ester, acetic acid 2-{3-[(R)-(4-{amino[2-methylallyloxycarbonylimino]methyl]phenylamino)-(5-isopropoxycarbonyloxymethoxy-1-pyrimidin-2-yl-1H-[1,2,4]triazol-3-yl)methyl]-2-fluoro-5-methoxyphenoxy}ethyl ester, acetic acid 2-(3-{(R)-(4-{amino[butoxycarbonylimino]methyl}phenylamino)-[5-(1-ethylpropoxycarbonyloxymethoxy)-1-pyrimidin-2-yl-1H-[1,2,4]triazol-3-yl]methyl}-2-fluoro-5-methoxyphenoxy)ethyl ester, acetic acid 2-(3-{(R)-(4-{amino[isobutoxycarbonylimino]methyl}phenylamino)-[5-(1-ethylpropoxycarbonyloxymethoxy)-1-pyrimidin-2-yl-1H-[1,2,4]triazol-3-yl]methyl}-2-fluoro-5-methoxyphenoxy)ethyl ester, carbonic acid 5-{(R)-(4-{amino-42-methylallyloxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester, acetic acid 2-(3-{(R)-(4-{amino[2-methylallyloxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester, carbonic acid 5-{(R)-(4-{amino-[2-ethoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester, carbonic acid 5-{(R)-(4-{amino-[2-propoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester, carbonic acid 5-{(R)-(4-{amino-[2-butoxycarbonylimino]methyl}phenylamino)-[2-fluoro-3-(2-hydroxyethoxy)-5-methoxyphenyl]methyl}-2-pyrimidin-2-yl-2H-[1,2,4]triazol-3-yloxymethyl ester 2-fluoro-1,1-dimethylethyl ester, acetic acid 2-(3-{(R)-(4-{amino[ethoxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester, acetic acid 2-(3-{(R)-(4-{amino [propoxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester, acetic acid 2-(3-{(R)-(4-{amino [butoxycarbonylimino]methyl}phenylamino)-[5-(2-fluoro-1,1-dimethylethoxycarbonyloxymethoxy)-1-pyrimidin-2-yl-2H-[1,2,4]triazol-3-yl]methyl}-2-fluoro-5-methoxyphenoxy)ethyl ester, acetic acid 2-{3-[(R)-(4-{amino [butoxycarbonylimino]methyl} phenylamino)-(5-isopropoxycarbonyloxymethoxy-1-pyrimidin-2-yl-1H-[1,2,4]triazol-3-yl)methyl]-2-fluoro-5-methoxyphenoxy)ethyl ester, or acetic acid 2-{3-[(R)-(4-{amino [isobutoxycarbonylimino]methyl}phenylamino)-(5-isopropoxycarbonyloxymethoxy-1-pyrimidin-2-yl-1H-[1,2,4]triazol-3-yl)methyl]-2-fluoro-5-methoxyphenoxy)ethyl ester, or a pharmaceutically acceptable salt thereof.

13. A pharmaceutical composition comprising the compound or the pharmaceutically acceptable salt thereof according to claim 1.

14. A method of treating a disease caused by thrombus formation, comprising administering to a human subject in need thereof the compound or the pharmaceutically acceptable salt thereof according to claim 1, wherein the disease caused by thrombus formation is thrombosis, deep vein thrombosis, pulmonary embolism, cerebral infarction, myocardial infarction, acute coronary syndrome, vascular restenosis, or disseminated intravascular coagulation syndrome.

15. A method of treating a disease caused by thrombus formation, comprising administering to a human subject in need thereof the compound or the pharmaceutically acceptable salt thereof according to claim 10, wherein the disease caused by thrombus formation is thrombosis, deep vein thrombosis, pulmonary embolism, cerebral infarction, myocardial infarction, acute coronary syndrome, vascular restenosis, or disseminated intravascular coagulation syndrome.

16. A method of treating a disease caused by thrombus formation, comprising administering to a human subject in need thereof the compound or the pharmaceutically acceptable salt thereof according to claim 11, wherein the disease caused by thrombus formation is thrombosis, deep vein thrombosis, pulmonary embolism, cerebral infarction, myocardial infarction, acute coronary syndrome, vascular restenosis, or disseminated intravascular coagulation syndrome.

17. A pharmaceutical composition comprising the compound or the pharmaceutically acceptable salt thereof according to claim 10.

18. A pharmaceutical composition comprising the compound or the pharmaceutically acceptable salt thereof according to claim 11.

* * * * *